US009392976B2

(12) United States Patent
Rodriguez-Llorente et al.

(10) Patent No.: US 9,392,976 B2
(45) Date of Patent: Jul. 19, 2016

(54) METHODS AND SYSTEMS FOR DETERMINING PHYSIOLOGICAL INFORMATION BASED ON A COMBINED AUTOCORRELATION SEQUENCE

(75) Inventors: Fernando Rodriguez-Llorente, London (GB); Nicholas James Wooder, Royston (GB)

(73) Assignee: Covidien LP, Mansfield, MA (US)

( * ) Notice: Subject to any disclaimer, the term of this patent is extended or adjusted under 35 U.S.C. 154(b) by 723 days.

(21) Appl. No.: 13/609,533

(22) Filed: Sep. 11, 2012

(65) Prior Publication Data

US 2014/0073960 A1 Mar. 13, 2014

(51) Int. Cl.
*A61B 5/024* (2006.01)
*A61B 6/00* (2006.01)
*A61B 5/00* (2006.01)
*A61B 5/1455* (2006.01)

(52) U.S. Cl.
CPC .......... *A61B 5/7246* (2013.01); *A61B 5/14551* (2013.01); *A61B 5/02416* (2013.01); *A61B 5/725* (2013.01); *A61B 5/7207* (2013.01)

(58) Field of Classification Search
CPC combination set(s) only.
See application file for complete search history.

(56) References Cited

U.S. PATENT DOCUMENTS

| | | | |
|---|---|---|---|
| 4,911,167 A | 3/1990 | Corenman et al. | |
| 4,938,228 A | 7/1990 | Righter et al. | |
| 4,955,379 A | 9/1990 | Hall | |
| 5,188,108 A | 2/1993 | Secker | |
| 5,853,364 A | 12/1998 | Baker, Jr. et al. | |
| 6,002,952 A | 12/1999 | Diab et al. | |
| 6,178,343 B1 | 1/2001 | Bindszus et al. | |
| 6,339,715 B1 | 1/2002 | Bahr et al. | |
| 6,463,311 B1 | 10/2002 | Diab | |
| 6,519,486 B1 | 2/2003 | Edgar, Jr. et al. | |
| 6,564,077 B2 | 5/2003 | Mortara | |
| 6,684,090 B2 | 1/2004 | Ali et al. | |
| 6,850,787 B2 | 2/2005 | Weber et al. | |
| 6,905,470 B2 | 6/2005 | Lee et al. | |

(Continued)

FOREIGN PATENT DOCUMENTS

WO 2009023524 A1 2/2009

OTHER PUBLICATIONS

Kamshilin Alexei A. et al. "Photoplethysmographic Imaging of High Spatial Resolution," Biomedical Optics Express, vol. 2, No. 4, Apr. 1, 2011, pp. 996-1006.

(Continued)

*Primary Examiner* — Katherine Fernandez
*Assistant Examiner* — Farshad Negarestan
(74) *Attorney, Agent, or Firm* — Shvarts & Leiz LLP

(57) ABSTRACT

A physiological monitoring system may process a physiological signal such a photoplethysmograph signal from a subject. The system may determine physiological information, such as a physiological rate, from the physiological signal. The system may use search techniques and qualification techniques to determine one or more initialization parameters. The initialization parameters may be used to calculate and qualify a physiological rate. The system may use signal conditioning to reduce noise in the physiological signal and to improve the determination of physiological information. The system may use qualification techniques to confirm determined physiological parameters. The system may also use autocorrelation techniques, cross-correlation techniques, fast start techniques, and/or reference waveforms when processing the physiological signal.

28 Claims, 55 Drawing Sheets

(56) References Cited

U.S. PATENT DOCUMENTS

| | | |
|---|---|---|
| 7,018,338 B2 | 3/2006 | Vetter et al. |
| 7,315,753 B2 | 1/2008 | Baker, Jr. et al. |
| 7,373,194 B2 | 5/2008 | Weber et al. |
| 7,530,955 B2 | 5/2009 | Diab et al. |
| 7,534,212 B2 | 5/2009 | Baker, Jr. et al. |
| 7,904,132 B2 | 3/2011 | Weber et al. |
| 7,922,665 B2 | 4/2011 | Baker, Jr. |
| 7,931,599 B2 | 4/2011 | Baker, Jr. et al. |
| 8,007,441 B2 | 8/2011 | Baker, Jr. |
| 8,226,568 B2 | 7/2012 | Watson et al. |
| 8,285,352 B2 | 10/2012 | Addison et al. |
| 2007/0233468 A1 | 10/2007 | Ozdas et al. |
| 2009/0326393 A1 | 12/2009 | Sethi et al. |
| 2010/0191118 A1* | 7/2010 | Kabakov ............... 600/453 |
| 2012/0179011 A1 | 7/2012 | Moon et al. |
| 2013/0079656 A1* | 3/2013 | Dripps et al. ............ 600/529 |

OTHER PUBLICATIONS

International Search Report and Written Opinion of the International Searching Authority for application No. PCT/US2013/059290, mailed on Dec. 26, 2013.

Karlen, W. et al. "Photoplethysmogram signal quality estimation using repeated Gaussian filters and cross-correlation." 2012, Physiol. Meas. 33, pp. 1617-1629.

Communication pursuant to Rule 164(1) EPC and partial supplementary European search report issued by the European Patent Office in connection with counterpart European Patent Application No. 13837097.8, dated Apr. 15, 2016, 7 pages.

* cited by examiner

METHODS AND SYSTEMS FOR DETERMINING PHYSIOLOGICAL INFORMATION BASED ON A COMBINED AUTOCORRELATION SEQUENCE

The present disclosure relates to determining physiological information. More particularly, the present disclosure relates to determining physiological information, such as physiological rate information, based on a combined autocorrelation sequence.

SUMMARY

A physiological monitor may determine one or more physiological parameters such as, for example, a physiological rate based on signals received from one or more physiological sensors. The physiological monitor may analyze physiological signals (e.g., photoplethysmographic (PPG) signals) for oscillometric behavior characterized by a pulse rate, a respiration rate, or both. Physiological signals may include one or more noise components, which may include the effects of ambient light, electromagnetic radiation from powered devices (e.g., at 60 Hz or 50 HZ), subject movement, and/or other non-physiological or undesired physiological signal components. In some circumstances, the determination of a pulse rate from photoplethysmographic information may present challenges. Factors such as, for example, noise, subject movement, the shape of physiological pulses, subjects having low perfusion with small physiological pulses, and/or other factors may present challenges in determining a pulse rate.

The physiological monitor in accordance with the present disclosure may include a sensor, having a detector, which may generate an intensity signal (e.g., a PPG signal) based on light attenuated by the subject. Processing equipment of the monitor, a processing module, and/or other suitable processing equipment may determine a value indicative of a physiological rate based on the intensity signal. For example, the processing equipment may determine a pulse rate based on analysis of the intensity signal.

In some embodiments, the processing equipment may use a search mode and a locked mode to determine a physiological parameter of a subject. The search mode may be used to determine one or more initialization parameters and the locked mode may use the one or more initialization parameters to determine the physiological parameter (e.g., pulse rate) of the subject. The locked mode may use, for example, a relatively narrow band-pass filter that is initially tuned based on the one or more initialization parameters and is subsequently tuned based on previously determined physiological parameters. A relatively narrow, adjustable band-pass filter is good at rejecting noise when it is tuned to the correct rate. The search and locked modes may include qualification techniques to qualify the one or more initialization parameters and the physiological parameters. The qualification techniques can prevent the band-pass filter from being initially tuned to noise and can prevent the band-pass filter from deviating away from the correct physiological rate. In addition, in the event that the band-pass is tuned incorrectly, the processing equipment may determine to return to the search mode based on qualification failure information to reset the one or more initialization parameters. Accordingly, physiological parameters (e.g., pulse rate) may be reliably determined in the presence of noise.

In some embodiments, the processing equipment may determine one or more initialization parameters (e.g., an algorithm setting) based on the intensity signal, and determine a value indicative of a physiological rate of the subject based on the intensity signal and based on the algorithm setting. Determining the value indicative of the physiological rate may include performing a correlation calculation such as an autocorrelation, and/or filtering a signal based on the algorithm setting, wherein the signal is based on the intensity signal. The filtering may include applying a bandpass filter based on the algorithm settings. In some embodiments, the processing equipment may generate a threshold based on the correlation signal and/or algorithm setting, and identify threshold crossings. For example, the processing equipment may determine a difference (e.g., a time interval or number of samples) associated with at least two threshold crossings, and then determine the value indicative of the physiological rate based on the difference.

In some embodiments, the processing equipment may calculate an autocorrelation sequence based on the intensity signal, and identify a number of times the autocorrelation sequence crosses a threshold at each of a plurality of threshold settings. In some embodiments, the number of crossings may be converted to a value indicative of a physiological rate based on the length of the autocorrelation sequence. In some embodiments, the intensity signal may be conditioned using, for example, a detrending calculation. The autocorrelation sequence may be generated by selecting a first and a second portion of the conditioned intensity signal and performing a correlation calculation at a plurality of different lags. Analysis of the stability of the number of threshold crossings over two or more of the plurality of threshold settings may aid the processing equipment in determining the value indicative of a physiological rate. For example, the processing equipment may analyze the stability by determining and/or selecting a stable region where the number of threshold crossing remains substantially the same for a range of threshold values. In some embodiments, the processing equipment may identify one or more peaks of the autocorrelation sequence, and determine the value indicative of a physiological rate of the subject based on an analysis of the shape of the one or more peaks. The shape analysis may be based on a symmetry of the one or more peaks, a width of the one or more peaks, an amplitude of the one or more peaks, or other shape information. In some embodiments, the analysis may include identifying a plurality of peaks of the autocorrelation sequence, disqualifying peaks that do not meet one or more criteria, and then determining the value indicative of the physiological rate based on one or more of the non-disqualified peaks. In some embodiments, the number of crossing may be converted to one or more initialization settings (e.g., an algorithm setting).

In some embodiments, the processing equipment may perform a first modulation on an intensity signal to generate a first modulated intensity signal using a first modulation signal, and a second modulation on an intensity signal to generate a second modulated intensity signal using a second modulation signal. The first and second modulation signals may be sinusoids relatively shifted in phase such as, for example, a sine signal and a cosine signal. In some embodiments, the modulated signals may be low-pass filtered. Analysis of a phase signal based on the first modulated intensity signal and the second modulated intensity signal may aid in determining a value indicative of a physiological rate of the subject based on the phase signal. In some embodiments, a plurality of first modulated intensity signals and second modulated intensity signals may be generated over a range of modulation frequencies. The analysis may include analyzing phase signals based on the plurality of first modulated intensity signals and the plurality of second modulated intensity signals, and the value indicative of the physiological rate may be determined based on the phase differences. For example, a modulation frequency that provides a substantially stable phase difference may be used to determine the value indicative of a physiological rate. In some embodiments, the analysis of one or more phase signals may aid in determining one or more initialization settings (e.g., an algorithm setting).

In some embodiments, the processing equipment may calculate an autocorrelation sequence based on the intensity signal, which may be conditioned, and then calculate a cross-correlation sequence of the autocorrelation sequence and a cross-correlation waveform to determine a value indicative of a physiological rate of the subject. In some embodiments, the conditioning may include generating a signal to fit a segment of the intensity signal such as a line fit, a quadratic curve fit, or a cubic curve fit, and then modifying the intensity signal by subtracting the generated signal. In some embodiments, an absolute value of the cross-correlation sequence may be used for analysis. The analysis may be based on a peak in the calculated absolute values. In some embodiments, a cross-correlation waveform having a plurality of segments having different frequency components may be used. For example, the plurality of segments may include one or more base waveforms, having a different associated frequency, for each of the plurality of segments. In a further example, one or more base waveforms for a particular segment may be a temporal-scaled and/or amplitude-scaled version of one or more base waveforms for another one of the plurality of segments. One or more of the plurality of segments may include temporal dithering of associated base waveform(s). In some embodiments, a second cross-correlation may be calculated, having segments each with different characteristics, and different from the first cross-correlation waveform. Accordingly, the one or both of the cross-correlations may be used to determine the value indicative of the physiological rate. In some embodiments, a peak based on the cross-correlation sequence may be identified and analyzed. In some embodiments, an envelope based on the cross-correlation sequence may be generated, and the peak may be identified from the envelope. In some embodiments, values in the cross-correlation sequence that correspond to each of the plurality of segments may be summed, and the peak may be identified based on the sums. Peaks may be compared to a threshold, which may be determined based on the cross-correlation sequence, and/or compared to the next largest identified peak. In some embodiments, the cross-correlation sequence may be used to determine one or more initialization settings (e.g., an algorithm setting).

In some embodiments, a first autocorrelation sequence and a second autocorrelation sequence may be calculated, and then combined to determine one or more initialization settings (e.g., an algorithm setting) or a value indicative of physiological information of the subject. The first and second autocorrelation sequences may be calculated using templates, which may be portions of data, having different sizes, or the same size. In some embodiments, the first and second auto-correlation sequences may be averaged and/or bandpass filtered. One or more peaks in the combined autocorrelation sequence may be identified. For example, the difference (e.g., in time or sample number) between two peaks may be used to determine the initialization settings or the value indicative of the physiological rate.

In some embodiments, after determining a value indicative of a physiological rate of the subject, the processing equipment may determine whether to qualify or disqualify the value. A cross-correlation sequence based on the intensity signal and a reference waveform may be calculated. The reference waveform may be based on the value indicative of the physiological rate of the subject, and may optionally include a pulse shape. A metric indicative of a symmetry associated with the cross-correlation sequence may be determined and the qualification may be based on the metric. The metric may be based on symmetry between two segments, which may be, for example, adjacent segments centered on a peak or valley of the cross-correlation sequence, or segments that may begin at points in the cross-correlation sequence that are spaced apart from each other and are at approximately equal amplitudes. The value indicative of the physiological rate may be filtering based on the qualification. In some embodiments, two segments from the cross-correlation sequence may be selected that are approximately the same size, each having starting points offset by a certain amount (e.g., quarter of a period). The period may be associated with the value indicative of the physiological rate, and the segment sizes may be smaller than, equal to, or larger than the period. In some embodiments, the processing equipment may calculate a sequence of differences, where each is based on a value from a first of the two segments and a value from a second of the two segments. The qualification of the value indicative of the physiological rate may be based on a maximum and a minimum of the calculated differences. In some embodiments, the processing equipment may calculate angles, where each is based on a value from a first of the two segments and a value from a second of the two segments. The qualification may be based on a sum of the angles. In some embodiments, the foregoing techniques may be used to qualify or disqualify one or more initialization settings.

In some embodiments, qualification may include selecting two signal segments having different lengths based on the intensity signal. A first of the two different lengths may be approximately double a second of the two different lengths, and be approximately equal to, or twice, a period associated with the value indicative of the physiological rate. In some embodiments, a positive area and a negative area for each of the two signal segments may be calculated, and the difference between the areas may be calculated. A threshold may be generated based on the difference, and a value based on the difference for a second of the two signal segments may be compared to the threshold. In some embodiments, a first metric may be determined based on the intensity signal. After performing a filtering calculation based on the intensity signal to generate a filtered intensity signal, a second metric based on the filtered intensity signal may be determined. The filtering may include applying a high-pass filter having a cutoff of about double the value indicative of the physiological rate. The first and second metrics may each include one of a standard deviation, root-mean-square deviation, an amplitude, a sum, and an integral. Qualification may be based on a comparison of the first and second metrics. For example, a ratio of the first metric to the second metric may be determined and compared to a threshold, and qualification may be based on the comparison. In some embodiments, qualification may include selecting two signal segments, which may be adjacent, of approximately equal length based on the intensity signal. An area for each of the two segments may be determined and compared to determine whether to qualify the value indicative of the physiological rate. In some embodiments, a cross-correlation sequence based on the intensity signal and a cross-correlation waveform may be calculated, and the two signal segments may be selected from the cross-correlation sequence. In some embodiments, the foregoing qualification techniques may be used to qualify or disqualify one or more initialization settings.

In some embodiments, qualification may include analyzing selected positive and negative values based on a mean-subtracted intensity signal. Statistical properties of the positive and negative values may be calculated, and compared to determine whether to qualify the value indicative of the physiological rate. In some embodiments, a cross-correlation sequence based on the intensity signal and a cross-correlation waveform may be calculated, and the two signal segments may be selected from the cross-correlation sequence. In some embodiments, the foregoing qualification techniques may be used to qualify or disqualify one or more initialization settings.

In some embodiments, qualification may include calculating a first cross-correlation sequence based on the intensity signal and a first reference waveform, and a second cross-correlation sequence based on the intensity signal and a second reference waveform. The first and second reference waveforms may optionally have different lengths, pulse shapes, or other properties. In some embodiments, a first qualification metric and a second qualification metric may be determined based on the first cross-correlation sequence and second cross-correlation sequence, respectively, and the metrics may be used to determine whether to qualify the value indicative of the physiological rate. In some embodiments, the foregoing qualification techniques may be used to qualify or disqualify one or more initialization settings.

In some embodiments, when the value indicative of the physiological rate is disqualified, qualification failure information may be analyzed, and a second calculation technique (e.g., which may be different than the first technique) may be used to determine a subsequent value indicative of the physiological rate of the subject. In some embodiments, at least one qualification metric based on the physiological rate and the intensity signal may be determined. When the value is disqualified, the corresponding at least one qualification metric may be indicative of the actual physiological rate of the subject, and the selected second calculation technique may be configured such that it is more likely to identify the actual physiological rate of the subject than the first calculation technique. In some embodiments, the qualification failure information may include a plurality of disqualified values and corresponding qualification metrics. In some embodiments, the analysis may include identifying a pattern based on historical qualification information. The second calculation technique may optionally include a low pass, high pass, and/or notch filtering calculation based on the intensity signal that is not included in the first calculation technique. In some embodiments, when the value indicative of the physiological rate is disqualified, qualification failure information may be analyzed, and a different value indicative of the physiological rate may be used for subsequent processing. In some embodiments, at least one qualification metric may be determined based on the value indicative of the physiological rate and the intensity signal, and may be indicative of the actual physiological rate of the subject. Accordingly, the different value may correspond to the actual physiological rate. In some embodiments, the analysis may determine that the value indicative of the physiological rate is indicative of a harmonic of the physiological rate and that the different value corresponds to a fundamental frequency of the physiological rate. In some embodiments, subsequent processing may include performing a filtering calculation based on the intensity signal, in which the filtering coefficients used in the filtering calculation may be based on the different value. In some embodiments, subsequent processing may include using a second calculation technique based on the intensity signal and the different value to determine a second value indicative of the physiological rate. In some embodiments, the forego-ing techniques may be used to improve the determination of one or more initialization settings.

In some embodiments, a first initialization setting may be determined based on an intensity signal using a first calculation technique, and a second initialization setting may be determined based on the intensity signal using a second calculation technique. The processing equipment may determine whether to qualify each of the first initialization setting and the second initialization setting. A resulting initialization setting may be determined based on whether the first and second initialization settings are qualified, and the resulting initialization setting may be used to determine a value indicative of a physiological rate of the subject. The resulting initialization setting may be the first initialization setting when the first initialization setting is qualified and the second initialization is disqualified, or the resulting initialization setting may be a combination of the first initialization setting and the second initialization setting when both are qualified. The initialization settings may be an algorithm setting and may include a filter configuration, and/or one or more settings used in generating a threshold.

In some embodiments, an envelope may be generated based on a segment of the intensity signal, and the intensity signal may be modified based on the envelope. The envelope may include an upper envelope and a lower envelope, in which the upper envelope includes values greater than the lower envelope, and the upper and lower envelopes do not cross. In some embodiments, the upper envelope may include at least one point of the intensity signal and the lower envelope may include at least one point of the intensity signal. The modification may include subtracting the lower envelope from a segment of the intensity signal to generate a first signal, scaling the first signal based on a difference between the upper envelope and the lower envelope to generate a second signal, and subtracting the mean of the second signal from the second signal to generate the modified intensity signal. The first signal may be scaled to vary in amplitude between one and negative one, or zero and one, or other suitable range. In some embodiments, generating the envelope may include fitting a function to the intensity signal. In some embodiments, a signal may be generated to fit a segment of the intensity signal, and the intensity signal may be modified by subtracting the generated signal. The generated signal may include a linear signal, a quadratic signal, and/or a polynomial signal having an order of three or more. In some embodiments, outlier points in the segment and/or points at each end of the segment may be downweighted in the fitting process. An autocorrelation sequence may be calculated based on the modified intensity signal, and used to determine one or more initialization parameters or a value indicative of a physiological rate of the subject. A threshold may be generated based on the autocorrelation sequence, and threshold crossings may be identified. The value indicative of a physiological rate may be determined based on a difference (e.g., in time or sample number) associated with at least two threshold crossings.

In some embodiments, a value indicative of a physiological rate of the subject may be determined by calculating an autocorrelation sequence based on the intensity signal, determining a threshold window having a center portion not used in the determination of a threshold, determining a threshold at each of a plurality of points of the autocorrelation sequence based on the threshold window to generate a threshold sequence, and determining two or more crossings of the autocorrelation sequence and the threshold sequence. The threshold window may include a center portion including a sample under test and at least two guard samples adjacent to the sample under test located on each side of the sample under test. The threshold window may also include at least two base samples located outside of the center portion located on each side of the center portion. In some embodiments, the number of guard samples and/or base samples may be based on an initialization parameter or a previously determined value indicative of the physiological rate. The two or more crossings may include a least one pair of crossings that correspond to a peak in the autocorrelation sequence, where the peak intersects the threshold sequence at the pair crossings. In some embodiments, a binary signal may be generated based on the threshold crossings.

In some embodiments, a correlation sequence may be calculated based on a portion of the intensity signal and a stored reference waveform, and physiological rate information may be determined based on the correlation sequence. A new reference waveform that is derived from the intensity signal may be selected based on the physiological rate information and/or based on a period associated with the rate information. The new reference waveform may be qualified, stored, and used for calculating a subsequent correlation sequence based on a more recent portion of the intensity signal and the new reference waveform. Determination of whether to qualify the new reference waveform may be based on shape analysis of the new reference waveform. Subsequent physiological rate information may be determined based on the subsequent correlation sequence. If the new reference waveform is not qualified, the new reference waveform may be discarded, and a subsequent correlation sequence may be calculated based on a more recent portion of the intensity signal and a previously stored reference waveform. In some embodiments, physiological rate information may be determined by generating a threshold based on the correlation sequence, identifying threshold crossings, and determining a difference (e.g., in time or sample number) associated with at least two threshold crossings.

In some embodiments, an intensity signal may be classified based on one or more classifications such as a dicrotic notch classification, a neonate classification, and/or any other suitable classification. A calculation technique for determining an initialization parameter or a value indicative of a physiological rate may be selected from a plurality of calculation techniques based on the classification. For example, the selected calculation technique may include a high pass filter when the classification of the intensity signal is a neonate classification. In a further example, the selected calculation technique may include stricter qualification criteria when the classification of the intensity signal is a dicrotic notch classification. In some embodiments, the selected calculation technique may be configured to determine when an initialization parameter or a calculated value corresponds to a harmonic of the physiological rate and/or modify the initialization parameter or calculated value to correspond to the physiological rate when the classification of the intensity signal is a dicrotic notch classification.

In some embodiments, a value indicative of a physiological rate of a subject may be determined by filtering an intensity signal into a low frequency component and a high frequency component, determining one or more metrics for each of the low frequency component and the high frequency component, comparing the one or more metrics, and selecting either the low frequency component or the high frequency component. The one or more metrics may include, for example, a kurtosis value, a standard deviation value, a root mean square value, and/or any other suitable metric. The intensity signal may be filtered, for example, into a low frequency component by attenuating frequencies greater than approximately 75 BPM, or into a high frequency component by attenuating frequencies lesser than approximately 75 BPM. The 75 BPM cut-off is exemplary and any other suitable BPM cutoff can be used to separate the intensity signal into high and low frequency components. In some embodiments, the value indicative of the physiological rate may be determined by calculating an autocorrelation sequence based on the selected frequency component, generating a threshold based on the autocorrelation sequence, identifying threshold crossings, and determining a difference (e.g., in time or sample number) associated with at least two threshold crossings. In some embodiments, the foregoing techniques may be used to determine one or more initialization settings.

In some embodiments, at least one value indicative of a physiological rate of a subject may be determined based on one or more fast start parameters. An autocorrelation sequence may be calculated based on the intensity signal and the one or more fast start parameters. The autocorrelation sequence may be analyzed to determine the at least one value indicative of a physiological rate of the subject. The one or more fast start parameters may include, for example, an autocorrelation template size and/or an autocorrelation template size increment. In some embodiments, more than one autocorrelation sequence may be calculated in series using autocorrelation templates of different sizes. The autocorrelation templates may optionally increase in size as the series progresses. Analysis of the autocorrelation sequence may include generating a threshold based on the autocorrelation sequence, and identifying a threshold crossing. In some embodiments, the fast start parameters may be used to determine one or more initialization settings.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
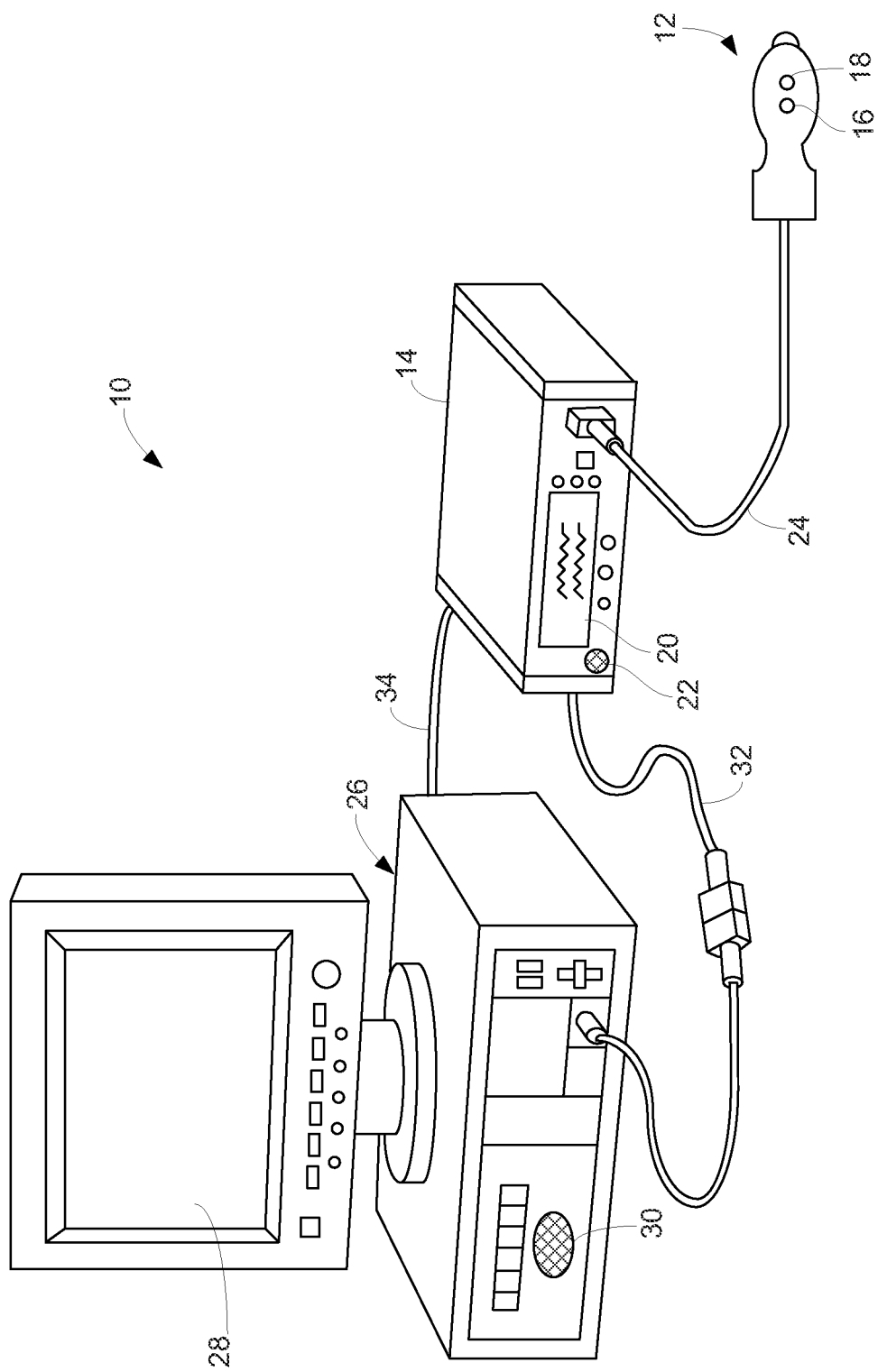
FIG. 1 shows an illustrative physiological monitoring system, in accordance with some embodiments of the present disclosure.

The present disclosure is directed towards determining physiological information including a physiological rate. A physiological monitor may determine one or more physiological parameters such as, for example, pulse rate, respiration rate, blood oxygen saturation, blood pressure, or any other suitable parameters, based on signals received from one or more sensors. For example, a physiological monitor may analyze photoplethysmographic (PPG) signals for oscillometric behavior characterized by a pulse rate, a respiration rate, or both. Physiological signals may include one or more noise components, which may include the effects of ambient light, 60 Hz electromagnetic radiation from powered devices, subject movement, any other non-physiological signal component or undesired physiological signal component, or any combination thereof.

In some circumstances, the determination of a pulse rate from photoplethysmographic information may present challenges. Typical pulse rates range from about 20 to 300 BM for human subjects. For example, the pulse rate of a neonate may be relatively high (e.g., 130-180 BPM) compared to that of a resting adult (e.g., 50-80 BM). Various sources of noise may obscure the pulse rate. For example, motion artifacts from subject movement may occur over time scales similar to those of the pulse rate of the subject (e.g., on the order of 1 Hertz). Subject movement can prove especially troublesome in measuring pulse rates of neonates, who tend to exhibit significant movement at times during measurements. Significant movement can cause the noise component of the PPG signal to be larger and in some cases significantly larger than the physiological pulse component.

Other factors may also present challenges in determining pulse rate. For example, the shape of physiological pulses can vary significantly not only between subjects, but also with time, position, and physical orientation for a given subject. Moreover, certain pulse shapes in particular may make it difficult to determine the correct pulse rate. As an example, deep dicrotic notches may cause a single pulse to appear similar to two consecutive pulses and thus it may cause one to believe that the pulse rate is double the actual rate. Low perfusion is another factor that can present challenges. A subject with low perfusion typically has low-amplitude physiological pulses and therefore PPG signals derived from such subjects may be more susceptible to noise than PPG signals derived from other subjects.

The present disclosure discloses techniques for reliably determining rate information from a physiological signal and in particular to determining pulse rate from photoplethysmographic information. While the techniques are disclosed in some embodiments as being implemented in the context of oximeters, it will be understood that any suitable processing device may be used in accordance with the present disclosure.

An oximeter is a medical device that may determine the oxygen saturation of the blood. One common type of oximeter is a pulse oximeter, which may indirectly measure the oxygen saturation of a subject's blood (as opposed to measuring oxygen saturation directly by analyzing a blood sample taken from the subject). Pulse oximeters may be included in physiological monitoring systems that measure and display various blood flow characteristics including, but not limited to, the oxygen saturation of hemoglobin in arterial blood. Such physiological monitoring systems may also measure and display additional physiological parameters, such as a subject's pulse rate, respiration rate, and blood pressure.

An oximeter may include a light sensor that is placed at a site on a subject, typically a fingertip, toe, forehead or earlobe, or in the case of a neonate, across a foot. The oximeter may use a light source to pass light through blood perfused tissue and photoelectrically sense the transmission of the light in the tissue (e.g., which may be indicative of absorbed light). In addition, locations which are not typically understood to be optimal for pulse oximetry may be used in some embodiments. For example, additional suitable sensor locations include, without limitation, the neck to monitor carotid artery pulsatile flow, the wrist to monitor radial artery pulsatile flow, the inside of a subject's thigh to monitor femoral artery pulsatile flow, the ankle to monitor tibial artery pulsatile flow, and around or in front of the ear. Suitable sensors for these locations may include sensors for sensing absorbed light based on detecting reflected light (e.g., a forehead sensor). In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue), a transmission signal (i.e., representing the amount of light transmitted by the tissue), or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda, t) = I_0(\lambda) \exp(-(s\beta_o(\lambda) + (1-s)\beta_r(\lambda))l(t)) \quad (1)$$

where:
$\lambda$=wavelength;
t=time;
I=intensity of light detected;
$I_0$=intensity of light transmitted;
s=oxygen saturation;
$\beta_o, \beta_r$=empirically derived absorption coefficients; and
l(t)=a combination of concentration and path length from emitter to detector as a function of time.

The traditional approach measures light absorption at two wavelengths (e.g., Red and IR), and then calculates saturation by solving for the "ratio of ratios" as follows.

1. The natural logarithm of Eq. 1 is taken ("log" will be used to represent the natural logarithm) for IR and Red to yield $$\log I = \log I_0 - (s\beta_o + (1-s)\beta_r)l. \quad (2)$$

2. Eq. 2 is then differentiated with respect to time to yield $$\frac{d \log I}{dt} = -(s\beta_o + (1-s)\beta_r)\frac{dl}{dt}. \quad (3)$$

3. Eq. 3, evaluated at the Red wavelength $\lambda_R$, is divided by Eq. 3 evaluated at the IR wavelength $\lambda_{IR}$ in accordance with $$\frac{d \log I(\lambda_R)/dt}{d \log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})}. \quad (4)$$

4. Solving for s yields $$s = \frac{\frac{d \log I(\lambda_{IR})}{dt}\beta_r(\lambda_R) - \frac{d \log I(\lambda_R)}{dt}\beta_r(\lambda_{IR})}{\frac{d \log I(\lambda_R)}{dt}(\beta_o(\lambda_{IR}) - \beta_r(\lambda_{IR})) - \frac{d \log I(\lambda_{IR})}{dt}(\beta_o(\lambda_R) - \beta_r(\lambda_R))}. \quad (5)$$

5. Note that, in discrete time, the following approximation can be made:

$$\frac{d \log I(\lambda, t)}{dt} \simeq \log I(\lambda, t_2) - \log I(\lambda, t_1). \quad (6)$$

6. Rewriting Eq. 6 by observing that log A–log B=log(A/B) yields $$\frac{d \log I(\lambda, t)}{dt} \simeq \log\left(\frac{I(t_2, \lambda)}{I(t_1, \lambda)}\right). \quad (7)$$

7. Thus, Eq. 4 can be expressed as $$\frac{\frac{d \log I(\lambda_R)}{dt}}{\frac{d \log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R, \quad (8)$$

where R represents the "ratio of ratios."

8. Solving Eq. 4 for s using the relationship of Eq. 5 yields $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}. \quad (9)$$

9. From Eq. 8, R can be calculated using two points (e.g., PPG maximum and minimum), or a family of points. One method applies a family of points to a modified version of Eq. 8. Using the relationship $$\frac{d \log I}{dt} = \frac{dI/dt}{I}, \quad (10)$$

Eq. 8 becomes $$\frac{\frac{d \log I(\lambda_R)}{dt}}{\frac{d \log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (11)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R,$$

which defines a cluster of points whose slope of y versus x will give R when $$x = [I(t_2, \lambda_{IR}) - I(t_1, \lambda_{IR})]I(T_1, \lambda_R), \quad (12)$$

and $$y = [I(t_2, \lambda_R) - I(t_1, \lambda_R)]I(t_1, \lambda_{IR}). \quad (13)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

Pulse rate can be determined from the IR light signal, the Red light signal, any other suitable wavelength light signal, or a combination of light signals.

FIG. 1 is a perspective view of an embodiment of a physiological monitoring system 10. System 10 may include sensor unit 12 and monitor 14. In some embodiments, sensor unit 12 may be part of an oximeter. Sensor unit 12 may include an emitter 16 for emitting light at one or more wavelengths into a subject's tissue. A detector 18 may also be provided in sensor 12 for detecting the light originally from emitter 16 that emanates from the subject's tissue after passing through the tissue. Any suitable physical configuration of emitter 16 and detector 18 may be used. In an embodiment, sensor unit 12 may include multiple emitters and/or detectors, which may be spaced apart. System 10 may also include one or more additional sensor units (not shown) which may take the form of any of the embodiments described herein with reference to sensor unit 12. An additional sensor unit may be the same type of sensor unit as sensor unit 12, or a different sensor unit type than sensor unit 12. Multiple sensor units may be capable of being positioned at two different locations on a subject's body; for example, a first sensor unit may be positioned on a subject's forehead, while a second sensor unit may be positioned at a subject's fingertip.

Sensor units may each detect any signal that carries information about a subject's physiological state, such as arterial line measurements or the pulsatile force exerted on the walls of an artery using, for example, oscillometric methods with a piezoelectric transducer. According to another embodiment, system 10 may include a plurality of sensors forming a sensor array in lieu of either or both of the sensor units. Each of the sensors of a sensor array may be a complementary metal oxide semiconductor (CMOS) sensor. Alternatively, each sensor of an array may be a charged coupled device (CCD) sensor. In some embodiments, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. In some embodiments, each pixel may have a photodetector and an active amplifier. In some embodiments, a group of pixels may share an amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is attenuated by the tissue and transmitted to detector 18, such as in a sensor designed to obtain pulse oximetry data from a subject's forehead.

In some embodiments, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., pulse rate, blood pressure, blood oxygen saturation) based on data relating to light emission and detection received from one or more sensor units such as sensor unit 12. In an alternative embodiment, the calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a subject's physiological parameters are not within a predefined normal range. In some embodiments, the monitor 14 includes a blood pressure monitor. In some embodiments, the system 10 includes a stand-alone blood pressure monitor in communication with the monitor 14 via a cable or a wireless network link.

In some embodiments, sensor unit 12 may be communicatively coupled to monitor 14 via a cable 24. In some embodiments, a wireless transmission device (not shown) or the like may be used instead of or in addition to cable 24.

In the illustrated embodiment, system 10 includes a multi-parameter physiological monitor 26. The monitor 26 may include a cathode ray tube display, a flat panel display (as shown by display 28) such as a liquid crystal display (LCD) or a plasma display, or may include any other type of monitor now known or later developed. Multi-parameter physiological monitor 26 may be configured to calculate physiological parameters and to provide a display 28 for information from monitor 14 and from other medical monitoring devices or systems (not shown). For example, multi-parameter physiological monitor 26 may be configured to display pulse rate information from monitor 14, an estimate of a subject's blood oxygen saturation generated by monitor 14 (referred to as an "SpO$_2$" measurement), and blood pressure from monitor 14 on display 28. Multi-parameter physiological monitor 26 may include a speaker 30.

Monitor 14 may be communicatively coupled to multi-parameter physiological monitor 26 via a cable 32 or 34 that is coupled to a sensor input port or a digital communications port, respectively and/or may communicate wirelessly (not shown). In addition, monitor 14 and/or multi-parameter physiological monitor 26 may be coupled to a network to enable the sharing of information with servers or other workstations (not shown). Monitor 14 and/or multi-parameter physiological monitor 26 may be powered by a battery (not shown) or by a conventional power source such as a wall outlet. In some embodiments, monitor 14, monitor 26, or both, may include one or more communications ports (not shown in FIG. 1) such as, for example, universal serial bus (USB) ports, ethernet ports, WIFI transmitters/receivers, RS232 ports, any other suitable communications ports, or any combination thereof. In some embodiments, monitor 14, monitor 26, or both, may include memory (not shown in FIG. 1) such as, for example, a hard disk, flash memory (e.g., a multimedia card (MMC), a Secure Digital (SD) card), read only memory, any other suitable memory, any suitable communications ports for communicating with memory (e.g., a USB port for excepting flash memory drives, an Ethernet port for communicating with a remote server), or any combination thereof.

Figure 2:
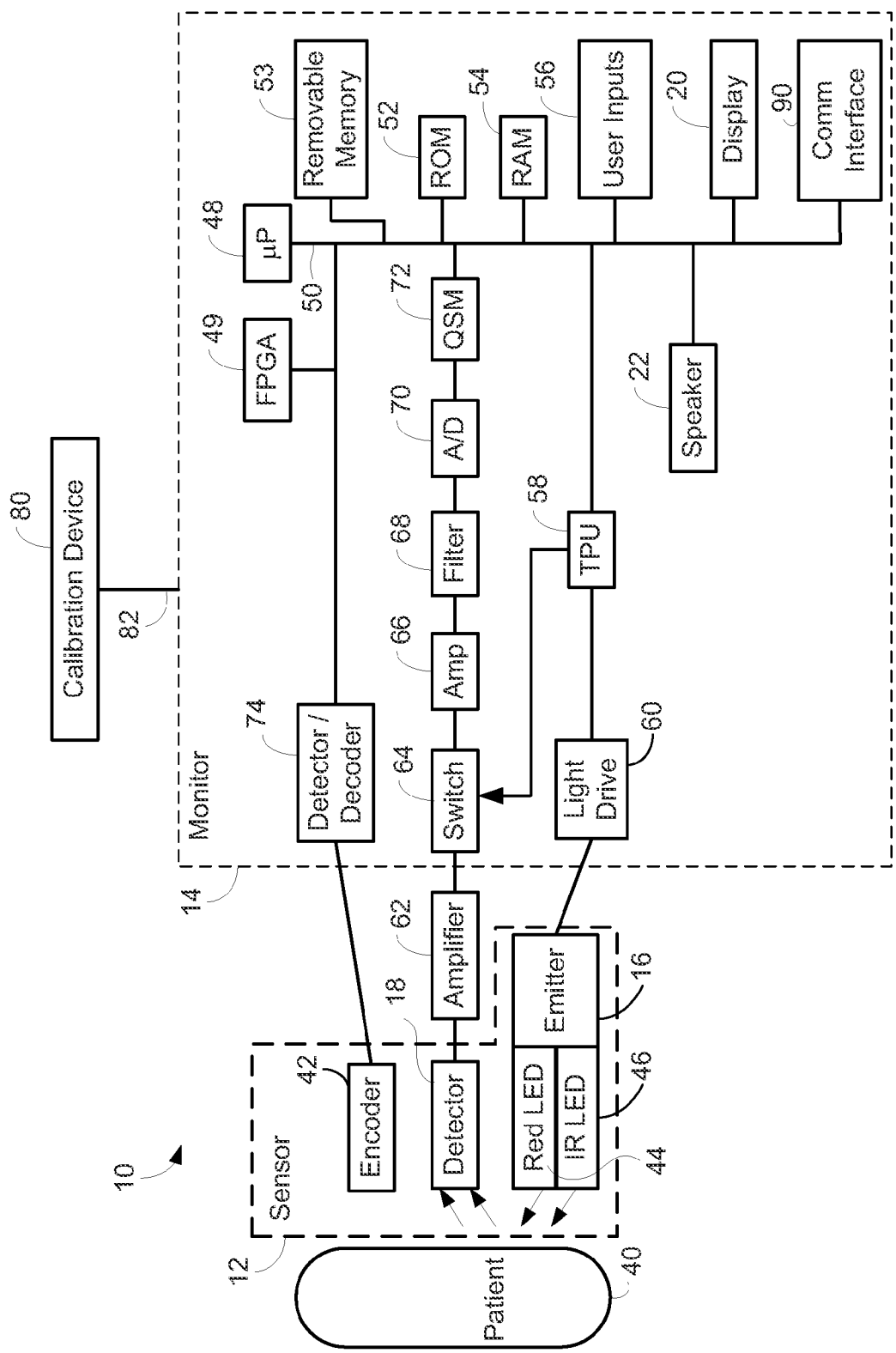
FIG. 2 is a block diagram of the illustrative physiological monitoring system of FIG. 1 coupled to a subject, in accordance with some embodiments of the present disclosure.

FIG. 2 is a block diagram of a physiological monitoring system, such as physiological monitoring system 10 of FIG. 1, which may be coupled to a subject 40 in accordance with an embodiment. Certain illustrative components of sensor unit 12 and monitor 14 are illustrated in FIG. 2.

Sensor unit 12 may include emitter 16, detector 18, and encoder 42. In the embodiment shown, emitter 16 may be configured to emit at least two wavelengths of light (e.g., Red and IR) into a subject's tissue 40. Hence, emitter 16 may include a Red light emitting light source such as Red light emitting diode (LED) 44 and an IR light emitting light source such as IR LED 46 for emitting light into the subject's tissue 40 at the wavelengths used to calculate the subject's physiological parameters. In some embodiments, the Red wavelength may be between about 600 nm and about 700 nm, and the IR wavelength may be between about 800 nm and about 1000 nm. In some embodiments, in which a sensor array is used in place of a single sensor, each sensor may be configured to emit a single wavelength. For example, a first sensor emits only a Red light while a second emits only an IR light. In another example, the wavelengths of light used are selected based on the specific location of the sensor.

It will be understood that, as used herein, the term "light" may refer to energy produced by radiation sources and may include one or more of radio, microwave, millimeter wave, infrared, visible, ultraviolet, gamma ray or X-ray electromagnetic radiation. As used herein, light may also include electromagnetic radiation having any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In some embodiments, detector 18 may be configured to detect the intensity of light at the Red and IR wavelengths. Alternatively, each sensor in the array may be configured to detect intensity at a single wavelength. In operation, light may enter detector 18 after being attenuated (e.g., absorbed, scattered) by the subject's tissue 40. Detector 18 may convert the intensity of the received light into an electrical signal. The light intensity is related to the absorption and/or reflected of light in the tissue 40. That is, when more light at a certain wavelength is absorbed or reflected, less or more light of that wavelength is received from the tissue by the detector 18. After converting the received light to an electrical signal, detector 18 may send the signal to monitor 14, where physiological parameters may be calculated based on the absorption of the Red and IR wavelengths in the subject's tissue 40.

In some embodiments, encoder 42 may contain information about sensor 12, such as sensor type (e.g., whether the sensor is intended for placement on a forehead or digit), the wavelengths of light emitted by emitter 16, power requirements or limitations of emitter 16, or other suitable information. This information may be used by monitor 14 to select appropriate algorithms, lookup tables and/or calibration coefficients stored in monitor 14 for calculating the subject's physiological parameters.

In some embodiments, encoder 42 may contain information specific to subject 40, such as, for example, the subject's age, weight, and diagnosis. Information regarding a subject's characteristics may allow monitor 14 to determine, for example, subject-specific threshold ranges in which the subject's physiological parameter measurements should fall and to enable or disable additional physiological parameter algorithms. This information may also be used to select and provide coefficients for equations from which, for example, pulse rate, blood pressure, and other measurements may be determined based on the signal or signals received at sensor unit 12. For example, some pulse oximetry sensors rely on equations to relate an area under a portion of a PPG signal corresponding to a physiological pulse to determine blood pressure. These equations may contain coefficients that depend upon a subject's physiological characteristics as stored in encoder 42. Encoder 42 may, for instance, be a coded resistor which stores values corresponding to the type of sensor unit 12 or the type of each sensor in the sensor array, the wavelengths of light emitted by emitter 16 on each sensor of the sensor array, and/or the subject's characteristics. In some embodiments, encoder 42 may include a memory on which one or more of the following information may be stored for communication to monitor 14: the type of the sensor unit 12; the wavelengths of light emitted by emitter 16; the particular wavelength each sensor in the sensor array is monitoring; a signal threshold for each sensor in the sensor array; any other suitable information; or any combination thereof. In some embodiments, encoder 42 may include an identifying component such as, for example, a radio-frequency identification (RFID) tag that may be read by decoder 74.

In some embodiments, signals from detector 18 and encoder 42 may be transmitted to monitor 14. In the embodiment shown, monitor 14 may include a general-purpose microprocessor 48, FPGA 49, or both, connected to an internal bus 50. In some embodiments, monitor 14 may include one or more microprocessors, digital signal processors (DSPs), or both. Microprocessor 48 may be adapted to execute software, which may include an operating system and one or more applications, as part of performing the functions described herein. Also connected to bus 50 may be a read-only memory (ROM) 52, a random access memory (RAM) 54, removable memory 53, user inputs 56, display 20, and speaker 22.

RAM 54, ROM 52, and removable memory 53 are illustrated by way of example (e.g., communications interface 90, flash memory, digital logic array, field programmable gate array (FPGA), or any other suitable memory), and not limitation. Any suitable computer-readable media may be used in the system for data storage. Computer-readable media are capable of storing information that can be interpreted by microprocessor 48, FPGA 49, or both. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, writable and non-writable, and removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to light drive circuitry 60, which may control when emitter 16 is illuminated and multiplexed timing for Red LED 44 and IR LED 46. TPU 58 may also control the gating-in of signals from detector 18 through amplifier 62 and switching circuit 64. These signals are sampled at the proper time, depending upon which light source is illuminated. In some embodiments, microprocessor 48, FPGA 49, or both, may de-multiplex the signal from detector 18 using de-multiplexing techniques such as time-division, frequency-division, code division, or any other suitable de-multiplexing technique. In some embodiments, microprocessor 48, FPGA 49, or both, may perform the functions of TPU 58 using suitable timing signals and multiplexing/de-multiplexing algorithms, and accordingly TPU 58 need not be included. The received signal from detector 18 may be passed through amplifier 66, low pass filter 68, and analog-to-digital converter 70. The digital data may then be stored in a queued serial module (QSM) 72 (or buffer such as a first in first out (FIFO) buffer) for later downloading to RAM 54 as QSM 72 fills up. A window of data may be selected from the data stored in the buffer for further processing. In some embodiments, there may be multiple separate parallel paths having components equivalent to amplifier 62, switching circuit 64, amplifier 66, filter 68, and/or A/D converter 70 for multiple light wavelengths or spectra received. In some embodiments, a filter (e.g., an analog filter) may be included (not shown) between amplifier 62 and switching circuit 64.

In an embodiment, microprocessor 48 may determine the subject's physiological parameters, such as pulse rate, $SpO_2$, and/or blood pressure, using various algorithms and/or lookup tables based on the value of the received signals and/or data corresponding to the light received by detector 18. Signals corresponding to information about subject 40, and particularly about the intensity of attenuated light emanating from a subject's tissue over time, may be transmitted from encoder 42 to decoder 74. These signals may include, for example, encoded information relating to subject characteristics. Decoder 74 may translate these signals to enable the microprocessor to determine the thresholds based on algorithms or look-up tables stored in ROM 52. In some embodiments, user inputs 56 may be used enter information, select one or more options, provide a response, input settings, any other suitable inputting function, or any combination thereof. User inputs 56 may be used to enter information about the subject, such as age, weight, height, diagnosis, medications, treatments, and so forth. In some embodiments, display 20 may exhibit a list of values which may generally apply to the subject, such as, for example, age ranges or medication families, which the user may select using user inputs 56.

Calibration device 80, which may be powered by monitor 14 via a coupling 82, a battery, or by a conventional power source such as a wall outlet, may include any suitable signal calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system). Calibration device 80 may be coupled to one or more components of monitor 14 to calibrate monitor 14.

Communications ("Comm") interface 90 may include any suitable hardware, software, or both, which may allow physiological monitoring system 10 (e.g., monitor 14, monitor 26) to communicate with electronic circuitry, a device, a network, or any combinations thereof. Communications interface 90 may include one or more receivers, transmitters, transceivers, antennas, plug-in connectors, ports, communications buses, communications protocols, device identification protocols, any other suitable hardware or software, or any combination thereof. Communications interface 90 may be configured to allow wired communication (e.g., using USB, RS-232 or other standards), wireless communication (e.g., using WiFi, IR, WiMax, BLUETOOTH, UWB, or other standards), or both. For example, communications interface 90 may be configured using a universal serial bus (USB) protocol (e.g., USB 1.0, USB 2.0, USB 3.0), and may be configured to couple to other devices (e.g., remote memory devices storing templates) using a four-pin USB standard Type-A connector (e.g., plug and/or socket) and cable. In a further example, communications interface 90 may be configured to access a database server, which may contain a template database. In some embodiments, communications interface 90 may include an internal bus such as, for example, one or more slots for insertion of expansion cards (e.g., to expand the capabilities of monitor 14, monitor 26, or both).

As described above, the optical signal attenuated by the tissue can be degraded by noise, among other sources, an electrical signal derived thereof can also be degraded by noise. One source of noise is ambient light that reaches the light detector. Another source of noise in an intensity signal is electromagnetic coupling from other electronic instruments. Movement of the subject also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from subject movement) can degrade a sensor signal relied upon by a care provider, without the care provider's awareness. This is especially true if the monitoring of the subject is remote, the motion is too small to be observed, or the care provider is watching the instrument or other parts of the subject, and not the sensor site. Analog and/or digital processing of sensor signals (e.g., PPG signals) may involve operations that reduce the amount of noise present in the signals or otherwise identify noise components in order to prevent them from affecting measurements of physiological parameters derived from the sensor signals.

It will be understood that the present disclosure is applicable to any suitable signal and that PPG signals are used merely for illustrative purposes. Those skilled in the art will recognize that the present disclosure has wide applicability to other signals including, but not limited to, other biosignals (e.g., electrocardiograms, electroencephalograms, electrogastrograms, electromyograms, pulse rate signals, pathological signals, ultrasound signals, any other suitable biosignals), or any combination thereof.

Figure 3:
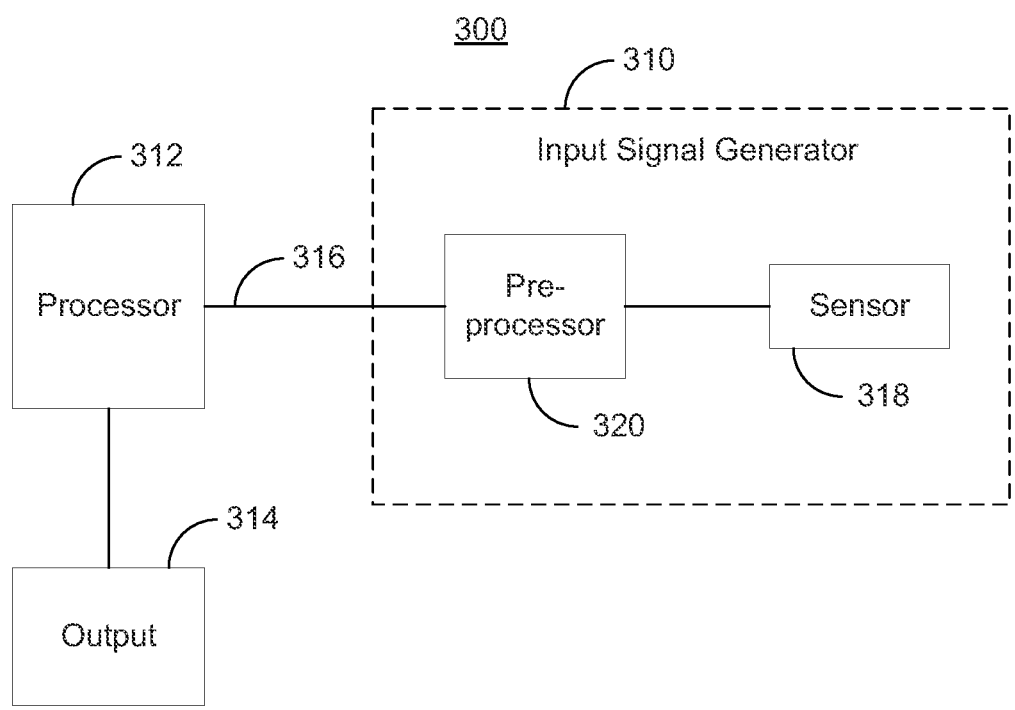
FIG. 3 shows a block diagram of an illustrative signal processing system in accordance with some embodiments of the present disclosure.

FIG. 3 is an illustrative signal processing system 300 in accordance with an embodiment that may implement the signal processing techniques described herein. In some embodiments, signal processing system 300 may be included in a physiological monitoring system (e.g., physiological monitoring system 10 of FIGS. 1-2). In the illustrated embodiment, input signal generator 310 generates an input signal 316. As illustrated, input signal generator 310 may include pre-processor 320 coupled to sensor 318, which may provide input signal 316. In some embodiments, input signal 316 may include one or more intensity signals based on a detector output. In some embodiments, pre-processor 320 may be an oximeter and input signal 316 may be a PPG signal. In an embodiment, pre-processor 320 may be any suitable signal processing device and input signal 316 may include PPG signals and one or more other physiological signals, such as an electrocardiogram (ECG) signal. It will be understood that input signal generator 310 may include any suitable signal source, signal generating data, signal generating equipment, or any combination thereof to produce signal 316. Signal 316 may be a single signal, or may be multiple signals transmitted over a single pathway or multiple pathways.

Pre-processor 320 may apply one or more signal processing operations to the signal generated by sensor 318. For example, pre-processor 320 may apply a pre-determined set of processing operations to the signal provided by sensor 318 to produce input signal 316 that can be appropriately interpreted by processor 312, such as performing A/D conversion. In some embodiments, A/D conversion may be performed by processor 312. Pre-processor 320 may also perform any of the following operations on the signal provided by sensor 318: reshaping the signal for transmission, multiplexing the signal, modulating the signal onto carrier signals, compressing the signal, encoding the signal, and filtering the signal. In some embodiments, pre-processor 320 may include a current-tovoltage converter (e.g., to convert a photocurrent into a voltage), an amplifier, a filter, and A/D converter, a de-multiplexer, any other suitable pre-processing components, or any combination thereof.

In some embodiments, signal 316 may include PPG signals corresponding to one or more light frequencies, such as an IR PPG signal and a Red PPG signal. In some embodiments, signal 316 may include signals measured at one or more sites on a subject's body, for example, a subject's finger, toe, ear, arm, or any other body site. In some embodiments, signal 316 may include multiple types of signals (e.g., one or more of an ECG signal, an EEG signal, an acoustic signal, an optical signal, a signal representing a blood pressure, and a signal representing a heart rate). Signal 316 may be any suitable biosignal or any other suitable signal.

In some embodiments, signal 316 may be coupled to processor 312. Processor 312 may be any suitable software, firmware, hardware, or combination thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may, for example, include an assembly of analog electronic components. Processor 312 may calculate physiological information. For example, processor 312 may compute one or more of a pulse rate, respiration rate, blood pressure, or any other suitable physiological parameter. Processor 312 may perform any suitable signal processing of signal 316 to filter signal 316, such as any suitable band-pass filtering, adaptive filtering, closed-loop filtering, any other suitable filtering, and/or any combination thereof. Processor 312 may also receive input signals from additional sources (not shown). For example, processor 312 may receive an input signal containing information about treatments provided to the subject. Additional input signals may be used by processor 312 in any of the calculations or operations it performs in accordance with processing system 300.

In some embodiments, all or some of pre-processor 320, processor 312, or both, may be referred to collectively as processing equipment. In some embodiments, any of the processing components and/or circuits, or portions thereof, of FIGS. 1-3 may be referred to collectively as processing equipment. For example, processing equipment may be configured to amplify, filter, sample and digitize input signal 316 (e.g., using an analog to digital converter), and calculate physiological information from the digitized signal. In some embodiments, all or some of the components of the processing equipment may referred to as a processing module.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 312 to, for example, store fiducial information or initialization information corresponding to physiological monitoring. In some embodiments, processor 312 may store physiological measurements or previously received data from signal 316 in a memory device for later retrieval. In some embodiments, processor 312 may store calculated values, such as a pulse rate, a blood pressure, a blood oxygen saturation, a fiducial point location or characteristic, an initialization parameter, or any other calculated values, in a memory device for later retrieval.

Processor 312 may be coupled to output 314. Output 314 may be any suitable output device such as one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as part of sensor unit 12 (of FIGS. 1 and 2) and monitor 14 (of FIGS. 1 and 2) and processor 312 may be implemented as part of monitor 14 (FIGS. 1 and 2). In some embodiments, portions of system 300 may be configured to be portable. For example, all or part of system 300 may be embedded in a small, compact object carried with or attached to the subject (e.g., a watch, other piece of jewelry, or a smart phone). In some embodiments, a wireless transceiver (not shown) may also be included in system 300 to enable wireless communication with other components of system 10 (FIGS. 1 and 2). As such, system 10 (FIGS. 1 and 2) may be part of a fully portable and continuous subject monitoring solution. In some embodiments, a wireless transceiver (not shown) may also be included in system 300 to enable wireless communication with other components of system 10. For example, pre-processor 320 may output signal 316 over BLUETOOTH, 802.11, WiFi, WiMax, cable, satellite, Infrared, or any other suitable transmission scheme. In some embodiments, a wireless transmission scheme may be used between any communicating components of system 300. In some embodiments, system 300 may include one or more communicatively coupled modules configured to perform particular tasks. In some embodiments, system 300 may be included as a module communicatively coupled to one or more other modules.

Pre-processor 320 or processor 312 may determine rate based on a periodicity within physiological signal 316 (e.g., a PPG signal) that is associated with a subject's pulse rate using one or more processing techniques. For ease of illustration, the following rate determination techniques will be described as performed by processor 312, but any suitable processing device (e.g., pre-processor 320, microprocessor 48, any other suitable components of system 10 and/or system 300, or any combination thereof) may be used to implement any of the techniques described herein.

Figure 4:
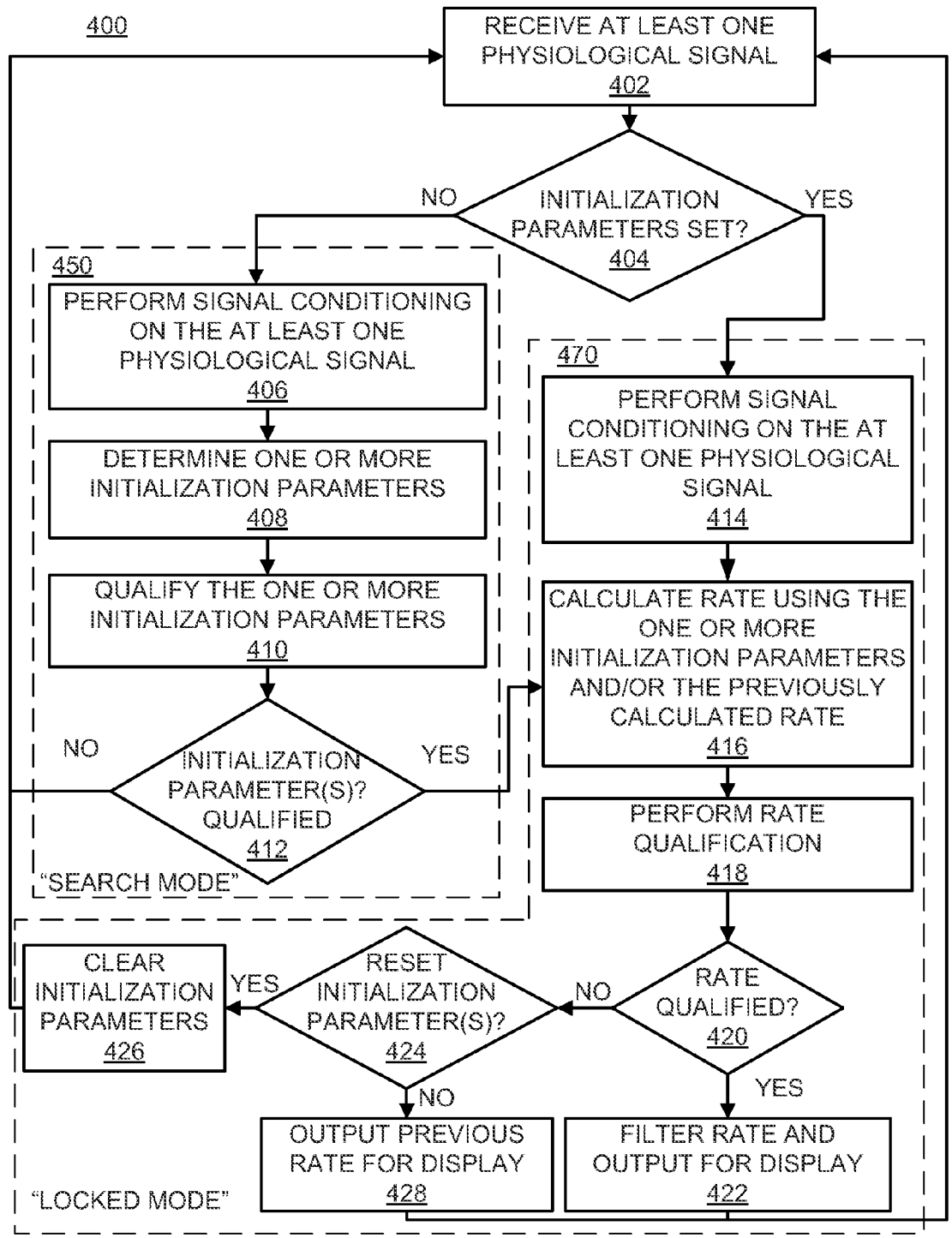
FIG. 4 is a flow diagram of illustrative steps for determining initialization parameters, calculating a physiological rate, and verifying the rate for output, in accordance with some embodiments of the present disclosure.

Physiological information such as pulse rate may be determined based on signals received from a physiological sensor. FIG. 4 is a flow diagram 400 showing illustrative steps for determining a physiological rate. Flow diagram 400 discloses a process for determining initialization parameters (referred to herein as "Search Mode"), and then using the initialization parameters to calculate a physiological rate and qualifying the calculated physiological rate prior to output (referred to herein as "Locked Mode"). In some embodiments, the physiological rate may be a pulse rate associated with a subject.

The steps of flow diagram 400, and all subsequent flow diagrams of this disclosure, may be performed using the physiological monitoring system 10 of FIGS. 1-2, system 300 of FIG. 3, any other suitable system, or any combination thereof. For example, in some embodiments, the steps may be performed by a particular central processing unit (CPU) of physiological monitoring system 10 (e.g., including microprocessor 48, bus 50, and any or all components coupled to bus 50). In a further example (not shown), physiological monitoring system 10 may be a modular system, including one or more functional modules (i.e., software, hardware, or a combination of both) configured to perform particular tasks or portions of tasks thereof. Any suitable arrangement of physiological monitoring system 10, any other suitable system, or any combination thereof, may be used in accordance with the present disclosure. For illustrative purposes, the flow diagrams of the present disclosure will be discussed in reference to processing equipment, which may include physiological monitoring system 10, system 300 of FIG. 3, any other suitable system, any suitable components thereof, or any combination thereof.

Step 402 may include processing equipment receiving at least one physiological signal from a physiological sensor, memory, any other suitable source, or any combination thereof. For example, referring to system 300 of FIG. 3, processor 312 may receive a physiological signal from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., ROM 52 of FIG. 2) after being pre-processed by pre-processor 320. In some such cases, step 402 may include recalling the signals from the memory for further processing. The portion of the physiological signal used for further processing may be referred to as the window of data.

The physiological signal of step 402 may be a photoplethysmograph (PPG) signal, which may include a sequence of pulse waves (e.g., having AC, or AC-DC coupled components) and may exhibit motion artifacts, noise from ambient light (e.g., 120 Hz lighting flicker from a 60 Hz grid power), electronic noise, system noise, any other suitable signal component, or any combination thereof. Step 402 may include receiving a particular time interval or corresponding number of samples of the physiological signal (e.g., a six second window of a sampled physiological signal). In some embodiments, step 402 may include receiving a digitized, sampled, and pre-processed physiological signal.

Step 404 may include processing equipment (e.g., processor 312) determining whether initialization parameters have been set. In some embodiments, initialization parameters may include one or more algorithm settings such as, for example, indexes for inputting into a look-up table, filter settings, and/or templates (e.g., for cross-correlation, signal shape evaluation, or other calculations). In some embodiments, initialization parameters may include one or more settings of a filter (e.g., a band-pass filter) such as, for example, a high and low frequency cutoff value (e.g., a frequency range), a representative frequency value, a set of one or more coefficients, any other suitable parameters, or any combination thereof. Physiological monitoring system 10 may use initialization parameters to improve data processing (e.g., reduce computational requirements, improve accuracy, reduce the effects of noise) to extract physiological information in the presence of noise. This may be accomplished by effectively limiting the bandwidth of data to be analyzed, performing a rough calculation to estimate a physiological rate or pulse, or otherwise mathematically manipulating physiological data.

While executing steps 406-412, the processing equipment (e.g., processor 312) will be referred to as being in "Search Mode," during which time the processing equipment may search for, and qualify, a set of one or more initialization parameters. Search Mode will also be described in further detail during the discussion of FIGS. 5-71 of the present disclosure.

Step 406 may include processing equipment performing signal conditioning on the at least one received physiological signal of step 402. Signal conditioning may include filtering (e.g., low pass, high pass, band pass, notch, or any other suitable filter), amplifying, performing an operation on the received signal (e.g., taking a derivative, averaging), performing any other suitable signal conditioning, or any combination thereof. For example, in some embodiments, step 406 may include removing a DC offset, low frequency components, or both, of the received physiological signal. In a further example, step 406 may include smoothing the received physiological signal (e.g., using a moving average or other smoothing technique).

Step 408 may include the processing equipment determining one or more initialization parameters. Step 408 may be used by the processing equipment to estimate one or more characteristics of a received physiological signal such as, for example, physiological rates, periods, or likely ranges thereof. In some embodiments, initialization parameters may include one or more settings of a filter such as, for example, a high and low frequency cutoff value of a band pass filter (e.g., a frequency range), a representative frequency value, a set of one or more coefficients (e.g., weights for filter weighting), one or more settings of a threshold calculation, any other suitable parameters, or any combination thereof. The initialization parameters may be determined based on the received physiological signal of step 402. Some illustrative techniques of step 408, referred to herein as "Search Techniques", will be described in further detail during the discussion of FIGS. 5-37 of the present disclosure.

In some embodiments, step 408 may include performing calculations on the received physiological signal of step 402 (e.g., autocorrelations, cross-correlations, modulations, statistical computations), accessing information stored in memory (e.g., templates, look-up tables), executing algorithms, selecting particular initialization parameters from a collection of initialization parameters, any other suitable processing, or any combination thereof.

Step 410 may include the processing equipment qualifying the one or more determined initialization parameters of step 408, while step 412 may include the processing equipment determining whether the qualification of step 410 is sufficient. Step 410 may include calculating one or more qualification metrics indicative of an estimated quality of the determined initialization parameters. For example, a particular initialization parameter may be determined at step 408, using any suitable technique of the present disclosure. The particular initialization parameters may be evaluated, and if it is determined that the parameters do not qualify at step 412 (e.g., exhibit a low confidence value), then the processing equipment may remain in "Search Mode" and repeat any or all of steps 400-412. Some illustrative techniques of step 410, referred to as "Qualification Techniques", will be described in further detail herein during the discussion of FIGS. 38-60 of the present disclosure.

While executing steps 414-428, the processing equipment will be referred to as being in "Locked Mode," during which time the processing equipment may use a particular set of initialization parameters or previously calculated rates for further calculation and output of a physiological rate such as pulse rate. Locked Mode will also be described in further detail during the discussion of FIGS. 72-80 of the present disclosure.

Step 414 may include the processing equipment performing signal conditioning on the at least one received physiological signal of step 402. Signal conditioning may include filtering (e.g., low pass, high pass, band pass, notch, or any other suitable filter), amplifying, performing an operation on the received signal (e.g., taking a derivative, averaging), performing any other suitable signal conditioning, or any combination thereof. For example, in some embodiments, step 414 may include removing a DC offset, low frequency components, or both, of the received physiological signal (e.g., de-trending). In a further example, step 414 may include smoothing (e.g., using a moving average or other smoothing technique) the received physiological signal.

Step 416 may include the processing equipment calculating a physiological rate using the one or more initialization parameters of step 412 or step 404. The initialization parameters may be used at step 416 to aid in calculating a physiological rate by filtering the received physiological signal, providing an estimate of a physiological rate of the received signal, or otherwise aiding in calculating the physiological rate. In some embodiments, the conditioned signal may be processed using an autocorrelation technique and the resulting autocorrelation output may be filtered based on one or more initialization parameters. The initialization parameters may also be used to extract a rate from the filtered autocorrelation signal. For example, a threshold may be calculated based on the initialization parameters and the rate may be calculated based on threshold crossings. Once an initial rate is determined, the subsequent calculations of rate can be based on the previously calculated rates. Some illustrative techniques of step 416, referred to herein as "Rate Calculation Techniques", will be described in further detail during the discussion of FIGS. 72-80 of the present disclosure.

Step 418 may include the processing equipment performing Qualification for the calculated rate of step 416. Qualification may include calculating a confidence value indicative of the likelihood that the calculated rate is the "true" physiological rate. Step 420 may include determining whether the Qualification of step 418 satisfies particular criteria.

If the calculated rate of step 416 is determined to be qualified at step 420, then the processing equipment may filter the calculated rate, and may output the filtered rate for display (e.g., on display 20 of physiological monitoring system 10) at step 422. For example, step 422 may include low pass filtering of the calculated rate to limit the rate of change of the outputted rate to physiological ranges. In a further example, step 422 may include applying an infinite impulse response (IIR) filter to the calculated rate of step 416. In some embodiments, step 422 may include storing the filtered rate values in memory such as, for example, RAM 54 or other suitable memory of physiological monitoring system 10.

If the calculated rate of step 416 is determined to be disqualified at step 420, then the processing equipment may determine whether to reset the one or more initialization parameters at step 424. If the processing equipment determines at step 424 that the one or more initialization parameters are to be reset, then the processing equipment may reset the one or more initialization parameters at step 426. Resetting the one or more initialization parameters may include deleting one or more stored initialization parameters from memory, and replacing them with other parameters (e.g., use a default set of initialization parameters). If the processing equipment determines at step 424 that the one or more initialization parameters are not to be reset, then the processing equipment may output the previous rate for display at step 428.

It will be understood that FIG. 4 is merely illustrative and that various modifications can be made to FIG. 4 that are within the scope of the present disclosure. For example, while the rate calculation of FIG. 416 is described as using one or more initialization parameters, the initialization parameters may also be used or instead be used to influence the signal conditioning performed at step 414.

In some embodiments, initialization parameters may be used to 1) tune a dynamic threshold (e.g., a CFAR threshold used at step 416) and 2) tune a bandpass (BP) filter (e.g., a BP filter used at step 414). The use of one or more Search Techniques and Qualification Techniques to determine and qualify initialization parameters may aid in setting the BP filter that may be used in Locked Mode. The BP filter may be applied before or after an autocorrelation, but before a threshold is generated and/or applied. The BP filter may, for example, have a width of the rate+/−a percentage or a fixed amount of BPM. Exemplary percentages may be +/−10%, 15%, 20%, 25%, and so on. Exemplary BPMs may be +/−10 BPM, 20 BPM, 30 BPM, and so on, and the percentage and BPMs may be fixed or variable. For example, at low rates the percentage may be higher and then relatively lower as the rate increases. The percentage may vary linearly, non-linearly, based on a step function, based on any other suitable function, or any combination thereof.

A relatively narrow, adjustable BP filter is good at rejecting noise when it tuned to the correct rate. However, if the BP filter is tuned incorrectly to noise, or if noise enters the range of the BP filter, the filter may start to track the noise instead of the physiological rate, which would be undesired. The use of robust Qualification Techniques such as, for example, those disclosed herein, can prevent the BP filter from initially being tuned to noise. If at some point noise begins to cause the filter to deviate away from the physiological rate, the incorrect rates will be disqualified and prevent this from happening. Even if the filter begins to deviate from the physiological rate, the system will eventually depart from Locked Mode and return to Search Mode to relock back onto the physiological rate.

It will be understood that any of the techniques of Search Mode may be used with any techniques of Locked Mode, and vice-versa. In some embodiments, Search Mode need not be separate from Locked Mode. For example, system 300 may operate in a single mode using various techniques during operation. For example, Locked Mode may start by not using a tuned BP filter, and using a fixed threshold instead of CFAR threshold. Once a rate is qualified, the adjustable BP filter and CFAR may be used. System 300 may use any suitable combination of Search Mode techniques and Locked Mode techniques to determine a physiological rate. In some embodiments, because the techniques of Search Mode may determine an indication of the physiological rate, any of the techniques of Search Mode may be used in Locked Mode to determine the physiological rate.

Figure 5:
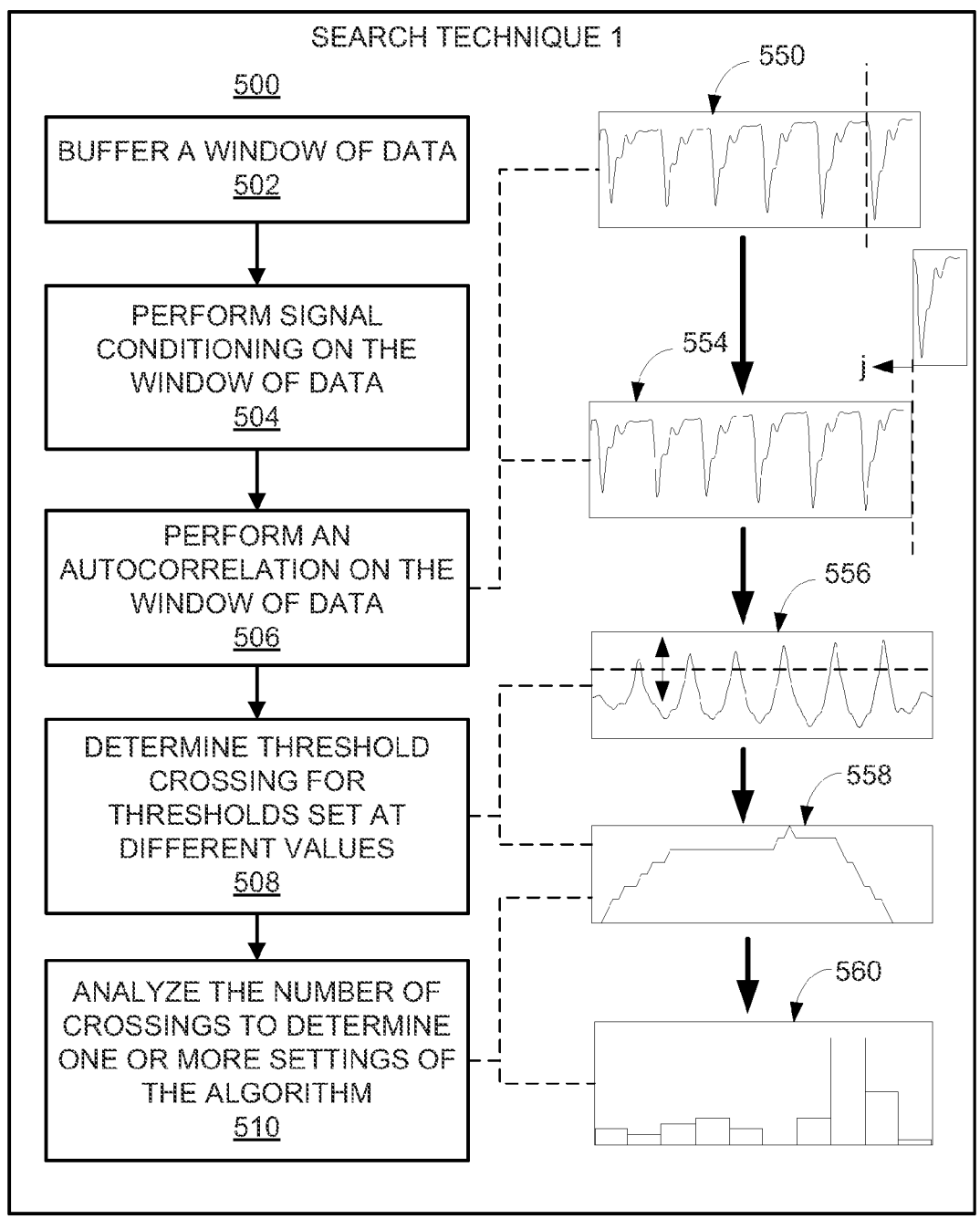
FIG. 5 is a flow diagram of illustrative steps for determining one or more settings based on a number of threshold crossings of an autocorrelation, in accordance with some embodiments of the present disclosure.

In some embodiments, Search Mode may include calculating an autocorrelation of a received physiological signal, and determining a number of threshold crossings of the autocorrelation to estimate a physiological rate or range thereof. FIG. 5 is a flow diagram 500 (Search Technique 1) for determining one or more algorithm settings (i.e., one or more initialization parameters) based on the number of threshold crossings.

Step 502 may include processing equipment buffering a window of data, derived from a physiological signal. In some embodiments, the window may include a particular time interval of the physiological signal (e.g., the most recent six seconds of a processed physiological signal). Step 502 may include pre-processing (e.g., using pre-processor 320) the output of a physiological sensor, and then storing a window of the processed data in any suitable memory or buffer (e.g., queue serial module 72 of FIG. 2), for further processing by the processing equipment. In some embodiments, the window of data may be recalled from data stored in memory (e.g., RAM 54 of FIG. 2 or any other suitable memory) for subsequent processing. In some embodiments, the window size (e.g., the number of samples or time interval of data to be buffered) of data is selected to capture multiple periods of oscillatory physiological activity. For example, a six second window of data, as shown illustratively by plot 550, may be used to capture about six pulse waves of a photoplethysmograph of a nominal resting adult with a pulse rate of approximately 1 Hz (i.e., 60 BPM). It will be understood that any suitable window size may be used in accordance with the present disclosure, and six seconds is used for illustrative purposes.

Step 504 may include the processing equipment performing signal conditioning on the window of data of step 502. Signal conditioning may include, for example, removing DC components, removing low frequency components, removing high frequency components, or a combination thereof, from the window of data. In some embodiments, a varying baseline may be removed from the window of data (i.e., de-trending) to constrain the data average to zero or some other fixed value.

Step 506 may include the processing equipment performing an autocorrelation on the conditioned window of data of step 504. Shown in Eq. 14:

$$A_{xx}(j) = \sum_{n=0}^{N-1} x_n x_{n-j} \quad (14)$$

is an illustrative expression for computing a discrete autocorrelation coefficient $A_{xx}$ for N samples $x_n$ for a range of lag values indexed by j, respectively. The autocorrelation output may include a sequence of points, and may be referred to as an autocorrelation sequence. The term autocorrelation, as used herein, shall also refer to a partial autocorrelation. For example, the term autocorrelation may be used to describe a correlation between segments of a given window of data, whether or not the segments share any data points. Accordingly, as used herein, the term autocorrelation may be used to describe a correlation between segments of a window of data sharing zero points, all points, or some points. The term cross-correlation, as used herein, shall refer to a correlation between two sets of data points not included in the same window of data. In some embodiments, the first portion of data, the second portion of data, or both, may be padded with zeros (e.g., at either or both ends of the portion) to equate the lengths of the first and second portions to aid in performing an autocorrelation.

In some embodiments, the autocorrelation of step 506 may include correlating a first portion of the window of data with a second portion of the window of data. The first and second portions may be exclusive of one another, may share one or more samples, or may be selected by any other suitable partition of the window of data. For example, referencing a six second window of data 550, the most recent one second of data may be correlated with the entire six seconds of data (as shown by autocorrelation setup 554, with lag j, which may originate at either endpoint). In a further example (not shown), the one second of data may be correlated with the previous five seconds of data (exclusive of the one second of data). In some embodiments, there may be a time gap between the first and second portions. For example, the most recent one second of data may be correlated with previous data not immediately preceding the one second of data.

Step 508 may include the processing equipment determining a number of threshold crossings of the autocorrelation of step 506 for different threshold values. The autocorrelation may exhibit one or more peaks. A threshold may include a fixed ordinate value (i.e., a horizontal line across a plot of the autocorrelation as shown in plot 556). The threshold may cross a number peaks (e.g., zero or more), as determined by a calculating a suitable intersection of the threshold with a suitable portion of each peak that is crossed. For example, a crossing may be defined as the intersection of the autocorrelation with the threshold, at a point where the first derivative of the autocorrelation is positive (i.e., an up-slope). In a further example, a crossing may be defined as the intersection of the autocorrelation with the threshold, at a point where the first derivative of the autocorrelation is negative (i.e., a down-slope). In a further example, a crossing may be defined as the midpoint of two points of intersection of the autocorrelation with the threshold where the first derivative of the autocorrelation is negative and positive at the respective points (i.e., a point between up-slope and down-slope). Any suitable reference point may be used to define a crossing. The threshold value may be varied, as shown by the double-tipped arrow of plot 556, causing a different number of peak crossings to be calculated, as shown by plot 558. Plot 558 may include the number of threshold crossings of the autocorrelation as a function of threshold value.

Figure 6:
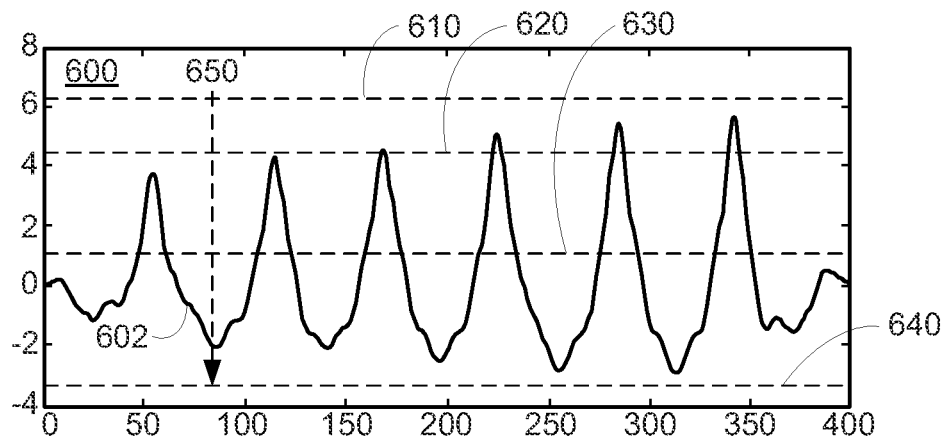
FIG. 6 is a plot of an illustrative autocorrelation of a physiological signal, along with a threshold, in accordance with some embodiments of the present disclosure.

In some embodiments, step 508 may be performed by initializing a threshold above the autocorrelation (i.e., a threshold value greater than any value of the autocorrelation), as shown in FIG. 6. FIG. 6 is a plot 600 of an illustrative autocorrelation 602 of a window of data, along with several thresholds 610, 620, 630, and 640, in accordance with some embodiments of the present disclosure. The abscissa of plot 600 is presented in units of sample number, while the ordinate is scaled in arbitrary units. Initially, referencing the origin of arrow 650, threshold 610 corresponds to an initial threshold value, having no intersections with the autocorrelation. As the threshold value is varied in the direction of arrow 650, the autocorrelation will cross the threshold value. For example, there are four peak crossings for threshold 620, while there are six peak crossings for threshold 630. For threshold 640, there are again zero peak crossings, similar to threshold 610, because the threshold value is less than every value of the autocorrelation. Any suitable variation in threshold may be used in accordance with the present disclosure (e.g., the threshold value may be initialized at a value less than every value of the autocorrelation and increased).

Figure 7:
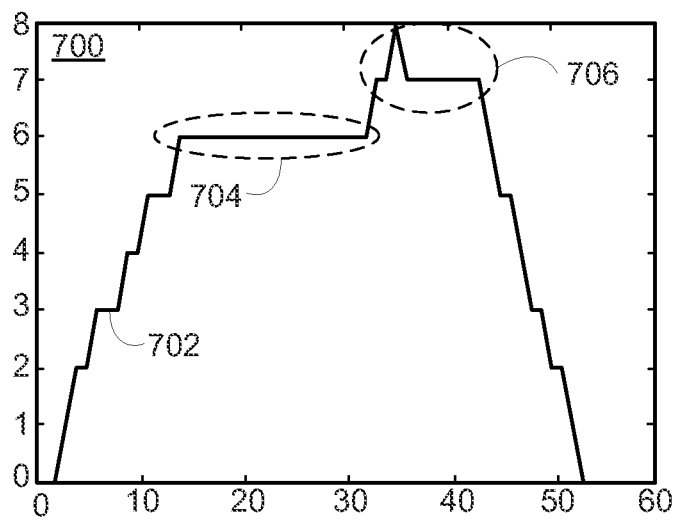
FIG. 7 is an illustrative plot of the number of threshold crossings of the autocorrelation of FIG. 6 as a function of threshold position, in accordance with some embodiments of the present disclosure.

In some embodiments, the output of step 508 may include a dataset of number of threshold crossings as a function of threshold value. One example of illustrative output of step 508 is shown in FIG. 7. FIG. 7 is an illustrative plot 700 of the number of threshold crossings 702 of an autocorrelation as a function of threshold position, in accordance with some embodiments of the present disclosure. The abscissa of plot 700 corresponds to threshold position in arbitrary units, with zero corresponding to a threshold position above the autocorrelation (i.e., non-intersecting), and increasing abscissa values corresponding to lower positions of the threshold. The units of the ordinate of plot 700 are the number of threshold crossings by the autocorrelation. Observing from left to right, it can be seen from plot 700 that the number of crossings starts at zero (i.e., threshold above the autocorrelation), increases as threshold position lowers, plateaus at six crossings as shown by highlight 704, increases over relatively shorter duration to seven and eight crossings as shown by highlight 706, and then decreases again to zero (i.e., threshold below the autocorrelation). The plateau indicated by highlight 704 may be attributed to relatively pronounced peaks in the autocorrelation. The shorter duration excursions indicated by highlight 706 may be attributed to noise or other relatively smaller features of the autocorrelation.

In some embodiments, the particular number of crossings with the longest duration in units of threshold position (i.e., plot 700 abscissa) may be provide an estimate of the number of peaks in the autocorrelation. For example, referencing plot 700, the longest plateau appears at six threshold crossings, which may indicate that six peaks are present in the autocorrelation. In some embodiments, the determination of six peaks may provide an estimate or rough approximation of pulse rate, or a range thereof (e.g., used to select settings of a band pass filter for processing the window of data). For example, six peaks in an autocorrelation of a six second window of data may indicate the pulse rate is in a range of about 5/6 Hz to 7/6 Hz (i.e., 50-70 BPM) or about 1 Hz (i.e., 60 BPM). Similarly, a determination of twelve peaks in an autocorrelation of a six second window of data may indicate that the pulse rate is in a range of about 11/6 Hz to 13/6 Hz (i.e., ~110-130 BPM) or about 2 Hz (i.e., 120 BPM).

Step 510 of flow diagram 500 may include the processing equipment analyzing the number of threshold crossings to determine one or more algorithm settings. As the threshold value of step 508 is varied, the number of threshold crossings by the autocorrelation may vary, as shown by plot 558. In some embodiments, the analysis of step 510 may include analyzing the stability of the number of threshold crossings over two or more threshold settings of multiple threshold settings. For example, the processing equipment may determine a plateau in the number of threshold crossings (e.g., as shown by highlight 704 of FIG. 7). In some embodiments, the analysis of step 510 may include analyzing more than one autocorrelation (i.e., of different windows of data) to generate a histogram of the number of crossings corresponding to a plateau for each autocorrelation (as shown by plot 560, and in more detail in FIG. 8). The use of a histogram for analyzing the number of crossings for multiple autocorrelations may reduce the effects of noise, signal excursions, or other sources of uncertainty in the number of peaks.

Figure 8:
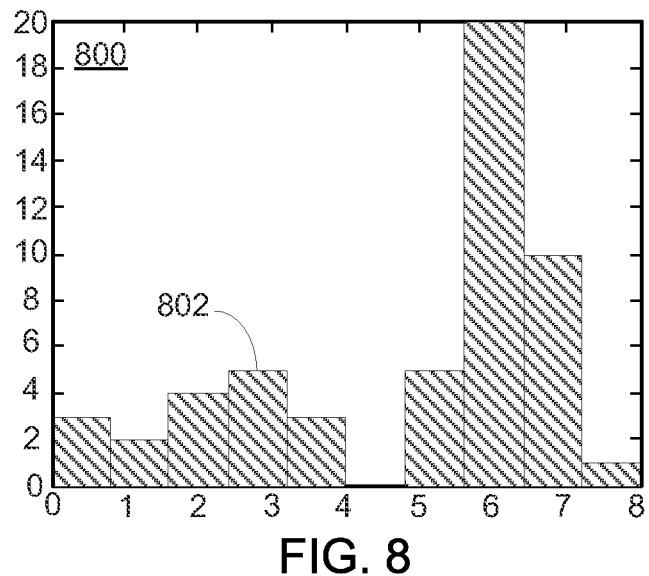
FIG. 8 is an illustrative histogram of instances of various numbers of threshold, in accordance with some embodiments of the present disclosure.

FIG. 8 is an illustrative histogram 800 of instances 802 of various numbers of threshold crossings, in accordance with some embodiments of the present disclosure. The abscissa of plot 800 corresponds to number of crossings. Note that the "bins" of the abscissa of the histogram are not necessarily bounded by integer values, but may be bounded by integer values in some embodiments. The units of the ordinate of plot 800 are instances of each number of crossings, as derived from multiple autocorrelations corresponding to multiple windows of data. The instances 802 of the illustrative histogram of plot 800 exhibit a maximum value at six crossings, indicating that six crossings is the most common number of crossings associated with an autocorrelation. Step 510 of flow diagram 500 may include using this value of six associated with the maximum in the histogram to estimate or approximate a pulse rate and/or pulse rate range. For example, a maximum value in instances 802 at six crossings, calculated from multiple windows of data each six seconds long, may roughly indicate a pulse rate in a range of about 5/6 Hz to 7/6 Hz (i.e., ~50-70 BPM) or about 1 Hz (i.e., 60 BPM).

It will be understood that noise and/or physiological characteristics of pulses (e.g., dicrotic notches) may cause other bins in the histogram to have large values and the processing of the threshold crossing information may take this into account. For example, a strong dicrotic notch may cause additional peaks to appear in the autocorrelation at the locations of the valleys shown in FIG. 6. As a result, there may be more than one stable region when the number of threshold crossings is plotted. Additional processing logic may be used to identify when there are two stable regions, where one stable region occurs at approximately double the number of crossings as the other stable region. The stable region at the lower number of crossings may be selected and used to estimate or approximate a pulse rate and/or pulse rate range.

Figure 9:
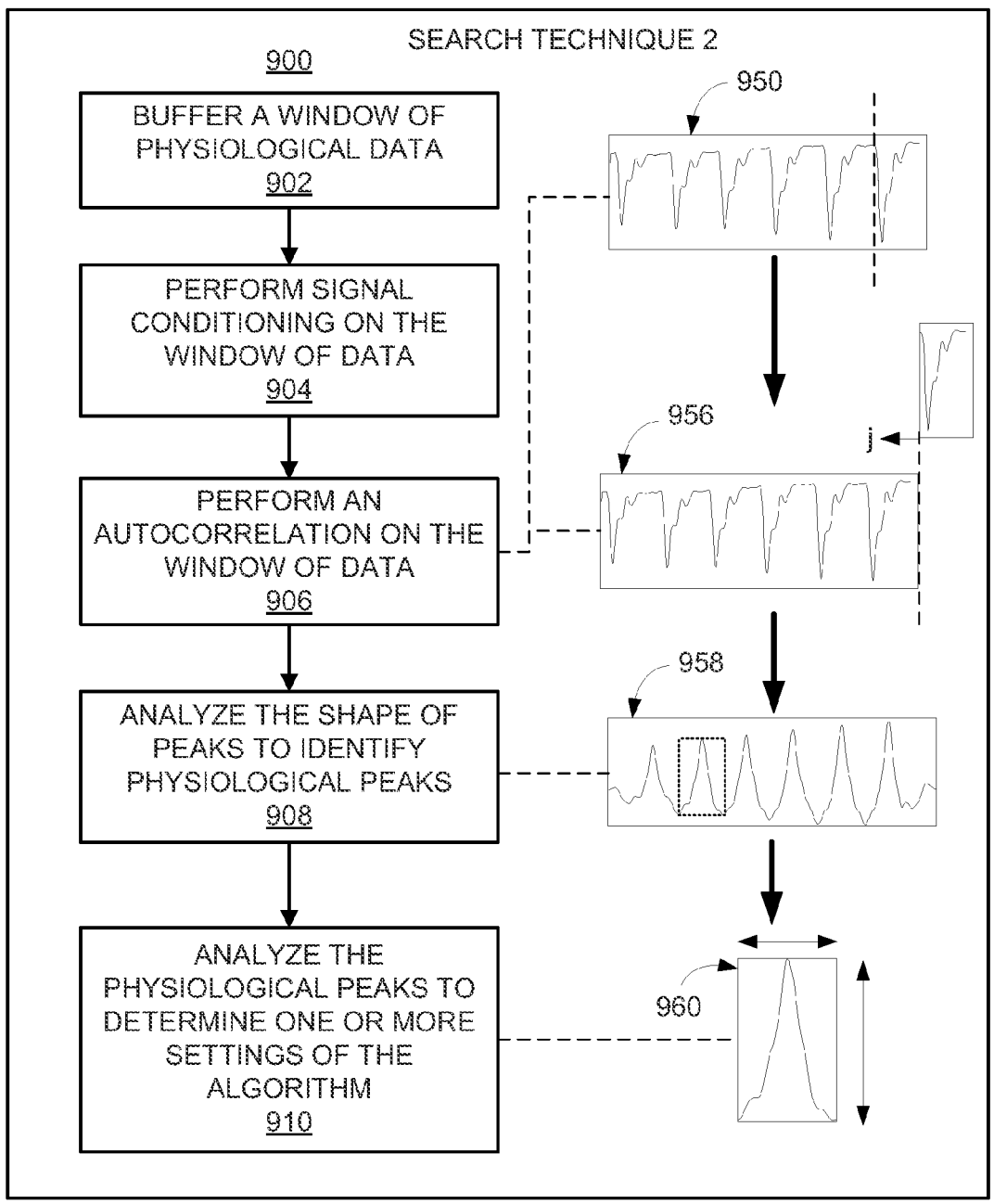
FIG. 9 is a flow diagram of illustrative steps for determining one or more settings based on analyzing physiological peaks, in accordance with some embodiments of the present disclosure.

In some embodiments, Search Mode may include calculating an autocorrelation of a received physiological signal, and analyzing peak shapes of the autocorrelation to estimate a physiological rate or range thereof. FIG. 9 is a flow diagram 900 (Search Technique 2) of illustrative steps for determining one or more algorithm settings (i.e., one or more initialization parameters) based on analyzing physiological peaks, in accordance with some embodiments of the present disclosure.

Step 902 may include the processing equipment buffering a window of data, derived from a physiological signal. In some embodiments, the window may include a particular time interval (e.g., the most recent six seconds of a processed physiological signal). Step 902 may include pre-processing (e.g., using pre-processor 320) the output of a physiological sensor, and then storing a window of the processed data in any suitable memory or buffer (e.g., queue serial module 72 of FIG. 2), for further processing by the processing equipment. In some embodiments, the window of data may be recalled from data stored in RAM (e.g., RAM 54 of FIG. 2) for subsequent processing. In some embodiments, the window size (e.g., the number of samples or time interval of data to be buffered) of data is selected to capture multiple periods of oscillatory physiological activity. For example, a six second window, as shown illustratively by plot 950, may be used to capture about six pulse wave periods of a photoplethysmograph of a nominal resting adult with a pulse rate of approximately 1 Hz (i.e., 60 BPM). It will be understood that any suitable window size may be used in accordance with the present disclosure, and six seconds is used for illustrative purposes. In some embodiments, the physiological signal may be an optical intensity signal, and the window of data may be indicative of an optical intensity detected by a suitable detector.

Step 904 may include the processing equipment performing signal conditioning on the window of data of step 902. Signal conditioning may include, for example, removing DC components, removing low frequency components, removing high frequency components, removing the mean, normalizing the standard deviation to one, performing any other suitable signal conditioning, or any combination thereof. In some embodiments, a varying baseline may be removed from the window of data (i.e., de-trending) to, for example, constrain the data average to zero or some other fixed value.

Step 906 may include the processing equipment performing an autocorrelation on the conditioned window of data of step 904. In some embodiments, the autocorrelation of step 906 may include correlating a first portion of the window of data with a second portion of the window of data, to generate an autocorrelation sequence. The first and second portions may be exclusive of one another, may share one or more samples, or may be selected by any other suitable partition of the window of data. For example, referencing a six second window of data 950, the most recent one second of data may be correlated with the entire six seconds of data (as shown by autocorrelation setup 956, with lag j, which may originate at either endpoint). In a further example (not shown), the one second of data may be correlated with the previous five seconds of data (exclusive of the one second of data). In some embodiments, there may be a time gap between the first and second portions. For example, the most recent one second of data may be correlated with previous data not immediately preceding the one second of data. In some embodiments, the first portion of data, the second portion of data, or both, may be padded with zeros to equate the lengths of the first and second portions to aid in performing the autocorrelation of step 906.

Step 908 may include the processing equipment analyzing the shape of peaks in the autocorrelation to identify physiological peaks. Physiological peaks may refer to peaks corresponding to a physiological rate. The autocorrelation of step 906 may exhibit one or more peaks, as shown by the autocorrelation of plot 958. Step 908 may include determining metrics of each peak such as the width, amplitude, symmetry (e.g., symmetry about a vertical axis), full width at half maximum (FWHM), any other suitable peak metric, or any combination thereof. Peaks demonstrating particular characteristics based on the determined metrics may be identified as physiological peaks, as opposed to noise or artifact peaks. A candidate peak of the autocorrelation of plot 958 is shown in panel 960. Further detail regarding peak shape and identification is provided in the discussion of FIG. 11 of this disclosure.

Step 910 may include the processing equipment analyzing the identified physiological peak(s) of step 908 to determine one or more algorithm settings. In some embodiments, step 910 may include estimating a physiological rate (e.g., a pulse rate), or range thereof, based on a peak shape. For example, the width of a peak (e.g., as shown by the horizontal double-tipped arrow of panel 960) may provide an indication of a pulse rate. In a further example, when more than one peak is identified at step 908, an average peak width may be calculated to provide an indication of a pulse rate. In a further example, when more than one peak is identified at step 908, a range of peak widths may be calculated to provide an indication of a range in pulse rate. In a further example, a FWHM value of a peak identified at step 908 may be calculated and used with a predetermined look-up table to determine one or more corresponding algorithm settings.

Figure 10:
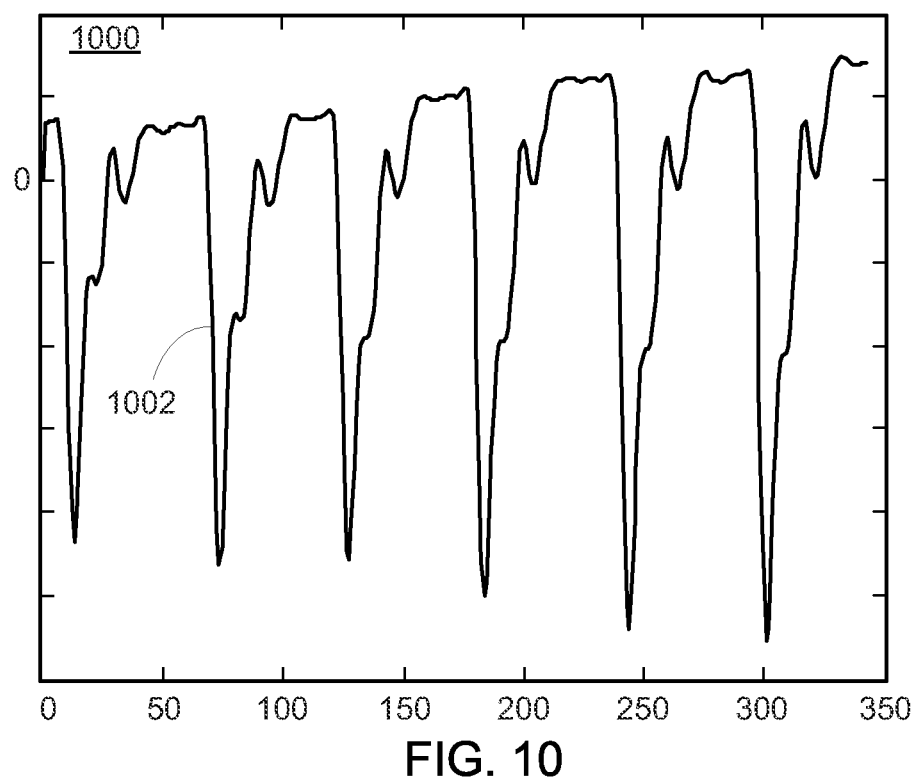
FIG. 10 is a plot of an illustrative filtered photoplethysmograph signal, in accordance with some embodiments of the present disclosure.
Figure 11:
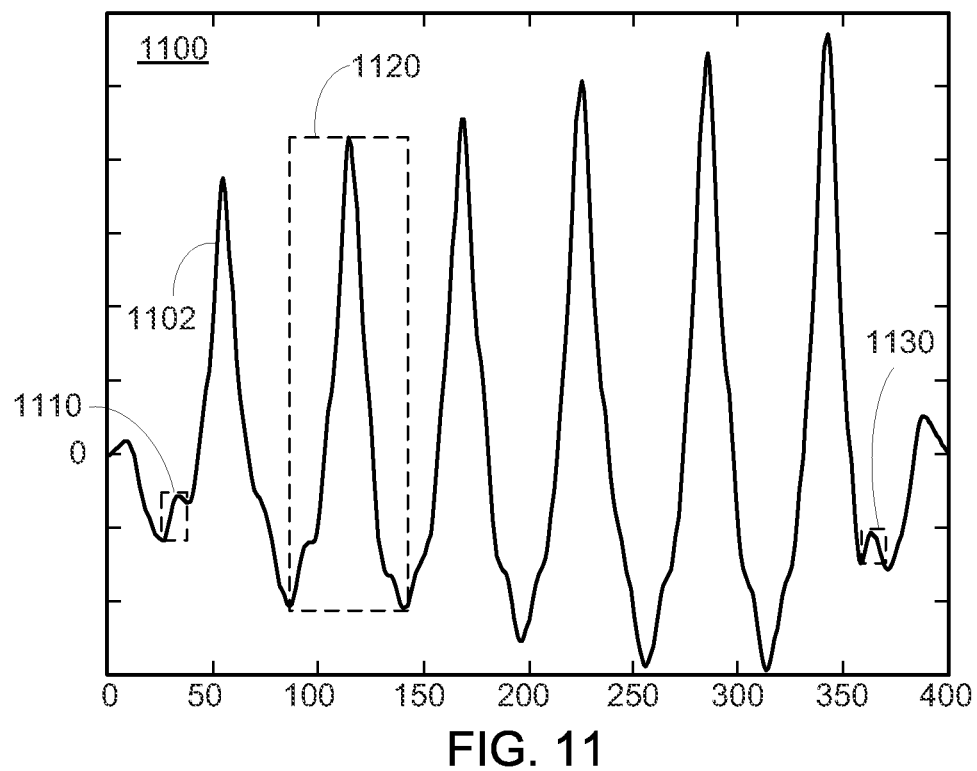
FIG. 11 is a plot of an illustrative autocorrelation of the photoplethysmograph signal of FIG. 10, with several peak shapes notated, in accordance with some embodiments of the present disclosure.

FIG. 10 is a plot 1000 of an illustrative filtered PPG signal 1002, in accordance with some embodiments of the present disclosure. The abscissa of plot 1000 is presented in units of sample number, while the ordinate is scaled in arbitrary units, with zero notated. In the illustrated embodiment, PPG signal 1002 is a window of six seconds of sampled intensity data (i.e., at a sampling rate of roughly 57 Hz) that was processed with a derivative filter. The most recent data corresponds to the right side of plot 1000, while more historical data corresponds to the left side of plot 1000. The oscillatory behavior of PPG signal 1002, due to pulse rate, is easily observed by the six negative peaks spaced about 1 second apart. An autocorrelation may be performed on PPG signal 1002, using any suitable partition of PPG signal 1002 and any suitable numerical technique. For example, the most recent one second of PPG signal 1002 may be correlated with the entire six second window to give a roughly seven second autocorrelation function, as shown in FIG. 11. FIG. 11 is a plot 1100 of an autocorrelation 1102 of PPG signal 1002 of FIG. 10, with several peak shapes notated by dashed boxes 1110, 1120, and 1130, in accordance with some embodiments of the present disclosure. The abscissa of plot 1100 is presented in units of autocorrelation lag position, while the ordinate is scaled in arbitrary units, with zero notated.

Several peaks have been notated by dashed boxes in FIG. 11. Box 1110 corresponds to a relatively small peak with respect to amplitude and width. This peak also exhibits poor symmetry, which indicates that this peak may be "riding" along a larger peak. In general, such a peak would not be identified as a physiological peak by the processing equipment, and may be a correlation artifact. Similarly, box 1130 corresponds to another relatively small peak with respect to amplitude and width, albeit exhibiting relatively more symmetry than the peak in box 1110. In general, the peak in box 1130 would also not be identified as a physiological peak by the processing equipment. Box 1120 corresponds to a relatively large peak with respect to amplitude and width, with sufficiently symmetrical character. In general, this peak would be identified as a physiological peak by the processing equipment. It will be understood that the identification of physiological peaks may be based on a comparison of one or peak metrics (e.g., amplitude, width, symmetry, FWHM, or other any other suitable metric, or any combination thereof) to threshold values, which may vary. For example, the amplitude of a peak (e.g., the height of a dashed box of FIG. 11) may be compared with a threshold value, and if the amplitude exceeds the threshold value, the peak may be determined to be a physiological peak. In a further example, the width of a peak (e.g., the width of a dashed box of FIG. 11) may be compared with a threshold value, and if the width exceeds the threshold value, the peak may be determined to be a physiological peak. In a further example, the amplitude to width ratio of a peak (e.g., the aspect ratio of a dashed box of FIG. 11) may be compared with a threshold value, and if the ratio exceeds the threshold value, the peak may be determined to be a physiological peak. In some embodiments, more than one threshold value may be used to categorize a peak. For example, a peak may be determined to be of physiological origin if both the amplitude and width exceed particular threshold values. In some embodiments, a peak identified as a physiological peak under a particular set of circumstances or settings need not be identified as a physiological peak under a different set of circumstances or settings.

Figure 12:
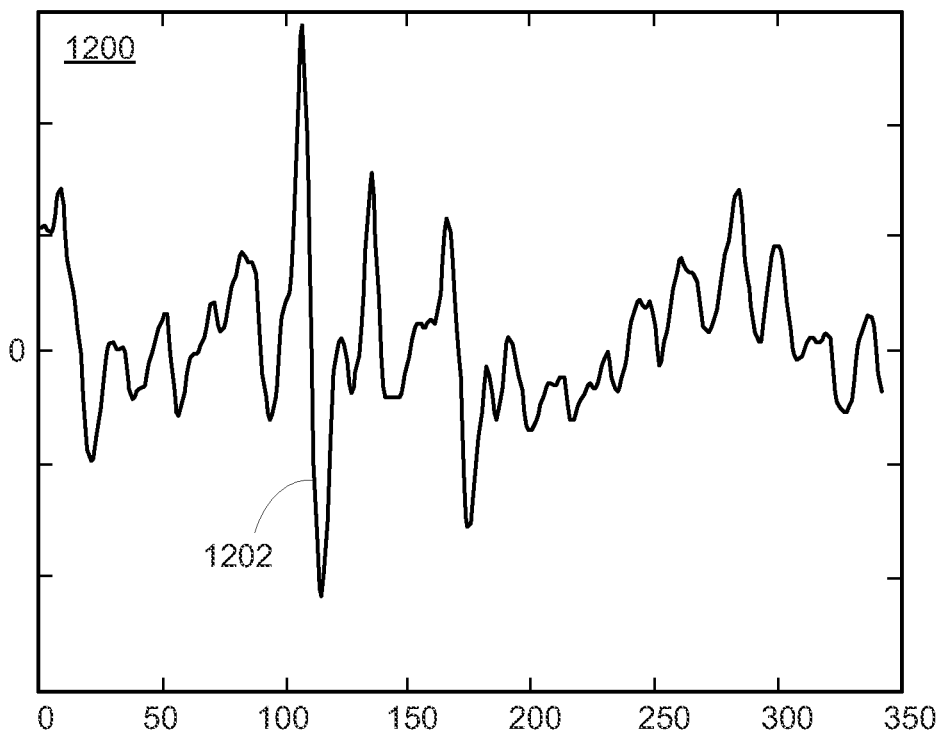
FIG. 12 is a plot of an illustrative filtered photoplethysmograph signal, relatively noisier than the photoplethysmograph signal of FIG. 10, in accordance with some embodiments of the present disclosure.
Figure 13:
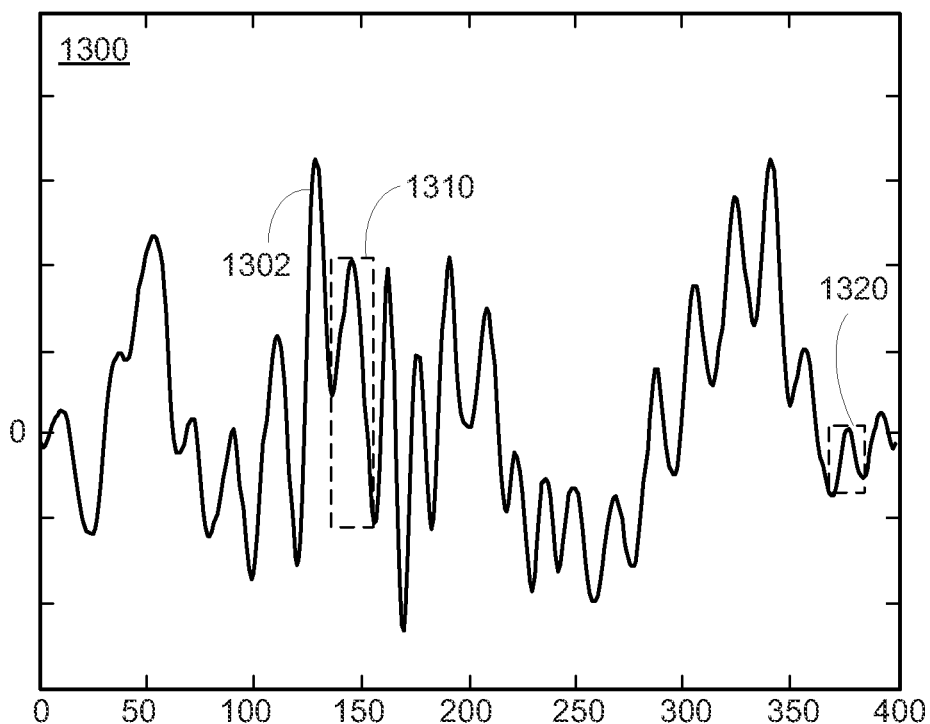
FIG. 13 is a plot of an illustrative autocorrelation of the photoplethysmograph signal of FIG. 12, with several peak shapes notated, in accordance with some embodiments of the present disclosure.

FIG. 12 is a plot 1200 of an illustrative filtered PPG signal 1202, relatively noisier than PPG signal 1002 of FIG. 10, in accordance with some embodiments of the present disclosure. The abscissa of plot 1200 is presented in units of sample number, while the ordinate is scaled in arbitrary units, with zero notated. In the illustrated embodiment, PPG signal 1202 is a window of six seconds of sampled intensity data (i.e., at a sampling rate of roughly 57 Hz) that was processed with a derivative filter. The most recent data corresponds to the right side of plot 1200, while more historical data corresponds to the left side of plot 1200. The oscillatory behavior of PPG signal 1202, due to pulse rate, is of higher frequency than that of PPG signal 1002, with large artifacts due to motion or other lower frequency components (e.g., characteristic of a neonate). An autocorrelation may be performed on PPG signal 1202, using any suitable partition of PPG signal and any suitable numerical technique. For example, the most recent one second of PPG signal 1002 may be correlated with the entire six second window to give a roughly seven second autocorrelation function, as shown in FIG. 13. FIG. 13 is a plot 1300 of an illustrative autocorrelation 1302 of PPG signal 1202 of FIG. 12, with several peak shapes notated by dashed boxes 1310 and 1320, in accordance with some embodiments of the present disclosure. The abscissa of plot 1300 is presented in units of autocorrelation lag, while the ordinate is scaled in arbitrary units, with zero notated.

The superposition of low frequency components of relatively large amplitude and a physiological pulse component of the same or smaller amplitude may present challenges in determining the pulse rate. Box 1310 corresponds to a peak exhibiting poor symmetry, having a steep baseline characteristic of lower frequency activity. Although the peak corresponding to box 1310 is due to a physiological pulse, the shape of the peak may present challenges during shape analysis. Additionally, box 1320 is associated with a peak exhibiting relatively low amplitude. Again, although the peak corresponding to box 1320 is due to a physiological pulse, the shape of the peak may present challenges during shape analysis. Under some circumstances, such as performing calculations on noisy PPG signal 1202, techniques other than, or in addition to, those described in flow diagram 900 may be preferred. In some embodiments, the processing equipment may be trained (e.g., by using a neural network) or otherwise programmed (e.g., with subject specific peak shapes and thresholds) to recognize peak shapes of noisy physiological data, as shown in FIG. 13. In addition, peaks may be analyzed in combination with other peaks or based on characteristics of other peaks. For example, metrics and/or statistics may be computed on all or a subset of the peaks identified in FIG. 13. For example, the peak widths may be analyzed to determine an average or median peak width and/or to compute a histogram of peak widths. A consistent or relatively consistent peak width among the peaks may indicate physiological pulse information even though other aspects of the peaks (e.g., symmetry) may be undesirable or lack consistency. The information from multiple peaks may then be used to determine the settings of the algorithm. Any of the techniques described herein may be used in concert with, or in lieu of, the illustrative techniques of flow diagram 900 during Search Mode.

Figure 14:
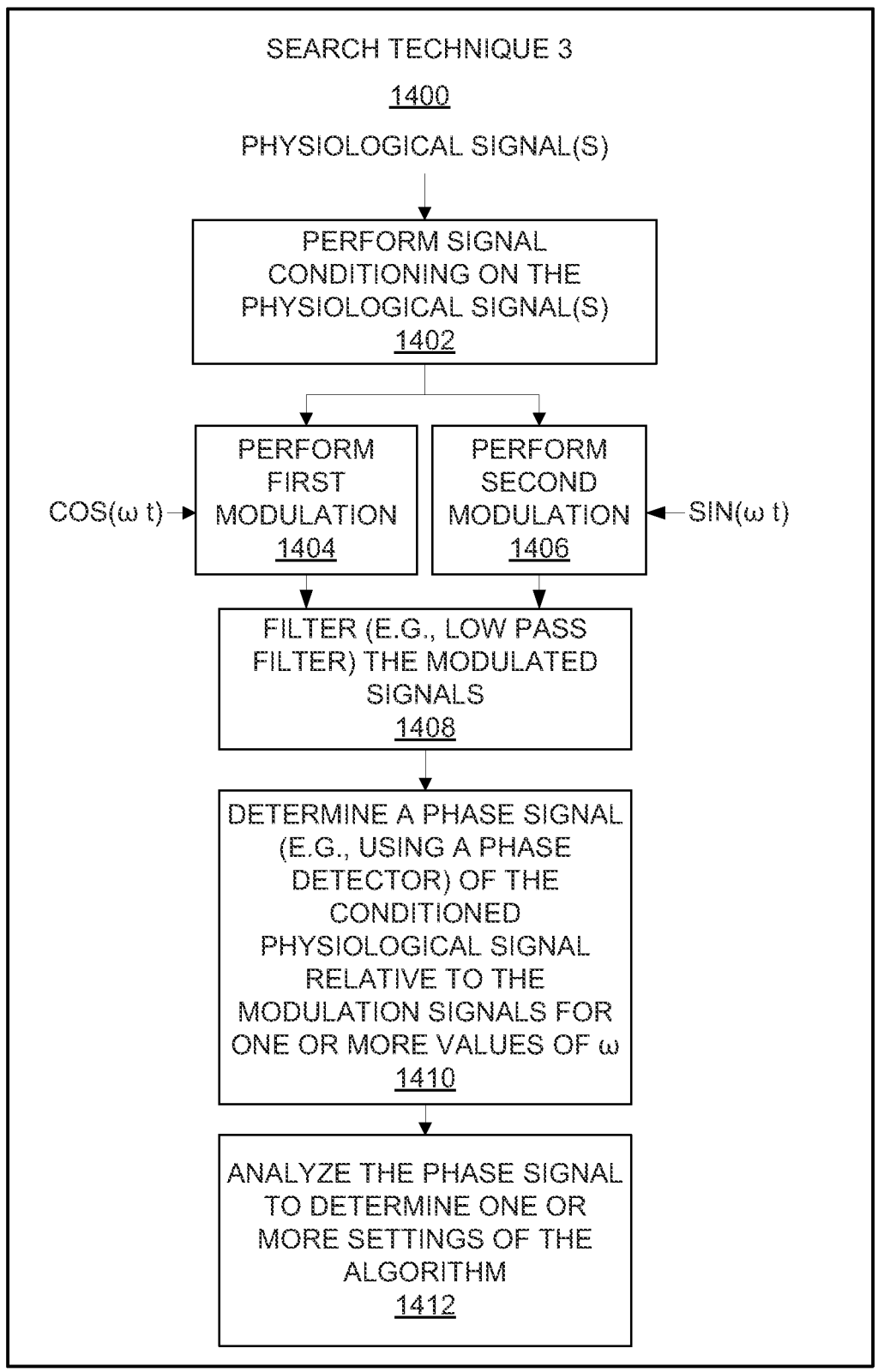
FIG. 14 is a flow diagram of illustrative steps for determining one or more settings based on a phase between a physiological signal and modulated signals, in accordance with some embodiments of the present disclosure.

In some embodiments, Search Mode may include performing cosine and sine modulation of a received physiological signal, and analyzing a phase difference of the modulated signals, to estimate a physiological rate or range thereof. FIG. 14 is a flow diagram 1400 (Search Technique 3) of illustrative steps for determining one or more algorithm settings (i.e., one or more initialization parameters) based on a phase between a physiological signal and modulated signals, in accordance with some embodiments of the present disclosure.

Step 1402 may include processing equipment performing signal conditioning on a physiological signal, or window thereof. Signal conditioning may include removing DC components, low frequency components, or both, from the window of data (e.g., by high-pass or band-pass filtering). In some embodiments, a varying baseline may be removed from the window of data (i.e., de-trending) to constrain the data average to zero. In some embodiments step 1402 may include calculating an ensemble average window of data of multiple windows of data. In some embodiments, step 1402 may include smoothing the physiological signal. For example, a moving average may be calculated and outputted as the conditioned signal.

Step 1404 may include the processing equipment performing a first modulation such as, for example, a cosine modulation as shown by Eq. 15a:

$$f_c(j) = f(j)\cos(\omega t_j) \tag{15a}$$

in which f(j) is the conditioned signal at sample j, $\omega$ is a characteristic frequency (e.g., in units of radians/s, and sometimes referred to as angular velocity), $t_j$ is a time associated with the sample j, and $f_c(j)$ is the cosine modulated signal. The cosine modulation may include multiplying the conditioned physiological signal by a cosine function of time, having some frequency $\omega$. In some embodiments, step 1404 may include performing the cosine modulation using multiple $\omega$ values. The values of $\omega$ may be bounded within a physiological range, such as about 0.33-5 Hz, corresponding to about 20-300 BPM. In some embodiments, processing equipment may determine one or more $\omega$ values that provide a substantially stable phase (e.g., a roughly constant phase).

Step 1406 may include the processing equipment performing second modulation such as, for example, a sine modulation as shown by Eq. 15b:

$$f_s(j) = f(j)\sin(\omega t_j) \tag{15b}$$

in which f(j) is the conditioned signal at sample j, $\omega$ is a characteristic frequency, $t_j$ is a time associated with the sample j, and $f_s(j)$ is the sine modulated signal. The sine modulation may include multiplying the conditioned physiological signal by a sine function of time, having some frequency $\omega$. In some embodiments, step 1406 may include performing the sine modulation using multiple $\omega$ values. The one or more values of $\omega$ may be the same as those of step 1404. It will be understood that while the first and second modulation signals are discussed herein illustratively in the context of cosine and sine modulations, any suitable modulation functions may be used to generate a first and a second modulated signals. Additionally, the modulation functions may have any suitable periodic character, including functions such as, for example, a sawtooth wave, a series of concatenated peak shapes, or other suitable functions.

Step 1408 may include the processing equipment filtering the modulated signals of steps 1404 and 1406. Step 1408 may include applying a low pass filter to the modulated signals of steps 1404 and 1406. In some embodiments, the filter used in step 1408 may depend on the value of $\omega$, reducing the presence of higher frequency activity in the modulated signals. In some embodiments, the filter used in step 1408 may be based on an expected physiological range (e.g., low-pass filtering to reduce components above 5 Hz/300 BPM). For example, the processing equipment may apply a heterodyne technique, in which the product of two original periodic signals (i.e., the physiological signal and a modulation signal) may be expressed as the sum of two periodic functions having respective frequencies equal to the difference and the sum of the frequencies of the two original periodic signals.

Step 1410 may include the processing equipment determining a phase between the modulated signals for the one or more values of $\omega$ used in steps 1404 and 1406. In some embodiments, the processing equipment may include, or communicate with, a phase detector (e.g., software, hardware, or both) which may detect a phase between the cosine and sine modulated signals. In some embodiments, a phase may be calculated at each sample point of the modulated signals, generating a phase signal. For example, referencing the heterodyne technique, shown below are Eqs. 16a and 16b:

$$f_c(j) = \cos(\omega t_j + \varphi)\cos(\omega t_j) = \frac{(\cos(\varphi) + \cos(2\omega t_j + \varphi))}{2} \rightarrow \frac{1}{2}\cos(\varphi) = I \tag{16a}$$

$$f_s(j) = \cos(\omega t_j + \varphi)\sin(\omega t_j) = \frac{(\sin(2\omega t_j + \varphi) - \sin(\varphi))}{2} \rightarrow \frac{-1}{2}\sin(\varphi) = Q \tag{16b}$$

$$\varphi = \arctan\left(-\frac{Q}{I}\right) \tag{16c}$$

in which modulated signals $f_c(j)$ and $f_s(j)$ are derived from an original signal $f(j) = \cos(\omega t_1 + \phi)$, which is used as a relatively simple example for illustration. The rightward pointing arrows represent low pass filtering of the modulated signals, which removes the relatively higher frequency component of the modulated signals. Shown in Eq. 16c is an illustrative expression for determining the phase between the original signal (e.g., a physiological signal) and the modulation signals (e.g., the sine and cosine functions). The processing equipment may determine the phase of a conditioned physiological signal relative to modulation signals by using Eqs. 16a-16c, where the conditioned physiological signal is substituted for f(j).

Figure 17:
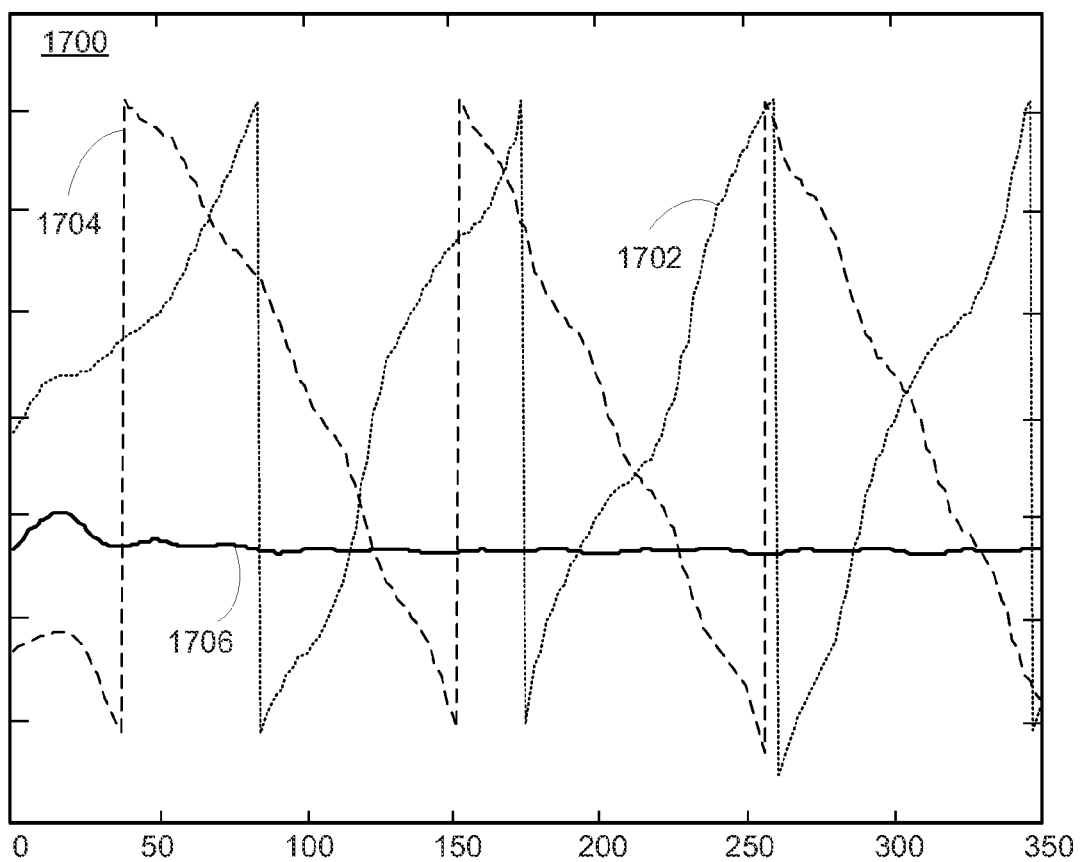
FIG. 17 is a plot of illustrative phase signals generated from modulated signals, in accordance with some embodiments of the present disclosure.

Step 1412 may include the processing equipment analyzing a phase signal based on the first modulated intensity signal and the second modulated intensity signal to determine one or more algorithm settings. In some embodiments, step 1412 may include selecting the ω value exhibiting the most constant phase over the domain (e.g., about 350 samples as illustrated in FIG. 17) as determined in step 1410. For example, in some embodiments, the processing equipment may calculate a mean value of the phase signal for each ω value and then calculate the root-mean-square difference between each phase signal and corresponding mean. If a particular ω value is too high or too low relative to a physiological frequency (e.g., a pulse rate) of the physiological signal, the phase signal may be observed to change over the domain (e.g., time or sample number). Values of ω closer to the physiological frequency are expected to exhibit phases that remain roughly constant over the domain for a subject that does not exhibit a temporal change in rate. For example, an equation such as Eq. 17:

$$R_\omega = \frac{1}{N}\sqrt{\sum_{n=0}^{N-1}(x_{n,\omega} - \bar{x}_\omega)^2} \qquad (17)$$

may be used to quantify the deviation of the phase signal from a constant value. In Eq. 17, $x_{n,\omega}$ is the nth sample of N samples, $\bar{x}_\omega$ is the phase mean value, and $R_\omega$ is the RMS deviation.

In a further example, the difference between the maximum and minimum values of the phase signal may provide an indication of the constancy of the phase signal. Any suitable metric may be used to determine the ω value that corresponds to the most constant phase between the physiological signal and the modulation signals. The selected ω value may be used to initialize parameters of the algorithm, including, for example, one or more settings of a band pass filter such a high and low frequency cutoff value (e.g., a frequency range), a representative frequency value, a set of one or more coefficients, any other suitable parameters, or any combination thereof.

Figure 15:
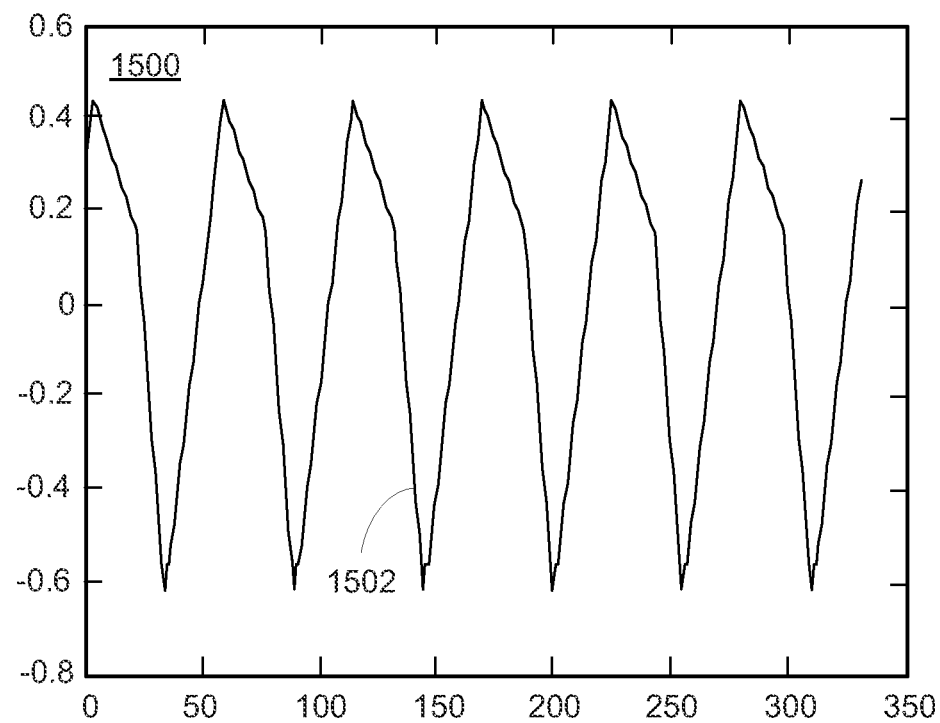
FIG. 15 is a plot of an illustrative filtered photoplethysmograph signal, in accordance with some embodiments of the present disclosure.

FIG. 15 is a plot 1500 of an illustrative filtered photoplethysmograph signal 1502, in accordance with some embodiments of the present disclosure. The abscissa of plot 1500 is presented in units of sample number, while the ordinate is scaled in arbitrary units.

Figure 16:
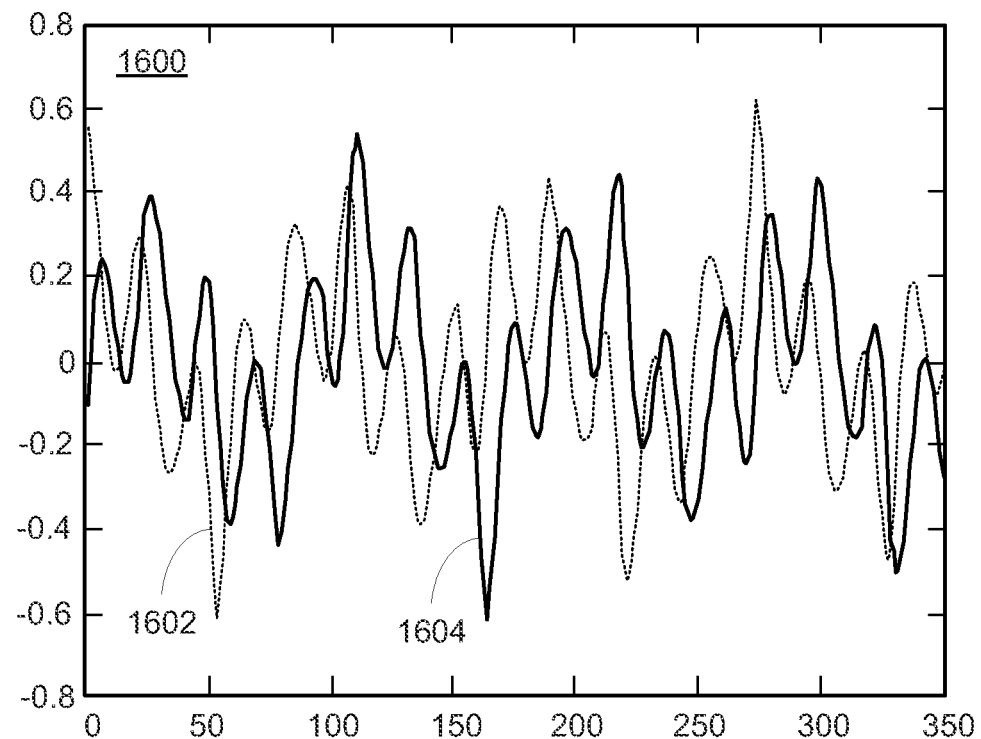
FIG. 16 is a plot of an illustrative filtered photoplethysmograph signal of modulated by both cosine and sine functions, in accordance with some embodiments of the present disclosure.

FIG. 16 is a plot 1600 of a physiological signal modulated by both sine (i.e., modulated signal 1602) and cosine (i.e., modulated signal 1604) functions, in accordance with some embodiments of the present disclosure. The abscissa of plot 1600 is presented in units of sample number, while the ordinate is scaled in arbitrary units. Modulated signals 1602 and 1604 may be generated, for example, by performing steps 1404 and 1406 of flow diagram 1400 of FIG. 14, respectively. The phase between the physiological signal and the modulated signals 1602 and 1604 is observed to be roughly constant between about 110-120 samples, across the entire domain of plot 1600 of about 350 samples.

FIG. 17 is a plot 1700 of the phase signals 1702, 1704, and 1706 between the physiological signal and the modulation signals for three different ω values, in accordance with some embodiments of the present disclosure. The abscissa of plot 1700 is presented in units of sample number, while the ordinate is scaled in arbitrary units. Phase signals 1702, 1704 and 1706 may be generated, for example, by performing step 1410 of flow diagram 1400 of FIG. 14. Phase signals 1704 and 1702 correspond to ω values that are either too high or too low relative to a physiological frequency (e.g., a pulse rate) of the physiological signal from which they were derived. This is exhibited by the significant changes in phase signal over the domain of plot 1700. Note that the sharp vertical changes in phase signals 1702 and 1704 occur when the phase exceeds $\pi$ or $-\pi$ rad, and the value is reset to between $\pi$ and $-\pi$ rad. Phase signal 1706 corresponds to a ω value that is closer to the physiological frequency relative to the ω values associated with phase signals 1702 and 1704. This is exhibited by the roughly constant phase over the entire domain of plot 1700. Any suitable metric, such as those disclosed above in the discussion of step 1412 of flow diagram 1400, may be used to determine the sufficiency of the constant character of a phase such as phase signal 1706.

Figure 18:
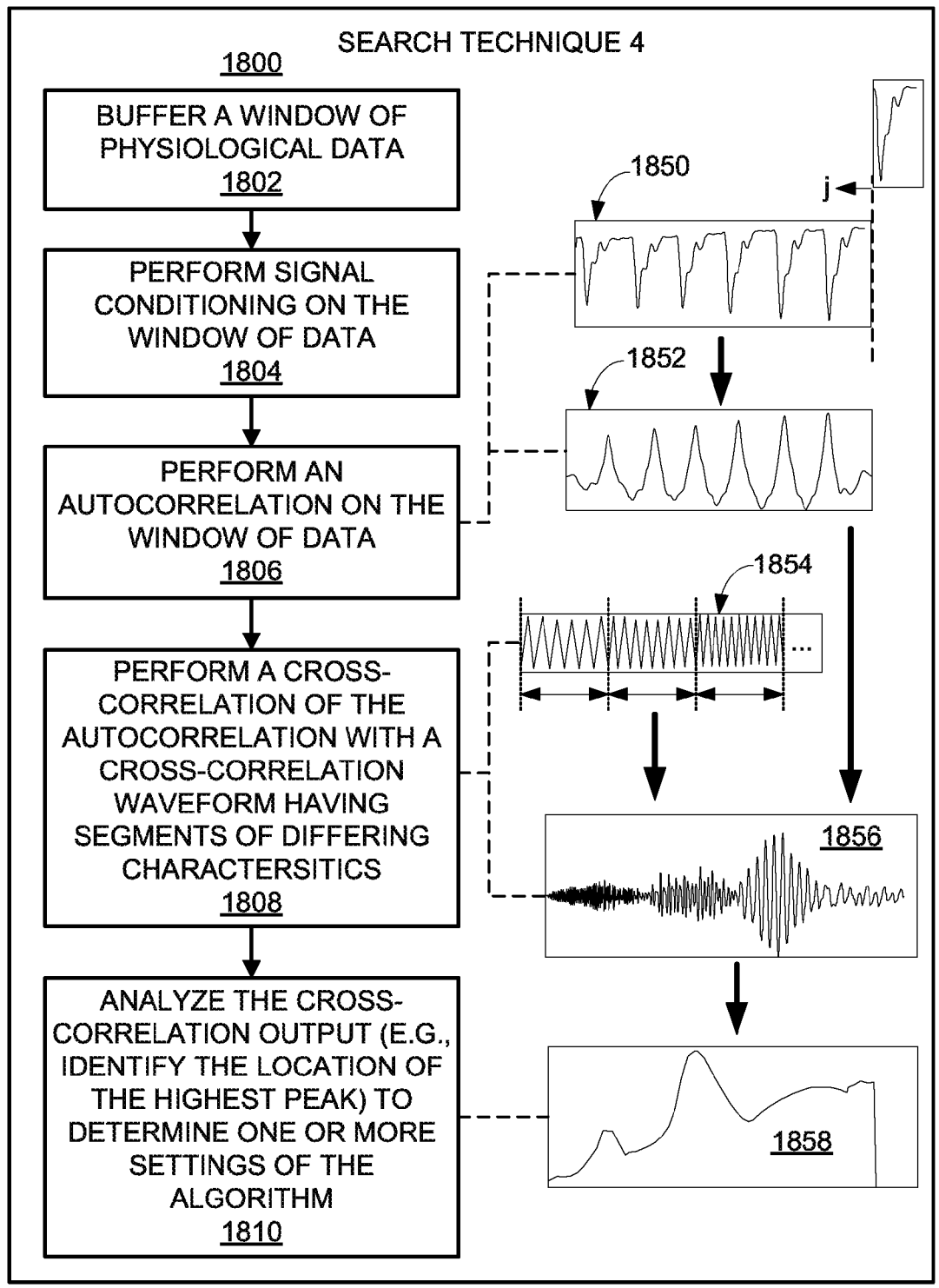
FIG. 18 is a flow diagram of illustrative steps for determining one or more settings based on a cross-correlation of a signal with a cross-correlation waveform, in accordance with some embodiments of the present disclosure.

In some embodiments, Search Mode may include performing an autocorrelation of a window of data and a cross-correlation with a pre-determined cross-correlation waveform, to estimate a physiological rate or range thereof. FIG. 18 is a flow diagram 1800 (Search Technique 4) of illustrative steps for determining one or more algorithm settings (i.e., one or more initialization parameters) based on a cross-correlation of a signal with a cross-correlation waveform, in accordance with some embodiments of the present disclosure.

Step 1802 may include processing equipment buffering a window of data, derived from a physiological signal. In some embodiments, the window may include a particular time interval (e.g., the most recent six seconds of a processed physiological signal). Step 1802 may include pre-processing (e.g., using pre-processor 320) the output of a physiological sensor, and then storing a window of the processed data in any suitable memory or buffer (e.g., queue serial module 72 of FIG. 2), for further processing by the processing equipment. In some embodiments, the window of data may be recalled from data stored in memory (e.g., RAM 54 of FIG. 2 or other suitable memory) for subsequent processing. In some embodiments, the window size (e.g., the number of samples or time interval of data to be buffered) of data is selected to capture multiple periods of oscillatory physiological activity. For example, a six second window may be used to capture about six pulse wave of a photoplethysmograph of a nominal resting adult with a pulse rate of approximately 1 Hz (i.e., 60 BPM). It will be understood that any suitable window size may be used in accordance with the present disclosure, and six seconds is used for illustrative purposes.

Step 1804 may include the processing equipment performing signal conditioning on the window of data of step 1802. Signal conditioning may include, for example, removing DC components, removing low frequency components, removing high frequency components, removing the mean, normalizing the standard deviation to one, performing any other suitable signal conditioning, or any combination thereof. In some embodiments, a varying baseline may be removed from the window of data (i.e., de-trending) to, for example, constrain the data average to zero or some other fixed value.

Step 1806 may include the processing equipment performing an autocorrelation on the conditioned window of data of step 1804. In some embodiments, the autocorrelation of step 1806 may include correlating a first portion of the window of data with a second portion of the window of data. The first and second portions may be exclusive of one another, may share one or more samples, or may be selected by any other suitable partition of the window of data. For example, referencing a six second window of data, the most recent one second of data may be correlated with the entire six seconds of data (as shown by autocorrelation setup 1850, with lag j, which may originate at either endpoint, and autocorrelation output 1852). In a further example (not shown), the one second of data may be correlated with the previous five seconds of data (exclusive of the one second of data). In some embodiments, there may be a time gap between the first and second portions. For example, the most recent one second of data may be correlated with previous data not immediately preceding the one second of data.

In some embodiments, step 1808 may include the processing equipment performing a cross-correlation of the autocorrelation of step 1806 with all or part of a cross-correlation waveform. In some embodiments, step 1808 may include the processing equipment performing a cross-correlation of the conditioned physiological signal of step 1804 with a cross-correlation waveform, and step 1806 need not be performed. The following discussion, and FIG. 18, will reference using the autocorrelation of step 1806 for illustration, although the same techniques will apply if step 1806 is omitted. The cross-correlation waveform may include multiple segments, each having different frequency components. For example, the cross-correlation waveform may include a concatenation of segments, each including a waveform of a particular characteristic frequency. Panel 1854 shows a portion of an illustrative cross-correlation waveform, in accordance with some embodiments of the present disclosure. Further detail regarding generation of, and properties of, the cross-correlation waveform is provided below in the discussion of FIG. 19 and FIG. 20, for example. The output of step 1808 may be a cross-correlation, exhibiting segments approximately corresponding to the segments of the cross-correlation waveform, as shown illustratively by panel 1856.

Step 1810 may include the processing equipment analyzing the cross-correlation output of step 1808 to determine one or more algorithm settings. In some embodiments, step 1810 may include determining a maximum in the cross-correlation, and identifying a segment of the cross-correlation waveform corresponding to the maximum. In some embodiments, step 1810 may include identifying a pattern in the cross-correlation. For example, panel 1856 shows a cross-correlation with one particular segment have a maximum value. The maximum value is located in the center of the segment, with roughly linear fall-offs in amplitude to either side within the segment (i.e., sawtooth or triangular type amplitude variation). This pattern, or other suitable patterns, may be identified by the processing equipment. Panel 1858 shows an illustrative upper envelope for the absolute value of a cross-correlation output. In some embodiments, characteristics of an upper envelope may be calculated, compared with threshold values, or otherwise analyzed to identify a physiological peak.

Figure 19:
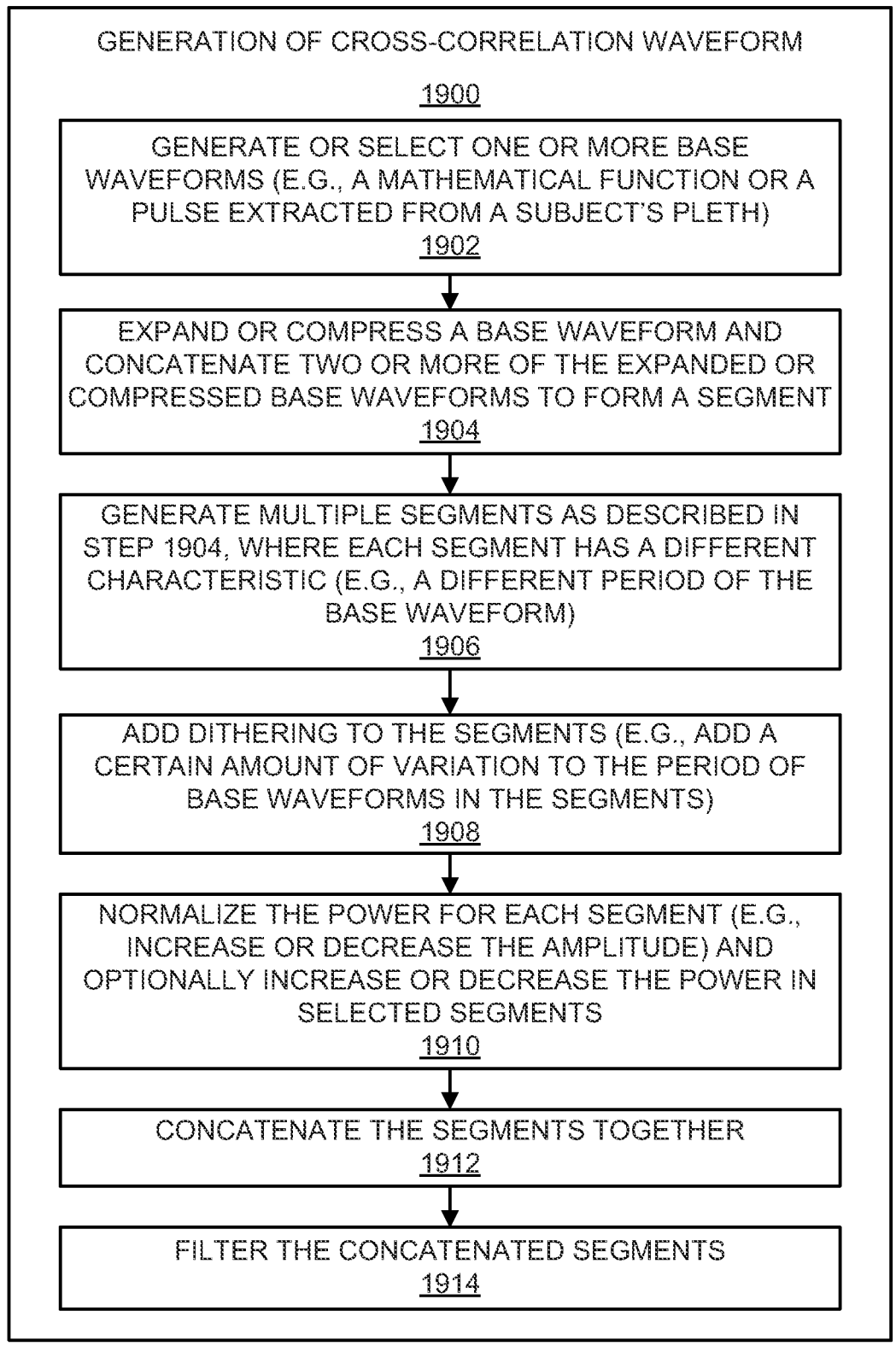
FIG. 19 is a flow diagram of illustrative steps for generating a cross-correlation waveform, in accordance with some embodiments of the present disclosure.

FIG. 19 is a flow diagram 1900 of illustrative steps for generating a cross-correlation waveform, in accordance with some embodiments of the present disclosure. It will be understood that any of the illustrative steps of flow diagram 1900 may be optionally performed, and accordingly some of the illustrative steps of flow diagram 1900 need not be performed.

Step 1902 may include the processing equipment, or other suitable processing equipment, generating or selecting one or more base waveforms. A base waveform will refer to a single period of a wave or pulse of any suitable type, although the base waveform may include higher frequency components relative to the frequency component corresponding to the single period (e.g., a single period of a base waveform may exhibit oscillatory behavior of smaller period). A base waveform may be a mathematical function, one or more pulse waves of a subject's PPG, any other suitable waveform, or any combination thereof. For example, in some embodiments, a base waveform may be a sine wave, cosine wave, triangular wave, square wave, wavelet, any other suitable mathematical function, any portions thereof, or any combination thereof. In a further example, in some embodiments, a base waveform may be a processed PPG signal (e.g., filtered, averaged, smoothed or otherwise processed), a component of a PPG (e.g., one or more scales of a wavelet-transformed PPG signal), any other suitable physiological signal, any portions thereof, or any combination thereof.

Step 1904 may include the processing equipment, or other suitable processing equipment, expanding or compressing the base waveform of step 1902 to adjust the period, and concatenation two or more of the base waveforms to form a segment. For example, a six second segment may include six concatenated base waveforms each having a period of one second. A different six second segment may include twelve concatenated base waveforms that have been each compressed to a period of a half second. In some embodiments, segments may include the same or different types of base waveforms, having any suitable period. In some embodiments, step 1904 need not be performed. For example, one or more pre-generated segments may be stored, and no expansion, compression, or concatenation need be required at step 1904 to form a segment.

Step 1906 may include the processing equipment generating multiple segments (e.g., as described in step 1904), each having a different characteristic (e.g., period of the base waveform). The multiple segments may be generated sequentially, or in parallel, and may each include any suitable type of base waveform. In some embodiments, step 1906 need not be performed each time a cross-correlation waveform is generated. For example, one or more segments may be generated and stored for later use, and accordingly, step 1906 need not be performed again at the later time.

Step 1908 may include the processing equipment adding dithering to one or more of the segments of step 1906. Dithering may include adding variation to the period of base waveforms within a segment. For example, a particular segment may originally include six concatenated, identical base waveforms, each having a period of one second. Dithering may be added to the particular segment by adjusting the period of the leftmost base waveform to 0.9 seconds and adjusting the period of the rightmost base waveform to 1.1 seconds. In a further example, dithering may be applied continuously across a segment, generating a chirp-like segment. Any suitable technique for adding dithering to a segment may be used, in accordance with the present disclosure. In some embodiments, step 1908 need not be performed. In some embodiments, the processing equipment may perform step 1908 as part of performing step 1904.

Step 1910 may include the processing equipment adjusting the amplitude of one or more segments. In some embodiments, the amplitude of a segment may be adjusted based on the period of the base waveforms included in the segment. In some embodiments, step 1910 may be performed as part of the base waveform generation of step 1902. In some embodiments, step 1910 may be performed as part of the segment generation of step 1906. In some embodiments, step 1910 need not be performed.

Step 1912 may include the processing equipment concatenating the segments of step 1910 together. Step 1912 may include positioning the multiple segments end to end in a linear arrangement. In some embodiments the linear arrangement may be organized by segment periodicity. For example, segments may be arranged from lowest to highest periodicity, or from highest to lowest periodicity. The concatenated segments will be referred to as a cross-correlation waveform. In some embodiments, a cross-correlation waveform may include concatenated segments with padding (e.g., inserted zeros) between the segments to reduce higher frequency components near the segment boundaries. For example, padding segments of zeros, equal in length (i.e., time interval, number of samples) to the waveform segments, may be inserted between each pair of adjacent segments, to minimize edge effects of the segment boundaries. In some embodiments, a cross-correlation waveform may include concatenated segments, which may each be scaled with a window function (e.g., at step 1910), such that each segment decays to zero near the segment's boundaries. In some embodiments, a cross-correlation waveform may include concatenated segments with dithering (e.g., at step 1908) at the boundaries of segments to reduce higher frequency components near the segment boundaries (e.g., due to abrupt changes in characteristic frequency). In some embodiments, the cross-correlation waveform may include at least one "chirp" type segment, which may include a gradual (i.e., linear) variation in frequency over the segment's domain. Any suitable technique may be used for generating the cross-correlation waveform from one or more segments, in accordance with the present disclosure.

Step 1914 may include the processing equipment filtering the concatenated segments of step 1912. In some embodiments, the processing equipment may apply a low-pass filter, band-pass filter, notch filter, any other suitable filter, or any combination thereof to the concatenated segments to form the cross-correlation waveform. For example, the processing equipment may apply a low-pass filter to reduce and/or eliminate high frequency components (e.g., associated with segment boundaries). In a further example, the cutoff frequency of the low-pas filter may be based on initialization parameters. In some embodiments, step 1914 need not be performed, and the concatenated segments of step 1912 may be referred to as the cross-correlation waveform.

Figure 20:
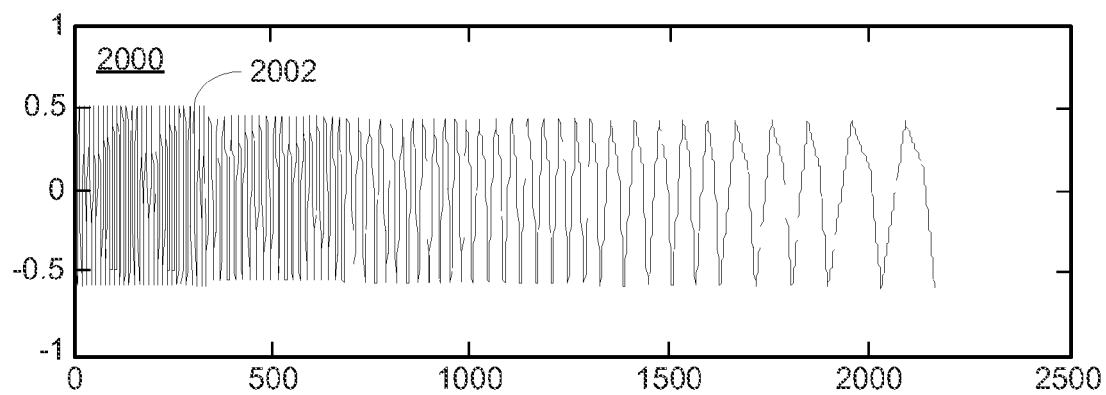
FIG. 20 is a plot of an illustrative cross-correlation waveform, in accordance with some embodiments of the present disclosure.

FIG. 20 is a plot 2000 of an illustrative cross-correlation waveform 2002, in accordance with some embodiments of the present disclosure. The abscissa of plot 2000 is presented in units of cross-correlation waveform sample number, while the ordinate is scaled in arbitrary units. Cross-correlation waveform 2002 includes multiple segments, each segment including a waveform having a particular characteristic frequency. Accordingly, cross-correlation waveform 2002 has varying frequency character, which may be used for comparison with a window of data, or autocorrelation derived thereof. In some embodiments, a cross-correlation waveform may include concatenated segments, each having a particular characteristic frequency. In the illustrated embodiment of FIG. 20, the characteristic period of the segments increases from left to right.

Figure 21:
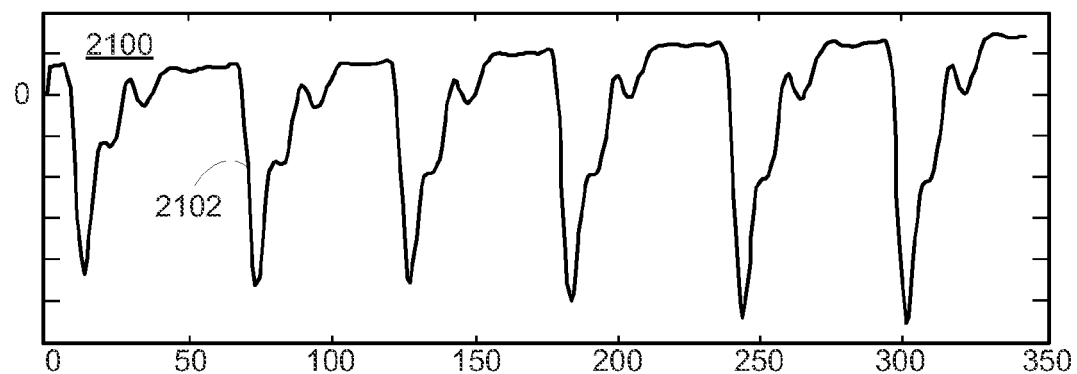
FIG. 21 is a plot of an illustrative window of data of a physiological signal, in accordance with some embodiments of the present disclosure.

FIG. 21 is a plot 2100 of an illustrative window of data 2102 of a physiological signal, in accordance with some embodiments of the present disclosure. The abscissa of plot 2100 is presented in units of sample number, while the ordinate is scaled in arbitrary units. In the illustrated embodiment, PPG signal 2102 is a window of six seconds of sampled intensity data (i.e., at a sampling rate of roughly 57 Hz) that was processed with a derivative filter. The oscillatory behavior of PPG signal 2102, due to pulse rate, is easily observed by the six negative peaks spaced about one second apart. An autocorrelation may be performed on PPG signal 2102, using any suitable partition of PPG signal and any suitable numerical technique.

Figure 22:
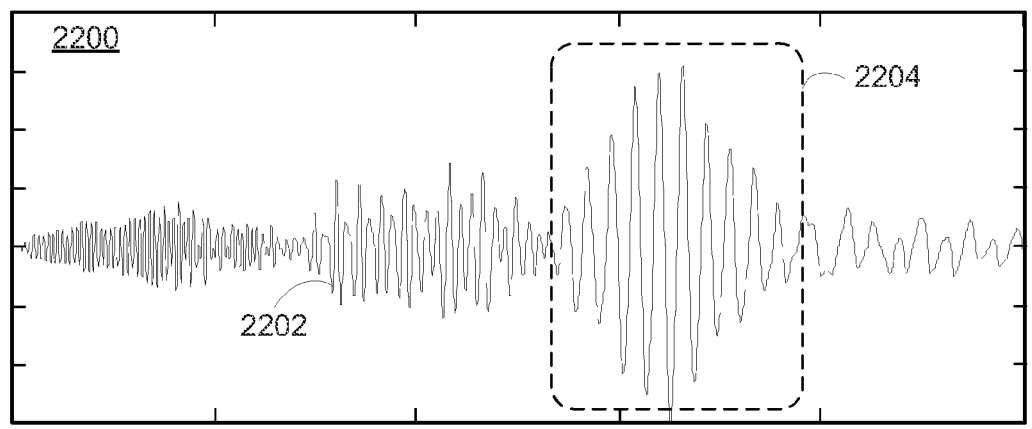
FIG. 22 is a plot of an illustrative cross-correlation of an autocorrelation of a window of data with a cross-correlation waveform, in accordance with some embodiments of the present disclosure.

FIG. 22 is a plot 2200 of an illustrative cross-correlation 2202 of an autocorrelation of a window of data with a cross-correlation waveform, in accordance with some embodiments of the present disclosure. The abscissa of plot 2200 is presented in units of cross-correlation lag, while the ordinate is scaled in arbitrary units. Region 2204 of cross-correlation 2202 highlights a particular portion of the cross-correlation having a relatively large amplitude, and pyramidal amplitude variation. The amplitude and shape of region 2204 may indicate a match or similarity in characteristic period between a particular segment and a window of data.

Figure 23:
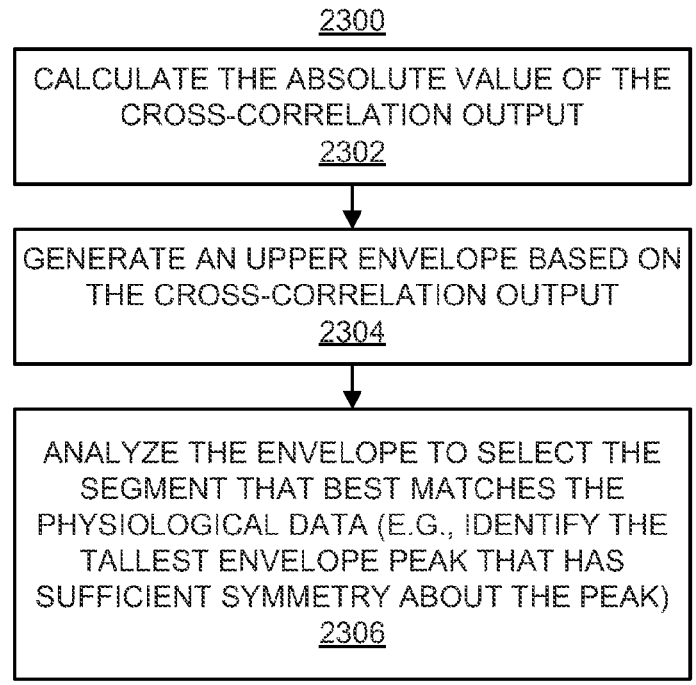
FIG. 23 is a flow diagram of illustrative steps for selecting a segment of a cross-correlation waveform based on envelope analysis, in accordance with some embodiments of the present disclosure.

FIG. 23 is a flow diagram 2300 of illustrative steps for selecting a segment of a cross-correlation waveform based on envelope analysis, in accordance with some embodiments of the present disclosure.

Step 2302 may include processing equipment calculating the absolute value of a cross-correlation output. The cross-correlation output may be generated by, for example, performing suitable steps of flow diagram 1800 of FIG. 18. Calculation of the absolute value may aid in determining characteristics of the cross-correlation output. In some embodiments, the cross-correlation output may be squared to ensure all positive values for further analysis. Any suitable mathematical technique may be used to condition the cross-correlation output.

Step 2304 may include the processing equipment generating an upper envelope based on the cross-correlation output, or output signal derived thereof (e.g., the absolute value of the cross-correlation output). The upper envelope may be an outline of the cross-correlation amplitudes, providing a convenient curve for further processing. In some embodiments, the upper envelope may be generated using a mathematical formalism such as, for example, a linear or spline fit through the cross-correlation data points. In some embodiments, the upper envelope may be fitted through a representative point of each segment of the cross-correlation output. For example, the upper envelope may be fitted through points located at $(x_s, y_s)$, in which $x_s$, is a midpoint in the domain of each segment and $y_s$ is an average amplitude in the segment. Any suitable technique may be used to generate an upper envelope of the cross-correlation output, or output signals derived thereof.

Step 2306 may include the processing equipment analyzing the envelope of step 2304 to select a desired segment that corresponds to the window of data used for the cross-correlation. In some embodiments, step 2306 may include locating one or more peaks in the envelope. In some embodiments, step 2306 may include analyzing a peak in the envelope to determine whether the peak corresponds to a physiological pulse. Peak analysis may include calculating a peak height, peak width (e.g., using any suitable calculation such as FWHM), peak symmetry (e.g., skewness), peak baseline, peak isolation (e.g., peak center locations relative to widths), peak up-slopes and down-slopes (e.g., maximum and minimum derivatives), peak aspect ratio (e.g., height to width ratio), any other suitable peak characteristic, or any combination thereof. In some embodiments, step 2306 may include comparing one or more peak characteristics with a threshold value to determine whether to select the peak. For example, the processing equipment may locate the peak with the largest amplitude and calculate one or more characteristics for comparison with a threshold. If the peak is determined to not correspond to a physiological pulse based on the comparison, the processing equipment may locate another peak for analysis. The discussion of FIG. 24 provides further detail and illustration of peak characteristics.

Figure 24:
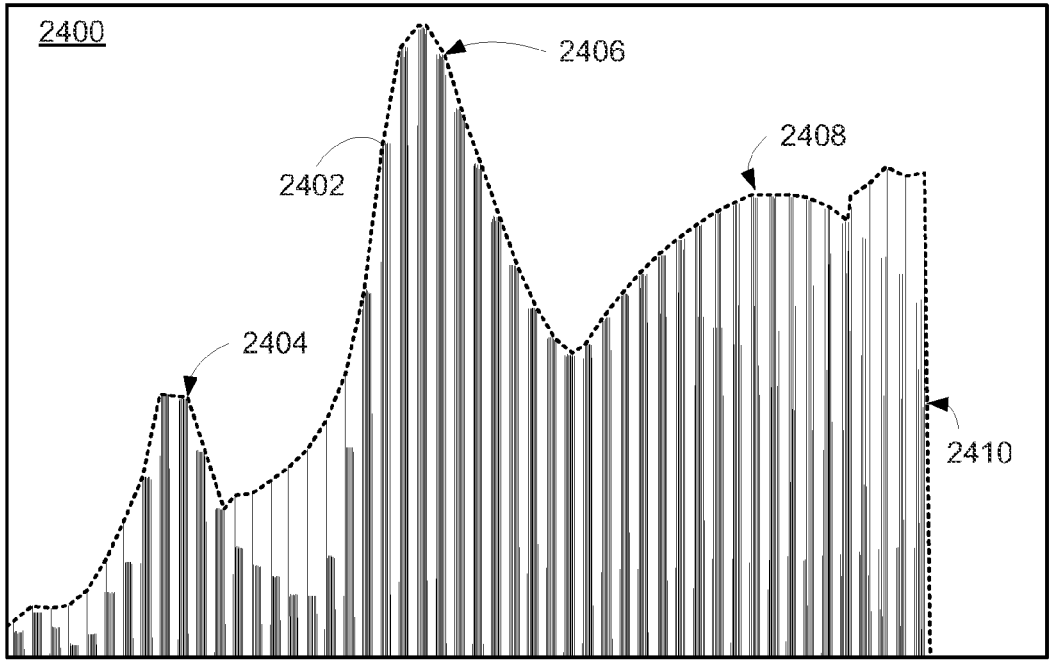
FIG. 24 is a plot of an illustrative cross-correlation output, in accordance with some embodiments of the present disclosure.

FIG. 24 is a plot 2400 of an illustrative cross-correlation output 2402 (with absolute value having already been taken of the output) and upper envelope 2410 (shown by the dotted line), in accordance with some embodiments of the present disclosure. The abscissa of plot 2400 is presented in units of cross-correlation lag, by segment, while the ordinate is scaled in arbitrary units, with zero baseline. Cross-correlation output 2402 includes fifty segments, corresponding to fifty segments in the cross-correlation waveform used to generate the cross-correlation output 2402. Each of the fifty segments of cross-correlation output 2402 includes multiple data points corresponding to particular time lags in the cross-correlation between the cross-correlation waveform and the window of data (or autocorrelation derived thereof).

Upper envelope 2410 includes three major peaks; peak 2404, peak 2406, and peak 2408. Peaks 2406 and 2404 have similar aspect ratios, while the height of peak 2406 is roughly twice that of peak 2404. Peak 2408 is observably wider than either peak 2404 or peak 2406, with a height intermediate to peak 2404 and peak 2406. In some embodiments, the processing equipment may analyze signals such as cross-correlation output 2402 to determine which, if any, peaks may correspond to a physiological rate.

In an illustrative example, processor 312 may determine that peak 2408 does not correspond to a physiological pulse because the aspect ratio of peak 2408 is too near unity (i.e., the height of peak 2408 is too small relative to the FWHM). Processor 312 may determine that peak 2406 has a larger height than peak 2404, and accordingly may initially analyze peak 2406. Under some circumstances, processor 312 may determine that peak 2406 corresponds to a physiological rate, and select the segment of the cross-correlation waveform that corresponds to maximum of peak 2406. In some embodiments, when processor 312 has selected a desired peak, further peaks need not be analyzed. Under some circumstances, peak 2408 may be designated as a noise peak, and processor 312 may determine that the presence of peak 2408 encroaching near peak 2406 may warrants another window of data to be analyzed. Similarly, under some circumstances, processor need not require a further window of data, and may select peak 2406.

Figure 25:
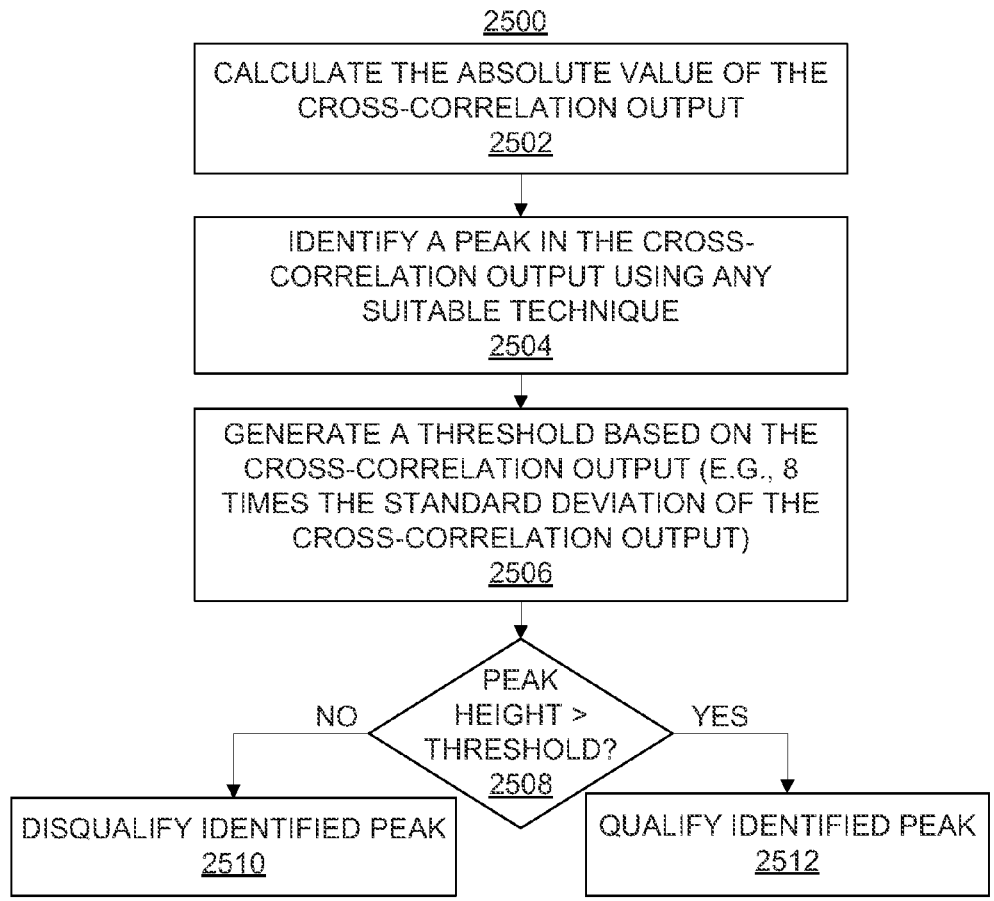
FIG. 25 is a flow diagram of illustrative steps for qualifying a peak of a cross-correlation waveform based on a standard deviation, in accordance with some embodiments of the present disclosure.

FIG. 25 is a flow diagram 2500 of illustrative steps for qualifying a peak of a cross-correlation waveform, in accordance with some embodiments of the present disclosure.

Step 2502 may include processing equipment calculating the absolute value of a cross-correlation output. The cross-correlation output may be generated by, for example, performing suitable steps of flow diagram 1800 of FIG. 18. Calculation of the absolute value may aid in determining characteristics of the cross-correlation output. In some embodiments, the cross-correlation output may be squared to ensure all positive values for further analysis. Any suitable mathematical technique may be used to condition the cross-correlation output.

Step 2504 may include the processing equipment identifying a peak in the cross-correlation output of step 2502 using any suitable technique. Step 2504 may include locating a maximum value in the cross-correlation output, locating a zero in the first derivative of the cross-correlation output, calculating a second derivative value (e.g., to determine whether any extrema are minima or maxima), any other suitable peak locating calculation, or any combination thereof. In some embodiments, step 2504 may include applying curve fitting to the cross-correlation output. For example, the processing equipment may fit a function, such as a Gaussian profile or a polynomial, to a candidate peak by calculating one or more parameters of the function. In some embodiments, identifying a peak may include identifying an interval in the cross-correlation domain corresponding to the peak, identifying a centerline of a peak, identifying any other suitable characteristic values, or any combination thereof.

Step 2506 may include the processing equipment generating a threshold based on the cross-correlation output of step 2502. In some embodiments, the threshold value may be calculated based on statistical analysis of the cross-correlation output. For example, the processing equipment may calculated a mean, standard deviation, or both, of the cross-correlation output and generate a threshold value based on this calculation. In an illustrative example, the processing equipment may generate a threshold equal to eight times the standard deviation of the cross-correlation output. In some embodiments, threshold values may be stored in a database (e.g., a look-up table), and may be recalled based on one or more signal metrics (e.g., statistical values), any other suitable information (e.g., subject identification), or any combination thereof. The threshold value of step 2506 may be a height threshold, height-to-width threshold, peak area (e.g., integral of cross-correlation output over peak domain) threshold, any other suitable threshold value of a peak characteristic, or any combination thereof.

Step 2508 may include the processing equipment determining whether the identified peak of step 2504 exceeds the threshold of step 2506. Step 2508 may include a comparison of the peak value (i.e., maximum value of the cross-correlation output in the peak domain) to the threshold value. For example, step 2508 may include computing a difference, ratio, any other suitable comparative quantity, or any combination thereof. If the peak value is determined to exceed the threshold value, the identified peak may be qualified as a physiological peak, as shown by step 2512. If the peak value is determined not to exceed the threshold value, the identified peak may be disqualified as a physiological peak, as shown by step 2510. In some embodiments, step 2508 may include comparing multiple characteristic of the identified peak to corresponding threshold values. For example, if the peak value is determined to exceed a threshold value and the height-to-width ratio value of the peak exceeds another threshold, the identified peak may be qualified as a physiological peak, as shown by step 2512.

Step 2510 may include the processing equipment disqualifying the identified peak of step 2504 based on the comparison of step 2508. In some embodiments, disqualification may include removing the identified peak from further consideration, calculation, or processing.

Step 2512 may include the processing equipment qualifying the identified peak of step 2504 based on the comparison of step 2508. In some embodiments, qualification may include subjecting the identified peak to further consideration, calculation, or processing.

Figure 26:
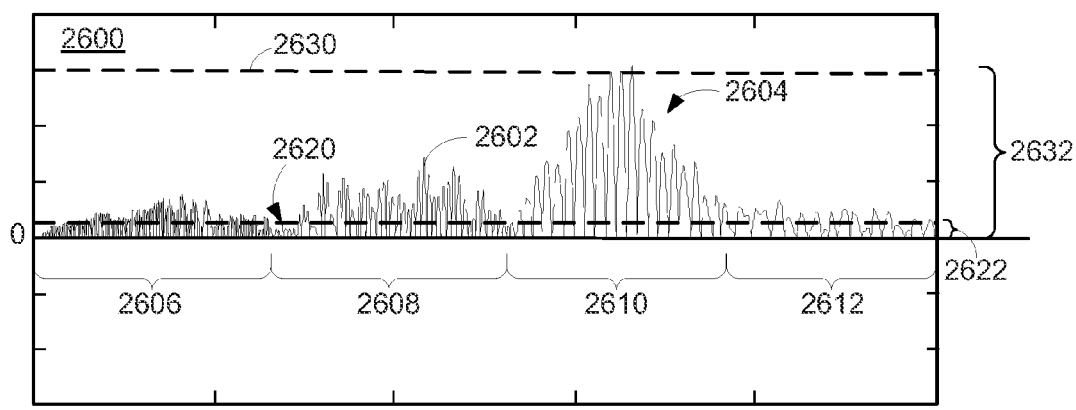
FIG. 26 is a plot of an illustrative cross-correlation output and a threshold value, in accordance with some embodiments of the present disclosure.

FIG. 26 is a plot 2600 of an illustrative cross-correlation output 2602 and a threshold 2630, in accordance with some embodiments of the present disclosure. The abscissa of plot 2600 is presented in units of cross-correlation lag, while the ordinate is scaled in arbitrary units, with zero notated. Note that cross-correlation output 2602 is the result of an absolute value calculation, and includes all positive values with a baseline of zero. Cross-correlation output 2602 includes at least four segments (i.e., segments 2606, 2608, 2610, and 2612, along with segments not shown). Peak 2604 is located within segment 2610, and includes a number of minor peaks within its envelope. The standard deviation of cross-correlation output 2602 is shown by line 2620, a difference 2622 from the baseline. In an illustrative example, threshold 2630 may be used to qualify a peak of cross-correlation 2602. In the illustrated embodiment, the difference 2632 of threshold 2630 from the baseline is eight times difference 2622. As illustrated, peak 2604 exceeds threshold 2630, and accordingly, the processing equipment may qualify peak 2604 based on this comparison. Under some circumstances, such as, for example, a higher threshold (not shown), the processing equipment may disqualify peak 2604.

Figure 27:
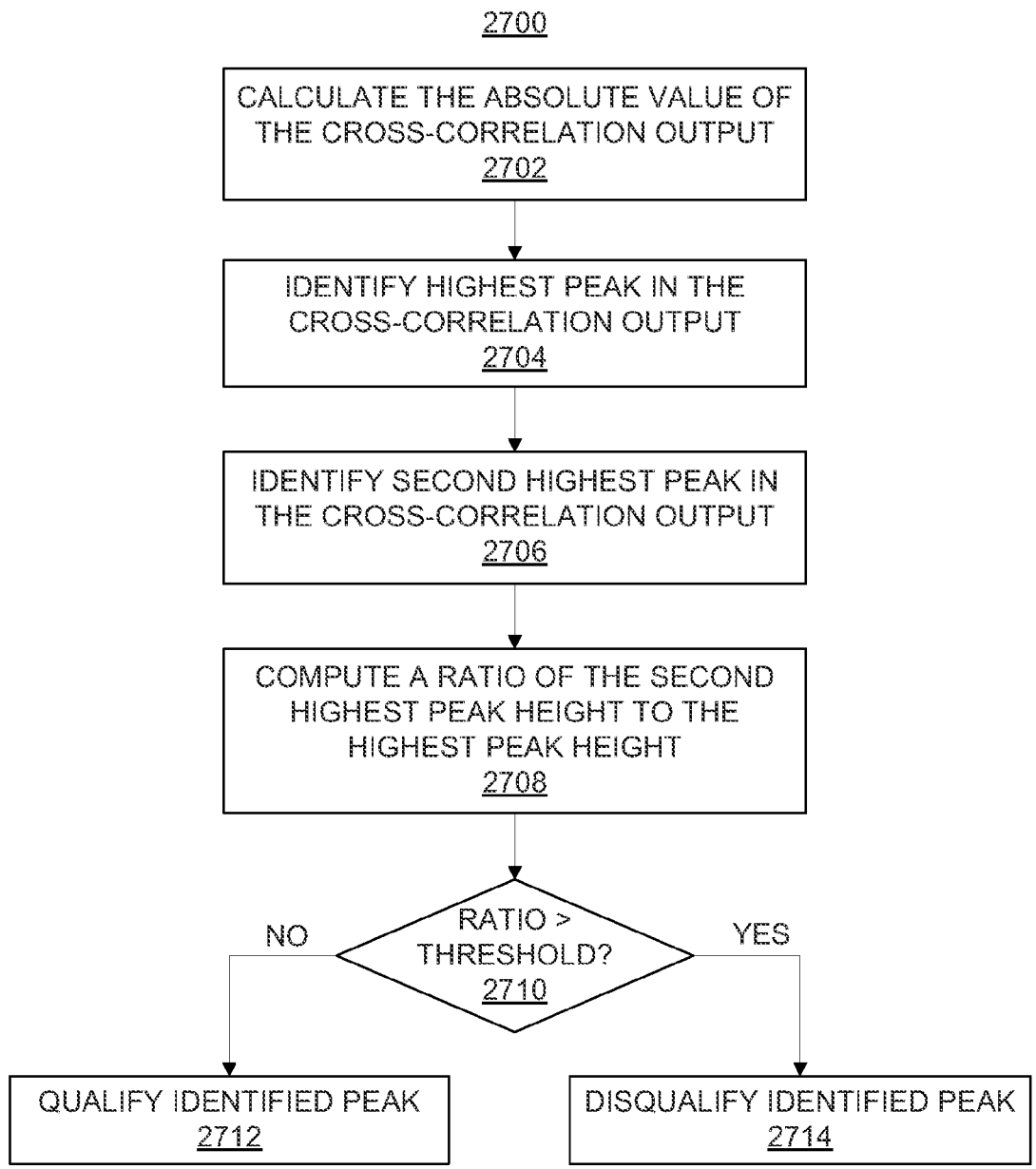
FIG. 27 is a flow diagram of illustrative steps for qualifying a peak of a cross-correlation waveform based on a peak comparison, in accordance with some embodiments of the present disclosure.

FIG. 27 is a flow diagram 2700 of illustrative steps for qualifying a peak of a cross-correlation waveform based on a peak comparison, in accordance with some embodiments of the present disclosure.

Step 2702 may include processing equipment calculating the absolute value of a cross-correlation output. The cross-correlation output may be generated by, for example, performing suitable steps of flow diagram 1800 of FIG. 18. Calculation of the absolute value may aid in determining characteristics of the cross-correlation output. In some embodiments, the cross-correlation output may be squared, and optionally re-scaled, to ensure all positive values for further analysis. Any suitable mathematical technique may be used to condition the cross-correlation output.

Step 2704 may include the processing equipment identifying the highest peak in the cross-correlation output of step 2702 using any suitable technique. Step 2704 may include locating a maximum value in the cross-correlation output, locating a zero in the first derivative of the cross-correlation output, calculating a second derivative value (e.g., to determine whether extrema are minima or maxima), any other suitable peak locating calculation, or any combination thereof. In some embodiments, step 2704 may include applying curve fitting to the cross-correlation output. For example, the processing equipment may fit a function, such as a Gaussian profile or a polynomial, to a candidate peak by calculating one or more parameters of the function. In some embodiments, identifying a peak may include identifying an interval in the cross-correlation domain corresponding to the peak, identifying a centerline of a peak, identifying any other suitable characteristic values, or any combination thereof. In some embodiments, step 2704 may include comparing multiple peaks to identify the highest peak.

Step 2706 may include the processing equipment identifying the second highest peak in the cross-correlation output of step 2702 using any suitable technique. Step 2706 may include locating a maximum value in the cross-correlation output, locating a zero in the first derivative of the cross-correlation output, calculating a second derivative value (e.g., to determine whether extrema are minima or maxima), performing any other suitable peak locating calculation, or any combination thereof. In some embodiments, step 2706 may include applying curve fitting to the cross-correlation output. For example, the processing equipment may fit a function, such as a Gaussian profile or a polynomial, to a candidate peak by calculating one or more parameters of the function. In some embodiments, identifying a peak may include identifying an interval in the cross-correlation domain corresponding to the peak, identifying a centerline of a peak, identifying any other suitable characteristic values, or any combination thereof. In some embodiments, step 2704 may include comparing multiple peaks to identify the second highest peak. In some embodiments, the processing equipment may exclude one or more portions of the cross-correlation output from being considered as including the second peak. For example, the processing equipment may require that the second peak not be part of the same segment as that of the highest peak of step 2704. In a further example, the processing equipment may require that the second peak not be part of the same segment as that of the highest peak of step 2704, nor neighboring segments.

In some embodiments, peak height may be calculated based on an absolute maximum value, calculated relative to a baseline, calculated relative to a negative peak minimum (e.g., positive peak to negative peak amplitude), calculated using any other suitable technique, or any combination thereof. For example, depending upon the local baseline of the cross-correlation output, the highest peak need not have an absolute value higher than the second highest peak (e.g., if the baseline of the second highest peak is sufficiently larger than the baseline of the highest peak). Any suitable criteria may be used to identify the highest and second highest peaks of steps 2704 and 2706, respectively.

Step 2708 may include the processing equipment computing a ratio of the second high highest peak height of step 2706 to the highest peak height of step 2704. Step 2710 may include determining whether the computed ratio of step 2708 is larger than a threshold value. If the ratio is determined to be greater than the threshold value at step 2710, indicating the second highest peak is not sufficiently small relative to the highest peak, the identified highest peak may be disqualified, as shown by step 2714. If the ratio is determined to be less than or equal to the threshold value at step 2710, indicating the second highest peak is sufficiently small relative to the highest peak, the identified highest peak may be qualified, as shown by step 2712. The threshold value may be any suitable value between zero and one. For example, the threshold value may be in the range of 0.6-0.8, in accordance with some embodiments of the present disclosure. In some embodiments, the threshold value may be generated based at least in part from the cross-correlation output. For example, although not shown in flow diagram 2700, step 2506 of flow diagram 2500 may be performed as part of, or prior to, performing step 2710.

Figure 28:
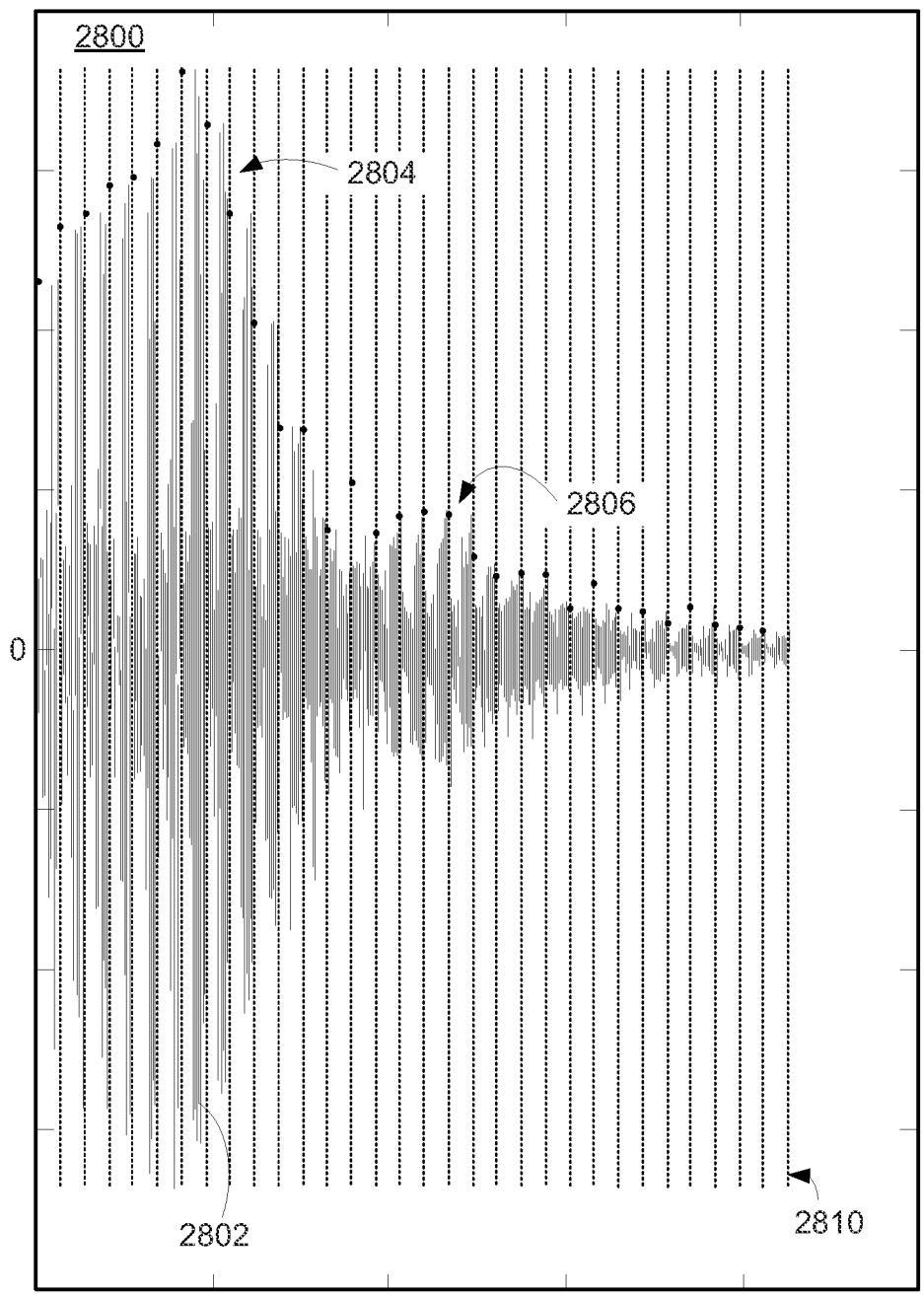
FIG. 28 is a plot of an illustrative cross-correlation output under noisy conditions, in accordance with some embodiments of the present disclosure.

FIG. 28 is a plot 2800 of an illustrative cross-correlation output 2802 under noisy conditions, in accordance with some embodiments of the present disclosure. The abscissa of plot 2800 is presented in units of cross-correlation lag, while the ordinate is scaled in arbitrary units. Segment boundaries 2810 are displayed in plot 2800 as dashed lines for reference. Cross-correlation output 2802 exhibits peak 2804 and relatively smaller peak 2806. Peak 2804 is due to noise, and not due to a physiological pulse. Peak 2806, observed to be significantly small than peak 2804, is due to a physiological pulse. In some circumstances, cross-correlation outputs that exhibit large noise components, such as cross-correlation output 2802, may lead to erroneous determination of physiological peaks. Accordingly, additional processing or analysis of the cross-correlation output may be performed to correctly identify the physiological peak.

Figure 29:
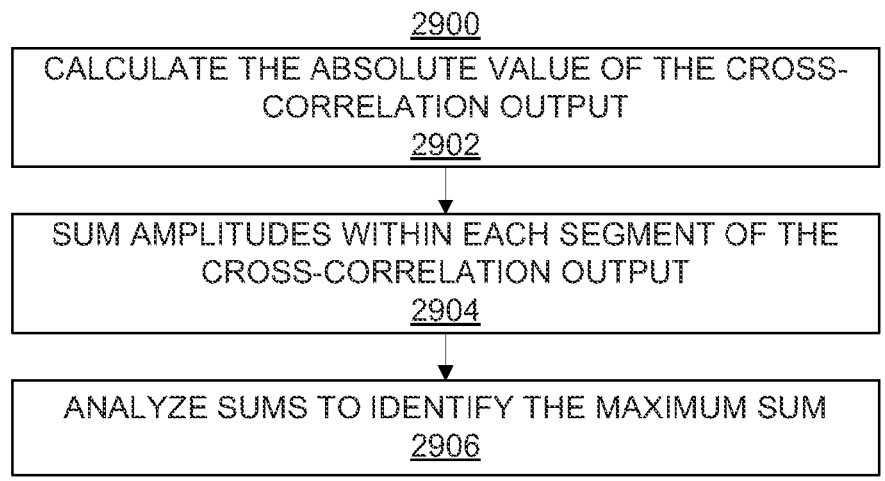
FIG. 29 is a flow diagram of illustrative steps for qualifying a peak of a cross-correlation waveform based on a segment sum, in accordance with some embodiments of the present disclosure.

FIG. 29 is a flow diagram 2900 of illustrative steps for qualifying a peak of a cross-correlation waveform based on a segment sum, in accordance with some embodiments of the present disclosure. The steps of flow diagram 2900 may be especially useful in circumstances in which a cross-correlation output exhibits relatively large noise components.

Step 2902 may include the processing equipment calculating the absolute value of a cross-correlation output. The cross-correlation output may be generated by, for example, performing suitable steps of flow diagram 1800 of FIG. 18.

Calculation of the absolute value may aid in determining characteristics of the cross-correlation output. In some embodiments, the cross-correlation output may be squared, and optionally re-scaled, to ensure all positive values for further analysis. Any suitable mathematical technique may be used to condition the cross-correlation output.

Step 2904 may include the processing equipment summing the amplitudes within each segment of the cross-correlation output. Within each segment may be various values of the cross-correlation output, computed at different time lags. While the input to step 2902 is the cross-correlation output of N values, the output of step 2902 is a set of m values (termed the "sum output"), in which m represents the number of segments (i.e., m is less than N). The summation of step 2904 allows the effects of large fluctuations in the cross-correlation output (e.g., due to noise) to be taken into account in identifying peaks. Accordingly, singular peaks (e.g., excursions) in the cross-correlation output having large heights but a relatively low number of high-height neighboring values (i.e., low density) will be diminished by performing the summing of step 2904. Accordingly, singular peaks in the cross-correlation output having large heights and a relatively high number of high-height neighboring values (i.e., high density) will be enhanced by performing the summing of step 2904.

Step 2906 may include the processing equipment analyzing the sum output of step 2904 to identify the maximum sum value. Any suitable peak location technique may be used in accordance with the present disclosure. Step 2906 may include locating a maximum value in the sum output, locating a zero in the first derivative of the sum output, calculating a second derivative value of the sum output (e.g., to determine whether extrema are minima or maxima), performing any other suitable peak locating calculation, or any combination thereof.

Figure 30:
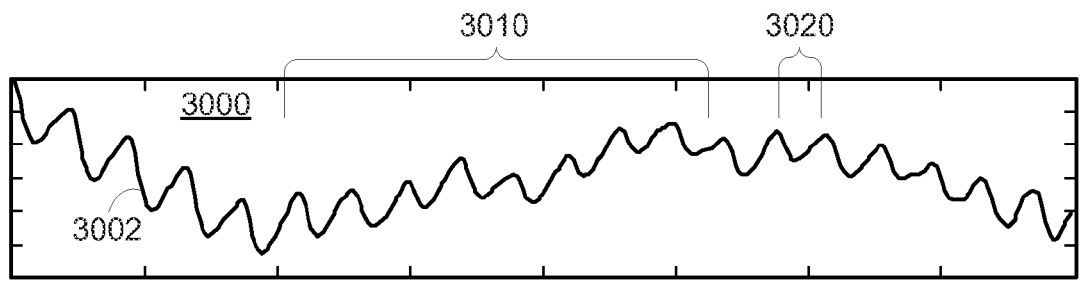
FIG. 30 is a plot of an illustrative pre-processed PPG signal, exhibiting low frequency noise, in accordance with some embodiments of the present disclosure.

FIG. 30 is a plot 3000 of an illustrative pre-processed PPG signal 3002, exhibiting low frequency noise, in accordance with some embodiments of the present disclosure. The abscissa of plot 3000 is presented in units proportional to sample number, while the ordinate is scaled in arbitrary units. PPG signal 3002 exhibits a relatively large noise component, as shown by the low frequency baseline oscillation (i.e., with half-period shown approximately by interval 3010). The physiological pulse of PPG signal 3002 is observed by the relatively higher frequency oscillations (i.e., with full period shown approximately by interval 3020) superimposed on the noise component.

Figure 31:
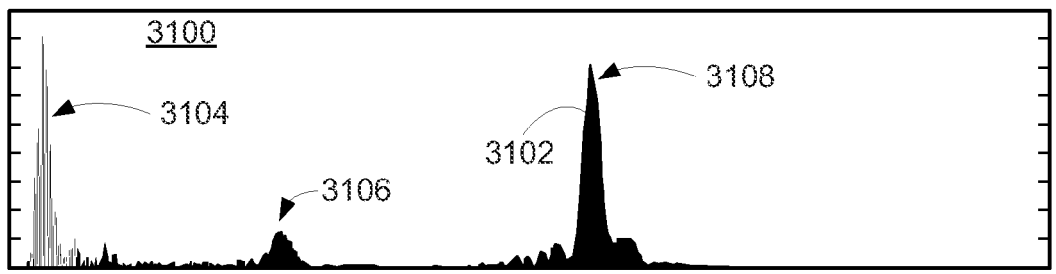
FIG. 31 is a plot of an illustrative cross-correlation output based in part on the PPG signal of FIG. 30, in accordance with some embodiments of the present disclosure.

FIG. 31 is a plot 3100 of an illustrative cross-correlation output 3102 based in part on the PPG signal 3002 of FIG. 30, in accordance with some embodiments of the present disclosure. The abscissa of plot 3100 is presented in units of cross-correlation lag, while the ordinate is scaled in arbitrary units, with a zero baseline. The three largest peaks of cross-correlation output 3102 (i.e., peak 3104, peak 3106, and peak 3108) all exhibit particular characteristics relative to one another. For example, peak 3104 is slightly taller than peak 3108, both of which are significantly taller than peak 3106. Peak 3108 has a higher density than peak 3104, which exhibits larger fluctuations of cross-correlation output within segments. Note that peak 3108 corresponds to a physiological rate, while peak 3104 corresponds to low frequency noise. The difference in density between peak 3104 and peak 3108 may be used to determine which peak likely corresponds to a physiological peak, as described illustratively by flow diagram 2900 of FIG. 29.

Figure 32:
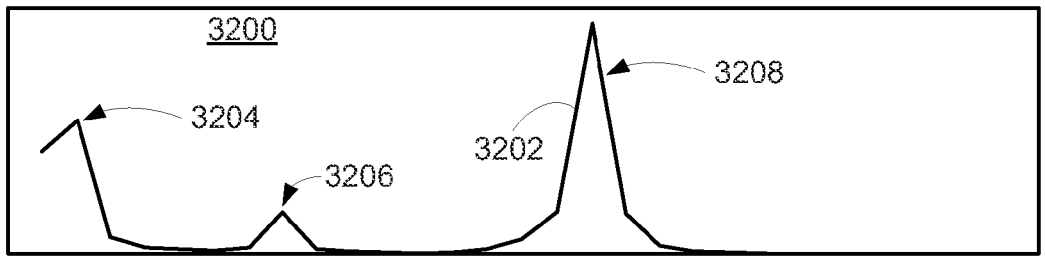
FIG. 32 is a plot of the sum within each segment of the illustrative cross-correlation output of FIG. 31, in accordance with some embodiments of the present disclosure.

FIG. 32 is a plot 3200 of the sums 3202 within each segment of the illustrative cross-correlation output 3102 of FIG. 31, in accordance with some embodiments of the present disclosure. The abscissa of plot 3200 is presented in units of segment number, while the ordinate is scaled in arbitrary units, with a zero baseline. Peak 3208, which corresponds to peak 3108 of FIG. 31, is the largest peak of plot 3200, with a larger peak height than peak 3204, which corresponds to peak 3104 of FIG. 31. Peak 3206, which corresponds to peak 3106 of FIG. 31, does not have the highest peak height with or without summing within each segment, and accordingly need not be considered a physiological rate under some circumstances. The use of summing, as described by flow diagram 2900 of FIG. 29, allows the peak associated with a physiological pulse to be identified for relatively noisy PPG signals. The identified peak may be automatically qualified or it may be further analyzed and qualified or disqualified using one or more techniques described in connection with flow diagrams 2300, 2500, and 2700.

Figure 33:
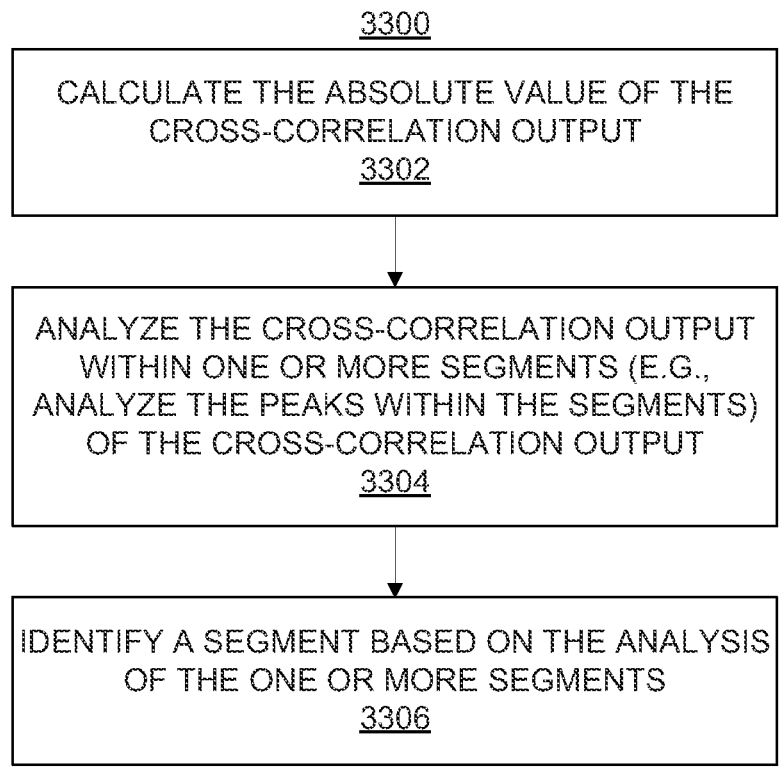
FIG. 33 is a flow diagram of illustrative steps for identifying a segment of a cross-correlation output based on a segment analysis, in accordance with some embodiments of the present disclosure.

FIG. 33 is a flow diagram 3300 of illustrative steps for identifying a segment of a cross-correlation output based on a segment analysis, in accordance with some embodiments of the present disclosure.

Step 3302 may include processing equipment calculating the absolute value of a cross-correlation output. The cross-correlation output may be generated by, for example, performing suitable steps of flow diagram 1800 of FIG. 18. Calculation of the absolute value may aid in determining characteristics of the cross-correlation output. In some embodiments, the cross-correlation output may be squared, and optionally re-scaled, to ensure all positive values for further analysis. Any suitable mathematical technique may be used to condition the cross-correlation output.

Step 3304 may include the processing equipment analyzing one or more segments of the cross-correlation output. Analyzing a segment of the cross-correlation output may include determining a maximum value, determining a shape of the cross-correlation output within the segment, performing any other suitable analysis, or any combination thereof. In some embodiments, step 3304 may include generating an upper envelope, of any suitable resolution, for the cross-correlation output within the segment. In some embodiments, step 3304 may include curve fitting the upper envelope (e.g., performing a least squares polynomial regression), performing a piecewise linear regression), of any suitable resolution. For example, a pair of ascending and descending best-fit (e.g., under any suitable constraints) lines through the peaks within the segment may be computed (e.g., see highlight 3404 of FIG. 34). In some embodiments, step 3304 may include calculating a slope of an envelope, or portion thereof, to determine a shape of the cross-correlation output within the segment. In some embodiments, step 3304 may include determining several characteristics of the cross-correlation output within the segment. For example, step 3304 may include determining a peak height, and determining a shape (e.g., up-slope, down-slope, shape of peak heights within the segment) of the peaks within the segment.

Step 3306 may include the processing equipment identifying a segment of the cross-correlation output based on the analysis of step 3304. In some embodiments, the segment may be identified based on a comparison of one or more characteristics of the cross-correlation output within the segment to corresponding threshold values. For example, the slope of a best-fit line (under any suitable constraints) through ascending minor peaks within the segment may be compared with a threshold, or range thereof, and identified based on the comparison. In some embodiments, identifying a segment of the cross-correlation output may include identifying a frequency corresponding to the segment. For example, the frequency associated with a segment of the cross-correlation output (e.g., frequency associated with the corresponding segment of the cross-correlation waveform used) may be identified.

Figure 34:
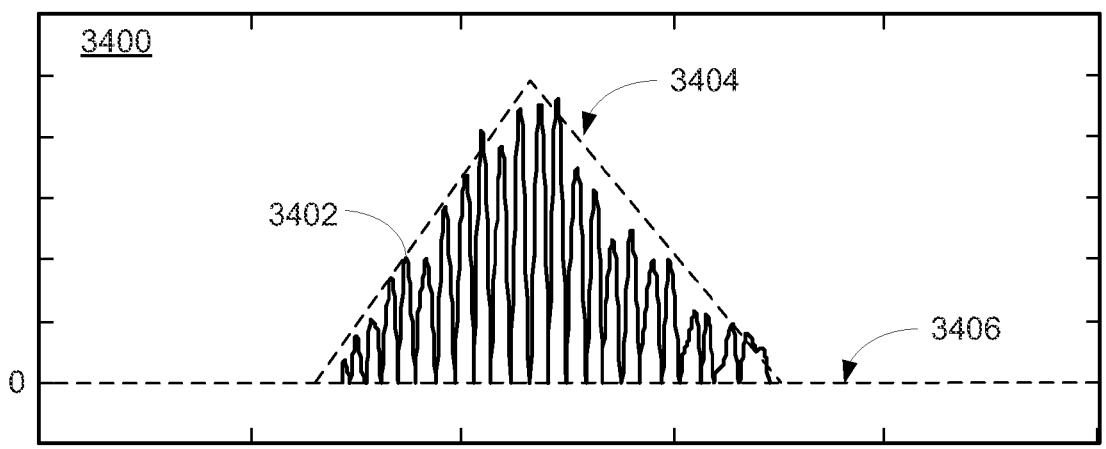
FIG. 34 is a plot showing one segment of an illustrative cross-correlation output with a segment shape highlighted, in accordance with some embodiments of the present disclosure.

FIG. 34 is a plot 3400 showing one segment of an illustrative cross-correlation output 3402 with a segment shape highlighted by highlight 3404, in accordance with some embodiments of the present disclosure. The abscissa of plot 3400 is presented in units of cross-correlation lag, while the ordinate is scaled in arbitrary units, with a zero baseline 3406. Baseline 3406 represents the axis about which an absolute value was calculated (i.e., an ordinate value of zero). The cross-correlation output within a segment may include multiple minor peaks that collectively form a peak, as shown by cross-correlation output 3402. The minor peaks of cross-correlation output 3402 at either boundary of the segment may be relatively small, and may increase towards the center of the segment. Highlight 3404 is a linear fit to the minor peak heights within the segment. Note that highlight 3404 need not be linear, and may be any suitable shape, or piecewise combination thereof. Any suitable shape characteristic of a cross-correlation output within a segment may be used to identify a segment as corresponding to a physiological pulse. For example, the symmetry of a peak of cross-correlation output 3402 may be determined by comparing the absolute values of the two slopes (i.e., positive up-slope and negative down-slope) of highlight 3404. In a further example, the deviation between the minor peaks of cross-correlation output 3402 and a highlight (e.g., highlight 3404 or other suitable highlight of any suitable shape) may be calculated and compared to a threshold.

Figure 35:
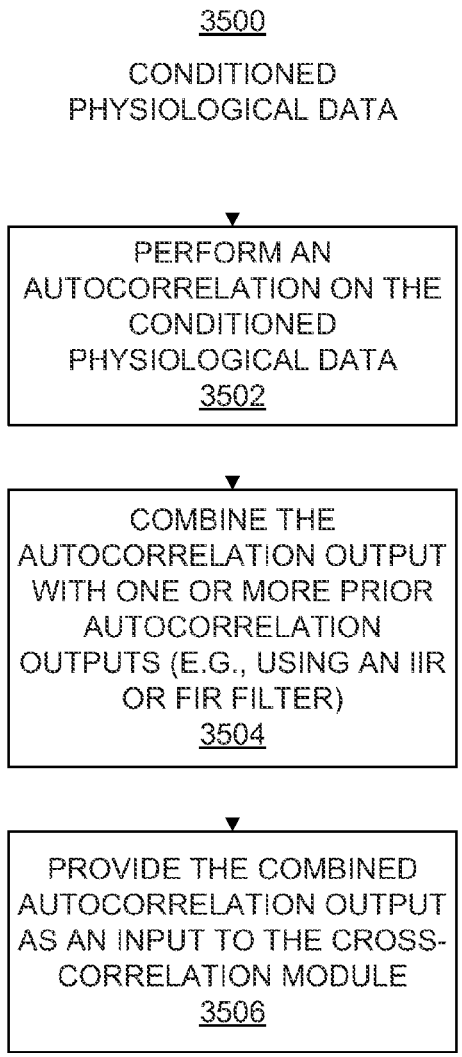
FIG. 35 is a flow diagram of illustrative steps for providing a combined autocorrelation of a physiological signal using one or more prior autocorrelations, in accordance with some embodiments of the present disclosure.

FIG. 35 is a flow diagram 3500 of illustrative steps for providing a combined autocorrelation of a physiological signal using one or more prior autocorrelations, in accordance with some embodiments of the present disclosure.

Step 3502 may include processing equipment performing an autocorrelation on conditioned physiological data (e.g., a window of data). In some embodiments, the autocorrelation of step 3502 may include correlating a first portion of the window of data with a second portion of the window of data. The first and second portions may be exclusive of one another, may share one or more samples, or may be selected by any other suitable partition of the window of data.

The window of data of step 3502 may be derived from the output of a physiological sensor, pre-processed (e.g., using pre-processor 320), and then stored in any suitable memory or buffer (e.g., queue serial module 72 of FIG. 2), for further processing by the processing equipment. In some embodiments, the window of data may be recalled from data stored in memory (e.g., RAM 54 of FIG. 2 or other suitable memory) for subsequent conditioning and processing. In some embodiments, the window size (e.g., the number of samples or time interval of data to be buffered) of data is selected to capture multiple periods of oscillatory physiological activity. For example, a six second window may be used to capture about six pulse wave of a photoplethysmograph of a nominal resting adult with a pulse rate of approximately 60 BPM (i.e., 1 Hz). It will be understood that any suitable window size may be used in accordance with the present disclosure, and six seconds is used for illustrative purposes. Signal conditioning may include removing DC components, low frequency components, or both, from the window of data. In some embodiments, a varying baseline may be removed from the window of data (i.e., de-trending) to constrain the data average to zero.

Step 3504 may include the processing equipment combining the autocorrelation output of step 3502 with one or more prior autocorrelation outputs, to generate a combined autocorrelation output. In some embodiments, the autocorrelation output may be averaged (e.g., using an ensemble average, weighted average, or any other suitable average) with one or more prior autocorrelation outputs. For example, step 3504 may include applying an infinite impulse response (IIR) filter, or a finite impulse response (FIR) filter, to the current and prior autocorrelation outputs. Combining autocorrelation output with prior autocorrelation output(s) may reduce the effects of sudden changes or noise while the processing equipment, for example, is in Search Mode.

Step 3506 may include the processing equipment providing the combined autocorrelation output as an input to a cross-correlation calculation (e.g., as described by step 1808 of flow diagram 1800 of FIG. 18). In some embodiments, the combined autocorrelation output may be queued in any suitable memory storage for use in calculating a cross-correlation output. In some embodiments, the combined autocorrelation may be generated by an autocorrelation module, and may be provided to a cross-correlation module. While the combined autocorrelation output is described as being inputted into a cross-correlation module, it will be understood that the combined autocorrelation output can be used in all modules and steps disclosed herein that use an autocorrelation.

Figure 36:
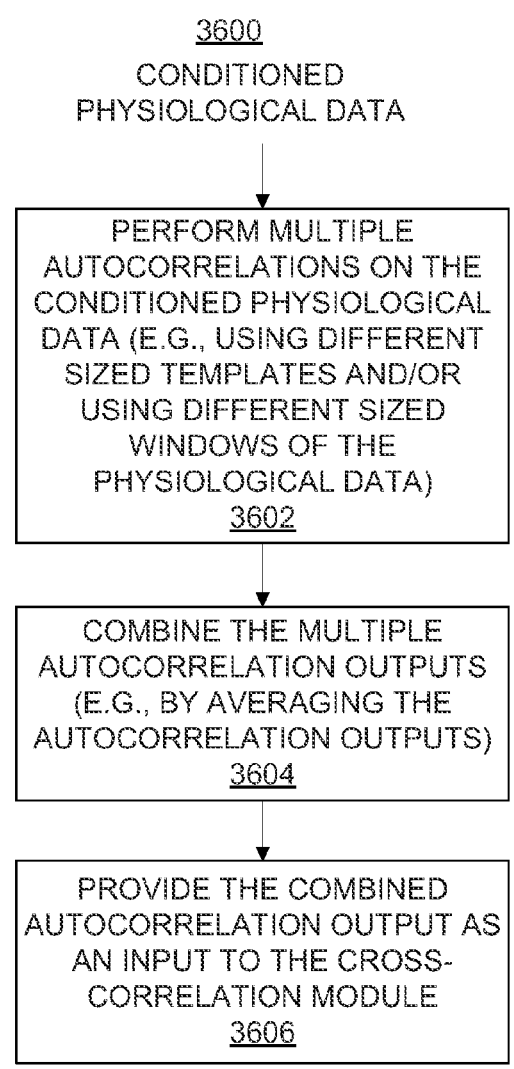
FIG. 36 is a flow diagram of illustrative steps for providing a combined autocorrelation using various window sizes and templates, in accordance with some embodiments of the present disclosure.

FIG. 36 is a flow diagram 3600 of illustrative steps for providing a combined autocorrelation using various window sizes and templates, in accordance with some embodiments of the present disclosure.

Step 3602 may include processor 312 performing multiple autocorrelations on conditioned physiological data. Step 3602 may include using different sized templates, different sized windows of data, or both, to generate multiple autocorrelation outputs. In some embodiments, different windows of data may be selected from the physiological data. An autocorrelation may be performed for each of the different windows, using any suitable autocorrelation templates. In some embodiments, a particular window of data may be partitioned into multiple sets of first and second portions, and an autocorrelation may be performed for each set. For example, a six second window of data may be buffered. The most recent one second of data of the window may be used as a first template, and the most recent two seconds of data of the window may be used as a second template. A first autocorrelation may be performed using the first template and the entire six second window, and a second autocorrelation may be performed using the second template and the entire six second window.

Step 3604 may include the processing equipment combining the multiple autocorrelation outputs of step 3602. In some embodiments, combining may include averaging (e.g., ensemble averaging, weighted averaging, any other suitable averaging) the multiple autocorrelation outputs to generate a single, combined autocorrelation output. Combining multiple autocorrelation outputs may reduce the effects of sudden changes or noise while the processing equipment is in, for example, Search Mode. Because autocorrelations will typically contain peaks at a lag of zero and a lags that correspond to the periodic component of a signal, it is possible to combine multiple autocorrelations of differently sized templates and of different window sizes to minimize noise such as non-periodic noise.

Step 3606 may include the processing equipment providing the combined autocorrelation output as an input to a cross-correlation calculation (e.g., as described by step 1808 of flow diagram 1800 of FIG. 18). In some embodiments, the combined autocorrelation output may be queued in any suitable memory storage for use in calculating a cross-correlation output. In some embodiments, the combined autocorrelation may be generated by an autocorrelation module, and may be provided as input to a cross-correlation module. While the combined autocorrelation output is described as being inputted into a cross-correlation module, it will be understood that the combined autocorrelation output may be used in all modules and steps disclosed herein that use an autocorrelation.

Figure 37:
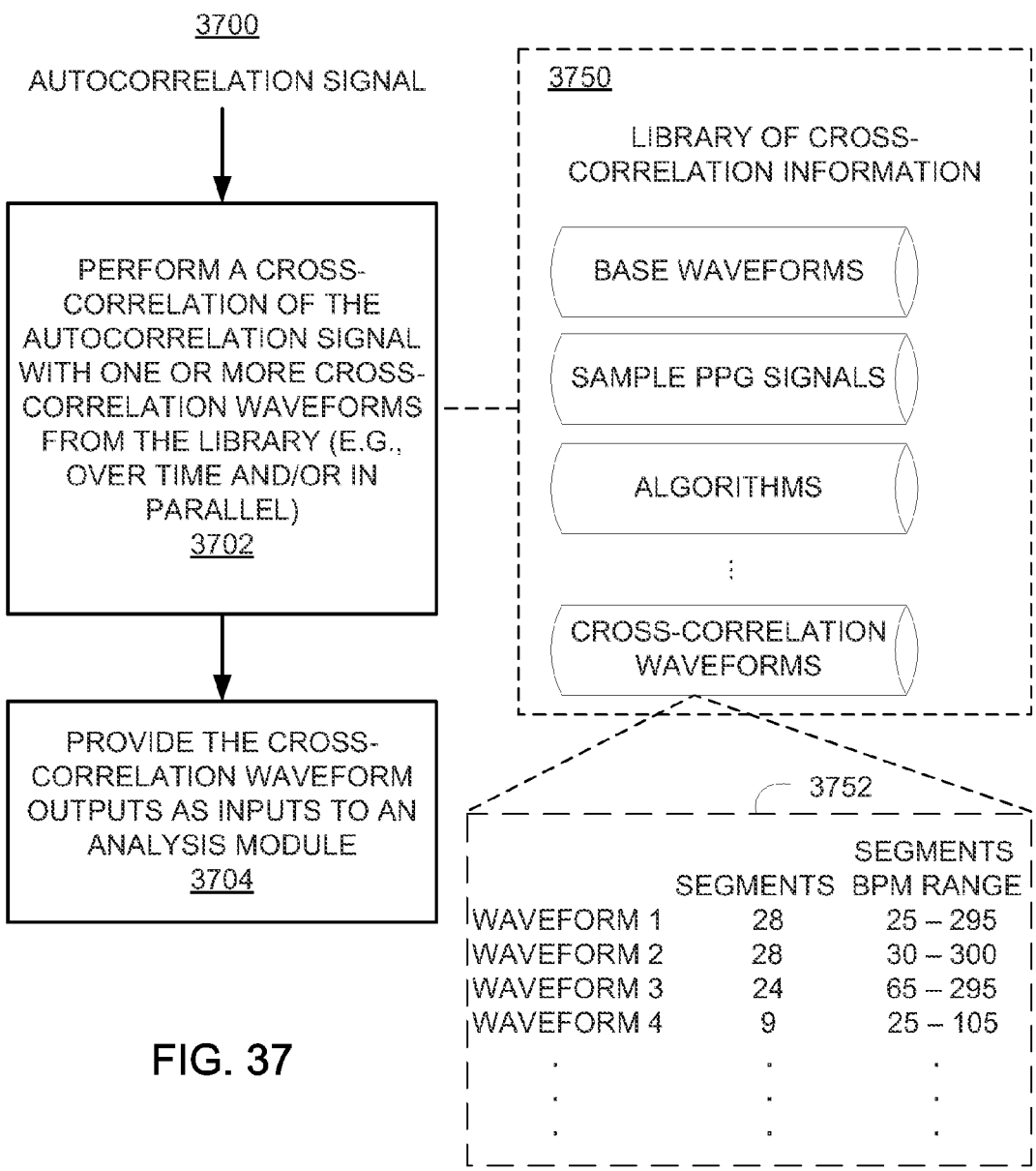
FIG. 37 is a flow diagram of illustrative steps for performing a cross-correlation using a library of cross-correlation waveforms, in accordance with some embodiments of the present disclosure.

FIG. 37 is a flow diagram 3700 of illustrative steps for performing a cross-correlation using a library 3750 of cross-correlation waveforms 3752, in accordance with some embodiments of the present disclosure. The illustrative steps of flow diagram 3700 may be used to generate a cross-correlation waveform, which may be used in Search Mode to determine initialization parameters.

Step 3702 may include processing equipment performing a cross-correlation of an autocorrelation output with one or more cross-correlation waveforms. In some embodiments, the one or more cross-correlation waveforms may be recalled, or otherwise accessed from library 3750. The autocorrelation output may be generated using any suitable technique such as the techniques disclosed herein (e.g., the illustrative steps of flow diagram 500 of FIG. 5, flow diagram 900 of FIG. 9, or other suitable technique). In some embodiments, the cross-correlation of step 3702 may include one or more segments, each having particular characteristics, as described by flow diagram 1900 of FIG. 19. In some embodiments, the cross-correlation waveform may include multiple segments, each including multiple pulses. In some embodiments, the cross-correlation of step 3702 may be performed sequentially over time with different cross-correlation waveforms. For example, the processing equipment may perform one cross-correlation every second and sequence through multiple cross-correlation waveforms over time. In some embodiments, the cross-correlation of step 3702 may be performed in parallel with the same autocorrelation output and different cross-correlation waveforms.

Library 3750 of cross-correlation information may include stored base waveforms (e.g., for generating cross-correlation waveforms), sample PPG signals (e.g., for use as base waveforms in generating cross-correlation waveforms), algorithms (e.g., computer-readable instructions for performing a cross-correlation), cross correlation waveforms, any other suitable information, or any combination thereof. Library 3750 may be stored in any suitable type of memory (e.g., ROM 52 of physiological monitoring system 10 of FIGS. 1-2), or combinations thereof, and may be formatted using any suitable database format.

Cross-correlation waveforms 3752 may be stored in suitable memory as part of library 3750. In some embodiments, cross-correlation waveforms 3752 may include one or more cross-correlation waveforms, each having a particular number of segments and spanning a particular range in physiological pulse frequency (e.g., a particular BPM range). In the illustrated example, cross-correlation waveforms 3752 include at least four waveforms, shown by "WAVEFORM 1"-"WAVEFORM 4." The waveforms each include a particular number of segments, ranging from, for example, 9 to 28 segments. Additionally, the waveforms each span a particular BPM range, from, for example, 25 to 300 BPM. WAVEFORM 1 spans the BPM range of 25 to 295 BPM, by 28 segments (e.g., in increments of 10 BPM), while WAVEFORM 4 spans the BPM range of 25-105 BPM, by 9 segments (e.g., in increments of 10 BPM). Accordingly, different cross-correlation waveforms may be preferred for use in different circumstances. By using different cross-correlation waveforms, either in parallel or sequentially, it is possible to more accurately identify a segment corresponding to a subject's physiological pulse rate. For example, WAVEFORM 4 may be preferred for use with physiological data from a resting adult, rather than a neonate or active adult because it contains segments in the range of 25-105 BPM. As a further example, WAVEFORM 2 may be preferred when a subject's heart rate is 60 BPM because it contains a segment corresponding to 60 BPM.

Step 3704 may include the processing equipment providing the cross-correlation output from step 3702 for further analysis. In some embodiments, the cross-correlation output may be generated by a cross-correlation module, and may be provided as an input to an analysis module (e.g., as shown by step 1810 of flow diagram 1800 of FIG. 18). In some embodiments, the analysis module may process the cross-correlation output according to one or more of flow diagrams 1800, 2300, 2500, 2700, 2900, and 3300 to identify a desired segment.

The foregoing discussion of FIGS. 18-37 relate to Search Mode embodiments that use a cross-correlation waveform and refer to identifying peaks, identifying segments, and determining one or more algorithm settings. It will be understood that the identification of segments is optional and the identified peak information may be directly used to determine one or more algorithm settings. For example, the peak information may be used to determine physiological rates, periods, or likely ranges thereof. As shown in FIG. 37, identification of a peak in WAVEFORM 1 may indicate that the pulse rate is within a specific 10 BPM range because the BPMs of segments are spaced 10 BPM apart. This information, or the peak information, may be used to set one or more algorithm settings. The algorithm settings may include settings of a filter such as, for example, a high and low frequency cutoff value of a band pass filter (e.g., a frequency range), a representative frequency value, a set of one or more coefficients, one or more settings of a threshold calculation, any other suitable parameters, or any combination thereof.

In some embodiments, Search Mode may include the processing equipment qualifying one or more initialization parameters (e.g., as shown by step 410 of flow diagram 400 of FIG. 4). Qualification of the determined initialization parameters may provide a more robust operation, and reduce the misidentification of noise activity as a physiological rate. For example, Qualification Techniques may be used to detect instances in which the system has locked on to one half, double, or other multiple of the actual physiological rate. Whereas determining initialization parameters may provide an estimate of a physiological rate, or range thereof, qualification may provide an indication of how consistent the estimate is, and how well the estimate characterizes a physiological pulse. In some embodiments, the Qualification Techniques discussed in the context of Search Mode may also be used to qualify a calculated rate in Locked Mode.

Figure 38:
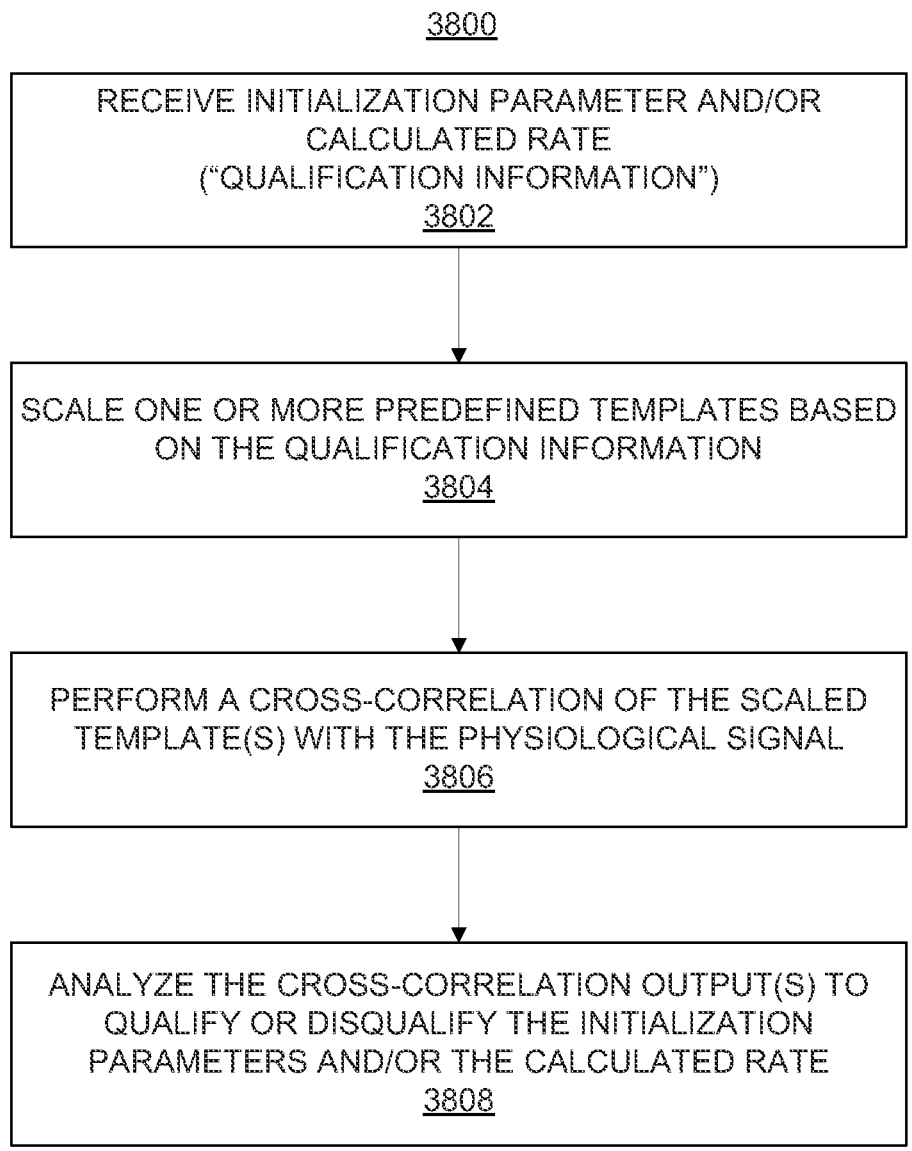
FIG. 38 is a flow diagram of illustrative steps for qualifying or disqualifying initialization parameters using a cross-correlation, in accordance with some embodiments of the present disclosure.

FIG. 38 is a flow diagram 3800 of illustrative steps for qualifying or disqualifying initialization parameters and/or calculated rates using a cross-correlation, in accordance with some embodiments of the present disclosure.

Step 3802 may include processing equipment receiving qualification information. Qualification information may include initialization parameters, a calculated rate, qualification metrics, any other suitable information used in qualifying initialization parameters and/or calculated rates, or any combination thereof. In some embodiments the qualification information may be generated at an earlier time, and stored in suitable memory (e.g., RAM 54, ROM 52, or other memory of physiological monitoring system 10 of FIGS. 1-2). Accordingly, in some embodiments, step 3802 may include recalling the qualification information from memory. In some embodiments, a single processor, module, or system may determine, store or otherwise process the qualification information and perform steps 3804-3808, and accordingly, step 3802 need not be performed.

Step 3804 may include the processing equipment scaling one or more predefined templates based on the qualification information. The predefined templates may include asymmetrical pulses without a dicrotic notch, asymmetrical pulses with a dicrotic notch, approximately symmetrical pulses without a dicrotic notch, pulses of any other classification, any other suitable type of template, or any combination thereof. In some embodiments, the predefined templates may be derived from a subject's PPG signals. In some embodiments, the predefined templates may be mathematical functions, mathematical approximations to a PPG signal, any other suitable mathematical formulation, or any combination thereof. In some embodiments, scaling a predefined template may include stretching or compressing the template in the time domain (or corresponding sample number domain) to match a characteristic time scale of the template to that associated with the qualification information. For example, if an initialization parameter estimates the physiological rate to be 1 Hz, a predefined template may be scaled to correspond to 1 Hz. The period associated with the initialization parameters, or the calculated rate, will be referred to herein as "P", and may be used for qualification. Scaled templates may be referred to herein as "reference waveforms."

Step 3806 may include the processing equipment performing a cross-correlation of the scaled template(s) of step 3804 and the physiological signal. The physiological signal may be conditioned before being used in the cross-correlation. The signal conditioning may include removing DC components, low frequency components, or both, from the signal. In some embodiments, a varying baseline may be removed from the signal (i.e., de-trending) to constrain the data average to zero. The signal may also be normalized so that the amplitude of the signal is one. The cross-correlation may be performed using any suitable algorithm. The output of step 3806 may be a cross-correlation output, which may include a series of cross-correlation values taken for a corresponding series of time lags (or sample number lags) between the predefined template and the physiological signal.

Step 3808 may include the processing equipment analyzing the cross-correlation output(s) of step 3806 to qualify or disqualify the initialization parameters, the calculated rate, or both. A conditioned cross-correlation output of step 3806 may include one or more peaks, indicative of high correlation between the physiological signal and a predefined template. In some embodiments, step 3808 may include analyzing one or more peaks. In some embodiments, step 3808 may include analyzing one or more segments of the cross-correlation output. For example, tests described herein below such as the Symmetry Test, Radius Test, Angle Test, Area Test, Area Similarity Test, Statistical Property Test, or any other suitable test, or combination thereof, may be performed at step 3808 to analyze the one or more cross-correlation outputs of step 3806. The processing equipment may perform any suitable analysis at step 3808 to qualify or disqualify initialization parameters, a calculated rate, or both, associated with the one or more cross-correlation outputs. In some embodiments, when a value is disqualified in Locked Mode, the value may still be used although a rate filter may be modified. For example, a filter weight associated with the disqualified value may be reduced as a result of disqualification.

Figure 39:
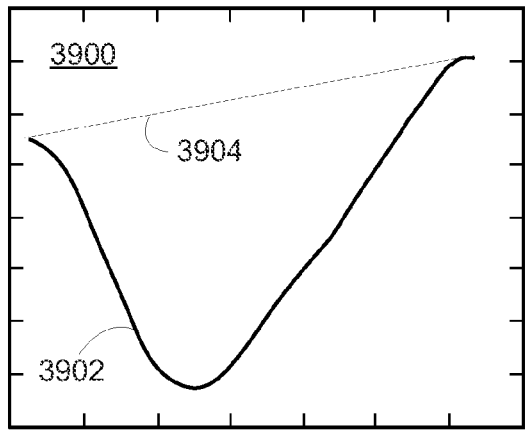
FIG. 39 is a plot of an illustrative PPG signal showing one pulse of a subject, in accordance with some embodiments of the present disclosure.

FIG. 39 is a plot 3900 of an illustrative PPG signal 3902 showing one pulse of a subject, in accordance with some embodiments of the present disclosure. The abscissa of plot 3900 is presented in arbitrary units, while the ordinate is also presented in arbitrary units. PPG signal 3902 exhibits non-zero baseline 3904, which may be, but need not be, a straight line. While PPG signal 3902 is relatively free of noise, sloped baseline 3904 indicates a relatively low frequency noise component. In some embodiments, PPG signal 3902 may be a raw PPG signal, a smoothed PPG signal, an ensemble averaged PPG signal, a filtered PPG signal, any other raw or processed PPG signal, or any combination thereof. In some embodiments, PPG signal 3902 may be approximated by a mathematical representation for further processing (e.g., step 3806, step 3808, or both, of flow diagram 3800).

Figure 40:
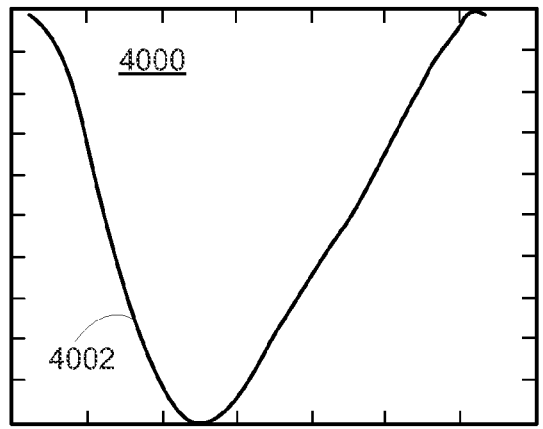
FIG. 40 is a plot of an illustrative template derived from the PPG signal of FIG. 39 with baseline removed, in accordance with some embodiments of the present disclosure.

FIG. 40 is a plot 4000 of a template 4002 derived from illustrative PPG signal 3902 of FIG. 39 with baseline 3904 removed (i.e., de-trended), in accordance with some embodiments of the present disclosure. The abscissa of plot 4000 is presented in arbitrary units, while the ordinate is also presented in arbitrary units. The conditioned signal derived from PPG signal 3902 is referred to as template 4002. De-trending, or other suitable conditioning, may be performed as part of step 3804 of flow diagram 3800. Although the ordinate of FIG. 40 is not numerated, template 4002 may be normalized or otherwise scaled along the ordinate of plot 4000 to range from [−1,0], [−1,1], [0,1], or any other suitable range. For example, the mean of template 4002 may be set to zero.

Figure 41:
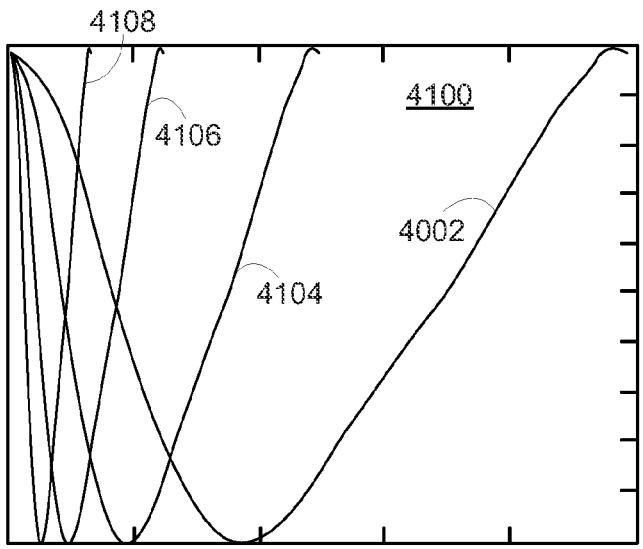
FIG. 41 is a plot of the illustrative template of FIG. 40 scaled over the domain to different sizes for use as templates in performing a cross-correlation, in accordance with some embodiments of the present disclosure.

FIG. 41 is a plot 4100 of illustrative template 4002 of FIG. 40 scaled to different sizes for use as templates in performing cross-correlations, in accordance with some embodiments of the present disclosure. The abscissa of plot 4100 is presented in arbitrary units, while the ordinate is also presented in arbitrary units. Illustrative scaled templates 4104, 4106, and 4108 are generated by scaling template 4002 by respective scale factors. In the illustrated example, with the abscissa beginning at zero, the pulse period is scaled by one-half, one-fourth, and one-eighth, to generate scaled templates 4104, 4106, and 4108, respectively.

The plots of FIGS. 39-41 illustrate one technique for creating templates for use in qualifying initialization parameters and/or calculated rates. The starting pulse in FIG. 39 may be selected from the subject being monitored or may be selected offline from a library of stored PPG signals from subjects. In some embodiments, the starting pulse may be generated mathematically (e.g., based on one or more functions) or manually. In some embodiments, the processing equipment may generate the one or more templates for each qualification calculation. In some embodiments, a library of templates for one or more pulse shapes may be pre-generated and/or pre-stored in memory and the processing equipment may select the appropriate template or templates for use in the qualification based on the received qualification information. For example, 281 templates may be stored for each pulse shape, one for each BPM in the range of 20-300 BPM. This is merely illustrative and any suitable number of templates may be stored of any suitable BPM resolution and covering any suitable range of BPMs. The processing equipment may select an appropriate template based on rate information in the qualification information. In some embodiments, the pulse shape of the templates may vary as a function of BPM. For example, at low BPM values (e.g., less than about 60 BPM) the pulse shape may be asymmetrical with a dicrotic notch. However, as the BPM value increases, the pulse shape may become more symmetrical and the dicrotic notch may become relatively smaller and eventually not included in the pulse shape.

Figure 42:
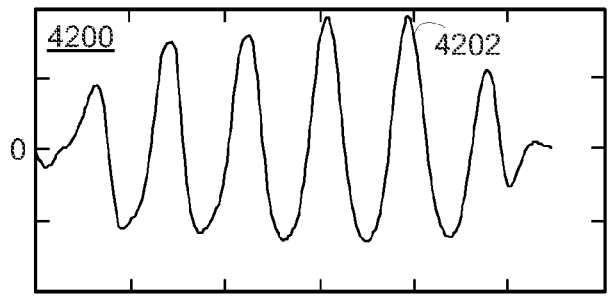
FIG. 42 is a plot of output of an illustrative cross-correlation between a photoplethysmograph signal and a predefined template, in accordance with some embodiments of the present disclosure.

FIG. 42 is a plot 4200 of output 4202 of an illustrative cross-correlation between a PPG signal or a signal derived thereof and a predefined template, in accordance with some embodiments of the present disclosure. The abscissa of plot 4200 is presented in units of cross-correlation lag, while the ordinate is presented in arbitrary units, with zero notated. The shape of cross-correlation output 4202 indicates a relatively close match between the template and the PPG signal. In some embodiments, more than one cross-correlation output may be generated by using more than one scaled template. Accordingly, in some embodiments, cross-correlation outputs corresponding to multiple templates may be evaluated (e.g., using any of the cross-correlation analyses of the present disclosure) to determine which template most closely matches the PPG signal.

Figure 43:
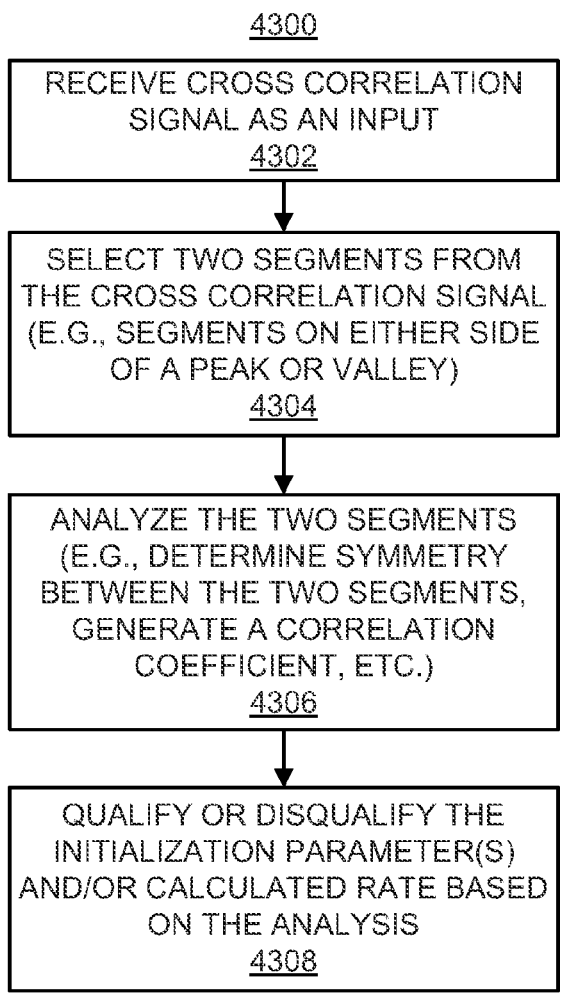
FIG. 43 is a flow diagram of illustrative steps for qualifying or disqualifying initialization parameters based on an analysis of two segments of a cross-correlation output, in accordance with some embodiments of the present disclosure.

FIG. 43 is a flow diagram 4300 of illustrative steps for qualifying or disqualifying initialization parameters and/or calculated rates based on an analysis of two segments of a cross-correlation, in accordance with some embodiments of the present disclosure. The illustrative steps of flow diagram 4300 may be referred to as the "Symmetry Test."

Step 4302 may include processing equipment receiving a cross-correlation signal (e.g., generated according to step 3806 of FIG. 38) as an input. In some embodiments, a cross-correlation signal may be a cross-correlation output (e.g., output of step 3806 of flow diagram 3800 of FIG. 38). In some embodiments, the cross-correlation signal may be generated by a cross-correlation module. In some embodiments the cross-correlation signal may be generated at an earlier time, and stored in suitable memory. Accordingly, in some embodiments, step 4302 may include recalling the stored cross-correlation signal from the memory. In some embodiments, a single processor, module, or system may perform the cross-correlation and steps 4304-4308, and accordingly, step 4302 need not be performed.

Step 4304 may include the processing equipment selecting any two suitable segments, having any suitable length (e.g., one full period, or more, or less), of the cross-correlation signal of step 4302. Period here refers to a period associated with an initialization parameter or a calculated rate. The cross-correlation signal may include a series of data points exhibiting peaks and valleys. The two segments may be selected on either side of a peak or valley, in symmetric locations (e.g., see FIGS. 44-45 for a more detailed discussion of the segments' symmetry). For example, the segments may share a single point at the zenith of a peak or the nadir of a valley, and the segments may extend in opposite directions. In a further example, the segments need not share any points, and a gap may exist between the segments.

Figure 44:
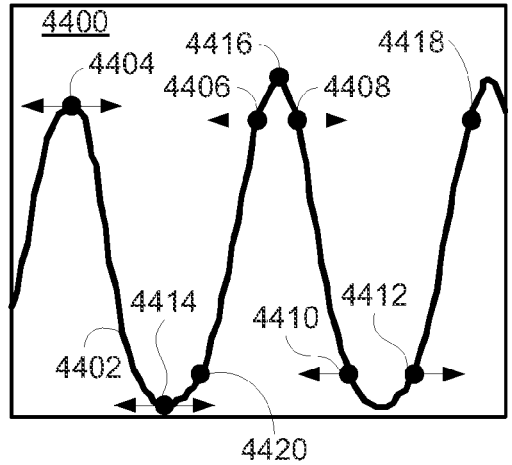
FIG. 44 is a plot of an illustrative cross-correlation output, showing several reference points for generating a symmetry curve, in accordance with some embodiments of the present disclosure.

FIG. 44 is a plot 4400 of an illustrative cross-correlation signal 4402, showing several reference points for selecting two segments and generating a symmetry curve, in accordance with some embodiments of step 4304 of the present disclosure. The reference points may be used to generate a series of points $(u_j, v_j)$ in a Cartesian plane (or other suitable coordinate system), termed a "symmetry curve," as shown by Eqs. 18 and 19.

$$u_j = f(x_0 + \Delta x_j) \qquad (18)$$

$$v_j = f(x_{00} - \Delta x_j) \qquad (19)$$

Reference points $x_0$ and $x_{00}$ may be the same point located at a peak or valley (i.e., $x_0 = x_{00}$ as shown by point 4404 or point 4414), or points $x_0$ and $x_{00}$ may be different points, for example, symmetrical about a peak (or valley) of cross-correlation signal values f(x) (e.g., as shown by points 4406 and 4408, or points 4410 and 4412). Note that x may include discrete values associated with a sampled signal. Shift $\Delta x_j$ may range from zero to any suitable number, generating two segments (i.e., the first and second segments, or vice versa) with data points at $(x_0 + \Delta x_j)$ and $(x_{00} - \Delta x_j)$ for a suitable span of index j values. If the cross-correlation signal is symmetric (about the midpoint of $x_0$ and $x_{00}$), as shift $\Delta x_j$ increases, $u_j$ and $v_j$ will be equal numerically. The series of points $(u_j, v_j)$ will accordingly generate a straight line of unity slope through the origin. Any deviation between $u_j$ and $v_j$ may be attributed to asymmetry of the cross-correlation output, and will accordingly cause the series of points $(u_j, v_j)$ to not fall in a straight line of unity slope through the origin.

Step 4304 may include the processing equipment selecting any two suitable segments, of any suitable length (e.g., one full period, or more, or less), of a cross-correlation output (e.g., cross-correlation signal 4402). For example, the portion of cross-correlation signal 4402 between points 4408 and 4410 may be a first segment, with the second segment extending leftward from point 4406 to point 4420. In a further example, the portion of cross-correlation signal 4402 between points 4408 and 4410 may be a first segment, with a second segment extending rightward from point 4412 to point 4418. In a further example, the portion of cross-correlation signal 4402 between points 4404 and 4414 may be a first segment, and a second segment may extend from point 4414 to points 4416.

Figure 45:
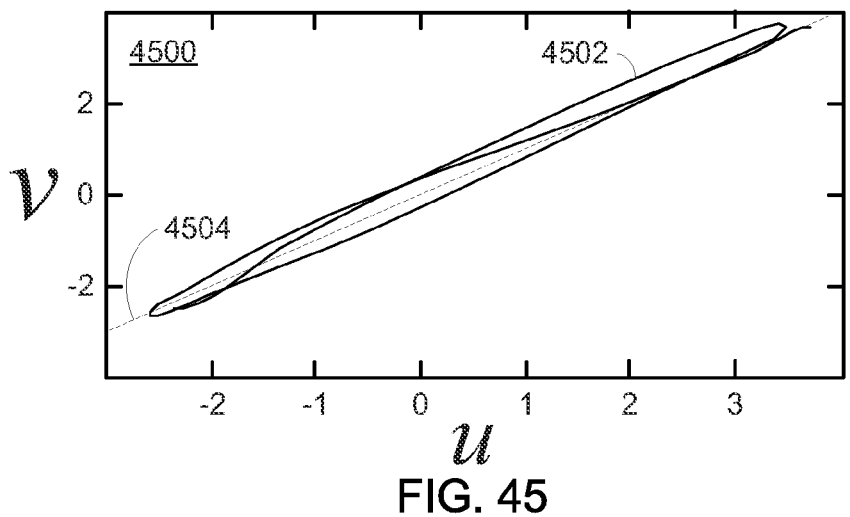
FIG. 45 is a plot of an illustrative symmetry curve generated using two segments of a cross-correlation, in accordance with some embodiments of the present disclosure.

Step 4306 may include the processing equipment analyzing the two segments of step 4304. In some embodiments, step 4306 may include analyzing the symmetry of the two segments. For example, step 4306 may include the processing equipment generating a symmetry curve to analyze the symmetry between the first and second segments. FIG. 45 is a plot 4500 of an illustrative symmetry curve 4502 generated using two segments of a cross-correlation signal, in accordance with some embodiments of the present disclosure. The demarcations of the abscissa and ordinate of plot 4500 are scaled in arbitrary, but similar, units. Symmetry curve 4502 may be generated, for example, by tracing out a series of points $(u_j, v_j)$ in a Cartesian plane (or other suitable coordinate system), as shown by Eqs. 18 and 19. Symmetry curve 4502 is observed to pass roughly through the origin at (0,0) and have a slope of roughly one, with some relatively small deviation. Line 4504 shows the line through the origin with a slope of unity, for reference. In some circumstances, symmetry curve 4502 may be determined to be shaped sufficiently well (e.g., based on the analysis of step 4306 of flow diagram 4300), and a set of initialization parameters may be qualified.

In some embodiments, step 4306 may include comparing a symmetry curve to a reference curve (e.g., a line through the origin with a slope of unity). For example, a variability metric such as $V_1$ may be computed according to Eq. 20a:

$$V_1 = \sum_{i=1}^{M} (S(x_i) - y(x_i))^2 \qquad (20a)$$

in which $S(x_i)$ is a symmetry curve value (e.g., a value of symmetry curve 4502) at point i of M data points, and $y(x_i)$ corresponds to a reference curve (e.g., line 4504 in which $y(x_i) = x_i$). Any suitable variability metric may be used to evaluate the symmetry curve, or otherwise the symmetry of the two segments.

In some embodiments, step 4306 may include comparing the two segments without first generating a symmetry curve or using a reference curve. For example, a variability metric such as may be computed according to Eq. 20b:

$$V_2 = \sum_{j=1}^{M} (u_j - v_j)^2. \qquad (20b)$$

As a further example, a correlation coefficient between the two segments may be computed. Any suitable correlation coefficient computation may be used including, for example, Pearson's correlation coefficient.

In some embodiments, multiple pairs of first and second segments may be selected at step 4304 and analyzed at step 4306. For example, a first pair of segments sharing a single common point may each extend for a full pulse period, while a second pair of segments sharing the same common point may extend for a half pulse period. In a further example, different pairs of segments may be selected each referenced to different peaks or valleys of the cross-correlation signal.

Step 4308 may include the processing equipment qualifying, or disqualifying, initialization parameters, a calculated rate, or both, based on the analysis of step 4306. In some embodiments, one or more metric may be inputted into a classifier (e.g., a neural network). In some embodiments, qualification (or disqualification) may depend on a comparison between one or metrics computed at step 4306 and one or more threshold values. For example, a variability metric (e.g., $V_1$ of Eq. 20a or any other suitable metric) may be compared with a threshold, and if the variability metric does not exceed the threshold value, the associated initialization parameters (or calculated rate) may be qualified. Accordingly, if the variability metric exceeds the threshold value, the associated (e.g., current, previously selected) initialization parameters, calculated rate, or both, may be disqualified (and vice versa). In some embodiments, a disqualification at step 4308 may trigger steps 4304-4308 to repeat (i.e., two different segments may be selected from the same cross-correlation signal for analysis). In some embodiments, a disqualification at step 4308 may trigger steps 4302-4308 to repeat (i.e., two segments are selected from a different cross-correlation signal for analysis). In some embodiments, a disqualification at step 4308 may trigger an analysis different than that of flow diagram 4300 to be performed to either qualify or disqualify the initialization parameters, calculated rate, or both, associated with the cross-correlation signal.

Figure 46:
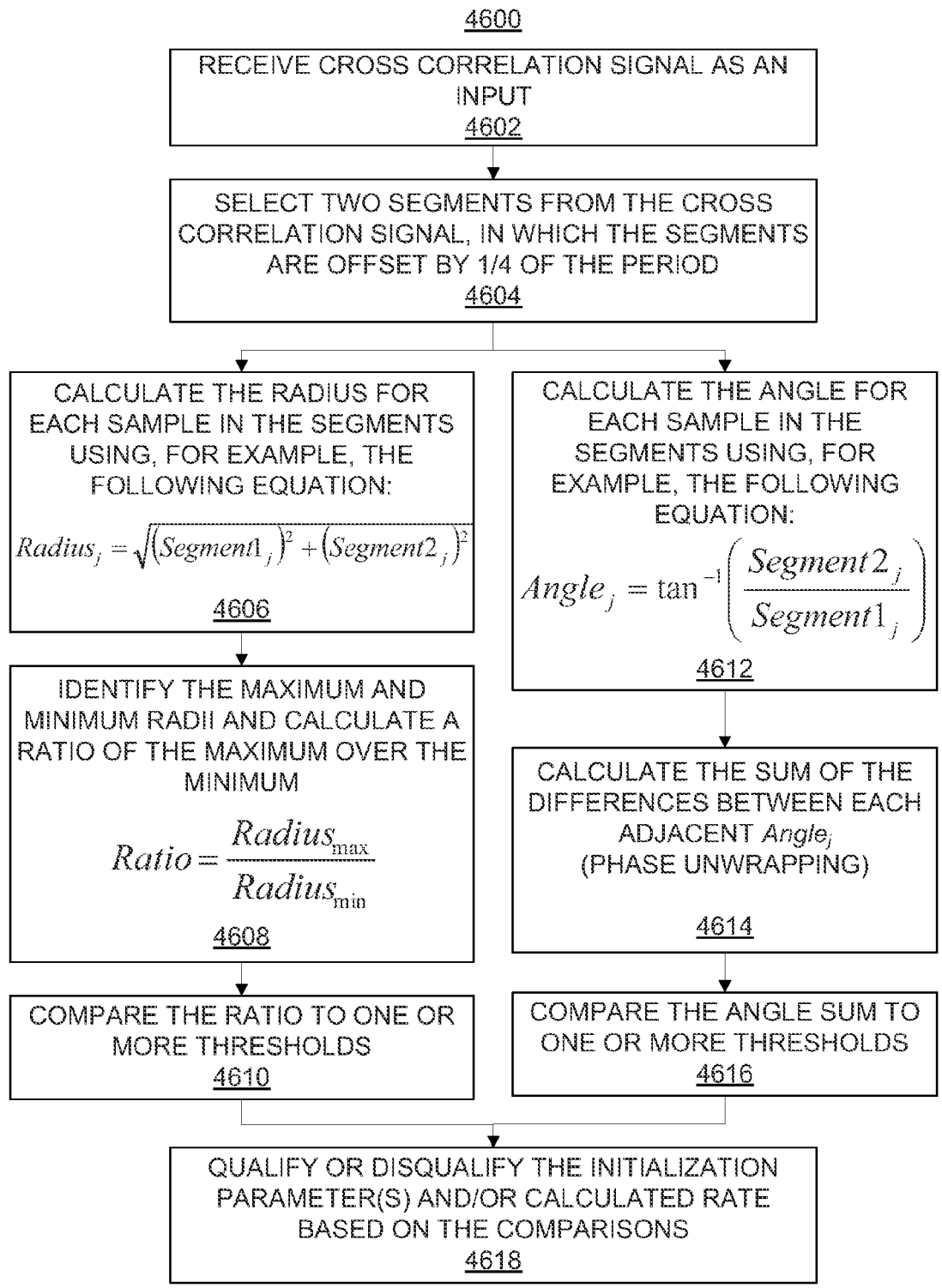
FIG. 46 is a flow diagram of illustrative steps for qualifying or disqualifying initialization parameters based on an analysis of offset segments of a cross-correlation output, in accordance with some embodiments of the present disclosure.

FIG. 46 is a flow diagram 4600 of illustrative steps for qualifying or disqualifying initialization parameters and/or calculated rates based on an analysis of offset segments of a cross-correlation signal, in accordance with some embodiments of the present disclosure. In some embodiments, the illustrative steps of flow diagram 4600 aid in preventing a double-rate/half-period condition, or other condition in which period P is not indicative of a physiological rate.

Step 4602 may include processing equipment receiving a cross-correlation signal (e.g., generated according to step 3806 of FIG. 38) as an input. In some embodiments, the cross-correlation signal may be generated by a cross-correlation module. In some embodiments the cross-correlation signal may be generated at an earlier time, and stored in suitable memory. Accordingly, in some embodiments, step 4602 may include recalling the stored cross-correlation signal from the memory. In some embodiments, a single processor, module, or system may perform the cross-correlation and steps 4604-4618, and accordingly, step 4602 need not be performed.

Step 4604 may include the processing equipment selecting two segments of the cross-correlation signal of step 4602. The cross-correlation signal may include a series of data points exhibiting peaks and valleys. The two segments may be of equal length, offset by a quarter length of the period P associated with the calculated rate, initialization parameters, or both. In some embodiments, the first and second segments may each have a length equal to period P, although they may be any suitable length as long as the segments are of approximately equal length. The two segments may be selected from any suitable portion of the cross-correlation signal. Note that the two segments will be referred to as Segment1 and Segment2, or the first segment and the second segment, although the designations are arbitrarily chosen for illustration purposes (e.g., the first and second segments may be interchanged in accordance with the present disclosure).

Following step 4604, the processing equipment may perform step 4606, 4612, or both (e.g., simultaneously or sequentially) in accordance with some embodiments of the present disclosure. In some embodiments, the "Radius Test" (i.e., steps 4606-4610) may be performed, and the "Angle Test" (i.e., steps 4612-4616) need not be performed. In some embodiments, the "Angle Test" may be performed, and the "Radius Test" need not be performed. In some embodiments, one of the "Radius Test" and the "Angle Test" may be performed initially, and depending upon the outcome of the test (e.g., qualify, disqualify) the other test may be performed.

Step 4606 may include the processing equipment calculating the radius based on the two segments of step 4604, using Eq. 21. In Eq. 21, Segment1$_j$ and Segment2$_j$ are the cross-correlation output f(x) values of the first and second segments, respectively, evaluated for index j, which ranges from zero to N−1 for segments with N data points. Note that x may include discrete values associated with a sampled signal. With reference to Eqs. 22 and 23, Segment1 originates at point $x_0$ and extends rightward with index j in the Cartesian plane, and the origin of Segment2 is offset by a quarter period P relative to the first segment. Also note that $\Delta x_j$ may increase linearly with j. For example, $\Delta x_j$ may be given by Eq. 24, in which $\Delta x$ is the data point spacing in the domain.

$$\text{Radius}_j = \sqrt{\text{Segment1}_j^2 + \text{Segment2}_j^2} \qquad (21)$$

$$\text{Segment1}_j = f(x_0 + \Delta x_j) \qquad (22)$$

$$\text{Segment2}_j = f\left(x_0 + \frac{P}{4} + \Delta x_j\right) \qquad (23)$$

$$\Delta x_j = j\Delta x \qquad (24)$$

The radius of step 4606, as computed using Eq. 21, will be a constant if the period P identically matches the period of the cross-correlation output f(x), and has strictly sinusoidal character. Variations in the radius with index j may be attributed to the shape of the cross-correlation output, deviations between period P and the characteristic period of the cross-correlation signal, any other suitable characteristic of the cross-correlation signal, or any combination thereof.

Step 4608 may include the processing equipment identifying the maximum and minimum radii step 4606, and calculating a ratio as shown, for example, by Eq. 25.

$$\text{Ratio} = \frac{\text{Radius}_{MAX}}{\text{Radius}_{MIN}} \qquad (25)$$

The ratio of the maximum (Radius$_{MAX}$) and minimum (Radius$_{MIN}$) radii provide a variability metric, indicating variability in the calculated radii values. Note that if the radii values have low variability (i.e., are all substantially the same value), the ratio is near one. The presence of variability will necessarily cause the ratio to assume a value greater than one. In some embodiments, variability metrics other than the ratio of Eq. 25 may be calculated from the radii values. Any suitable variability metric may be used in accordance with the present disclosure.

Step 4610 may include the processing equipment comparing the ratio of step 4608 to one or more threshold values. In some embodiments, a fixed threshold may be used for comparison. In some embodiments, a variable threshold may be used. For example, threshold value(s) may be based on the value of the period P, subject information (e.g., subject history, medical history, medical procedure), segment length, whether initialization parameters or calculated rates are being qualified, any other suitable information, or any combination thereof. In some embodiments, the threshold value(s) may be stricter in Search Mode versus Locked Mode. The stricter threshold(s) may prevent the algorithm from locking onto the wrong rate. Steps 4612-4616 may be performed in concert with, or in lieu of, steps 4606-4610, in accordance with some embodiments of the present disclosure.

Step 4612 may include the processing equipment calculating the angle for each index j of the two segments of step 4604, using Eq. 26. Each angle value, per index j, is the arctangent of the ratio of the first and second segment values, given Eqs. 22 and 23, respectively.

$$\text{Angle}_j = \tan^{-1}\left(\frac{\text{Segment2}_j}{\text{Segment1}_j}\right) \qquad (26)$$

Step 4614 may include the processing equipment calculating the sum of the differences between each adjacent angle of step 4612, also referred to as "phase unwrapping", as shown by Eq. 27:

$$\text{Sum}_{angle} = \sum_{j=1}^{N-1}(\text{Angle}_j - \text{Angle}_{j-1}), \qquad (27)$$

The sum may be approximately proportional to the length of the segments. Segments of length equal to period P should give a sum of roughly 360°, the period P is approximately equal to the characteristic period of the cross-correlation signal. If the cross-correlation exhibits a period half that of period P, then the sum may tend towards 720° for segment lengths equal to period P. The sum will depend, however, on the length of the segments. For example, longer segments (in terms of period P) tend to provide larger sums.

Step 4616 may include the processing equipment comparing the sum of step 4614 to one or more threshold values, or range thereof. In some embodiments, the one or more thresholds may include an upper and lower limit. In some embodiments, a threshold value may be based on the segment length. For example, a sum may be compared to a threshold range of 300-420°, for segments having a length equal to period P. In a further example, larger threshold values may be used with segments having a length longer than period P. In some embodiments, for a given segment length, a threshold value may vary. For example, threshold value(s) may be based on the value of the period P, subject information (e.g., subject history, medical history, medical procedure), whether initialization parameters or calculated rates are being qualified, any other suitable information, or any combination thereof. In some embodiments, the threshold value(s) may be stricter in Search Mode versus Locked Mode. In addition, in some embodiments, the threshold value(s) may be stricter for the first rate calculated in Locked Mode. The stricter threshold(s) may prevent the algorithm from locking onto the wrong rate.

Step 4618 may include the processing equipment qualifying or disqualifying the associated initialization parameters, calculated rate, or both, based on the comparison of step 4610, the comparison of step 4616, or both. If the ratio, angle sum, or both, exceed the respective threshold value, the initialization parameters, calculated rate, or both, may be disqualified. If the ratio, angle sum, or both, do not exceed the threshold value, the initialization parameters, calculated rate, or both, may be qualified.

Figure 47:
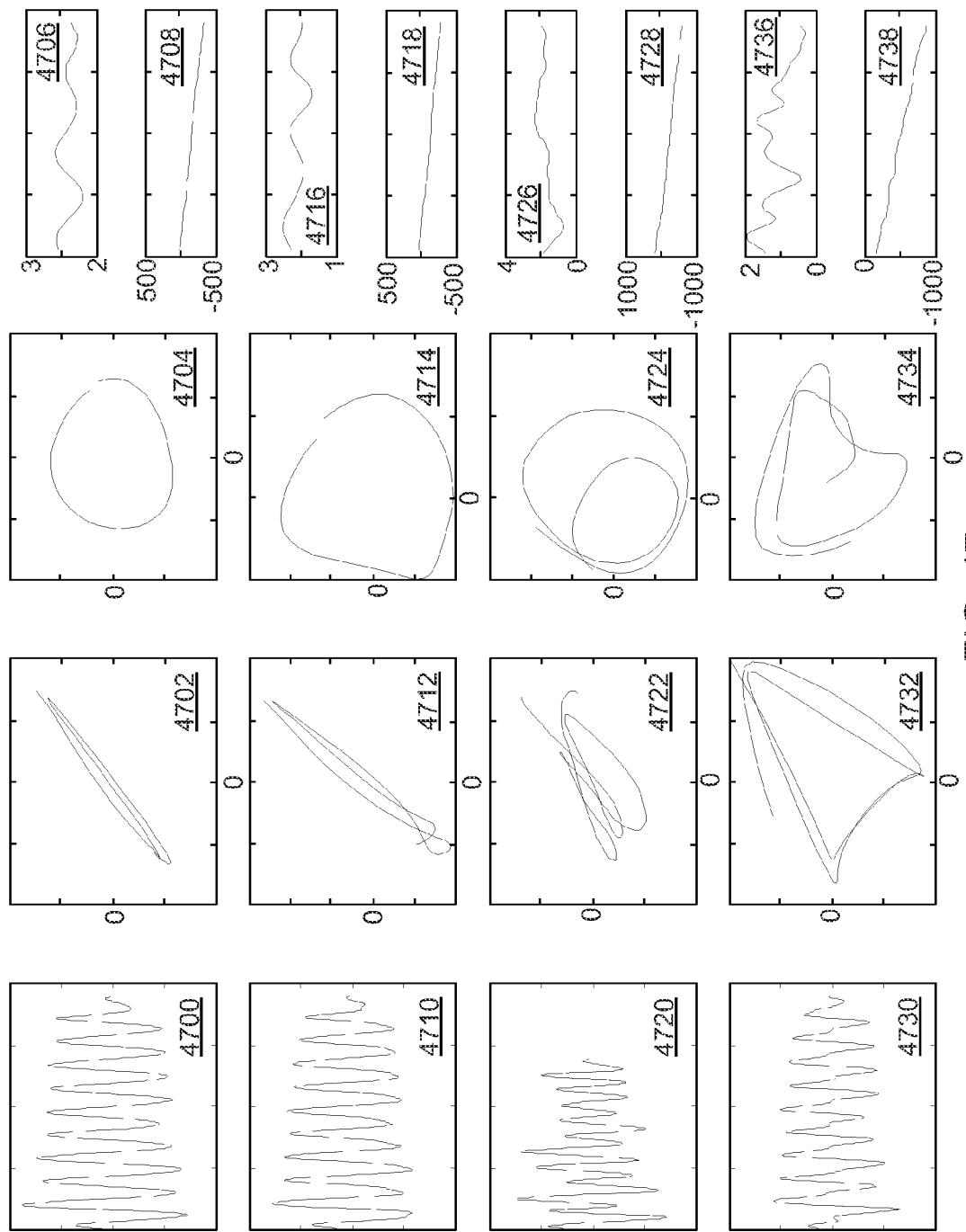
FIG. 47 shows multiple plots of illustrative cross-correlation outputs and corresponding symmetry curves, radial curves, radius calculations, and angle calculations, in accordance with some embodiments of the present disclosure.

FIG. 47 shows four sets of plots, arranged by row, of (from left to right) illustrative cross-correlation signals and corresponding symmetry curves, radial curves, radius calculations (top), and angle calculations (bottom), in accordance with some embodiments of the present disclosure.

Plots 4700, 4710, 4720, and 4730 show four respective, illustrative cross-correlation signals, in accordance with some embodiments of the present disclosure. The top two cross-correlation signals, of plots 4700 and 4710, do not exhibit notches and show relatively consistent periodic character. Plots 4702 and 4712 each show a symmetry curve, with lengths equal to 1.6 times period P, which corresponds to the cross-correlation signal of plots 4700 and 4710, respectively. The symmetry curves of plots 4702 and 4712 show substantially linear character, with respective slopes of nearly one, passing roughly through the origin. Accordingly, the peaks of the cross-correlation signals of plots 4700 and 4710 may be determined to be relatively symmetric, and an associated initialization parameters, calculated rate, or both, may be qualified based on the symmetry. Plots 4704 and 4714 each show a radial curve, using segment lengths equal to period P, which corresponds to the cross-correlation signal of plots 4700 and 4710, respectively. Plots 4706 and 4708 show respective radius and angle calculations based on the radial curve of plot 4704, while plots 4716 and 4718 show respective radius and angle calculations based on the radial curve of plot 4714. The radial curves of plots 4704 and 4714 are roughly circular, including a single loop. The radius calculations of plots 4706 and 4716 show some variation, with radius ratios (e.g., calculated using Eq. 25) of 1.18 and 1.54, respectively. The angle calculations of plots 4708 and 4718 give angle sums (e.g., calculated using Eq. 27) of 343.4° and 333.7°, respectively. The symmetry curves and radial curves associated with the cross-correlation results of plots 4700 and 4710, and calculations thereof, may indicate that the period P provides a relatively good estimate of the actual physiological period. Accordingly, under some circumstances, the initialization parameters, calculated rate, or both, associated with period P may be qualified.

The bottom two cross-correlation signals of FIG. 47, of plots 4720 and 4730, do not exhibit notches and show relatively consistent periodic character. Plots 4722 and 4732 each show a symmetry curve, with lengths equal to 1.6 times period P, which corresponds to the cross-correlation output of plots 4720 and 4730, respectively. The symmetry curves of plots 4722 and 4732 show substantially non-linear character, with varying slopes, and deviating relatively far from the origin. The peaks of the cross-correlation output of plot 4720 show varying amplitude, while the peaks of the cross-correlation signal of plot 4730 show an additional inflection likely caused by a dicrotic notch in the original physiological data. Accordingly, the peaks of the cross-correlation signals of plots 4720 and 4730 may be determined to be relatively asymmetric, and an associated initialization parameters, calculated rate, or both, may be disqualified based on the symmetry. Plots 4724 and 4734 each show a radial curve, using segment lengths equal to period P, which correspond to the cross-correlation signal of plots 4720 and 4730, respectively. Plots 4726 and 4728 show respective radius and angle calculations based on the radial curve of plot 4724, while plots 4736 and 4738 show respective radius and angle calculations based on the radial curve of plot 4734. The radial curve of plot 4724 shows two loops of substantially different radii, indicating that the period P may be roughly twice as long as the actual period of cross-correlation signal 4720. The radial curve of plot 4734 shows two non-circular loops, of varying radii, indicating that the period P may be roughly twice as long as the actual period of cross-correlation signal 4730. The radius calculations of plots 4726 and 4736 show significant variation, with radius ratios (e.g., calculated using Eq. 25) of 3.58 and 6.69, respectively. The angle calculations of plots 4728 and 4738 give angle sums (e.g., calculated using Eq. 27) of 757.6° and 703.9°, respectively. The symmetry curves and radial curves associated with the cross-correlation results of plots 4720 and 4730, and calculations thereof, may indicate that the period P provides a relatively poor estimate of the actual physiological period. In some embodiments, this may occur when the rate is locked onto low frequency noise or half the physiological rate or when the initialization parameters identity low frequency noise or half the physiological rate. Accordingly, under some circumstances, the initialization parameters, calculated rate, or both, associated with period P may be disqualified.

Figure 48:
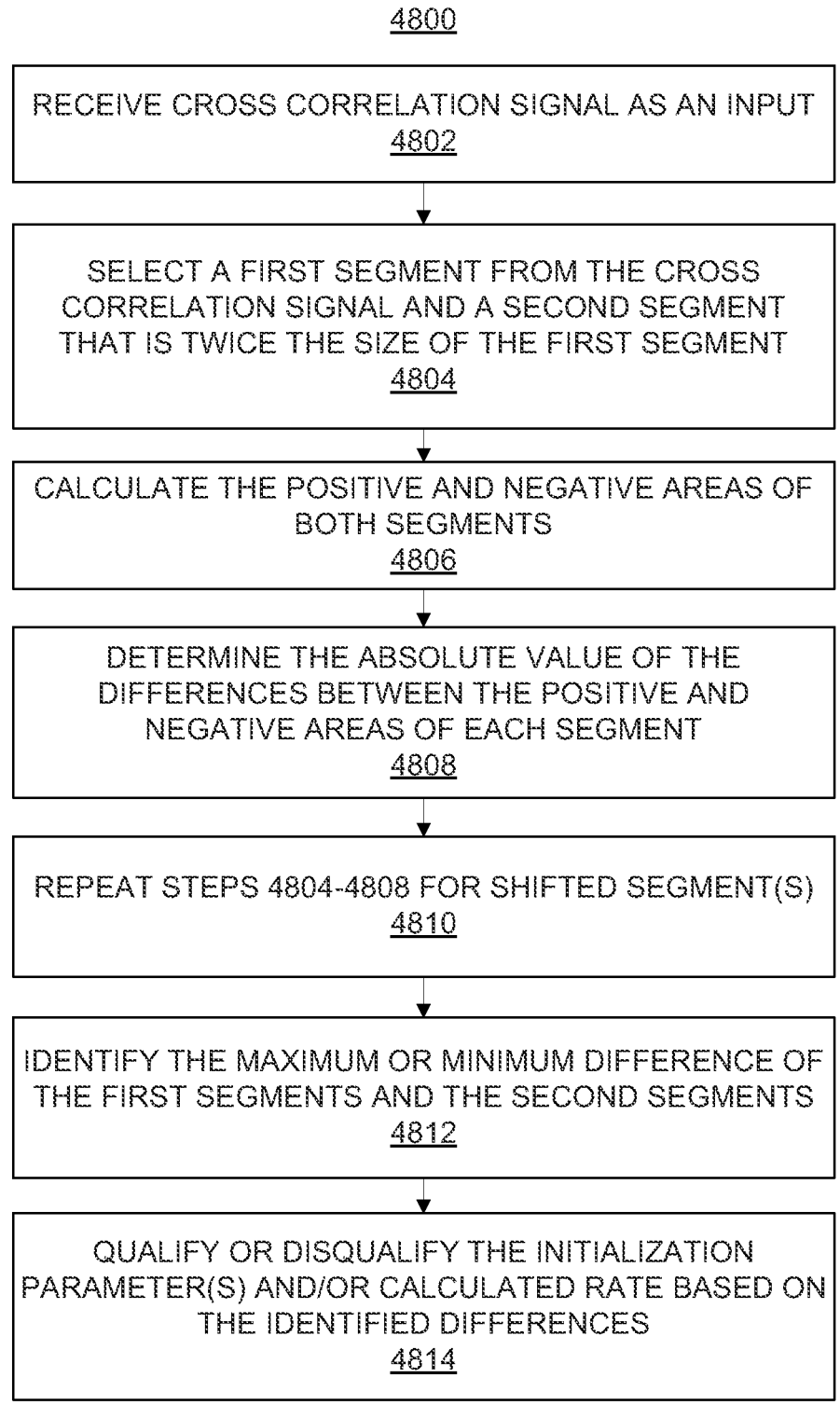
FIG. 48 is a flow diagram of illustrative steps for qualifying or disqualifying initialization parameters based on an areas of positive and negative portions of segments of a cross-correlation output, in accordance with some embodiments of the present disclosure.

FIG. 48 is a flow diagram 4800 of illustrative steps for qualifying or disqualifying initialization parameters and/or calculated rates based on areas of positive and negative portions of segments of a cross-correlation signal, in accordance with some embodiments of the present disclosure. In some embodiments, the illustrative steps of flow diagram 4800 aid in preventing a double-rate (half-period) condition, half-rate (double-period) condition, or other conditions in which period P is not indicative of a physiological rate. The illustrative steps of flow diagram 4800 may be referred to as the "Area Test."

Step 4802 may include processing equipment receiving a cross-correlation signal (e.g., generated according to step 3806 of FIG. 38) as an input. In some embodiments, the cross-correlation signal may be generated by a cross-correlation module. In some embodiments the cross-correlation signal may be generated at an earlier time, and stored in suitable memory. Accordingly, in some embodiments, step 4802 may include recalling the stored cross-correlation signal from the memory. In some embodiments, a single processor, module, or system may perform the cross-correlation and steps 4804-4814, and accordingly, step 4802 need not be performed.

Step 4804 may include the processing equipment selecting two signal segments of the cross-correlation signal of step 4802. The first segment may be half as large as the second segment. For example, the second segment may have a length equal to period P, while the first segment has a length equal to one half of period P and is included in the second segment. In a further example, the second segment may have a length equal to period 2P, while the first segment has a length equal to period P. The two segments may be selected from any suitable portion of the cross-correlation output.

Figure 49:
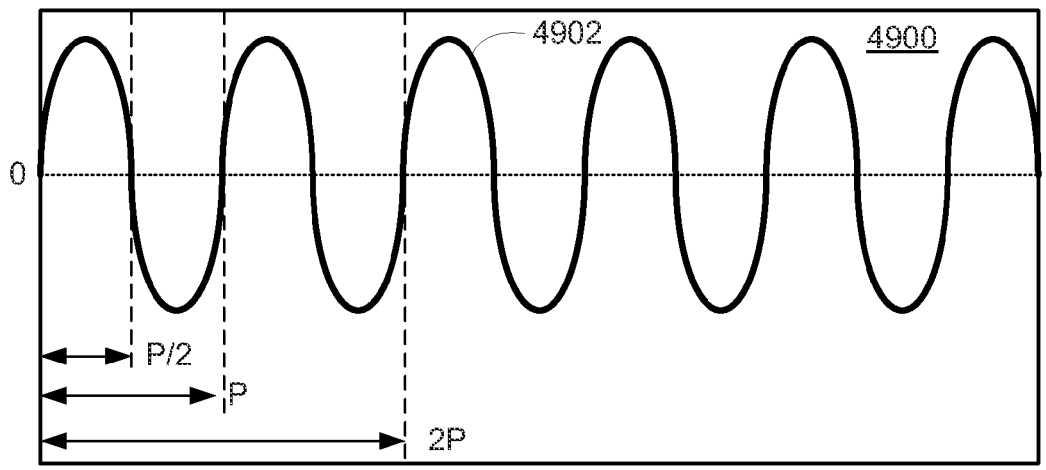
FIG. 49 is a plot of an illustrative cross-correlation output with the correct rate locked-in, in accordance with some embodiments of the present disclosure.
Figure 50:
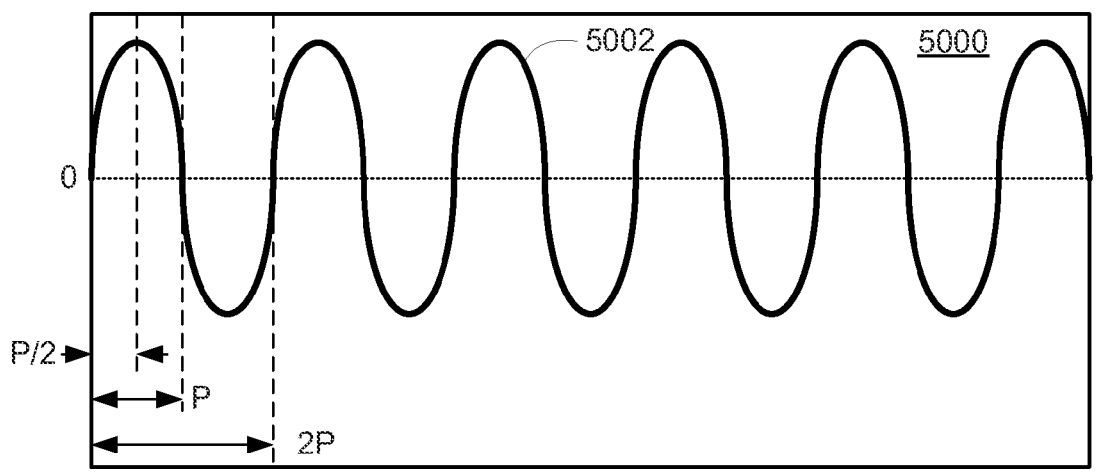
FIG. 50 is a plot of an illustrative cross-correlation output with double the correct rate locked-in, in accordance with some embodiments of the present disclosure.
Figure 51:
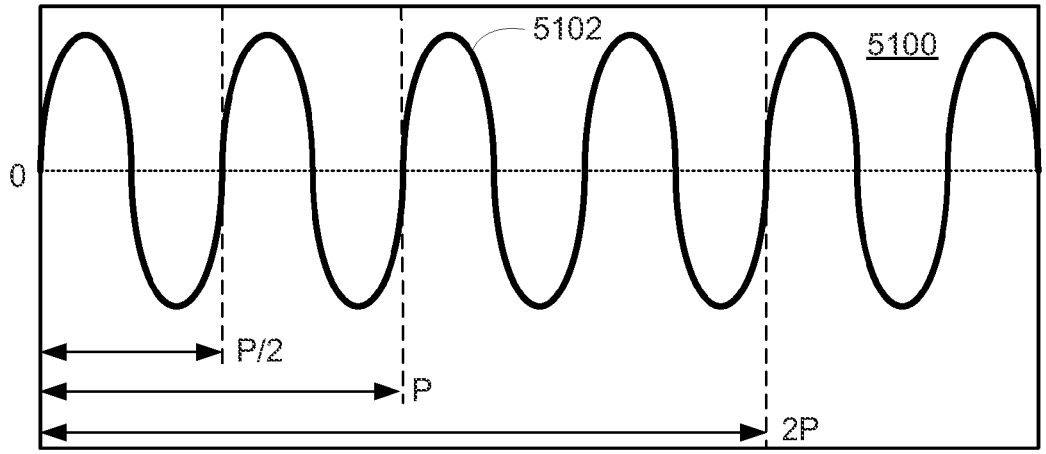
FIG. 51 is a plot of an illustrative cross-correlation output with one half the correct rate locked-in, in accordance with some embodiments of the present disclosure.

Step 4806 may include the processing equipment calculating the positive and negative areas of both the first and second segments. Each segment may include one or more oscillations, or portions thereof, and accordingly may include positive and negative portions (e.g., FIGS. 49-51 provides further illustration). In some embodiments, step 4806 may include performing a summation of the positive data points, and a summation of the negative data points for each segment. In some embodiments, step 4806 may include performing a piecewise discrete integration (e.g., a piecewise numerical quadrature or any other suitable analytical or numerical technique) of the positive and negative portions of each of the two segments of the cross-correlation signal. In some embodiments, the area values of step 4806 may both be positive values, with the areas of a negative portion of a segment calculated by taking the absolute value of the integral of the negative portion. In some embodiments, either or both areas may be normalized by the associated segment length. This normalization may allow for a particular threshold to be used for segments having different lengths. For example, the areas of a segment of length P may both be divided by P or one. In a further example, the areas of a segment of length 2P may both be divided by 2P or two.

Step 4808 may include the processing equipment determining the absolute value of the difference between the positive and negative areas (which may both be positive values) for each segment. In some embodiments, the processing equipment may calculate the difference between the areas of the positive and negative portions of each segment by subtracting the area of the negative portion, which may be a positive value, from the area of the positive portion (or vice versa), and then calculating the absolute value of the difference.

Step 4810 may include the processing equipment repeating steps 4804-4808, for various shifts in the segments relative to one another, relative to a varying origin point with the segments' relative positions fixed, or any other suitable shift. In some embodiments, the first and second segments may always originate at the same point, which may be shifted along the cross-correlation output at step 4810 to define the different pairs of segments. In some embodiments, the first segment may remain fixed and the second segment may be shifted at step 4810. For example, the first segment, with a length equal to P/2, may remain fixed and the second segment, with a length equal to P, may be shifted by one or more degree measures and the difference may be calculated at each degree measure. In a further example, the second segment, with a length equal to P, may remain fixed and the first segment, with a length equal to P/2, may be shifted by one quarter of the period P, and the difference may be calculated at this new segment location. Either or both of the first and second segments may be shifted any suitable amount to generate one or more pairs of first and second segments. In some embodiments, step 4808, step 4810, or both, may include storing the one or more respective difference values of steps 4808 and 4810 in any suitable memory, using any suitable data-basing or filing protocol.

Step 4812 may include the processing equipment identifying maximum values, minimum values, or both, of the differences among both the first segments and the second segments. For example, in some embodiments, the processing equipment may identify the maximum difference of the first segment(s) and the minimum difference of the second segment(s). In some embodiments, the processing equipment may identify the maximum difference of the first segment(s) and the minimum difference of the second segment(s). Any suitable technique may be used to identify the respective maximum and minimum values. In some embodiments, step 4812 may be performed concurrent with steps 4808 and 4810. For example, initial maximum and minimum difference values may be calculated at step 4808 and stored. As subsequent difference values are calculated at step 4810, the stored values may be replaced as larger or smaller values, as appropriate, are calculated.

Step 4814 may include the processing equipment qualifying or disqualifying the initialization parameters, calculated rate, or both, based on the identified maximum and minimum differences of step 4812. In some embodiments, the processing equipment may calculate a difference between the maximum difference for the first segments and the minimum difference for the second segments. For example, one or more thresholds may be set based on the value of the minimum difference for the second segments (e.g., the threshold value may be equal to the minimum difference value or a scaling thereof). The maximum difference for the first segment may then be compared to the threshold. If the maximum difference is greater than the threshold, the processing equipment may qualify the initialization parameters, calculated rate, or both. If the maximum difference is less than the threshold, the processing equipment may disqualify the initialization parameters, calculated rate, or both. In some embodiments, the processing equipment may calculate a ratio of the maximum difference for the first segment to the minimum difference for the second segment. For example, one or more thresholds, which may be predetermined or may depend upon the difference values, may be set. The ratio may then be compared to the threshold. If the ratio is greater than the threshold, the processing equipment may qualify the initialization parameters, calculated rate, or both. If the ratio is less than the threshold, the processing equipment may disqualify the initialization parameters, calculated rate, or both. In some embodiments, the ratio may be calculated for each pair of first and second segments, and a maximum ratio value may be selected to be compared with one or more threshold values. In some embodiments, the areas, differences, or ratios may be normalized by dividing by a value corresponding to the segment length. In some embodiments, the thresholds may be scaled based on the segment lengths of the period P. In some embodiments, one or more metrics may inputted into a classifier.

In some embodiments, the illustrative steps of flow diagram 4800 may be performed using segments of length P/2 and P, which may provide particular benefits under some circumstances. In some embodiments, the illustrative steps of flow diagram 4800 may be performed using segments of length P and 2P, which may provide particular benefits under some circumstances. Any suitable first and second segments may be used to perform the Area Test. The following discussion, referencing FIGS. 49-51, provides further detail regarding flow diagram 4800, in accordance with some embodiments of the present disclosure. The abscissa of each of plots 4900, 5000, and 5100 of FIGS. 49-51, respectively, are presented in units proportional to cross-correlation lag, while the ordinate is presented in arbitrary units, with zero notated.

FIG. 49 is a plot 4900 of an illustrative cross-correlation output 4902, centered about zero with correctly determined initialization parameters or rates, in accordance with some embodiments of the present disclosure. The period P is close to the period exhibited by cross-correlation signal 4902. As shown in plot 4900, cross-correlation signal 4902 may include portions above the baseline (i.e., values greater than zero), and portions below the baseline (i.e., values less than zero). Depending on a how a segment of cross-correlation signal 4902 is selected, the areas of the positive and negative portions may change relative to one another.

Three illustrative segment lengths are shown in FIG. 49, including period P, one half of period P, and double period P. The difference in the areas of the positive and negative portions of segments of length P or 2P may be expected to be relatively small for any suitable shift because the segments approximately cover a complete period or double period exhibited by cross-correlation output 4902. The difference between the areas of the positive and negative portions of segments of length P/2 may be expected to range from small values (e.g., when a segment is centered near a zero of cross-correlation signal 4902) to relatively larger values (e.g., when the segment lies substantially between zeros of cross-correlation signal 4902).

In some cases, in which the initialization parameters or rates are correctly determined, a first segment may have a length equal to P/2 and the second segment may have a length equal to period P. Differences in areas of positive and negative portions of cross-correlation signal 4902 may be calculated for multiple first and second segments, having constant respective lengths but varying shift. In some such cases, the maximum difference among first segments may be compared to the minimum difference among second segments, or a threshold derived thereof. For example, the maximum difference among first segments may be compared to a threshold equal to four times the minimum difference of the second segments. If the maximum difference among first segments is larger than the threshold, then the initialization parameters, calculated rate, or both, may be qualified.

In some cases, in which the initialization parameters or rates are correctly determined, a first segment may have a length equal to P and the second segment may have a length equal to period 2P. Unlike the previously discussed cases, in which first and second segments had respective lengths of P/2 and P, the differences of the present cases are now both expected to be small values. Accordingly, in some such cases, the maximum difference among first segments may be compared to the minimum difference among second segments, or a threshold derived thereof. For example, the maximum difference among first segments may be compared to a threshold equal to two times the minimum difference of the second segments. If the maximum difference among first segments is smaller than the threshold, then the initialization parameters, calculated rate, or both, may be qualified.

FIG. 50 is a plot 5000 of an illustrative cross-correlation output 5002 with initialization parameters or rates incorrectly determined to be double the correct rate, in accordance with some embodiments of the present disclosure. The period P is close to one half of the period exhibited by cross-correlation signal 5002. Three illustrative segment lengths are shown in FIG. 50, including period P, one half of period P, and double period P. As illustrated, the difference in the areas of the positive and negative portions of segments of length 2P may be expected to be relatively small for any suitable shift. The difference in the areas of the positive and negative portions of segments of lengths P/2 or P may be expected to range from small values (e.g., when a segment is centered near a zero of cross-correlation signal 5002) to relatively larger values (e.g., when the segment lies substantially between zeros of cross-correlation signal 5002).

In some cases, in which the initialization parameters or rates are incorrectly determined, a first segment may have a length equal to P/2 and the second segment may have a length equal to period P. Differences in areas of positive and negative portions of cross-correlation signal 5002 may be calculated for multiple first and second segments, having constant respective lengths but varying shift. In some such cases, the maximum difference among first segments may be relatively large compared to the minimum difference among second segments. Accordingly, under some circumstances, the use of first and second segments with respective lengths P/2 and P may allow a double-rate condition to qualify if similar threshold conditions are used as when the initialization parameters or rates are correctly determined.

In some cases, in which the initialization parameters or rates are incorrectly determined, a first segment may have a length equal to period P and the second segment may have a length equal to period 2P. In some such cases, the maximum difference of the first segment may be compared to the minimum difference of the second segment, or a threshold derived thereof. If the maximum difference among first segments is larger than a suitable threshold (e.g., the same threshold condition as used when the initialization parameters or rates are correctly determined), as may be expected, then the initialization parameters, calculated rate, or both, may be disqualified. Accordingly, in some embodiments, the Area Test may provide techniques to disqualify a double-rate condition.

FIG. 51 is a plot 5100 of an illustrative cross-correlation signal 5102 with initialization parameters or rates incorrectly determined to be half the correct rate, in accordance with some embodiments of the present disclosure. The period P is close to twice the period exhibited by cross-correlation signal 5102. Three illustrative segment lengths are shown in FIG. 51, including period P, one half of period P, and double period P. As illustrated, the difference in the areas of the positive and negative portions of segments of lengths P/2, P, and 2P may be expected to be relatively small for any suitable shift. In some cases, any full period of cross-correlation signal 5102 may provide a relatively low difference value, regardless of shift.

In some cases, in which the initialization parameters or rates are incorrectly determined to be one half the correct rate, a first segment may have a length equal to P/2 and the second segment may have a length equal to period P. Differences in areas of positive and negative portions of cross-correlation signal 5102 may be calculated for multiple first and second segments, having constant respective lengths but varying shift. In some such cases, the maximum difference among first segments may be comparable to the minimum difference among second segments. If the maximum difference among first segments is smaller than the threshold (e.g., the same threshold condition as used when the initialization parameters or rates are correctly determined), then the initialization parameters, calculated rate, or both, may be disqualified. Accordingly, the Area Test may provide techniques to disqualify a half-rate condition.

In some cases, in which the initialization parameters or rates are incorrectly determined to be one half the correct rate, a first segment may have a length equal to period P and the second segment may have a length equal to period 2P. In some such cases, the maximum difference of the first segment may be compared to the minimum difference of the second segment, or threshold derived thereof. If the maximum difference among first segments is smaller than a suitable threshold (e.g., the same threshold condition as used when the initialization parameters or rates are correctly determined), as may be expected, then the initialization parameters, calculated rate, or both, may be qualified. Accordingly, under some circumstances, the use of first and second segments with respective lengths P and 2P may allow a half-rate condition to qualify if similar threshold conditions are used as when the initialization parameters or rates are correctly determined.

In view of the foregoing, first and second segments with respective lengths P/2 and P may prevent qualification of a half-rate condition and first and second segment lengths of P and 2P may prevent qualification of a double-rate condition. Accordingly, in some embodiments, the Area Test may provide techniques to prevent qualification of double-rate, half-rate, or any other rate condition that is not indicative of a physiological rate.

Figure 52:
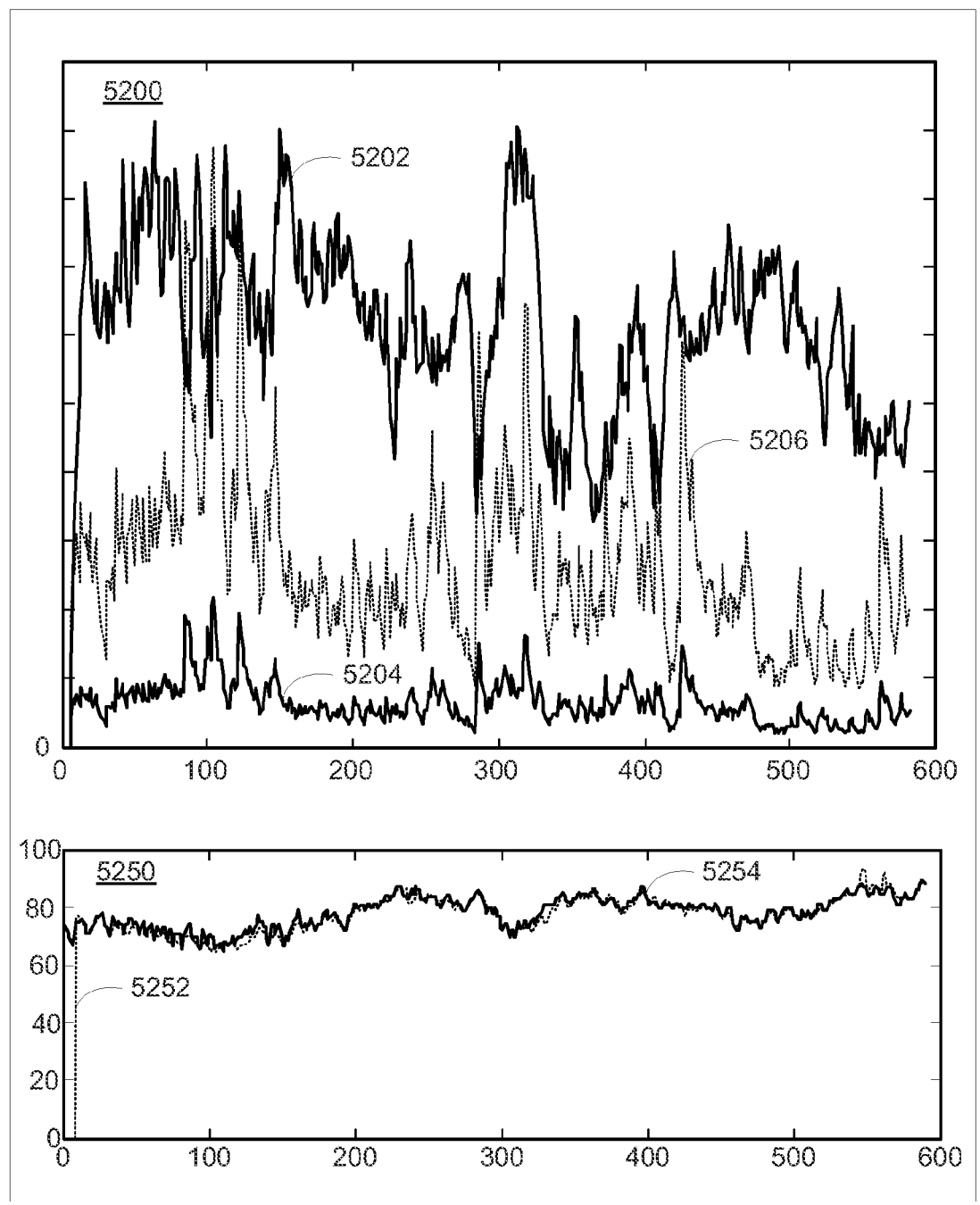
FIG. 52 is a plot of illustrative difference calculations of the Area Test, and a plot of illustrative calculated rates indicative of an actual physiological pulse, in accordance with some embodiments of the present disclosure.

FIG. 52 is a plot 5200 of illustrative difference calculations of the Area Test with correctly determined initialization parameters or rates, and a plot 5250 of illustrative calculated rates indicative of an actual physiological pulse, in accordance with some embodiments of the present disclosure. The abscissa of plot 5200 is presented in units of seconds, while the ordinate is presented in arbitrary units, with zero notated. Series 5202 is the maximum difference in first segments, with lengths equal to one half of period P. Series 5204 is the minimum difference in second segments, with lengths equal to period P. Threshold 5206 is an illustrative threshold equal to four times series 5204 (i.e., scaled from series 5204 by a multiplicative factor of four). As shown in FIG. 52, series 5202 lies above threshold 5206, indicating that the initialization parameters, calculated rate, or both, may be qualified. Plot 5250 of illustrative calculated rates indicative of an actual physiological rate, in accordance with some embodiments of the present disclosure. The abscissa of plot 5250 is presented in units of seconds, while the ordinate is presented in units of BPM. Time series 5252 is the pulse rate (i.e., BPM) as calculated by a subject monitoring system tracking the actual rate, shown by time series 5254.

Figure 53:
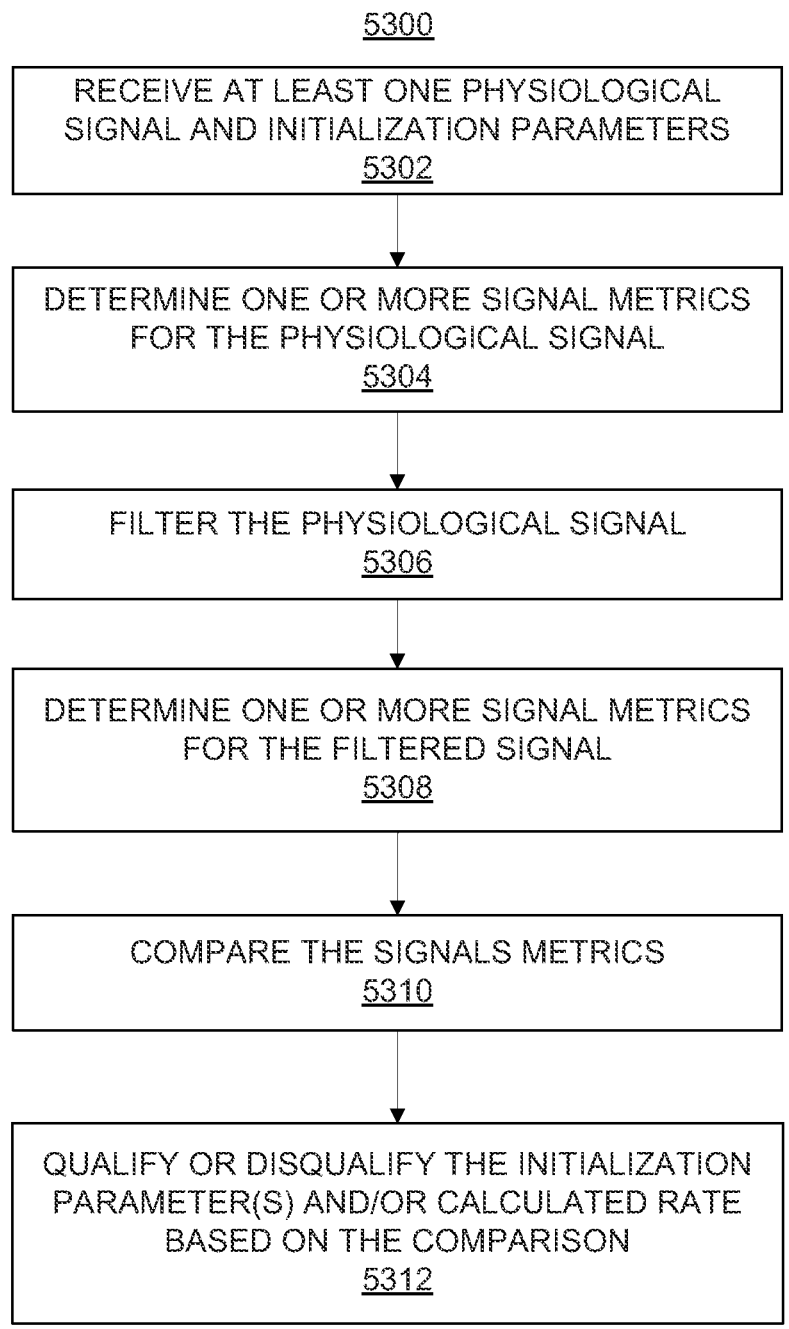
FIG. 53 is a flow diagram of illustrative steps for qualifying or disqualifying initialization parameters based on a filtered physiological signal, in accordance with some embodiments of the present disclosure.

FIG. 53 is a flow diagram of illustrative steps for qualifying or disqualifying initialization parameters and/or calculated rates based on a filtered physiological signal, in accordance with some embodiments of the present disclosure. In some embodiments, performance of the illustrative steps of flow diagram 5300 may provide an indication of the relative energy in a high frequency component of a physiological signal. Accordingly, in some circumstances, relatively large amounts of energy at rates much larger than the rate associated with the initialization parameters or a calculated rate may indicate that low-frequency noise has been locked onto. The illustrative steps of flow diagram 5300 may be referred to as the "High Frequency Residual Test."

Step 5302 may include processing equipment receiving at least one physiological signal from a physiological sensor, memory, any other suitable source, or any combination thereof. For example, referring to system 300 of FIG. 3, processor 312 may receive a physiological signal from input signal generator 310. Sensor 318 of input signal generator 310 may be coupled to a subject, and may detect physiological activity such as, for example, RED and IR light attenuation by tissue, using a photodetector. In some embodiments, for example, physiological signals generated by input signal generator 310 may be stored in memory (e.g., memory of system 10 of FIGS. 1-2) after being pre-processed by pre-processor 320. In such cases, step 5302 may include recalling the signals from the memory for further processing. The physiological signal of step 5302 may include a PPG signal, which may include a sequence of pulse waves and may exhibit motion artifacts, noise from ambient light, electronic noise, system noise, any other suitable signal component, or any combination thereof. Step 5302 may include receiving a particular time interval or corresponding number of samples of the physiological signal. In some embodiments, step 5302 may include receiving a digitized, sampled, and pre-processed physiological signal.

Step 5304 may include the processing equipment determining one or more signal metrics for the physiological signal of step 5302. Signal metrics may include a standard deviation of the physiological signal, an RMS of the physiological signal, an amplitude of the physiological signal, a sum or integral of the physiological signal over time or samples, any other suitable metric indicative of a magnitude of a signal or change thereof, or any combination thereof. In some embodiments, the processing equipment may compute the standard deviation of the physiological signal, which may indicate the relative amplitude of excursions in the signal about the mean. In a further example, the processing equipment may take an absolute value of a physiological signal with zero mean, and then integrate the resulting signal over time or sample number to provide an indication of the magnitude of signal excursions about the mean (e.g., zero).

Step 5306 may include the processing equipment filtering the physiological signal of step 5302. In some embodiments, the processing equipment may apply a high-pass filter to the physiological signal of step 5302. For example, the processing equipment may apply a high-pass filter (e.g., having any suitable order and spectral characteristics) having a cutoff at double the rate associated with the one or more initialization parameters. In some embodiments, the processing equipment may apply a notch filter to the physiological signal of step 5302. For example, the processing equipment may apply a notch filter (e.g., having any suitable spectral characteristics) having a notch centered at double the rate associated with the one or more initialization parameters. In some embodiments, the processing equipment may apply a high-pass filter and a notch filter to the physiological signal of step 5302. For example, the processing equipment may apply a high-pass filter having a cutoff at double the rate associated with the one or more initialization parameters, and a notch filter having a notch centered at double the rate associated with the one or more initialization parameters. The resulting high frequency (HF) signal may be further analyzed at step 5308. It will be understood that the physiological signal may undergo additional filtering before or after step 5306. Accordingly, the "filtered signal" of step 5306 refers to the filtering performed at step 5306, and not any previous or subsequent filtering.

Step 5308 may include the processing equipment determining one or more signal metrics for the filtered signal of step 5306. Signal metrics may include a standard deviation of the filtered signal, an RMS of the filtered signal, an amplitude of the filtered signal, a sum or integral of the filtered signal over time or samples, any other suitable metric indicative of a magnitude of a signal or change thereof, or any combination thereof. In some embodiments, the processing equipment may compute the standard deviation of the filtered signal, which may indicate the relative amplitude of excursions in the signal about the mean. In a further example, the processing equipment may take an absolute value of a filtered signal with zero mean, and then integrate the resulting signal over time or sample number to provide an indication of the magnitude of signal excursions about the mean (e.g., zero).

Step 5310 may include the processing equipment comparing the one or more signal metrics for the physiological signal of step 5302 with the one or more signal metrics for the filtered signal of step 5306. In some embodiments, the processing equipment may determine a comparison metric. In some embodiments, the processing equipment may determine the ratio of the signal metric(s) for the filtered signal to the signal metric(s) for the physiological signal. For example, the processing equipment may calculate the ratio of standard deviations of the filtered signal to the physiological signal. In some embodiments, the processing equipment may determine the difference between the signal metric(s) for the filtered signal and the signal metric(s) for the physiological signal.

Step 5312 may include the processing equipment qualifying or disqualifying initialization parameters, a calculated rate, or both, based on the comparison of step 5310. In some embodiments, the processing equipment may compare the comparison metric of step 5310 with one or more threshold values. For example, the processing equipment may compare the ratio of standard deviations of the filtered signal to the physiological signal to a ratio threshold. The ratio threshold may be any suitable fixed or adjustable value. For example, the ratio threshold may depend on the initialization parameters. If the ratio is higher than the ratio threshold, the processing equipment may disqualify the initialization parameters. If the ratio is lower than the ratio threshold, the processing equipment may qualify the initialization parameters. Accordingly, the processing equipment may use the High Frequency Residual Test to determine conditions having relatively large amounts of signal energy at rates much larger than the rate associated with initialization parameters or a calculated rate.

Figure 54:
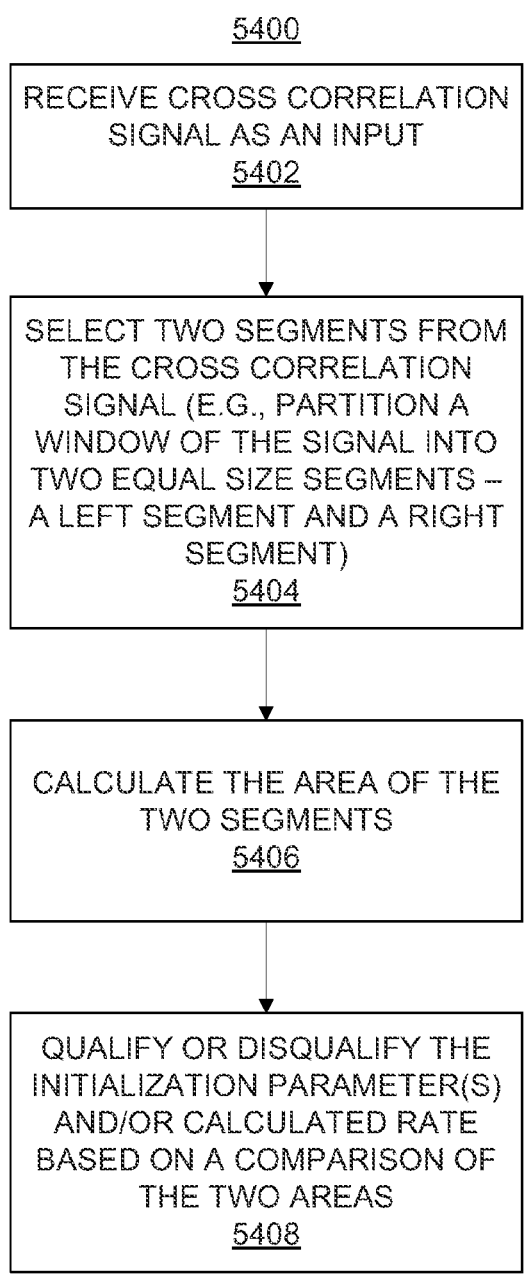
FIG. 54 is a flow diagram of illustrative steps for qualifying or disqualifying initialization parameters based on a comparison of areas of two segments of a cross-correlation output, in accordance with some embodiments of the present disclosure.
Figure 55:
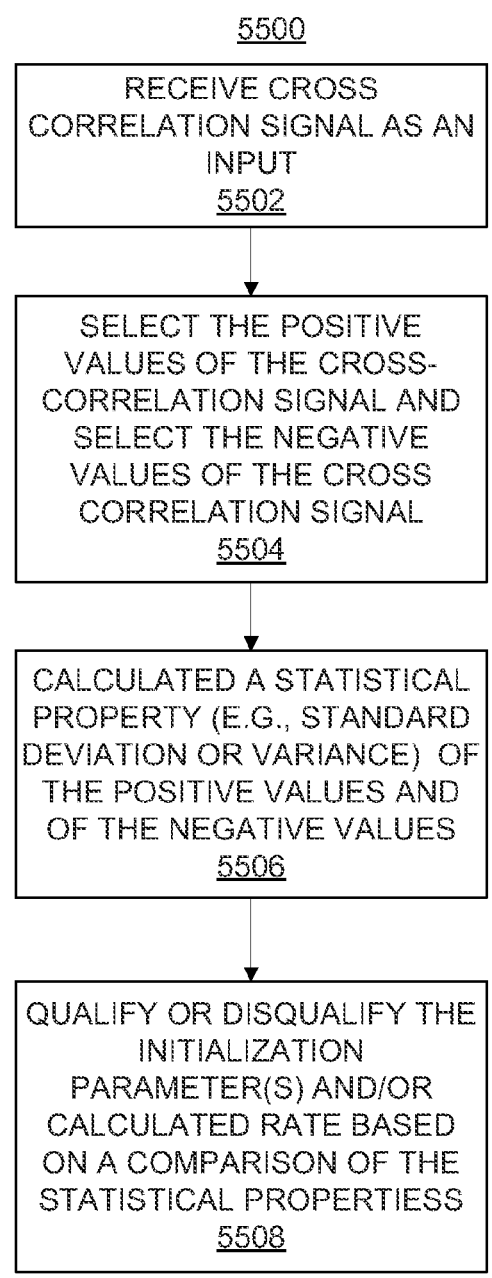
FIG. 55 is a flow diagram of illustrative steps for qualifying or disqualifying initialization parameters based on statistical properties of a cross-correlation output, in accordance with some embodiments of the present disclosure.

FIGS. 54 and 55 are illustrative flow diagrams of techniques that may also be used to qualify or disqualify initialization parameters, a calculated rate, or both. In some embodiments, the illustrative steps of flow diagrams 5400 and 5500 of FIGS. 54 and 55, respectively, may be performed based on initialization parameters, a calculated rate, or both. In some embodiments, the illustrative steps of flow diagrams 5400 and 5500 of FIGS. 54 and 55, respectively, may be performed independent of initialization parameters, a calculated rate, or both (e.g., to quantify noise and/or consistency in a buffered signal).

FIG. 54 is a flow diagram 5400 of illustrative steps for qualifying or disqualifying initialization parameters based on a comparison of areas of two segments of a cross-correlation signal, in accordance with some embodiments of the present disclosure. In some embodiments, performance of the illustrative steps of flow diagram 5400 may provide an indication of the similarity between different segments of a cross-correlation signal. The illustrative steps of flow diagram 5400 may be referred to as the "Area Similarity Test."

Step 5402 may include processing equipment receiving a cross-correlation signal (e.g., generated according to step 3806 of FIG. 38) as an input. In some embodiments, the cross-correlation signal may be generated by a cross-correlation module. In some embodiments the cross-correlation signal may be generated at an earlier time, and stored in suitable memory. Accordingly, in some embodiments, step 5402 may include recalling the stored cross-correlation signal from the memory. In some embodiments, a single processor, module, or system may perform the cross-correlation and steps 5404-5408, and accordingly, step 5402 need not be performed.

Step 5404 may include the processing equipment selecting two segments of the cross-correlation signal of step 5402. In some embodiments, the two segments may be of equal length. In some such embodiments, the cross-correlation signal may be equi-partitioned into a right segment and a left segment. For example, if the cross-correlation signal is six seconds in length, the left segment may be the left three seconds and the right segment may be adjacent right three seconds of the signal. In a further example, the first and second segments may each have a length equal to period P. Any suitable segments may be selected in accordance with the present disclosure. Note that the two segments will be referred to as Segment1 and Segment2, or the first segment and the second segment, although the designations are arbitrarily assigned for illustration purposes (e.g., the first and second segments may be interchanged in accordance with the present disclosure).

Step 5406 may include the processing equipment calculating the area of each of the first and second segments of step 5404. In some embodiments, step 5406 may include calculating an integral (e.g., a quadrature or any other suitable analytical or numerical technique), sum, or both, of the first and second segments. In some embodiments, the calculated area may be additive among the positive and negative areas. For example, the area of positive portions and the absolute value of the area of negative portions may be summed, resulting in a positive result. In some embodiments, the calculated area may be subtractive, in which the area of positive portions and negative portions of each segment are respective positive and negative numbers (e.g., integral of the segment values in which negative portions contribute negative integrals), and a resulting sum may be positive or negative.

Step 5408 may include the processing equipment qualifying or disqualifying initialization parameters, a calculated rate, or both, based on a comparison of the calculated areas of step 5406. Any suitable comparison technique, including the calculation of any suitable comparison metric (e.g., difference, ratio), may be used to compare the areas of the two segments. In some embodiments, the processing equipment may calculate a difference between the area of the first segment and the area of the second segment (or vice versa). In some embodiments, the processing equipment may calculate a ratio of the area of the first segment to the area of the second segment (or vice versa). In some embodiments, qualification or disqualification may include comparing a comparison metric to a threshold value. For example, the difference between (or ratio of) the areas of the two segments may be calculated and if above a threshold value, the initialization parameters, calculated rate, or both, may be disqualified. Using suitable segment selection, the areas of the two segments may be expected to be similar, if period P provides a relatively accurate indication of a physiological pulse period.

In some embodiments, step 5408 need not be performed with steps 5402-5406. In some embodiments, steps 5402-5406 may be performed independent of initialization parameters or a calculated rate. For example, a cross-correlation signal of a buffered window of data may be analyzed using steps 5402-5406. The areas of two segments (e.g., fixed length segments) of the cross-correlation signal may be compared using a comparison metric, and under some circumstances the buffered data may be qualified or disqualified (e.g., based on a comparison of the comparison metric with a threshold). This may be particularly useful when the physiological signal is relatively noise free and then noise suddenly appears in the signal. This may also be particularly useful when strong non-periodic noise is present in the signal.

FIG. 55 is a flow diagram 5500 of illustrative steps for qualifying or disqualifying initialization parameters based on statistical properties of a cross-correlation signal, in accordance with some embodiments of the present disclosure. In some embodiments, performance of the illustrative steps of flow diagram 5500 may provide an indication of the similarity between positive and negative portions of a cross-correlation signal. The illustrative steps of flow diagram 5500 may be referred to as the "Statistical Property Test."

Step 5502 may include processing equipment receiving a cross-correlation signal (e.g., generated according to step 3806 of FIG. 38) as an input. In some embodiments, the cross-correlation signal may be generated by a cross-correlation module. In some embodiments the cross-correlation signal may be generated at an earlier time, and stored in suitable memory. Accordingly, in some embodiments, step 5502 may include recalling the stored cross-correlation signal from the memory. In some embodiments, a single processor, module, or system may perform the cross-correlation and steps 5504-5508, and accordingly, step 5502 need not be performed.

Step 5504 may include the processing equipment selecting the positive values of the cross-correlation signal, and selecting the negative values of the cross-correlation signal. For example, the processing equipment may compare each value of the cross-correlation signal to zero, and use the comparison to select positive and/or negative values.

Step 5506 may include the processing equipment calculating a statistical property of the positive values and of the negative values of step 5504. The statistical property may include a mean, standard deviation, variance, root-mean-square (RMS) deviation (e.g., relative to zero), any other suitable statistical property, or any combination thereof. In some embodiments, the positive values and negative values may be processed separately at step 5506.

Step 5508 may include the processing equipment qualifying or disqualifying initialization parameters, a calculated rate, or both, based on a comparison of the statistical properties of step 5506. Any suitable comparison technique, including the calculation of any suitable comparison metric (e.g., difference, ratio), may be used to compare the statistical properties of the positive and negative values. In some embodiments, the processing equipment may calculate a difference between the statistical properties of the positive and negative values (or vice versa). In some embodiments, the processing equipment may calculate a ratio of the statistical properties of the positive and negative values (or vice versa). In some embodiments, qualification or disqualification may include comparing a comparison metric to a threshold value. For example, the difference between (or ratio of) the statistical properties of the positive and negative values may be calculated and if above a threshold value, the initialization parameters, calculated rate, or both, may be disqualified.

In some embodiments, step 5508 need not be performed with steps 5502-5506. In some embodiments, steps 5502-5506 may be performed independent of initialization parameters or a calculated rate. For example, a cross-correlation signal of a buffered window of data may be analyzed using steps 5502-5506. The statistical properties of the positive and negative values of the cross-correlation output may be compared using a comparison metric, and under some circumstances the buffered data may be qualified or disqualified (e.g., based on a comparison of the comparison metric with a threshold).

Figure 56:
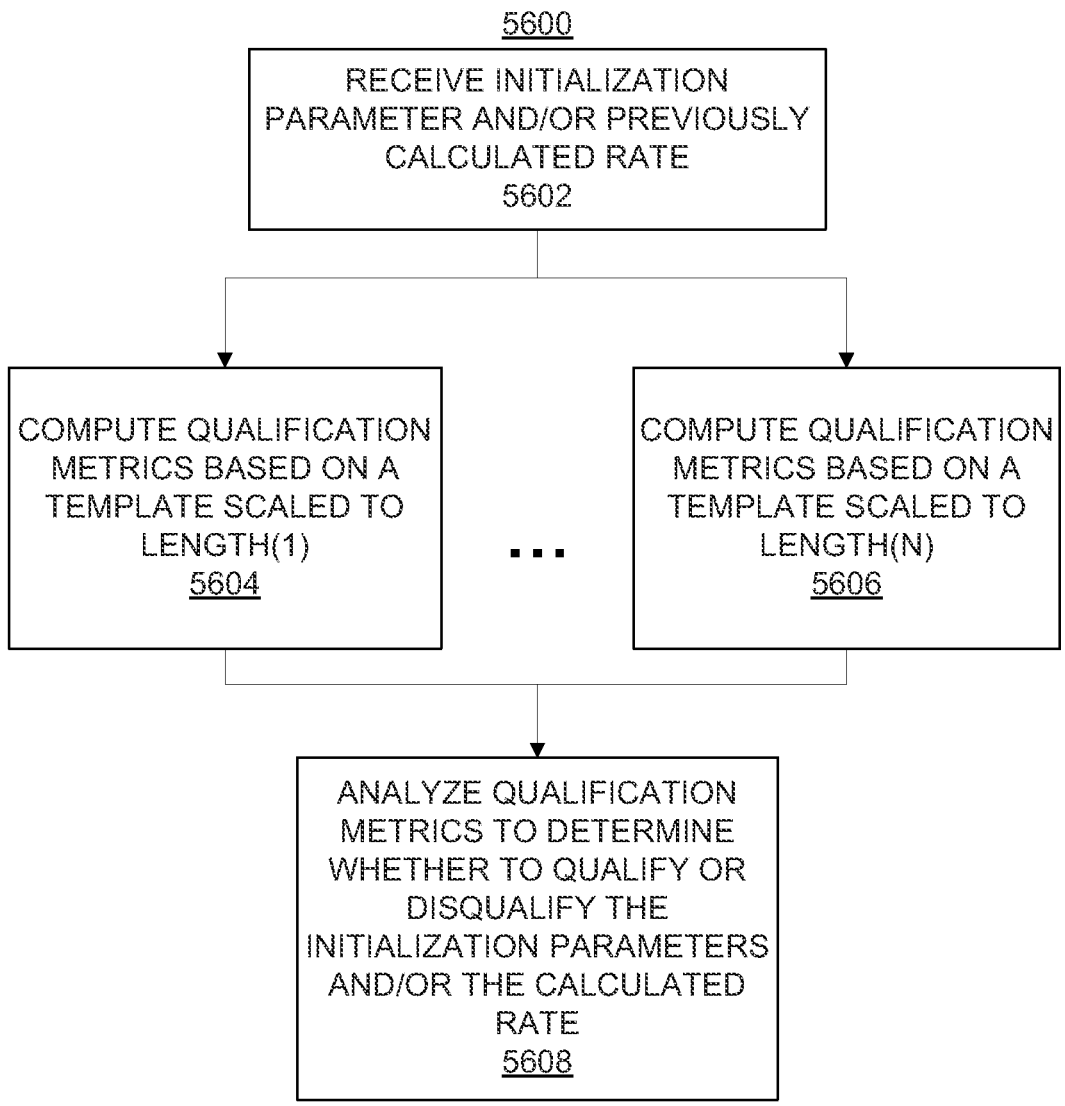
FIG. 56 is a flow diagram of illustrative steps for analyzing qualification metrics based on scaled templates of different lengths, in accordance with some embodiments of the present disclosure.
Figure 57:
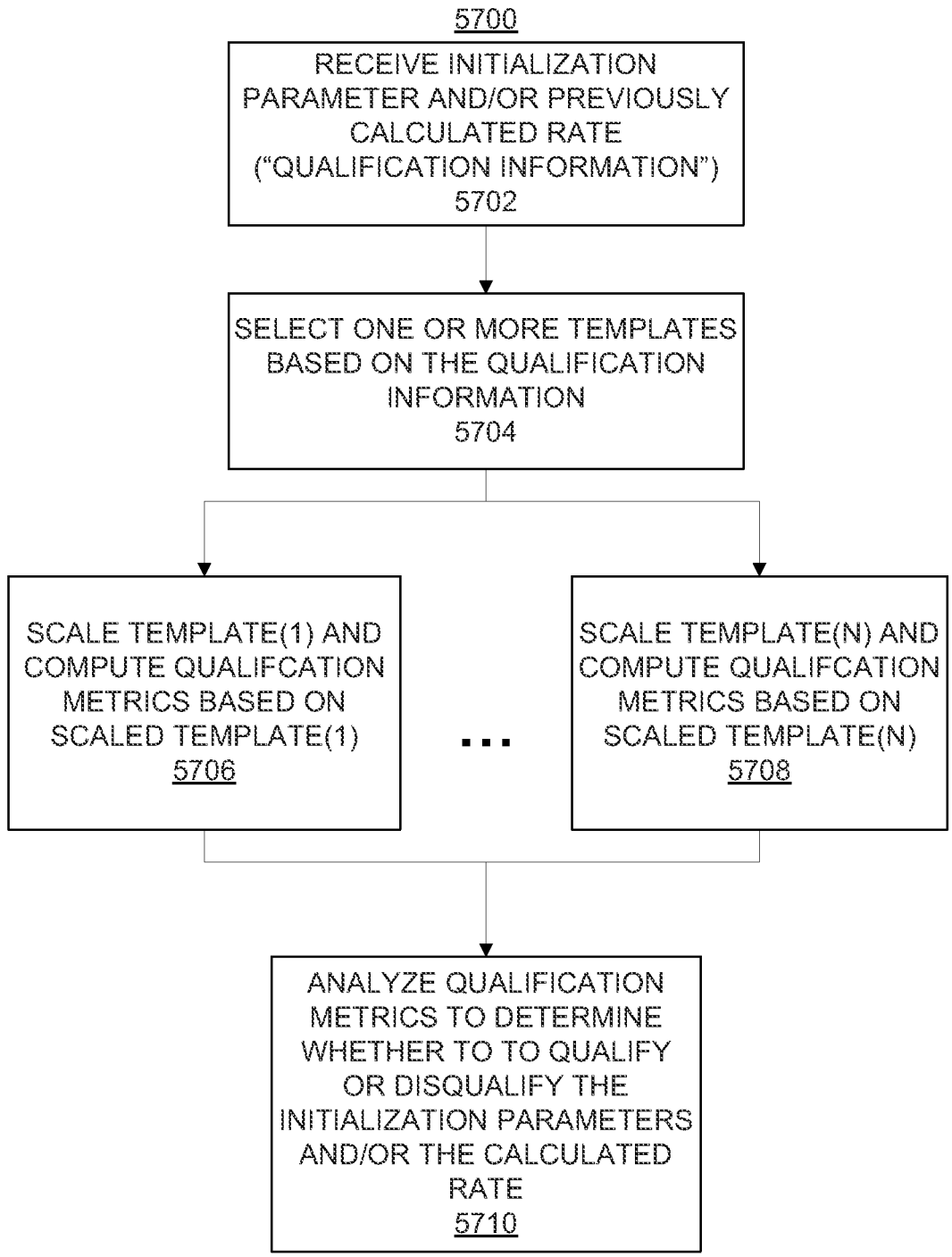
FIG. 57 is a flow diagram of illustrative steps for selecting one or more templates, and analyzing qualification metrics based on scaled templates, in accordance with some embodiments of the present disclosure.

In some embodiments, the illustrative steps of flow diagrams 5600 and 5700 of FIGS. 56 and 57, respectively, may be performed to qualify or disqualify initialization parameters, a calculated rate, or both. In some embodiments, the illustrative analyses of flow diagrams 5600 and 5700 of FIGS. 56 and 57, respectively, may be performed to increase confidence in a qualified rate. In some embodiments, flow diagrams 5600 and 5700 of FIGS. 56 and 57, respectively, may use a combination of any or all of the previously discussed qualification techniques. For example, the steps of flow diagrams 5600 and 5700 may be performed to further investigate whether initialization parameters and calculated rates correspond to a physiological rate of interest (e.g., pulse rate) by using multiple types of templates, multiple lengths of templates, or both.

FIG. 56 is a flow diagram 5600 of illustrative steps for analyzing qualification metrics based on scaled templates of different lengths, in accordance with some embodiments of the present disclosure. In some embodiments, performance of the illustrative steps of flow diagram 5600 may provide an evaluation of the qualification, or disqualification, of initialization parameters, a calculated rate, or both. The illustrative steps of flow diagram 5600 may be referred to as "Qualification Analysis."

Step 5602 may include processing equipment receiving an initialization parameter, previously calculated rate, any other suitable qualification information, or any combination thereof. In some embodiments, step 5602 may include recalling the stored initialization parameter, previously calculated rate, or both, from suitable memory. In some embodiments, a single processor, module, or system may calculate, store, or both, initialization parameters and the previously calculated rate, and perform steps 5604-5608, and accordingly, step 5602 need not be performed.

Step 5604 may include the processing equipment computing one or more qualification metrics based on a template scaled to a first length. In some embodiments, the scaled template may be used to generate a cross-correlation signal (e.g., using any suitable steps of flow diagram 3800 of FIG. 38), which may be analyzed according to any of the Qualification Techniques. In some embodiments, step 5604 may include performing a Symmetry Test, performing a Radius Test, performing an Angle Test, performing an Area Test, performing an Area Similarity Test, performing a Statistical Property Test, performing a High Frequency Residual Test, performing any other suitable test, performing any portions thereof, or any combination thereof. For example, a qualification metric may include a variability metric (e.g., calculated using Eq. 20a or 20b), a radius value (e.g., calculated using Eq. 25), and angle sum value (e.g., calculated using Eq. 27), an area of a segment, a statistical property, any other suitable metric, any metric derived thereof, or any combination thereof.

Step 5606 may include the processing equipment computing one or more qualification metrics based on a template scaled to a particular length different than the length of step 5604. In some embodiments, step 5606 may include performing a Symmetry Test, performing a Radius Test, performing an Angle Test, performing an Area Test, performing an Area Similarity Test, performing a Statistical Property Test, performing a High Frequency Residual Test, performing any other suitable test, performing any portions thereof, or any combination thereof. Step 5606 may be performed any suitable number of times with templates of different lengths, as indicated by the ellipsis of flow diagram 5600.

In some embodiments, using templates scaled to different lengths at steps 5604-5606 may aid in determining whether the initialization parameters, calculated rate, or both, are the true physiological rate. In some embodiments, a template may be scaled to a first length, based on the calculated rate or associated period (e.g., scaled to one half, one third, or double the rate). In some embodiments, the scaling used may be based on the calculated rate, initialization parameters, or both. In a further example, a template may be scaled based on a noise component. For example, if the calculated rate is 50 BPM, a template need not be scaled to the half-rate because 25 BPM is an unlikely physiological pulse rate. For relatively lower rates, templates scaled to higher rates may be used to determine if the initialization parameters or calculated rates are locked onto low-frequency noise. In a further example, for higher rates (e.g., 90 BPM and above) a template may be scaled to one half, one third, or other fraction of the calculated rate to determine if the initialization parameters or calculated rates are locked onto a harmonic of the physiological rate.

Step 5608 may include the processing equipment analyzing the qualification metrics of steps 5604 and 5606 to determine whether to qualify or disqualify the initialization parameter, previously calculated rate, or both, of step 5602. For example, the Angle Test may give a calculated angle sum of about 700° when a template is scaled to the calculated rate. If the Angle Test gives a calculated angle sum of about 360° when a template is scaled to one half of the period corresponding to the calculated rate, then the processing equipment may determine that there is a half-rate condition, and accordingly may qualify the half-rate and/or disqualify the rate. In a further example, two templates of the same length may be used at steps 5604 and 5606, one having a dicrotic notch and the other having no dicrotic notch. If the processing equipment qualifies at least one of the two templates, then the initialization parameters, calculated rate, or both, may be qualified.

FIG. 57 is a flow diagram 5700 of illustrative steps for selecting one or more templates, and analyzing qualification metrics based on scaled templates, in accordance with some embodiments of the present disclosure. In some embodiments, performance of the illustrative steps of flow diagram 5700 may provide an evaluation of the qualification, or disqualification, of initialization parameters, a calculated rate, or both.

Step 5702 may include processing equipment receiving an initialization parameter, previously calculated rate, any other suitable qualification information, or any combination thereof. In some embodiments, step 5702 may include recalling the stored initialization parameter, previously calculated rate, or both, from suitable memory. In some embodiments, a single processor, module, or system may calculate, store, or both, initialization parameters and the previously calculated rate, and perform steps 5704-5710, and accordingly, step 5702 need not be performed.

Step 5704 may include the processing equipment selecting one or more templates based on the qualification information of step 5702. In some embodiments, a variety of template shapes may be available to the processing equipment (e.g., stored in suitable memory accessible to the processing equipment). For example, some templates may exhibit a dicrotic notch while others do not exhibit a dicrotic notch. In a further example, some templates may exhibit symmetric peaks, while others do not exhibit symmetric peaks. In some embodiments, the template type may depend on a representative rate or period, which may be associated with initialization parameters, a calculated rate, or both. For example, in some embodiments, the processing equipment may select the one or more templates depending on the value of period P. For example, at relatively lower values of period P, a relatively more symmetrical template, without a dicrotic notch, may be selected. In some embodiments, a predefined number of templates may be used (e.g., all templates are always used), and accordingly, the selection of step 5704 need not be performed.

Step 5706 may include the processing equipment scaling a first template, of the one or more templates of step 5704, and calculating one or more qualification metrics based on the scaled first template. In some embodiments, the scaled first template may be used to generate a cross-correlation signal (e.g., using any suitable steps of flow diagram 3800 of FIG. 38), which may be analyzed according to any of the Qualification Techniques. In some embodiments, step 5706 may include performing a Symmetry Test, performing a Radius Test, performing an Angle Test, performing an Area Test, performing an Area Similarity Test, performing a Statistical Property Test, performing a High Frequency Residual Test, performing any other suitable test, performing any portions thereof, or any combination thereof.

Step 5708 may include the processing equipment scaling a second template, of the one or more templates of step 5704, and calculating one or more qualification metrics based on the scaled second template. In some embodiments, the scaled second template may be used to generate a cross-correlation signal (e.g., using any suitable steps of flow diagram 3800 of FIG. 38), which may be analyzed according to any of the Qualification Techniques. In some embodiments, step 5708 may include performing a Symmetry Test, performing a Radius Test, performing an Angle Test, performing an Area Test, performing an Area Similarity Test, performing a Statistical Property Test, performing a High Frequency Residual Test, performing any other suitable test, performing any portions thereof, or any combination thereof. Step 5708 may be performed any suitable number of times with different template shapes, as indicated by the ellipsis of flow diagram 5700.

Step 5710 may include the processing equipment analyzing the quantification metrics of steps 5706 and 5708 to determine whether to qualify or disqualify initialization parameters, a calculated rate, or both. The use of templates having different shapes may allow for more confidence in the results of a qualification. For example, if a calculated rate is 120 BPM or higher, then a symmetric template may be used. Further, if the calculated rate is below 120 BPM, then four templates may be used (e.g., symmetric and asymmetric, both with and without a dicrotic notch) to determine which template provides the best results during qualification.

In some embodiments, any or all of the illustrative steps of flow diagrams 5600 and 5700 may be suitably combined. The illustrative steps of flow diagrams 5600 and 5700 may be performed sequentially, simultaneously, alternately, or any other suitable combination. In some embodiments, variation in both the length and shape of a template may be used to aid in qualifying or disqualifying initialization parameters, a calculated rate, or both. In some embodiments, the shape of a template may depend on the length of the template. For example, templates of shorter length (i.e., shorter period), may exhibit more symmetry than templates of longer length. In some embodiments, a set of templates may be used, which each may have a particular length and shape. For example, a coarse set of templates (e.g., spanning a relatively large range of lengths, shapes, or both) may be used initially to determine a region of interest among the lengths and shapes (e.g., which templates provide the best result). A more refined set of templates, selected based on the region of interest, may then be used to calculate the rate with more accuracy, confidence, or both.

It will be understood that the Qualification Techniques disclosed herein are merely illustrative and any suitable variations may be implemented in accordance with the present disclosure. In some embodiments, the Qualification Techniques may be performed on signals other than cross-correlation signals. For example, the Qualification Techniques may be performed on any suitable physiological signal or any suitable signal derived thereof, such as a raw intensity signal, a conditioned intensity signal, and an autocorrelation signal. In some embodiments, it may be desired that the signal used in the Qualification Techniques includes a periodic component that corresponds to a physiological rate.

It will be understood that the templates used in the Qualification Techniques need not be scaled. In some embodiments, a library of templates may be stored in memory and accessible by the processing equipment. For each template, the library may store a complete range of desired template lengths (e.g., lengths corresponding to the range of 20-300 BPM, with a resolution of 1 BPM). Therefore, instead of scaling a template, the processing equipment may select a template with a desired length from the library. Regardless of how the template is selected or generated, the template may be referred to herein as a "reference waveform."

Any suitable variation of Search Mode may be implemented in accordance with the present disclosure. Several illustrative examples are provided and discussed in the context of FIGS. 58-60.

Figure 58:
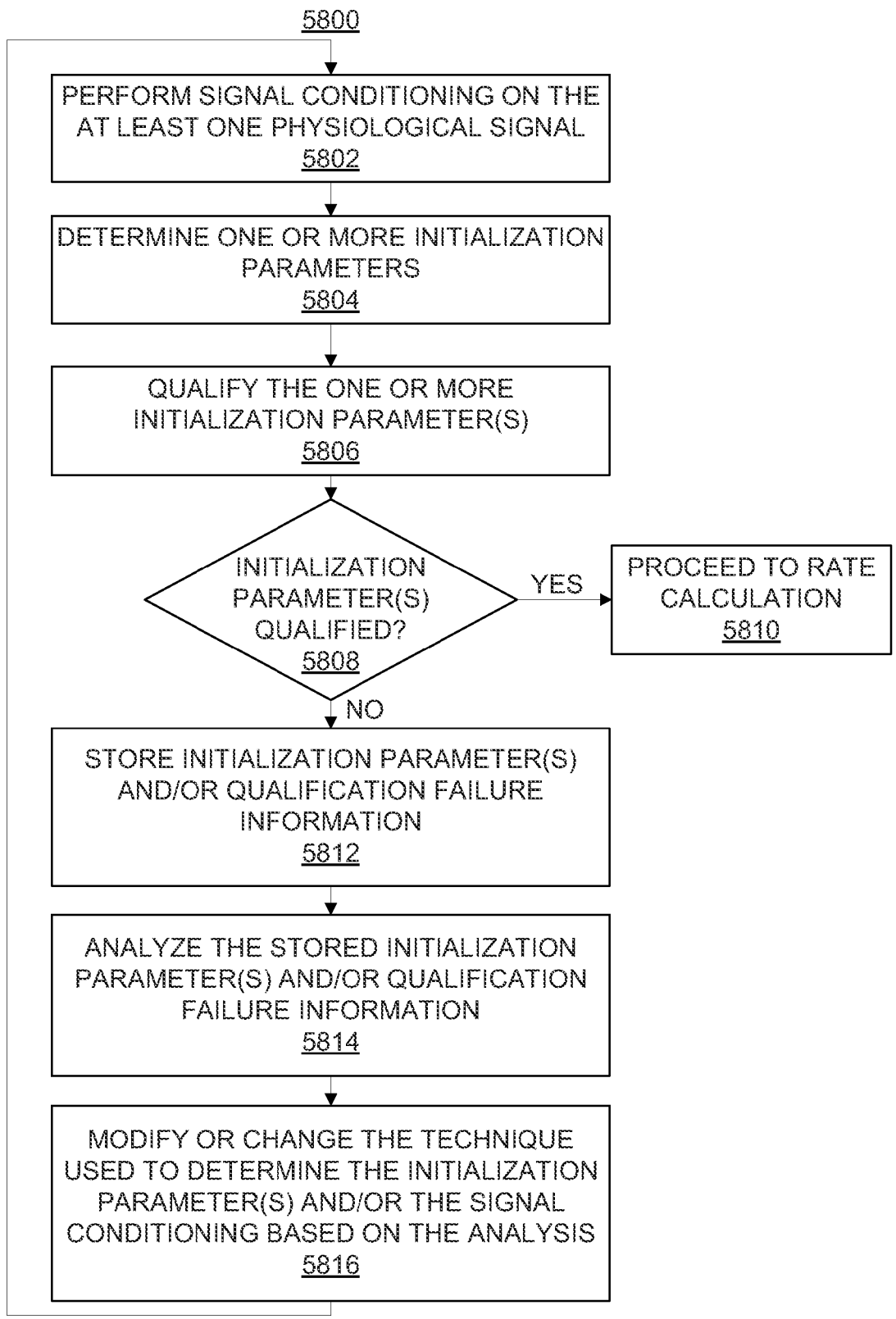
FIG. 58 is a flow diagram of illustrative steps for determining whether to change the Search Mode technique or to transition from Search Mode to Locked Mode, in accordance with some embodiments of the present disclosure.

FIG. 58 is a flow diagram 5800 of illustrative steps for determining whether to change the Search Technique or to transition from Search Mode to Locked Mode, in accordance with some embodiments of the present disclosure. In some embodiments, the illustrative steps of flow diagram 5800 may aid in preventing continual (e.g., repeated) disqualification of initialization parameters determined during Search Mode (e.g., by adjusting conditioning, processing, or both, of the signal).

Step 5802 may include processing equipment, pre-processor 320, or both, performing signal conditioning on at least one physiological signal. Signal conditioning may include filtering (e.g., low pass, high pass, band pass, notch, or any other suitable filter), amplifying, performing an operation on the received signal (e.g., taking a derivative, averaging), performing any other suitable signal conditioning, or any combination thereof. For example, in some embodiments, step 5802 may include removing a DC offset, low frequency components, or both, of the received physiological signal. In a further example, step 5802 may include smoothing the received physiological signal (e.g., using a moving average or other smoothing technique).

Step 5804 may include the processing equipment determining one or more initialization parameters. Step 5804 may be used by the processing equipment to estimate characteristics of the received physiological signal such as, for example, physiological rates, periods, or likely ranges thereof. In some embodiments, initialization parameters may include one or more settings of a band pass filter such as, for example, a high and low frequency cutoff value (e.g., a frequency range), a representative frequency value (or period value), a set of one or more coefficients, any other suitable parameters, or any combination thereof. The initialization parameters may be determined based on the physiological signal of step 5802. Any suitable Search Mode techniques disclosed herein, combinations thereof, or portions thereof, may be used at step 5804.

Step 5806 may include the processing equipment qualifying the one or more determined initialization parameters of step 5804, while step 5808 may include the processing equipment determining whether the qualification of step 5806 is sufficient. Step 5806 may include calculating one or more qualification metrics indicative of an estimated quality or accuracy of the determined initialization parameters. For example, a particular initialization parameter may be determined at step 5804, using any suitable Search Technique of the present disclosure. The particular initialization parameters may be evaluated, and if it is determined that the parameters do not qualify at step 5808, then the processing equipment may continue on to step 5812. If it is determined that the parameters do qualify at step 5808, then the processing equipment may proceed to performing a rate calculation at step 5810.

Step 5810 may include the processing equipment proceeding to performing rate calculation in Locked Mode using the initialization parameters determined at step 5804. Any suitable rate calculation technique disclosed herein, combination thereof, or portion thereof, may be used at step 5810.

Step 5812 may include the processing equipment storing one or more initialization parameters, qualification failure information, any other suitable information, or any combination thereof in any suitable memory. In some embodiments, for a particular initialization parameter, qualification failure information such as failure type maybe stored and catalogued, providing a historical record of failures.

Step 5814 may include the processing equipment analyzing the stored information of step 5812 (e.g., initialization parameters, qualification failure information). Analysis of the stored information may include reviewing a historical record of failures to identify a pattern, analyzing the results of other qualification tests, any other suitable analysis, or any combination thereof.

Step 5816 may include the processing equipment modifying, changing, or both, the Search Technique used to determine initialization parameters, the signal conditioning of the physiological signal, or any other suitable processes of Search Mode. Following performance of step 5816, steps 5802-5808 may be repeated to determine whether to proceed to performing the rate calculation.

In an illustrative example, referencing flow diagram 5800, qualification may repeatedly fail (i.e., repeated disqualification) due to locking onto of low frequency noise (e.g., in the case of a neonate). Illustratively, the low frequency noise may have a component in the 40-60 BPM range. In some such cases, especially in the case of neonates, step 5816 may include adjusting the signal conditioning of step 5802 to include a high-pass filter (e.g., with a cutoff point of 90 BPM) to effectively remove the lower-frequency components when repeated failures occur for initialization parameters corresponding to low BPM rates.

In a further illustrative example, referencing flow diagram 5800, an initialization parameter may correspond to a rate greater than 80 BPM, and the Angle Test may repeatedly output an angle sum of around 720°, causing disqualification. In some such cases, especially in the case of subjects with dicrotic notches, step 5816 may include adjusting the signal conditioning of step 5802 to include a notch filter (e.g., centered at the rate that repeatedly fails) to effectively remove or attenuate the dicrotic notch.

In a further illustrative example, referencing flow diagram 5800, the use of a cross-correlation waveform, cross-correlation output, or both, may be modified at step 5816. In some embodiments, only some segments of a cross-correlation waveform may be used (e.g., low-rate, high-rate, or any other particular segments may be omitted). In some embodiments, only some segments of a cross-correlation output may be analyzed (e.g., low-rate, high-rate, or any other particular segments may be ignored). In some embodiments, amplitudes of pulses within particular segments of a cross-correlation waveform may be adjusted, to change the likelihood of a maximum occurring within those particular segments. For example, the amplitude of pulses of a particular segment may be reduced to reduce the likelihood of a maximum amplitude occurring in that particular segment.

Figure 59:
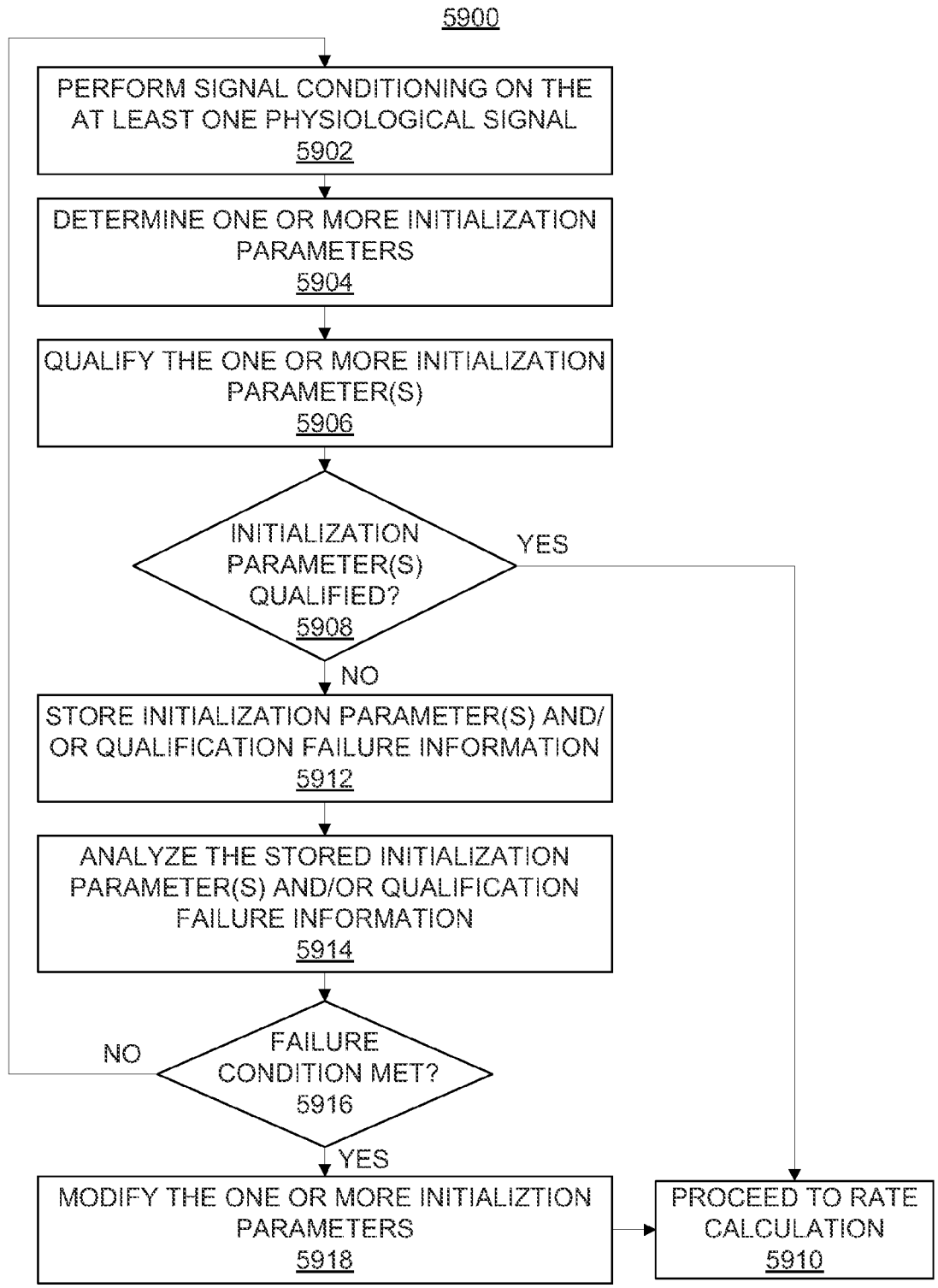
FIG. 59 is a flow diagram of illustrative steps for determining whether to transition from Search Mode to Locked Mode, in accordance with some embodiments of the present disclosure.

FIG. 59 is a flow diagram 5900 of illustrative steps for determining whether to transition from Search Mode to Locked Mode, in accordance with some embodiments of the present disclosure. In some embodiments, the illustrative steps of flow diagram 5900 may aid in preventing a repeated lock onto a rate other than a desired physiological rate (e.g., preventing locking on noise rather than a pulse rate).

Step 5902 may include processing equipment, pre-processor 320, or both, performing signal conditioning on at least one physiological signal. Signal conditioning may include filtering (e.g., low pass, high pass, band pass, notch, or any other suitable filter), amplifying, performing an operation on the received signal (e.g., taking a derivative, averaging), performing any other suitable signal conditioning, or any combination thereof. For example, in some embodiments, step 5902 may include removing a DC offset, low frequency components, or both, of the received physiological signal. In a further example, step 5902 may include smoothing the received physiological signal (e.g., using a moving average or other smoothing technique).

Step 5904 may include the processing equipment determining one or more initialization parameters. Step 5904 may be used by the processing equipment to estimate characteristics of the received physiological signal such as, for example, physiological rates, periods, or likely ranges thereof. In some embodiments, initialization parameters may include one or more settings of a band pass filter such as, for example, a high and low frequency cutoff value (e.g., a frequency range), a representative frequency value (or period value), a set of one or more coefficients, any other suitable parameters, or any combination thereof. The initialization parameters may be determined based on the physiological signal of step 5902. Any suitable Search Techniques disclosed herein, combinations thereof, or portions thereof, may be used at step 5904.

Step 5906 may include the processing equipment qualifying the one or more determined initialization parameters of step 5904, while step 5908 may include the processing equipment determining whether the qualification of step 5906 is sufficient. Step 5906 may include calculating one or more qualification metrics indicative of an estimated quality or accuracy of the determined initialization parameters. For example, a particular initialization parameter may be determined at step 5904, using any suitable Search Technique of the present disclosure. The particular initialization parameters may be evaluated, and if it is determined that the parameters do not qualify at step 5908, then the processing equipment may continue on to step 5912. If it is determined that the parameters do qualify at step 5908, then the processing equipment may proceed to performing a rate calculation at step 5910.

Step 5910 may include the processing equipment proceeding to performing a rate calculation in Locked Mode using the initialization parameters determined at step 5904. Any suitable Rate Calculation Technique disclosed herein, combination thereof, or portion thereof, may be used at step 5910.

Step 5912 may include the processing equipment storing one or more initialization parameters, qualification failure information, any other suitable information, or any combination thereof in any suitable memory. In some embodiments, for a particular initialization parameter, qualification failure information such as failure type maybe stored and catalogued, providing a historical record of failures.

Step 5914 may include the processing equipment analyzing the stored information of step 5912 (e.g., initialization parameters, qualification failure information). Analysis of the stored information may include reviewing a historical record of failures to identify a pattern, analyzing the results of other Qualification tests, any other suitable analysis, or any combination thereof.

Step 5916 may include the processing equipment determining whether one or more failure conditions have been met, based on the analysis of step 5914. If the processing equipment determines that one or more failure conditions have been met, the processing equipment then may proceed to step 5918. If the processing equipment determines that one or more failure conditions have not been met, the processing equipment then may proceed back to step 5902. In some embodiments, failure conditions may include particular results of particular tests. For example, the result of the Angle Test may be used to determine if one or more initialization parameters correspond to a half-rate condition.

Step 5918 may include the processing equipment modifying the one or more initialization parameters of step 5904. Step 5918 may include the processing equipment modifying the initialization parameter (e.g., a rate or range of rates) by a multiple (e.g., doubling or halving the rate) based on the analysis of step 5914. For example, the processing equipment may determine that initialization parameter(s) are indicative of a harmonic of the physiological rate at step 5914, and may modify the initialization parameter(s) to correspond to a fundamental frequency of the physiological rate at step 5918.

In an illustrative example, referencing flow diagram 5900, the processing equipment may consistently lock onto a one half, double, triple, or other multiple of the true physiological rate. If the initialization parameter corresponds to 50 BPM, and the Angle Test repeatedly outputs about 720°, step 5918 may include setting the initialization parameter to correspond to 100 BPM (i.e., doubling the rate, halving the period) and proceeding to a Rate Calculation Technique.

Figure 60:
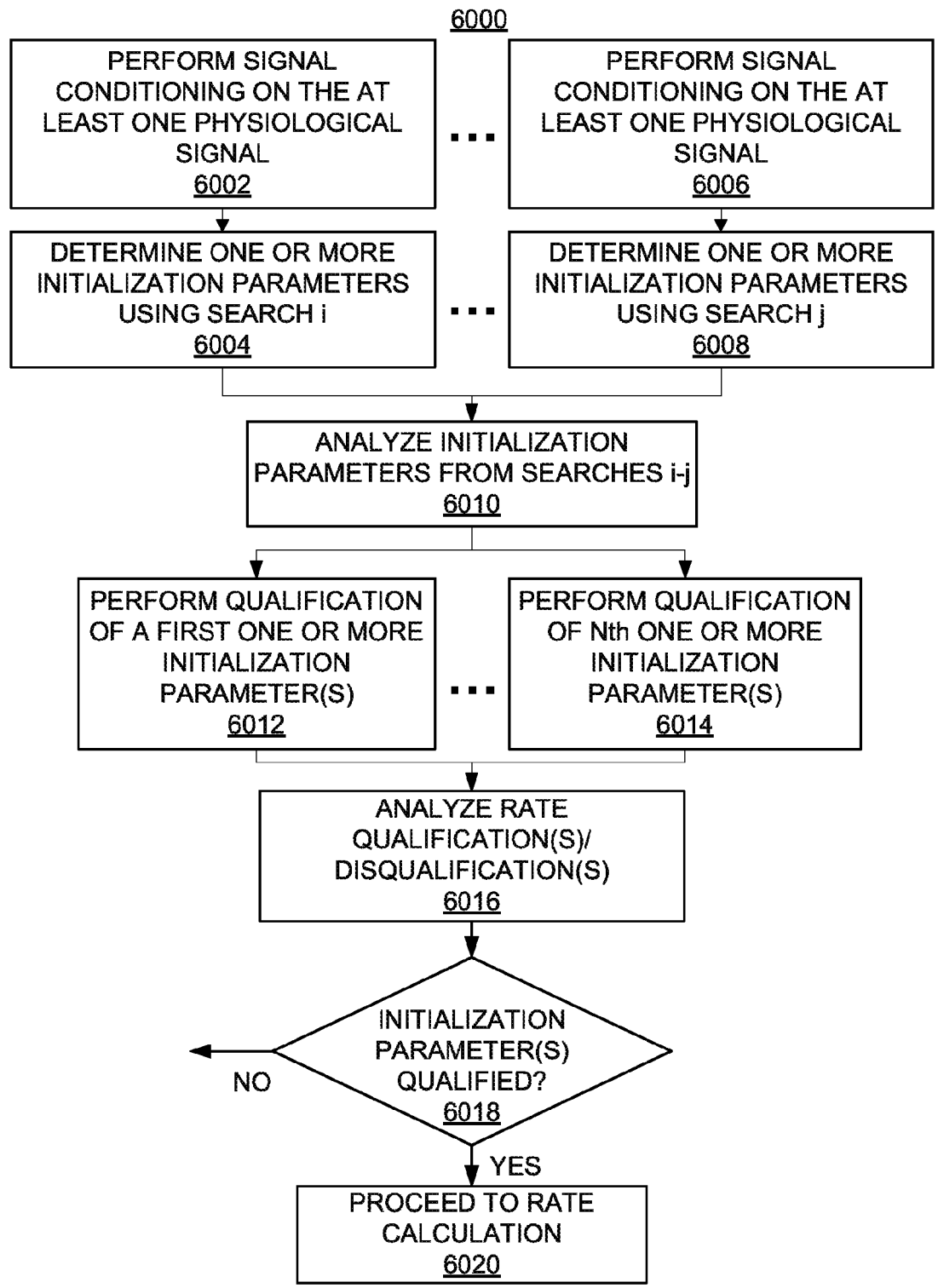
FIG. 60 is a flow diagram of illustrative steps for determining whether to transition from Search Mode to Locked Mode using multiple techniques, in accordance with some embodiments of the present disclosure.

FIG. 60 is a flow diagram 6000 of illustrative steps for determining whether to transition from Search Mode to Locked Mode using multiple techniques, in accordance with some embodiments of the present disclosure. In some embodiments, the illustrative steps of flow diagram 6000 may aid in determining a physiological rate by using more than one technique to condition a physiological signal, search for initialization parameters, qualify initialization parameters, or combinations thereof. In some embodiments, the use of multiple techniques may increase accuracy, confidence, or both of initialization parameters. In some embodiments, the use of multiple techniques may address any weaknesses in any single technique and accordingly provide a more robust calculation.

Step 6002 may include processing equipment, pre-processor 320, or both, performing signal conditioning on at least one physiological signal. Signal conditioning may include filtering (e.g., low pass, high pass, band pass, notch, or any other suitable filter), amplifying, performing an operation on the received signal (e.g., taking a derivative, averaging), performing any other suitable signal conditioning, or any combination thereof. For example, in some embodiments, step 6002 may include removing a DC offset, low frequency components, or both, of the received physiological signal. In a further example, step 6002 may include smoothing the received physiological signal (e.g., using a moving average or other smoothing technique).

Step 6004 may include the processing equipment determining one or more initialization parameters, or other algorithm settings (e.g., such as those used to generate a threshold), using a particular Search Technique. Step 6004 may be used by the processing equipment to estimate characteristics of the received physiological signal such as, for example, physiological rates, periods, or likely ranges thereof. In some embodiments, initialization parameters may include one or more settings of a band pass filter such as, for example, a high and low frequency cutoff value (e.g., a frequency range), a representative frequency value (or period value), a set of one or more coefficients, any other suitable parameters, or any combination thereof. The initialization parameters may be determined based on the physiological signal of step 6002. Any suitable Search Techniques disclosed herein (e.g., Search Techniques 1, 2, 3, or 4), combinations thereof, or portions thereof, may be used at step 6004.

Step 6006 may include the processing equipment, pre-processor 320, or both, performing signal conditioning on the same at least one physiological signal of step 6002. Signal conditioning may include filtering (e.g., low pass, high pass, band pass, notch, or any other suitable filter), amplifying, performing an operation on the received signal (e.g., taking a derivative, averaging), performing any other suitable signal conditioning, or any combination thereof. For example, in some embodiments, step 6006 may include removing a DC offset, low frequency components, or both, of the received physiological signal. In a further example, step 6006 may include smoothing the received physiological signal (e.g., using a moving average or other smoothing technique).

In some embodiments, step 6006 may include different signal conditioning techniques than those used at step 6002. For example, step 6002 may include applying a low-pass filter to the physiological signal, while step 6006 may include applying a high-pass filter to the physiological signal. In a further example, step 6002 may include removing 60 Hz noise, 50 Hz noise, and harmonics using band-stop filters or notch filters, while step 6006 may include applying a low-pass filter to remove high-frequency noise. Although only two signal conditioning steps are shown in flow diagram 6000, any suitable number of signal conditioning steps may be performed, as indicated by the ellipsis.

Step 6008 may include the processing equipment determining one or more initialization parameters, or other algorithm settings (e.g., such as those used to generate a threshold), using a particular Search Technique. Step 6008 may be used by the processing equipment to estimate characteristics of the received physiological signal such as, for example, physiological rates, periods, or likely ranges thereof. In some embodiments, initialization parameters may include one or more settings of a band pass filter such as, for example, a high and low frequency cutoff value (e.g., a frequency range), a representative frequency value (or period value), a set of one or more coefficients, any other suitable parameters, or any combination thereof. The initialization parameters may be determined based on the physiological signal of step 6006. Any suitable Search Techniques disclosed herein (e.g., Search Technique 1, 2, 3, or 4), combinations thereof, or portions thereof, may be used at step 6008.

In some embodiments, step 6008 may include the same Search Technique used at step 6004. For example, step 6004 may include performing Search Technique 4, in which a cross-correlation output is analyzed, while step 6008 may also include performing Search Technique 4 (e.g., with a different cross-correlation waveform than step 6004), in which a cross-correlation output is analyzed.

In some embodiments, step 6008 may include a different Search Technique than that used at step 6004. For example, step 6004 may include performing Search Technique 1, in which peak crossings are analyzed, while step 6008 may include performing Search Technique 2, in which peak shapes are analyzed. In some embodiments, the Search Technique used may depend on the signal conditioning technique used, and vice versa. For example, if Search Technique 2 is performed at step 6004, step 6008, or both, a respective high-pass filter may be used to reduce or eliminate low-frequency noise that would likely affect peak shape.

In some embodiments, steps 6004 and 6008 may be performed sequentially. In some embodiments, depending upon the result of step 6004, step 6008 may, but need not, be performed. In some embodiments, steps 6004 and 6008 may be performed in parallel (e.g., simultaneously or near simultaneously). Although only two initialization parameter determination steps are shown in flow diagram 6000, any suitable number of initialization parameter determination steps may be performed, as indicated by the ellipsis.

Step 6010 may include the processing equipment analyzing the initialization parameters (e.g., corresponding rates), or other algorithm settings, resulting from the determinations (e.g., Searches) of steps 6004 and 6008. In some embodiments, the analysis of step 6010 may include combining the initialization parameters of steps 6004 and 6008. For example, at step 6010, the initialization parameters of steps 6004 and 6008 may be averaged with or without adjustable weighting. In a further example, at step 6010, the initialization parameters of steps 6004 and 6008 may be input into a histogram (e.g., with historical results, or results from additional determinations) and the initialization parameters, or range thereof, exhibiting the maximum occurrence may be selected. In a further example, at step 6010, the average and standard deviation of the initialization parameters of steps 6004 and 6008 may be calculated. If the standard deviation is too large relative to the average (e.g., as compared to a threshold), step 6010 may require that any or all of steps 6002-6008 be repeated. In some embodiments, the analysis of step 6010 may include disregarding one or more initialization parameters. For example, at step 6010, the initialization parameters of steps 6004 and 6008 may be averaged without outliers (e.g., initialization parameters outside of a particular number of standard deviations from the mean).

In some embodiments, the initialization parameters of both step 6004 and 6008 may be analyzed at step 6010, and both may be subjected to Qualification following step 6010. For example, both steps 6004 and 6008 may result in initialization parameters that may be subjected to qualification at steps 6012 or 6014, and step 6010 need not be performed. In some embodiments, during the analysis of step 6010, none of the initialization parameters may be subjected to Qualification, and the process may end at step 6010, or may repeat (not shown) beginning at any of steps 6002-6008.

Step 6012 may include the processing equipment qualifying (or disqualifying) a first set of one or more initialization parameters, or other algorithm settings, using any suitable Qualification Technique. In some embodiments, step 6012 may include performing a Symmetry Test, performing a Radius Test, performing an Angle Test, performing an Area Test, performing an Area Similarity Test, performing a Statistical Property Test, performing any other suitable analysis, performing any portions thereof, or any combination thereof. In some embodiments, the output of step 6012 may be one or more qualification metrics (e.g., a radius calculation, an angle sum calculation, cross-correlation area, or other suitable metric or combination thereof)

Step 6014 may include the processing equipment qualifying (or disqualifying) an Nth set of one or more initialization parameters, or other algorithm settings, using any suitable Qualification Technique. In some embodiments, the qualification of step 6014 may be of the same type as the qualification of step 6012. For example, both steps 6012 and 6014 may include performing an Area Test. In some embodiments, the qualification of step 6014 may be of a different type than the qualification of step 6012. For example, step 6012 may include performing a Radius Test and an Angle Test, while step 6014 may include performing a Statistical Property Test.

In some embodiments, the qualifications of steps 6012 and 6014 may be performed using the same qualification information (e.g., initialization parameters, calculated rate), different initialization parameters, or any combination thereof. For example, both steps 6012 and 6014 may include performing a Symmetry Test, each using a particular period P associated with initialization parameters from steps 6004 and 6008. Any suitable number of sets of one or more initialization parameters may be qualified (or disqualified) at steps 6012 and 6014.

In some embodiments, steps 6012 and 6014 may be performed sequentially. In some embodiments, depending upon the result of step 6012, step 6014 may, but need not, be performed. In some embodiments, steps 6012 and 6014 may be performed in parallel (e.g., simultaneously). Although only two qualification steps are shown in flow diagram 6000, any suitable number of qualification steps may be performed, as indicated by the ellipsis.

Step 6016 may include the processing equipment analyzing the qualifications and/or disqualifications of steps 6012 and 6014. In some cases, steps 6012 and 6014 may give conflicting results such as, for example, step 6012 may qualify an initialization parameter while 6014 may disqualify the initialization parameter. In some cases, steps 6012 and 6014 may both qualify respective initialization parameters. In some embodiments, the analysis of step 6016 may include determining whether the respective qualified initialization parameters of steps 6012 and 6014 are the same, and how to proceed. For example, if the qualified initialization parameters are the same, and are not an unreasonable (e.g., outside of expected ranges), step 6016 may output the qualified initialization parameters to step 6018. In some cases, only some initialization parameters may be qualified. In some embodiments, the processing equipment may determine a resulting algorithm setting (e.g., initialization parameters), based on whether the algorithm settings of step 6012 and 6014 are qualified. For example, if two algorithm settings are qualified at respective steps 6012 and 6014, the processing equipment may combine the two algorithm settings.

Step 6018 may include the processing equipment determining whether the qualification of steps 6012 and 6014 are sufficient based on the analysis of step 6016. Steps 6012-6016 may include calculating one or more qualification metrics indicative of an estimated quality or accuracy of the determined initialization parameters. For example, a particular initialization parameter may be determined at steps 6004 and 6008, using any suitable Search Technique(s) of the present disclosure. The particular initialization parameters may be evaluated, and if it is determined that the parameters do not qualify at steps 6012 and 6014, then the processing equipment may repeat any of the steps of flow diagram 6000 (e.g., steps 6002-6016), wait for the next window of data to be buffered (e.g., to partially or fully replace the current window of data), or both. If it is determined that the parameters do qualify at step 5908, then the processing equipment may proceed to performing a rate calculation at step 6020.

Step 6020 may include the processing equipment proceeding to performing a rate calculation in Locked Mode using the initialization parameters determined at steps 6004 and 6008. Any suitable Rate Calculation Technique disclosed herein, combination thereof, or portion thereof, may be used at step 6020.

In some embodiments, the processing equipment may combine metrics, qualifications/disqualifications, any other suitable information, or any combination thereof in a neural network to determine which Technique may be desired under some circumstances. In some embodiments, for example, as system 300 processes data over time, the processing equipment may use a neural network to adapt the Techniques and parameters thereof used by the processing equipment to determine physiological information of a subject. For example, as initialization parameters are qualified and/or disqualified at step 6018, the processing equipment may adjust or otherwise update thresholds, criterion, or analysis techniques to select initialization parameters having higher probabilities of being qualified.

In some embodiments, the processing equipment may evaluate metric magnitudes, margins by which a test is passed or failed, any other suitable information, or any combination thereof, to determine how to proceed. In some embodiments, as one or more Qualification Techniques are applied to the initialization parameters of steps 6004 and 6008, the processing equipment may compare results. For example, if steps 6004 and 6008 output different initialization parameters that are both qualified at step 6016, the processing equipment may evaluate whether one set of initialization parameters passed a particular test by a relatively higher margin. Accordingly, the processing equipment may select the initialization parameters passing a qualification test by the highest margin to use in a rate calculation.

In some embodiments, signal conditioning may be applied to a physiological signal to aid in processing the signal for rate information. As described above, signal conditioning may include filtering, de-trending, smoothing, any other suitable conditioning, or any combination thereof. Physiological pulse rates may generally fall into a particular range (e.g., 20-300 BPM for humans), and accordingly signal conditioning may be used to reduce the presence or effects of signal components outside of this particular range. Further, a narrower pulse range may be expected for a subject, based on previous data for example, and a signal may be conditioned accordingly. The presence of noise may be also be addressed using signal conditioning. For example, ambient radiation (e.g., from artificial lighting, monitors, or sunlight) may impart a noise component in a physiological signal. In a further example, electronic noise (e.g., system noise) may also impart a noise component in a physiological signal. In a further example, motion or other subject activity may alter a physiological signal, possible obscuring signal components of interest for extracting rate information. In some embodiments, the Signal Conditioning techniques discussed herein may apply to Search Mode, Locked Mode, or any other suitable task performed by the processing equipment that may involve a physiological signal.

Figure 61:
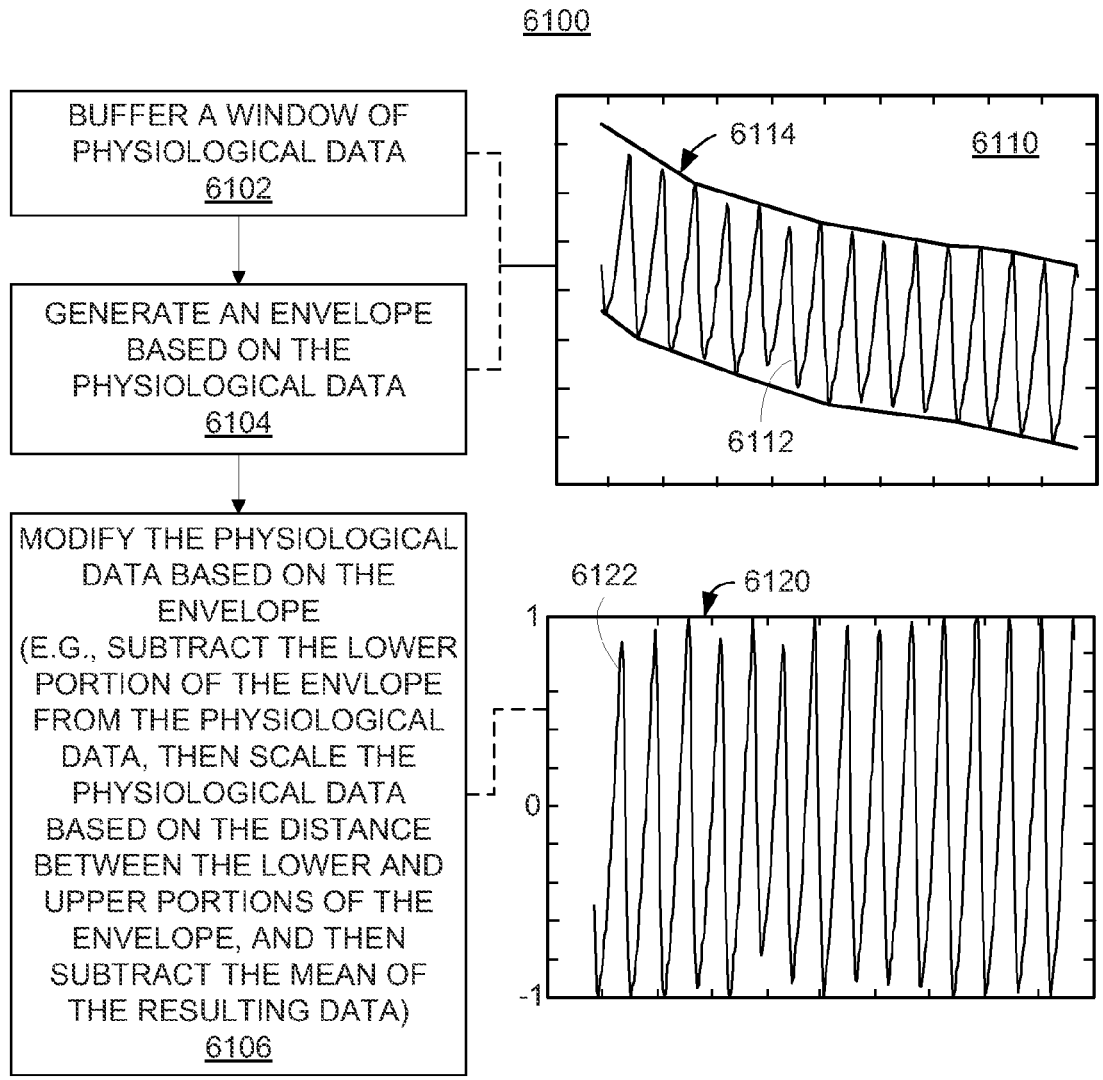
FIG. 61 is a flow diagram of illustrative steps for modifying physiological data using an envelope, in accordance with some embodiments of the present disclosure.

FIG. 61 is a flow diagram 6100 of illustrative steps for modifying a window of physiological data (e.g., a segment of an intensity signal) using an envelope, in accordance with some embodiments of the present disclosure. In some embodiments, the illustrative steps of flow diagram 6100 may aid in conditioning a physiological signal by adjusting a baseline, scaling at least some peaks, or both. In some embodiments, the illustrative steps of flow diagram 6100 may aid in reducing the effects of low frequency components (e.g., a constant or drifting baseline, peak amplitude changes) during subsequent processing of the window of data.

Step 6102 may include processing equipment buffering a window of data, derived from a physiological signal. In some embodiments, the window may include a particular time interval (e.g., the most recent six seconds of a processed physiological signal). Step 6102 may include pre-processing (e.g., using pre-processor 320) the output of a physiological sensor, and then storing a window of the processed data in any suitable memory or buffer (e.g., queue serial module 72 of FIG. 2), for further processing by the processing equipment. In some embodiments, the window of data may be recalled from data stored in memory (e.g., RAM 54 of FIG. 2 or other suitable memory) for subsequent processing. In some embodiments, the window size (e.g., the number of samples or time interval of data to be buffered) of data is selected to capture multiple periods of oscillatory physiological activity. Panel 6110 shows an illustrative window of data 6112 derived from a physiological signal.

Step 6104 may include the processing equipment generating an envelope (e.g., upper and lower bounding curves) based on the window of data of step 6102. The envelope may include an upper trace, which may be an outline of the peak data values, and a lower trace, which may be an outline of the valley data values. In some embodiments, the upper and lower traces may be generated using a mathematical formalism such as, for example, a linear or spline fit through the data points. The upper and lower traces may coincide with all, some, or no data points, depending on the enveloping technique used. Any suitable technique may be used to generate an envelope of the window of data. Panel 6110 shows an illustrative envelope 6114 generated for window of data 6112.

Step 6106 may include the processing equipment modifying the physiological data of step 6102 based on the envelope of step 6104. In some embodiments, step 6106 may include generating a new window of data. For example, The midpoint of the difference between the lower and upper trace at each location may be set as a new origin (e.g., a baseline). The upper and lower traces may then be scaled to respective desired values at each point (e.g., 1 and 0, respectively, or 1 and −1, respectively) and the window of data may be similarly amplitude scaled at each point. In a further example, the lower trace may be subtracted from the window of data. The window of data may then be scaled to respective desired values at each point (e.g., to between 2 and 0) based on the difference between the lower and upper traces. The mean may then be subtracted, centering the window of data about zero. Referencing Eq. 28 below, either of the two previous examples gives a modified window of data $M_{-1,1}(x_i)$ for each data point i at data point location $x_i$, ranging from −1 to 1, in which $f(x_i)$ is the initial window of data, $g(x_i)$ is the lower trace, and $h(x_i)$ is the upper trace. Referencing Eq. 29 below, either of the two previous examples gives a modified window of data $M_{0,1}(x_i)$ for each data point i at data point location $x_i$, ranging from 0 to 1, in which $f(x_i)$ is the initial window of data, $g(x_i)$ is the lower trace, and $h(x_i)$ is the upper trace. Any suitable mathematical formula, such as Eqs. 28 or 29, or any other suitable equation, may be used to modify a window of data based on an envelope.

$$M_{-1,1}(x_i) = \frac{2(f(x_i) - g(x_i))}{h(x_i) - g(x_i)} - 1 \tag{28}$$

$$M_{0,1}(x_i) = \frac{(f(x_i) - g(x_i))}{h(x_i) - g(x_i)} \tag{29}$$

In some embodiments, the processing equipment may down-weight outlier points in the buffered window of data. In some embodiments, the processing equipment may down-weight one or more points at each end of the buffered window of data. It will be understood that the envelope may be used to modify the physiological data to be within any suitable range, and that the ranges of 0 to 1, and −1 to 1, are included as illustrative examples.

Panel 6120 shows an illustrative modified window of data 6122, scaled to range from −1 to 1, centered about zero. Note that the lower and upper traces have been scaled to lie horizontal at −1 and 1, respectively, and window of data 6122 has been scaled accordingly. As compared to window of data 6112, modified window of data 6122 is shown to have a baseline of zero (rather than the trending baseline of window of data 6112), and a more consistent range of peak and valley values. Modified window of data 6122 may be used in any of the disclosed Search Techniques, Rate Calculation techniques, or any other suitable processes accepting a window of data derived from a physiological signal as an input.

Figure 62:
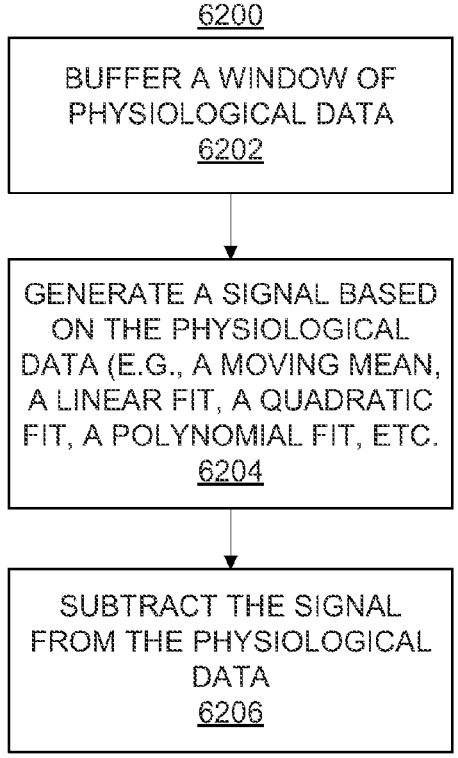
FIG. 62 is a flow diagram of illustrative steps for modifying physiological data by subtracting a trend, in accordance with some embodiments of the present disclosure.

FIG. 62 is a flow diagram 6200 of illustrative steps for modifying physiological data by subtracting a trend, in accordance with some embodiments of the present disclosure. In some embodiments, the illustrative steps of flow diagram 6200 may aid in conditioning a physiological signal by modifying a baseline. In some embodiments, the illustrative steps of flow diagram 6200 may aid in reducing the effects of low frequency components (e.g., a constant or drifting baseline) during subsequent processing of the window of data.

Step 6202 may include processing equipment buffering a window of data, derived from a physiological signal. In some embodiments, the window may include a particular time interval (e.g., the most recent six seconds of a processed physiological signal). Step 6202 may include pre-processing (e.g., using pre-processor 320) the output of a physiological sensor, and then storing a window of the processed data in any suitable memory or buffer (e.g., queue serial module 72 of FIG. 2), for further processing by the processing equipment. In some embodiments, the window of data may be recalled from data stored in memory (e.g., RAM 54 of FIG. 2 or other suitable memory) for subsequent processing. In some embodiments, the window size (e.g., the number of samples or time interval of data to be buffered) of data is selected to capture multiple periods of oscillatory physiological activity.

Step 6204 may include the processing equipment generating a signal based on the window of data of step 6202. The generated signal may represent a baseline or otherwise a trend in the window of data of step 6202. In some embodiments, the signal generated at step 6204 may include a moving mean, a linear fit (e.g., from a linear regression), a quadratic fit, any other suitable polynomial fit (e.g., using a "least-squares" regression), any other suitable functional fit (e.g., exponential, logarithmic, sinusoidal), any piecewise combination thereof, or any other combination thereof. Any suitable technique for generating a signal indicative of a trend may be used at step 6204. In some embodiments, each data point within the window of data may be given equal weighting. In some embodiments the processing equipment may down-weight outlier points or one or more points at each end of the buffered window of data.

Step 6206 may include the processing equipment subtracting the generated signal of step 6204 from the window of data of step 6202. In some embodiments, step 6206 may include generating a new window of data (e.g., the window data of step 6202 with the signal of step 6204 removed), which may be further processed, stored in any suitable memory, or both. Subtraction of the signal of step 6204 from the window of data of step 6202 may aid in processing the data for rate information by removing low frequency components. Further illustration of the signal subtraction of flow diagram 6200 is provided by FIGS. 63-65.

Figure 63:
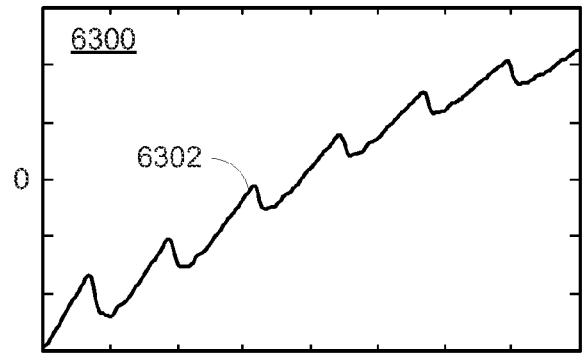
FIG. 63 is a plot of an illustrative window of data with the mean removed, in accordance with some embodiments of the present disclosure.

FIG. 63 is a plot 6300 of an illustrative window of data 6302 with the mean removed, in accordance with some embodiments of the present disclosure. The abscissa of plot 6300 is presented in units proportional to sample number, while the ordinate is presented in arbitrary units, with zero notated. Window of data 6302 is shown to include an increasing baseline, even with the mean value of the data removed. Accordingly, subtraction of the mean may provide unsatisfactory results when used with data having a changing baseline. In some such circumstances, a linear baseline, or other suitable trending baseline, may be subtracted from the window of data rather than a mean value. In some cases, in which the baseline of a window of data may be relatively constant, a mean subtraction may be preferred to a more complex baseline fit.

Figure 64:
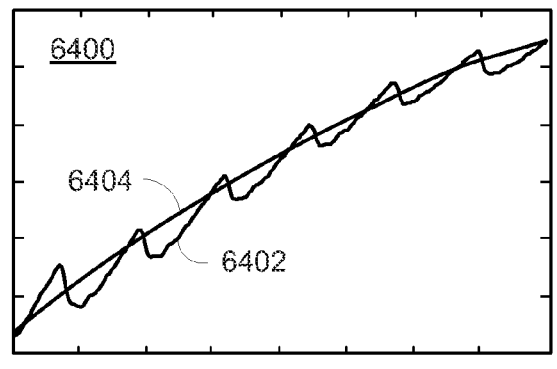
FIG. 64 is a plot of an illustrative window of data and a quadratic fit, in accordance with some embodiments of the present disclosure.
Figure 65:
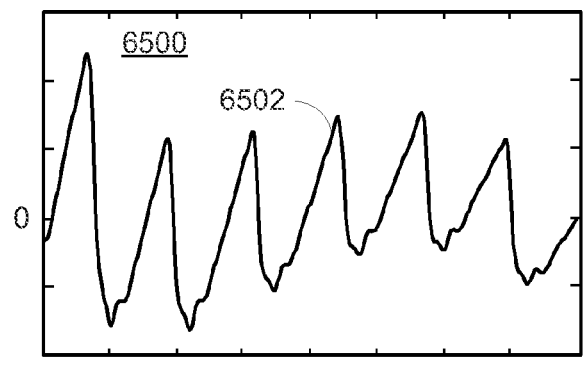
FIG. 65 is a plot of the illustrative window of data of FIG. 64 with the quadratic fit subtracted, in accordance with some embodiments of the present disclosure.

FIG. 64 is a plot 6400 of an illustrative window of data 6402 and a quadratic fit 6404, in accordance with some embodiments of the present disclosure. The abscissa of plot 6400 is presented in units proportional to sample number, while the ordinate is presented in arbitrary units. As compared to FIG. 63, quadratic fit 6404 follows the trending baseline of window of data 6402 more closely than a mean subtraction would be capable of. FIG. 65 a plot 6500 of modified window of data 6502 derived from illustrative window of data 6402 of FIG. 64 with quadratic fit 6404 subtracted, in accordance with some embodiments of the present disclosure. The abscissa of plot 6500 is presented in units proportional to sample number, while the ordinate is presented in arbitrary units, with zero notated. Modified window of data 6502 is substantially centered about zero, with a relatively constant baseline of zero.

Figure 66:
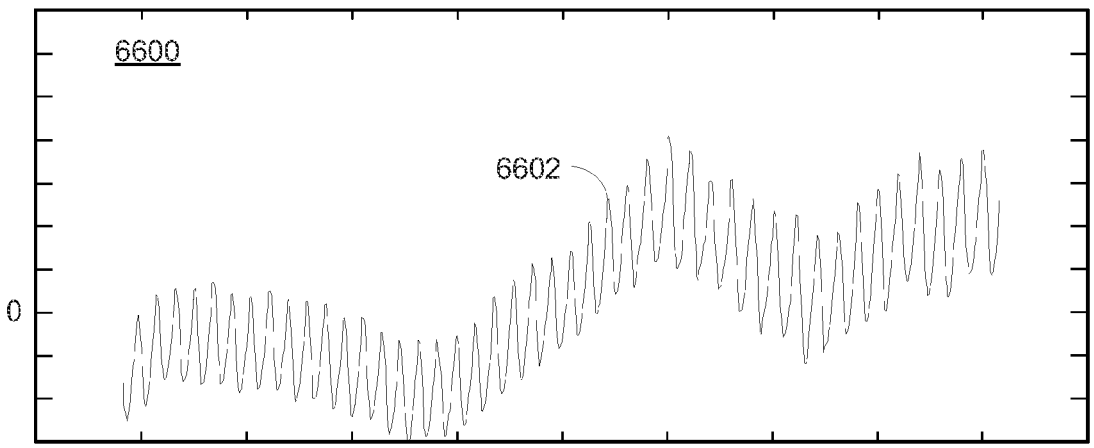
FIG. 66 is a plot of an illustrative modified window of data derived from an original window of data with the mean subtracted, in accordance with some embodiments of the present disclosure.
Figure 67:
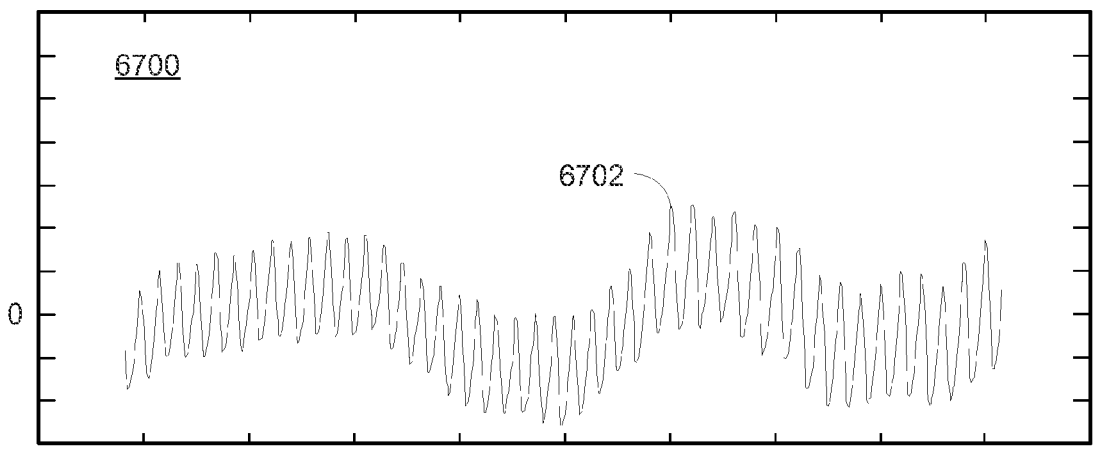
FIG. 67 is a plot of an illustrative modified window of data derived from the same original window of data as FIG. 66 with a linear baseline subtracted, in accordance with some embodiments of the present disclosure.
Figure 68:
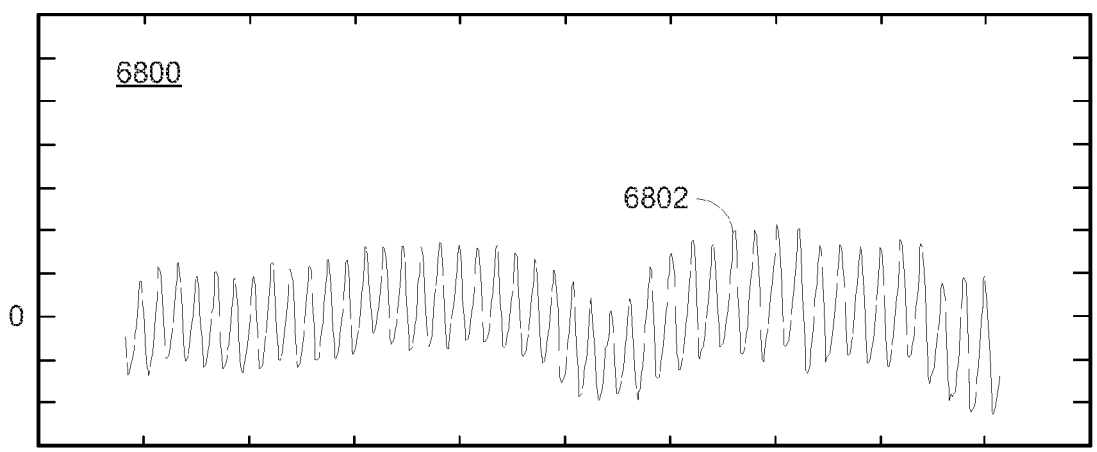
FIG. 68 is a plot of an illustrative modified window of data derived from the same original windows of data as FIGS. 66 and 67 with a quadratic baseline subtracted, in accordance with some embodiments of the present disclosure.

FIG. 66 is a plot 6600 of an illustrative modified window of data 6602 derived from an original window of data with the mean subtracted, in accordance with some embodiments of the present disclosure. The abscissa of plots 6600, 6700, and 6800 of FIGS. 66-68 are presented in units proportion to time (or sample number), while the ordinate is presented in arbitrary units, with zero notated. Modified window of data 6602 exhibits significant low frequency activity that is not substantially reduced nor eliminated by mean subtraction. Accordingly, modified window of data 6602 may present challenges for some techniques for extracting rate information. Note that modified window of data 6602 spans seven tick marks along the ordinate, in arbitrary units.

FIG. 67 is a plot 6700 of an illustrative modified window of data 6702 derived from the same original window of data as FIG. 66 with a linear baseline subtracted, in accordance with some embodiments of the present disclosure. Note that modified window of data 6702 spans almost six tick marks along the ordinate, in similar units of plot 6600, and accordingly exhibits relatively less (e.g., smaller amplitude) low frequency activity than modified windows of data 6602.

FIG. 68 is a plot 6800 of an illustrative modified window of data 6802 derived from the same original windows of data as FIGS. 66 and 67 with a quadratic baseline subtracted, in accordance with some embodiments of the present disclosure. Note that modified window of data 6802 spans almost four tick marks along the ordinate, in similar units of plots 6600 and 6700, and accordingly exhibits relatively less (e.g., smaller amplitude) low frequency activity than either of modified windows of data 6602 and 6702. In some circumstances, the subtraction of a quadratic fit may provide better results than a mean subtraction or linear subtraction. In some circumstances, the subtraction of a higher order polynomial fit, or any other suitable fit, may provide better results than a mean subtraction, linear subtraction, or quadratic subtraction. In some circumstances, a relatively simpler baseline fit may be preferred to a more complex baseline fit.

Figure 69:
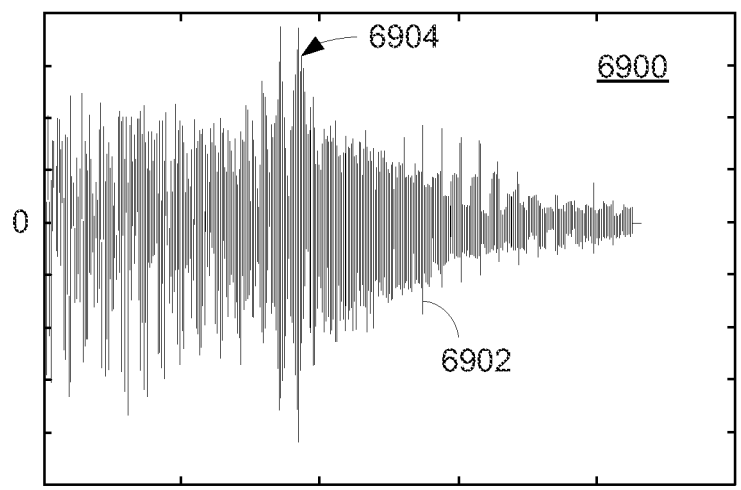
FIG. 69 is a plot of an illustrative cross-correlation output, calculated using a particular window of data with the mean removed, in accordance with some embodiments of the present disclosure.
Figure 70:
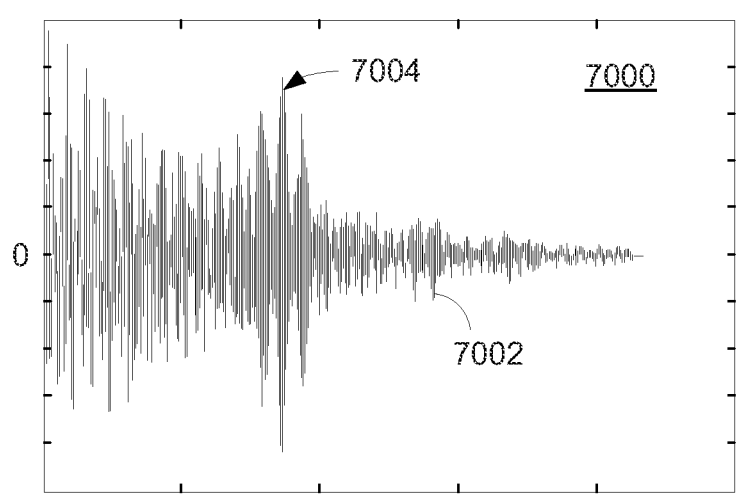
FIG. 70 is a plot of an illustrative cross-correlation output, calculated using the same particular window of data of FIG. 69 with a linear fit removed, in accordance with some embodiments of the present disclosure.
Figure 71:
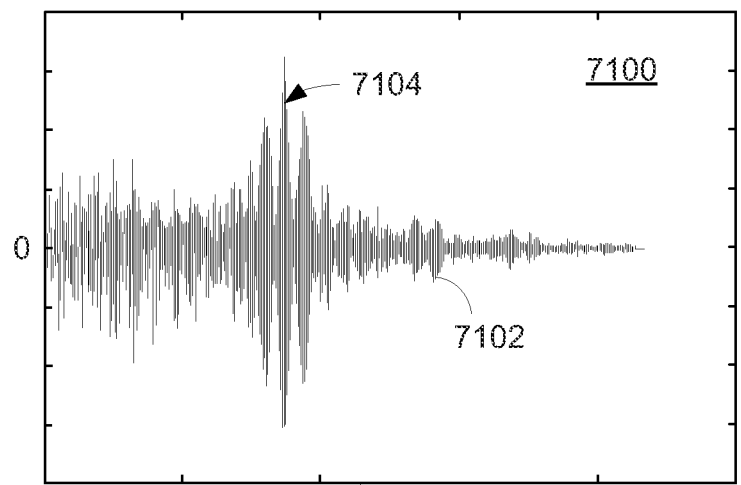
FIG. 71 is a plot of an illustrative cross-correlation output, calculated using the same particular window of data of FIGS. 69 and 70 with a quadratic fit removed, in accordance with some embodiments of the present disclosure.

Some illustrative effects of signal conditioning will be shown and discussed in the context of FIGS. 69-71.

FIG. 69 is a plot 6900 of an illustrative cross-correlation output 6902 (using a suitable cross-correlation waveform), calculated using a particular window of data with the mean removed, in accordance with some embodiments of the present disclosure. The abscissa of plots 6900, 7000, and 7100 of FIGS. 69-71 are presented in units of cross-correlation lag (e.g., in time or samples), while the ordinate is presented in arbitrary units, with zero notated. Cross-correlation output 6902 may be generated using any suitable technique (e.g., using flow diagram 1800 of FIG. 18, or flow diagram 3800 of FIG. 38, or any other technique disclosed herein). The one or more segments of cross-correlation output 6902 substantially corresponding to a physiological rate are indicated by region 6904. Relatively lower frequency components are evident (e.g., in the area to the left of region 6904), reducing the relative difference in amplitude between segments corresponding to a physiological rate and segments corresponding to noise.

FIG. 70 is a plot 7000 of an illustrative cross-correlation output 7002 (using a suitable cross-correlation waveform), calculated using the same particular window of data of FIG. 69 with a linear fit removed, in accordance with some embodiments of the present disclosure. Cross-correlation output 7002 may be generated using any suitable technique (e.g., using flow diagram 1800 of FIG. 18, or flow diagram 3800 of FIG. 38, or any other technique disclosed herein). The one or more segments of cross-correlation output 6902 substantially corresponding to a physiological rate are indicated by region 7004. Relatively lower frequency components are evident, forming a second peaking structure at the lowest frequencies. However, compared to cross-correlation output 6902, cross-correlation output 7002 exhibits increased separation between the physiological peak indicated by 7004 and lower frequency noise. The subtraction of a linear fit from a window of data may, in some circumstances, provide increased peak separation relative to subtraction of the mean.

FIG. 71 is a plot 7100 of an illustrative cross-correlation output 7102 (using a suitable cross-correlation waveform), calculated using the same particular window of data of FIGS. 69 and 70 with a quadratic fit removed, in accordance with some embodiments of the present disclosure. Cross-correlation output 7102 may be generated using any suitable technique (e.g., using flow diagram 1800 of FIG. 18, or flow diagram 3800 of FIG. 38, or any other technique disclosed herein). The one or more segments of cross-correlation output 7102 substantially corresponding to a physiological rate are indicated by region 7104. Relatively lower frequency components are evident, but of much reduced amplitude relative to cross-correlation outputs 6902 and 7002. The peaks near highlight 7104 are larger relative to the rest of cross-correlation output 7102, as is generally desired, which may allow the peaks to be identified more accurately, confidently, or both, by at least some of the techniques described herein. The subtraction of a quadratic fit from a window of data may, in some circumstances, reduce the amplitude of low frequency noise components relative to the subtraction of the mean or a linear fit.

It will be understood that the beneficial effects of signal conditioning are not limited to the examples depicted in FIGS. 69-71. For example, signal conditioning may provide benefits when applied prior to performing an autocorrelation of a signal and also in the Rate Calculation Techniques described below.

In some embodiments, once initialization parameters have been set (e.g., qualified), the processing equipment may transition to Locked Mode. While operating in Locked Mode, the processing equipment may use the qualified initialization parameters (e.g., filter settings) or other algorithm settings from Search Mode to condition, analyze, or both, a physiological signal to extract physiological rate information. In some embodiments, while operating in Locked Mode, the processing equipment may use a previously calculated rate to condition, analyze, or both, a physiological signal to extract physiological rate information. Performing a Rate Calculation may include further processing of the physiological signal.

The calculated rate may be qualified, using any suitable Qualification Technique. For example, any of the Qualification Techniques described herein may be used to qualify a calculated rate. When qualified, the calculated rate may be filtered and outputted for display.

Figure 72:
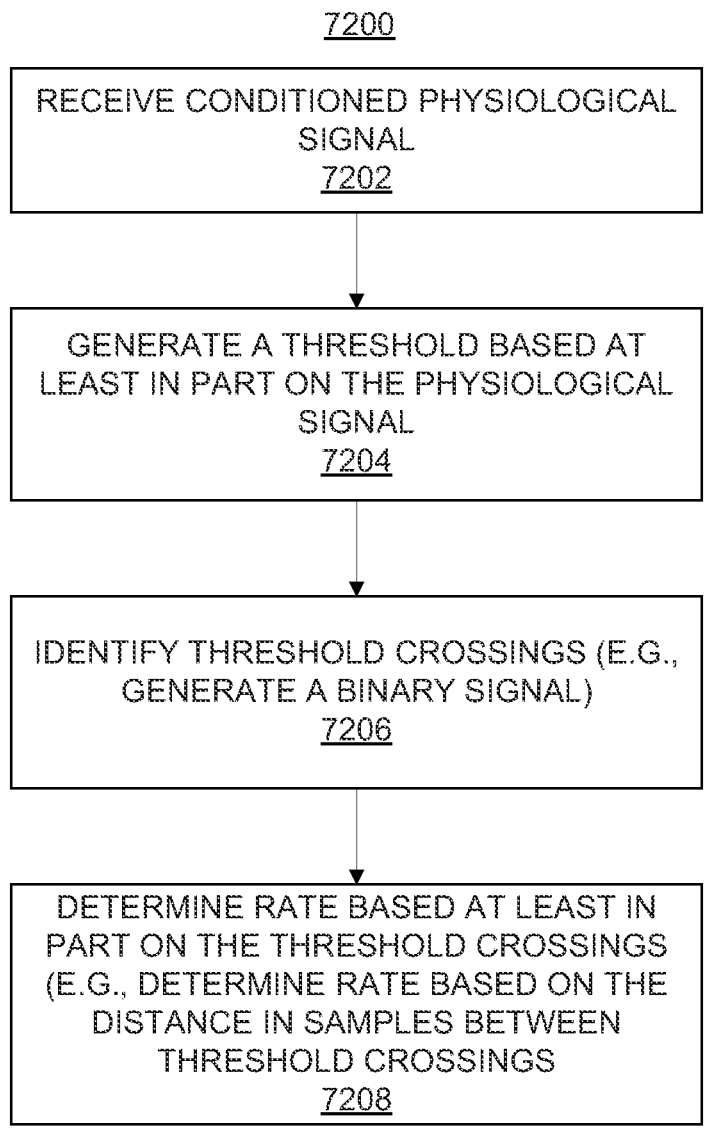
FIG. 72 is a flow diagram of illustrative steps for determining a physiological rate from threshold crossings based on a physiological signal, in accordance with some embodiments of the present disclosure.

FIG. 72 is a flow diagram 7200 of illustrative steps for determining a physiological rate from threshold crossings based on a physiological signal, in accordance with some embodiments of the present disclosure. A physiological signal (and signals derived thereof), whether analog or digital, may include a number of peaks (e.g., physiological pulse waves), over which the value of the signal may vary considerably. In some embodiments, a physiological signal, based on threshold crossings, may be converted into a binary signal, which includes only the values zero or one, to provide a convenient technique to extract rate information.

Step 7202 may include processing equipment receiving a conditioned physiological signal. The physiological signal may have undergone any of the signal conditioning techniques described herein (e.g., filtering, de-trending, modification using an envelope, smoothing), any other suitable signal conditioning techniques, any suitable signal pre-processing techniques, or any combination thereof. In some embodiments, the conditioned physiological signal may be a conditioned PPG signal, or a signal derived thereof. For example, the conditioned physiological signal may be a derivative of the IR PPG signal, having undergone suitable conditioning. In a further example, the conditioned physiological signal may be an autocorrelation generated from a PPG signal (e.g., as discussed by suitable steps of flow diagram 500 of FIG. 5, flow diagram 900 of FIG. 9, or other suitable techniques), and having undergone suitable conditioning. In some embodiments, the processing equipment may condition the physiological signal and perform the illustrative steps of flow diagram 7200, and accordingly step 7202 need not be performed.

Step 7204 may include the processing equipment generating a threshold sequence (i.e., a collection of threshold values referred to collectively here as a "threshold") based on the conditioned physiological signal of step 7202. The threshold may be used for comparison with the conditioned physiological signal to extract rate information. In some embodiments, the threshold may be a particular fixed value, which may be stored in any suitable memory. In some embodiments, the threshold may be a sequence of one or more adjustable values, which may be derived from a mathematical formula (e.g., a function, a statistical expression), look-up table, or other reference. For example, the adjustable threshold value may be equal to the standard deviation of the conditioned physiological signal or a portion thereof multiplied by a coefficient. In some embodiments, the threshold may by dynamic within each calculation of rate. For example, the threshold may be generated using a Constant False Alarm Rate (CFAR) technique (e.g., as discussed below with reference to FIGS. 75-80).

Figure 73:
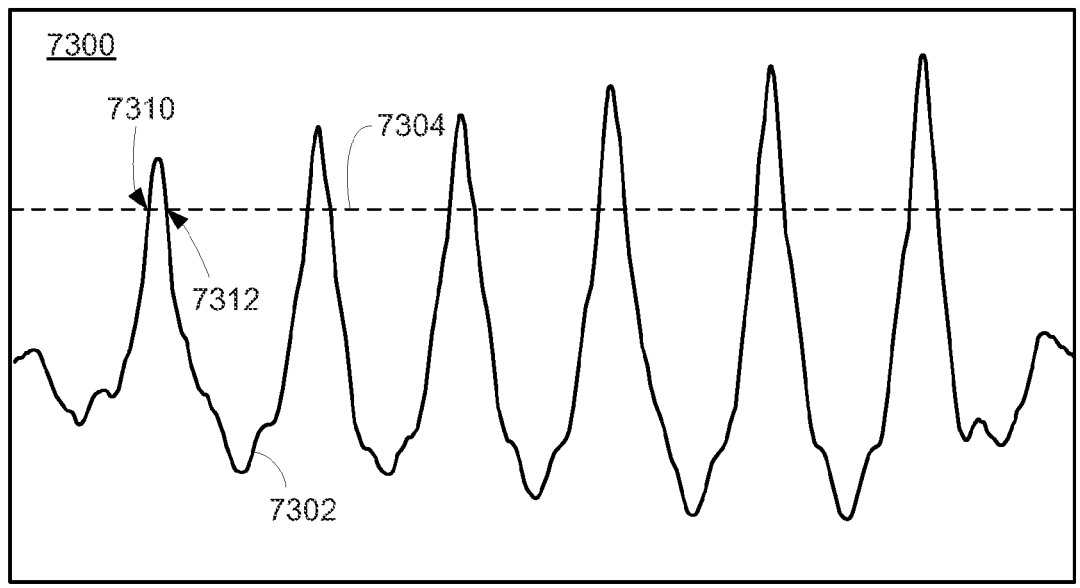
FIG. 73 is a plot of an illustrative autocorrelation output, with a Rate Calculation threshold shown, in accordance with some embodiments of the present disclosure.
Figure 74:
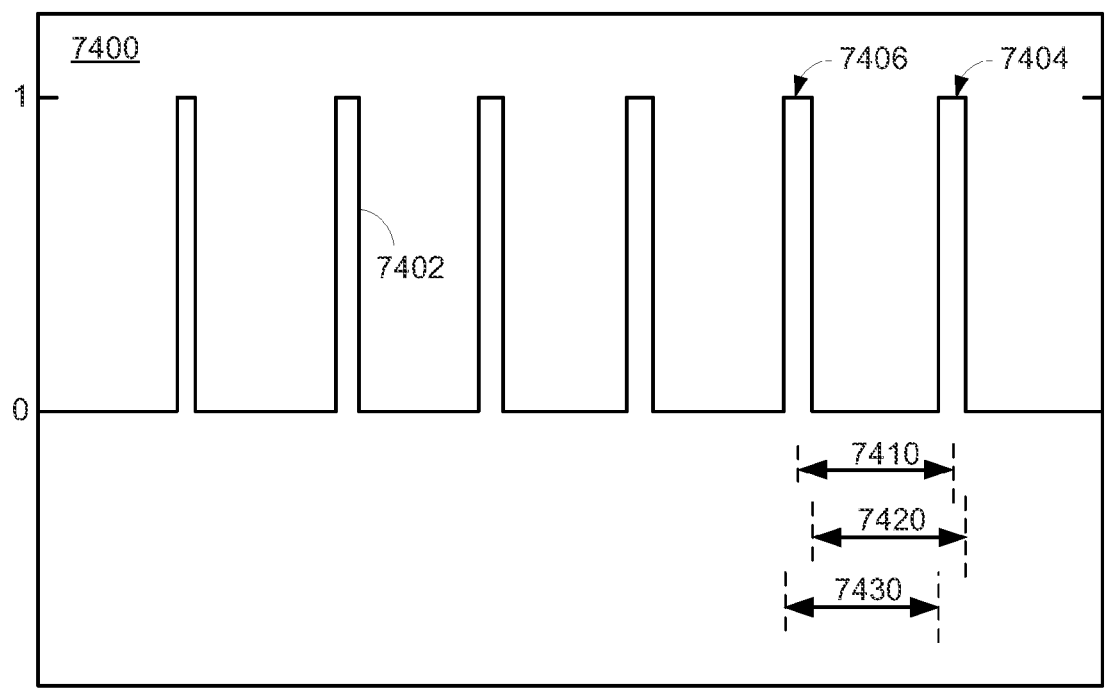
FIG. 74 is a plot of an illustrative binary signal, generated from the autocorrelation output of FIG. 73, which may be used to calculate a physiological pulse rate, in accordance with some embodiments of the present disclosure.

Step 7206 may include the processing equipment identifying threshold crossings of the conditioned physiological signal of step 7202. The conditioned physiological signal may include one or more peaks corresponding to a physiological pulse rate, which may cross the threshold on both an up-stroke and a down-stroke (e.g., providing two threshold crossings per peak). In some embodiments, a binary signal may be generated at step 7206 based on the threshold crossings (e.g., FIGS. 73-74 provide further illustration of generating a binary signal). For example, along the same abscissa as the conditioned physiological signal, the binary signal may be zero for the points where the conditioned physiological signal is less than the threshold and one for points where the conditioned physiological signal is greater than or equal to the threshold. Accordingly, the binary signal may include a series of rectangular pulses among a flat baseline. In some embodiments, the relatively simpler binary signal may be analyzed for rate information, rather than the conditioned physiological signal. In some embodiments, the threshold crossings may be identified and analyzed directly, and accordingly the binary signal need not be generated. In some circumstances, the binary signal may provide an illustrative graphic (e.g., displayed on display 20 of physiological monitoring system 10 of FIGS. 1-2) for a user or subject to view.

Step 7208 may include the processing equipment determining rate information based on the identified threshold crossings of step 7206. In some embodiments, a physiological pulse rate may be calculated based on the threshold crossings. For example, the time interval between up-stroke threshold crossings associated with adjacent pulse waves may provide a measure of the period of the physiological pulse rate. Similarly, the time interval between the down-stroke crossings, or midpoint of up-stroke and down-stroke crossings, of adjacent pulse waves may provide a measure of the period of the physiological pulse rate. Any suitable feature(s) of the threshold crossings, or a binary signal generated thereof, may be used to calculate a physiological pulse rate.

FIG. 73 is a plot 7300 of an illustrative autocorrelation output 7302, with a Rate Calculation threshold 7304 shown, in accordance with some embodiments of the present disclosure. The abscissa of plot 7300 is presented in units proportional to autocorrelation lag, while the ordinate is presented in arbitrary units. Illustrative autocorrelation output 7302 includes six major peaks, which cross threshold 7304. Referencing the leftmost peak of autocorrelation output 7302, the up-stroke crosses threshold 7304 at point 7310 and the down-stroke crosses threshold 7304 at point 7312. While autocorrelation 7302 is relatively clean and noise-free, there is signal structure (i.e., detailed shapes) present that does not necessarily provide any benefit during rate calculation. Generation of a binary signal based on autocorrelation 7302 may provide a simple signal for rate calculation.

FIG. 74 is a plot 7400 of an illustrative binary signal 7402, generated from autocorrelation output 7302 of FIG. 73, which may be used to calculate a physiological pulse rate, in accordance with some embodiments of the present disclosure. The abscissa of plot 7400 is presented in units proportional to autocorrelation lag, while the ordinate is presented in arbitrary units, with zero and one notated. Binary signal may include one or more rectangular peaks, such as peaks 7404 and 7406, which may be used to extract rate information. In part, because of the relatively simple structure of binary signal 7402 as compared to autocorrelation 7302, calculation of rate information may be accordingly simplified. In some embodiments, a rate may be calculated by determining an interval between adjacent peaks of binary signal 7402, using the interval length as a rate period, and then calculating the rate corresponding to the rate period. For example, interval 7410 stretches from the midpoint of peak 7404 (i.e., halfway between the up-stroke and down-stroke of a peak in the binary signal) to the midpoint of peak 7406. In a further example, interval 7420 stretches from the down-stroke of peak 7404 to the down-stroke of peak 7406. In a further example, interval 7430 stretches from the up-stroke of peak 7404 to the up-stroke of peak 7406. Any of intervals 7410, 7420, 7430, any other suitable intervals, or any combination thereof may be used to calculate rate information. In some embodiments, the two most recent peaks may be used to calculate rate information. In some embodiments, more than one pair of peaks may be used to calculate the rate information. For example, an average interval or median interval may be calculated based on multiple pairs of peaks. In a further example, a weighted average (e.g., weighted to down-weight outliers, weighted to up-weight more recent data) of interval length may be calculated. In a further example, a histogram may be generated of interval values, and the interval (or range thereof) occurring most often may be selected as the pulse period.

Figure 75:
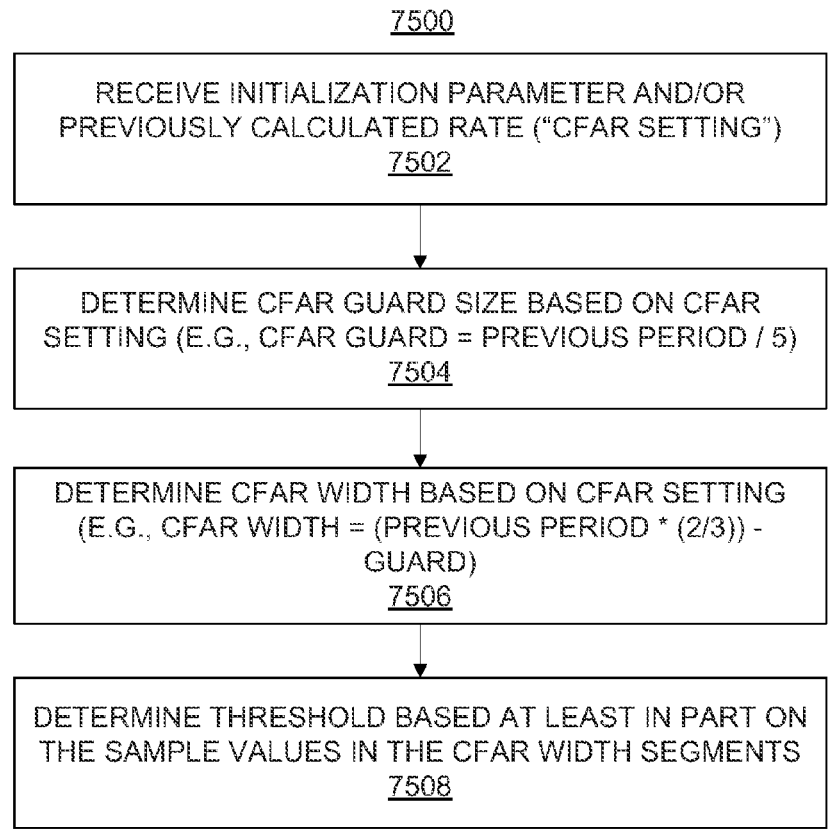
FIG. 75 is a flow diagram of illustrative steps for determining a threshold based on a Constant False Alarm Rate (CFAR) setting, in accordance with some embodiments of the present disclosure.

FIG. 75 is a flow diagram 7500 of illustrative steps for determining a Rate Calculation threshold based on a CFAR setting, in accordance with some embodiments of the present disclosure. The CFAR technique may use a CFAR window (which may be referred to as a "threshold window"), which may include the sample under test, guard samples, and base samples. The threshold window may include a center portion (e.g., the sample under test and guard samples) that is not used to generate the threshold value at each sample under test. Accordingly, the threshold value for the sample under test is based on the surrounding samples, and not, for example, on the sample under test and guard samples. The CFAR technique may be especially useful in identifying peaks in otherwise noisy signals.

Step 7502 may include the processing equipment receiving an initialization parameter, previously calculated rate, any other suitable qualification information, or any combination thereof. In some embodiments, step 7502 may include recalling the stored initialization parameter, previously calculated rate, or both, from suitable memory. In some embodiments, a single processor, module, or system may calculate, store, or both, initialization parameters and the previously calculated rate, and perform steps 7504-7508, and accordingly, step 7502 need not be performed. The rate associated with the received initialization parameters, calculated rate, or both will be referred to as a "CFAR Setting," which may be included as a part of algorithm settings.

Step 7504 may include the processing equipment determining a CFAR guard size based on the CFAR setting of step 7502. A guard is a set of one or more samples on either, or both, sides of the sample under test that are not included in the threshold calculation. The size of the guard may refer to the number of samples, the time interval, or any other size metric indicative of a guard. In some embodiments, the guard size may be based on the period of a previously calculated rate. For example, the guard size may be equal to one fifth of the period of the previously calculated rate. In some embodiments, the guard size may be predetermined.

Step 7506 may include the processing equipment determining a CFAR width of base samples based on the CFAR setting of step 7502. The CFAR width is the set of samples on either, or both, sides of the sample under test, outside of the guard, which are used in the threshold calculation (referred to herein as the "base samples"). The CFAR width may refer to the number of samples, the time interval, or any other size metric indicative of a width. In some embodiments, the CFAR width may be based on the period of a previously calculated rate (e.g., may be a linear or non-linear function of period P). For example, the CFAR width may be equal to two thirds of the period of the previously calculated rate, minus the guard size (i.e., CFAR width=($\frac{2}{3}$)P−guard size). In some embodiments, the CFAR guard size and CFAR width may decrease as period P decreases. The sizing of the CFAR components (e.g., the guard size and number of base samples) will also be referred to as a "CFAR Setting."

Step 7508 may include the processing equipment determining a threshold value based on the values of the base samples within the CFAR width for each sample under test. Step 7508 may include determining a threshold value at each sample under test, to generate a threshold sequence. The threshold sequence may be generated for comparison with a conditioned physiological signal, or signal derived thereof (e.g., an autocorrelation), to determine rate information. In some embodiments, the mean and standard deviation may be calculated for the base samples. For example, the local threshold value T ($x_k$) at point $x_k$ may be given by Eq. 30 below:

$$T(x_k) = \mu_k + K\sigma_k \quad (30)$$

in which $\mu_k$ is the mean of the base samples, K is a coefficient, and $\sigma_k$ is the standard deviation of the base samples. The coefficient K may have any suitable constant or variable value such as, for example, a predefined constant value, a value depending on the initialization parameters, a value varying with CFAR settings, or other suitable value. For example, K may depend linearly or non-linearly on the rate associated with the initialization parameters or a previously calculated rate. The coefficient K will also be referred to as a "CFAR Setting."

In some embodiments, the size and properties of a CFAR window may depend on characteristics of the underlying signal. For example, the number of guard samples, the number of base samples, the number of guard or base samples to either side of the sample under test (i.e., the symmetry of the CFAR window), the coefficient K, any other suitable CFAR window properties, or any combination thereof, may be adjusted based on the underlying signal. Any suitable CFAR property may be adjusted based on, for example, statistical properties of the underlying signal (e.g., mean, standard deviation), a trend of the underlying signal, a shape of the underlying signal, an initialization parameter, a previously calculated rate, any other suitable signal property, or any combination thereof. For example, as a physiological rate increases, the number of guard samples and the number of base samples may decrease for a fixed sampling rate.

Figure 76:
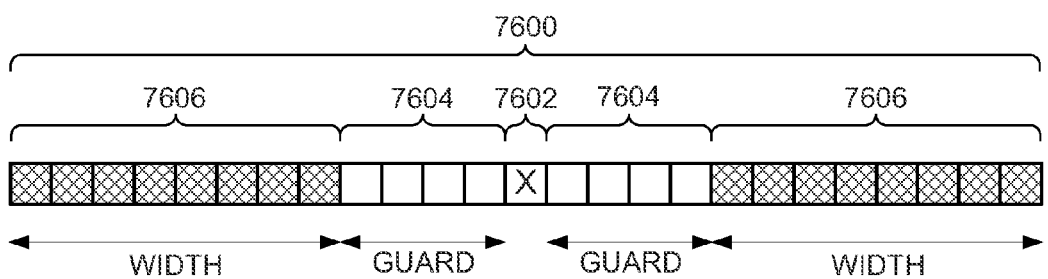
FIG. 76 shows an illustrative CFAR window, including the sample under test, guard samples, and base samples, in accordance with some embodiments of the present disclosure.

FIG. 76 shows an illustrative CFAR window 7600, including the sample under test 7602, guard samples 7604, and base samples 7606, in accordance with some embodiments of the present disclosure. CFAR window 7600, or portions thereof, may be used to generate a threshold value (e.g., using the illustrative steps of flow diagram 7500) at the location of the sample under test. Included in CFAR window 7600 may be sample under test 7602, immediately surrounded by guard samples 7604. Base samples 7606 lie outside of guard samples 7604 relative to sample under test 7602. In some embodiments, base samples 7606 are used to determine a threshold value for sample under test 7602. For example, Eq. 30 may be applied to base samples 7606 of CFAR window 7600 to generate a threshold value. A window similar to CFAR window 7600 may be generated at each point of a conditioned physiological signal, or signal derived thereof (e.g., an autocorrelation output), creating a threshold curve. A threshold curve may be used for comparison with, for example, the autocorrelation output from which the threshold was derived.

Figure 77:
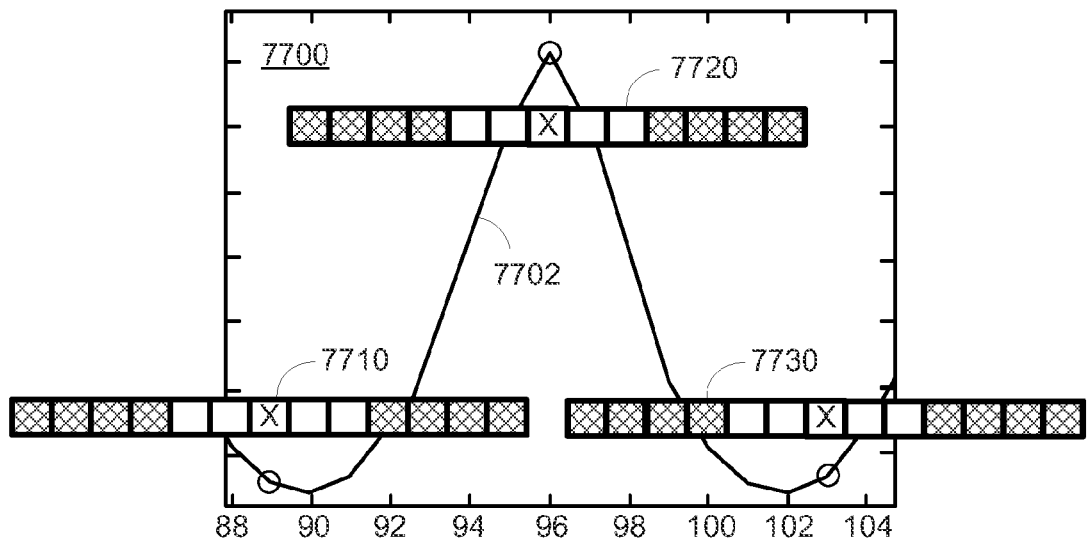
FIG. 77 is a plot of an illustrative autocorrelation output, with three CFAR windows shown, in accordance with some embodiments of the present disclosure.

FIG. 77 is a plot 7700 of an illustrative autocorrelation output 7702, with three illustrative CFAR windows 7710, 7720, and 7730 shown, in accordance with some embodiments of the present disclosure. The abscissa of plot 7700 is presented in units of autocorrelation lag, while the ordinate is presented in arbitrary units. The samples under test of CFAR windows 7710, 7720, and 7730 are highlighted by circles, corresponding to an "X" in the center of each window. The base samples of each CFAR window are shown with cross-hatching, while the guard samples on either side of the samples under test are shown with no hatching. The base samples of CFAR windows 7710 and 7730 are relatively larger vales than the respective samples under test of CFAR windows 7710 and 7730. Accordingly, in some embodiments, the threshold value calculated for CFAR windows 7710 and 7730 may be relatively large compared to the respective samples under test. The base samples of CFAR window 7720 are relatively smaller values than the sample under test of CFAR window 7720. Accordingly, in some embodiments, the threshold value calculated for CFAR window 7720 may be relatively small compared to the sample under test. In some embodiments, the number of samples used to determine statistical metrics may determine the minimum detection spacing. In some embodiments, guard samples may be used to prevent inclusion of a sample under test in a statistical calculation about the sample under test.

Figure 78:
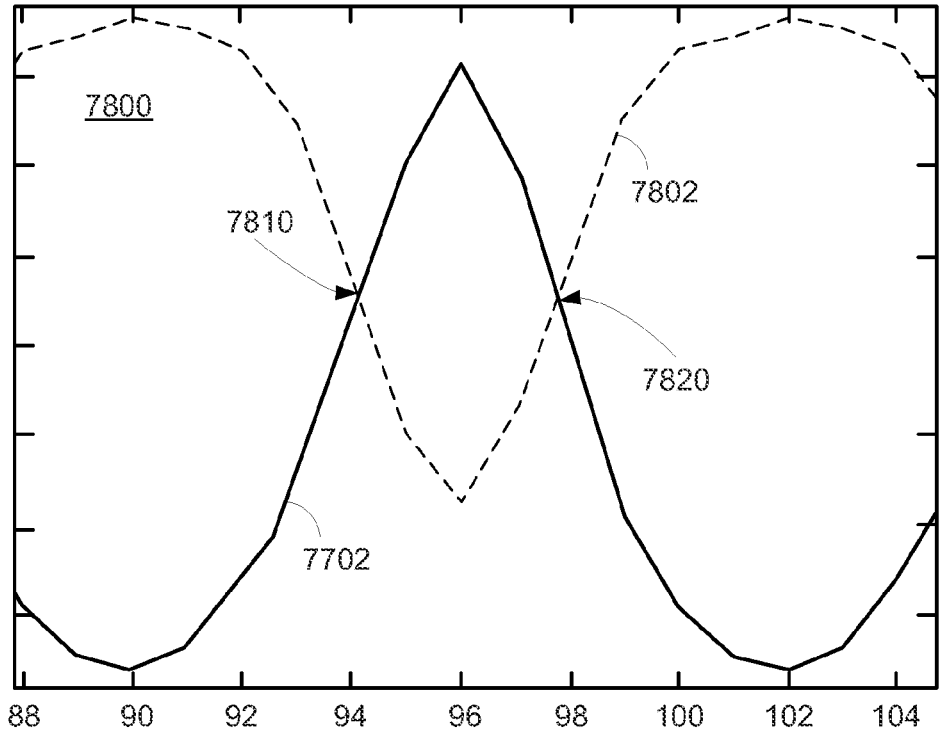
FIG. 78 is a plot of the illustrative autocorrelation output of FIG. 77, with a threshold generated based in part on the CFAR windows of FIG. 77, in accordance with some embodiments of the present disclosure.

FIG. 78 is a plot 7700 of the illustrative autocorrelation output 7702 of FIG. 77, with a threshold 7802 generated based in part on the CFAR windows of FIG. 77, in accordance with some embodiments of the present disclosure. The abscissa of plot 7800 is presented in units of autocorrelation lag, while the ordinate is presented in arbitrary units. As discussed in the context of FIG. 77, threshold values calculated for samples under test near a peak may be relatively smaller than threshold values calculated for samples under test near a trough. Threshold 7802 exhibits a relatively low value near the peak of autocorrelation output 7702, and relatively higher values away from the peak. Intersections 7810 and 7820 between autocorrelation output 7702 and threshold 7802 may be used to, for example, generate a binary pulse of a binary signal, which may be used to determine a physiological pulse rate.

Figure 79:
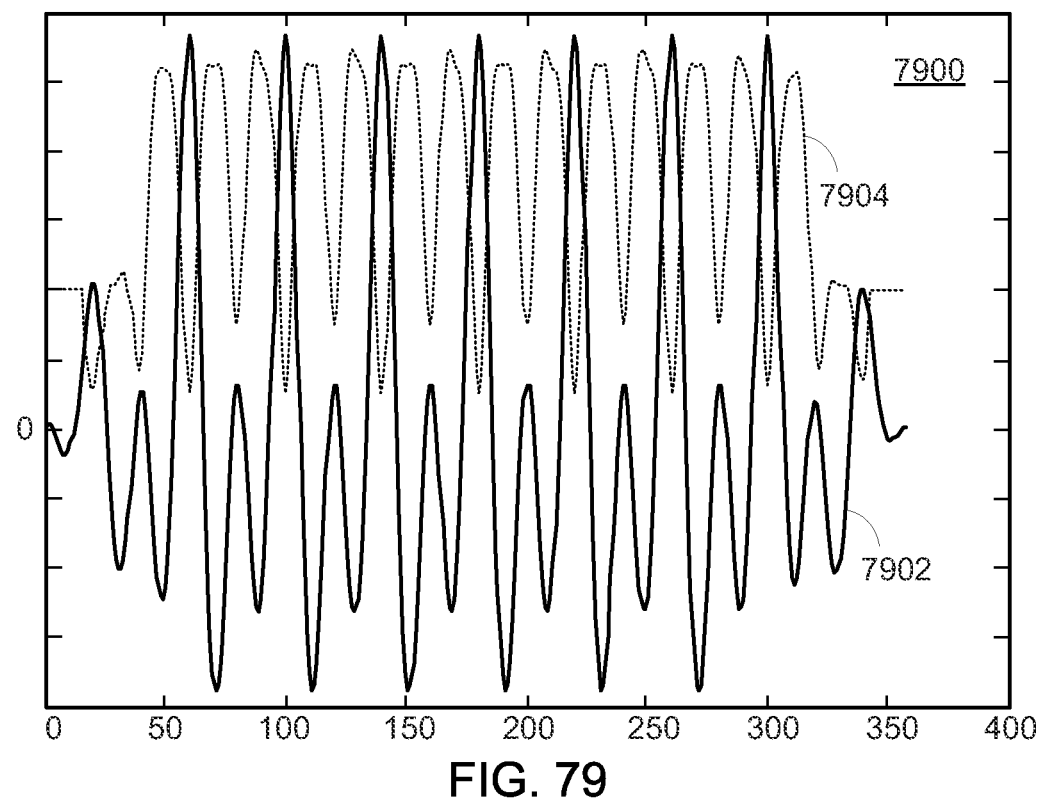
FIG. 79 is a plot of an illustrative autocorrelation output and a Rate Calculation threshold, in accordance with some embodiments of the present disclosure.
Figure 80:
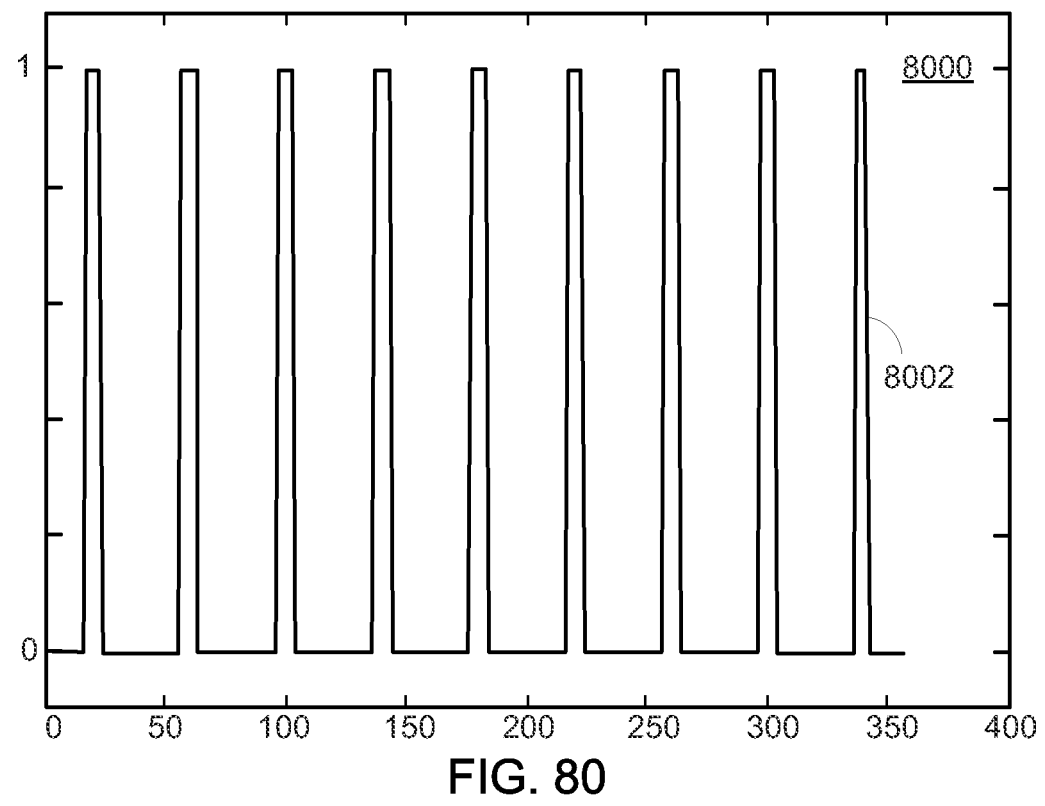
FIG. 80 is a plot of an illustrative binary signal generated based on the autocorrelation output and Rate Calculation threshold of FIG. 79, in accordance with some embodiments of the present disclosure.

FIG. 79 is a plot 7900 of an illustrative autocorrelation output 7902 and a Rate Calculation threshold 7904, in accordance with some embodiments of the present disclosure. The abscissa of plot 7900 is presented in units of autocorrelation lag, while the ordinate is presented in arbitrary units, with zero notated. Threshold 7904 is generated using a series of CFAR windows (e.g., as described by flow diagram 7500 of FIG. 75). The CFAR windows included a guard of four samples (on each side) and a width of twelve samples (on each side). Autocorrelation output 7902 exhibits a set of smaller peaks, indicative of physiological pulses that include dicrotic notches. Accordingly, the smaller peaks do not correspond to a physiological rate, but rather the larger peaks correspond to a physiological rate. The troughs of threshold 7904 are relatively higher than the zeniths of the corresponding smaller peaks. A binary signal generated from autocorrelation output 7902 and threshold 7904 (e.g., as shown in FIG. 80) may avoid including the smaller peaks that are indicative of dicrotic notches. Note that in FIG. 79, autocorrelation output 7902 is associated with a pulse rate of 85 BPM.

FIG. 80 is a plot 8000 of an illustrative binary signal 8002 generated based on the intersections of autocorrelation output 7902 and Rate Calculation threshold 7904 of FIG. 79, in accordance with some embodiments of the present disclosure. The abscissa of plot 8000 is presented in units of autocorrelation lag, while the ordinate is presented in arbitrary units, with zero and one notated. The smaller peaks of autocorrelation output 7902, indicating the presence of dicrotic notches, are not included as binary pulses in binary signal 8002. Accordingly, the CFAR windows used to generate threshold 7904 are correctly sized. In some embodiments, binary signal 8002 may be further analyzed to calculate a pulse rate.

Figure 81:
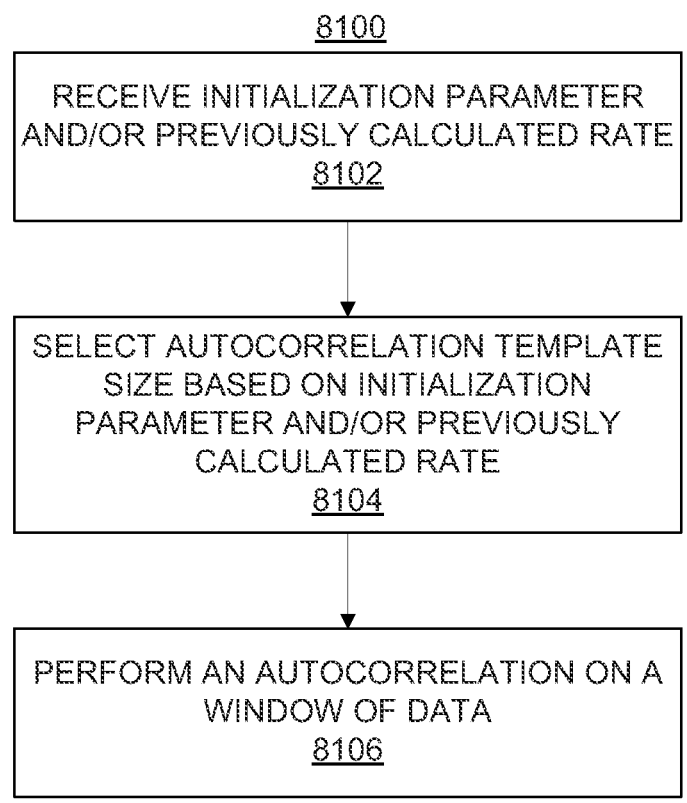
FIG. 81 is a flow diagram of illustrative steps for qualifying an autocorrelation template size to perform an autocorrelation, in accordance with some embodiments of the present disclosure.

FIG. 81 is a flow diagram 8100 of illustrative steps for selecting an autocorrelation template size to perform an autocorrelation, in accordance with some embodiments of the present disclosure. The size of an autocorrelation template may be based on initialization parameters, a calculated rate or other information. For example, the period P associated with initialization parameters and/or a calculated rate may be used to select an autocorrelation template size.

Step 8102 may include processing equipment receiving initialization parameters, a previously calculated rate, any other suitable rate information, or any combination thereof. In some embodiments, step 8102 may include recalling the stored initialization parameter, previously calculated rate, or both, from suitable memory. In some embodiments, a single processor, module, or system may calculate, store, or both, initialization parameters and the previously calculated rate, and perform steps 8104-8106, and accordingly, step 8102 need not be performed.

Step 8104 may include the processing equipment selecting an autocorrelation template size based on the received initialization parameters and/or previously calculated rate of step 8102. In some embodiments, the processing equipment may select an autocorrelation template size that is equal to the period associated with the received initialization parameters and/or previously calculated rate. In some embodiments, the processing equipment may select an autocorrelation template size that is greater than or less than the period associated with the received initialization parameters and/or previously calculated rate. For example, the processing equipment may input the received initialization parameters and/or previously calculated rate of step 8102 into a mathematical expression and/or look-up table, and determine an autocorrelation template size.

Step 8106 may include the processing equipment performing an autocorrelation on a window of data, using the autocorrelation template size selected at step 8104. In some embodiments, the autocorrelation of step 8106 may include correlating a first portion of the window of data (i.e., the template of selected size) with a second portion of the window of data (e.g., the remaining window of data). The first and second portions may be exclusive of one another, may share one or more samples, or may be selected by any other suitable partition of the window of data. For example, a six second window of data may be buffered from a physiological signal. The processing equipment may determine that the previously calculated rate is 60 BPM, and may determine that the period associated with the current rate is likely to be approximately 1 second. The processing equipment may select an autocorrelation template size of 1 second to perform the autocorrelation of step 8106, or use a look-up table (e.g., stored in memory of system 10) to select an autocorrelation template size to perform the autocorrelation of step 8106. In a further example, a six second window of data may be buffered from a physiological signal. The processing equipment may determine that the previously calculated rate is 120 BPM, and may determine that the period associated with the current rate is likely to be approximately 0.5 seconds. The processing equipment may select an autocorrelation template size of 0.5 second (e.g., about 1 period) to perform the autocorrelation of step 8106. In some embodiments, the resulting autocorrelation output of step 8106 may be further analyzed using any of the techniques disclosed herein.

Figure 82:
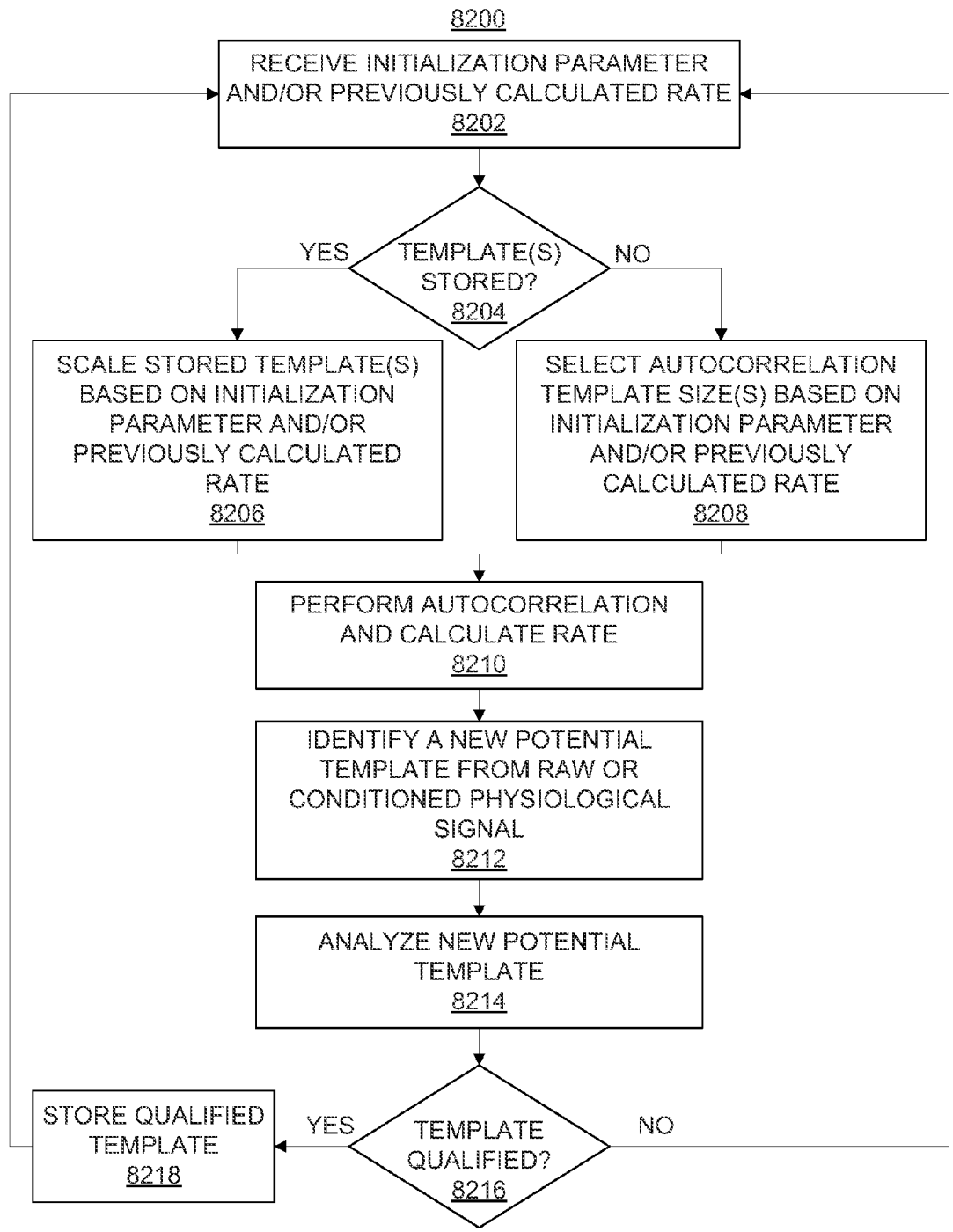
FIG. 82 is a flow diagram of illustrative steps for selecting an autocorrelation template, in accordance with some embodiments of the present disclosure.

FIG. 82 is a flow diagram 8200 of illustrative steps for qualifying an autocorrelation template, in accordance with some embodiments of the present disclosure. Qualification of a template may be used to select and store a template that provides desired performance, which may aid in system 300 determining initialization parameters and/or calculating a rate.

Step 8202 may include processing equipment receiving initialization parameters, a previously calculated rate, or both. In some embodiments, the initialization parameters, a previously calculated rate, or both, may be generated at an earlier time, and stored in suitable memory (e.g., RAM 54 of physiological monitoring system 10 of FIGS. 1-2). Accordingly, in some embodiments, step 8202 may include recalling the initialization parameters, a previously calculated rate, or both, from memory. In some embodiments, a single processor, module, or system may determine, store or otherwise process the initialization parameters and previously calculated rate, as well as perform steps 8204-8218, and accordingly, step 8202 need not be performed.

Step 8204 may include the processing equipment determining whether a template has been stored. In some embodiments, one or more templates may be stored in memory (e.g., ROM 52, RAM 54 of system 10 or other suitable memory). In some embodiments, the processing equipment may access one or more local memory devices, access one or more remote memory devices, perform a search of one or more stored templates, perform any other suitable operation to determine whether a template has been stored, or any combination thereof. At step 8204, the processing equipment may determine that a template has or has not been stored, and accordingly may proceed to step 8206 or step 8208, respectively. In some embodiments, the stored template may be a window of data derived from a physiological signal of the subject. For example, one or more templates derived from a window of data having relatively low-noise may be stored for future use (e.g., at step 8218). In some embodiments, the stored template may be derived from a standard template shape and/or a mathematical function. In some embodiments, step 8204 may include selecting the stored template from memory.

Step 8206 may include the processing equipment scaling the stored template of step 8204 based on initialization parameters and/or a previously calculated rate. The template may be scaled to exhibit a period equal to the period P associated with the initialization parameters and/or previously calculated rate. For example, if the period P associated with the initialization parameters is 1 second (e.g., for a 60 BPM rate), the template may be scaled to exhibit a period of 1 second.

In some embodiments, step 8206 may include the processing equipment selecting more than one stored autocorrelation templates based on initialization parameters and/or a previously calculated rate. In some embodiments, the processing equipment may average the templates to generate a composite template to be used in the remaining steps of flow diagram 8200. In some embodiments, the processing equipment may process the templates separately in the remaining steps of flow diagram 8200.

Step 8208 may include the processing equipment selecting an autocorrelation template size based on initialization parameters and/or a previously calculated rate. In circumstances where no suitable template has been stored, the processing equipment may select an autocorrelation template from a buffered window of data. For example, referencing a six second buffered window of data, the most recent one second of data may be selected as a template to be correlated with the entire six seconds of data. In some embodiments, the processing equipment may select the autocorrelation template size based on a period P associated with initialization parameters and/or a previously calculated rate. For example, if the period P associated with the initialization parameters is 1 second (e.g., for a 60 BPM rate), a template of 1 second may be selected.

Step 8210 may include the processing equipment performing an autocorrelation on a window of data, using an autocorrelation template of either step 8206 or 8208. The autocorrelation template and the window of data may be exclusive of one another, may share one or more samples, or may be selected by any other suitable partition of the physiological signal. The autocorrelation output of step 8210 may include one or more peaks, which may indicate correlation of the template with the window of data. Step 8210 may also include the processing equipment calculating a rate based on the autocorrelation. The processing equipment may implement any of the Search Mode and/or Locked Mode techniques disclosed herein to calculate the rate. In some embodiments, the processing equipment may perform more than one correlation operation at step 8210. For example, a correlation operation may be performed on multiple templates against the physiological signal. The template that has the highest correlation can be selected for use as the template in the autocorrelation. The stored templates may include templates with dicrotic notches of different sizes, amounts of skew, symmetry, any other suitable properties, or any combination thereof. In a further example, the processing equipment may perform an autocorrelation and CFAR analysis for each of multiple selected templates. The processing equipment may select the template associated with the highest confidence value. A confidence value may include, for example, the amount by which the autocorrelation exceeds a threshold (e.g., a CFAR threshold).

Step 8212 may include the processing equipment identifying a new reference waveform (e.g., a new potential template) from a raw or conditioned physiological signal (e.g., a photoplethysmograph signal). In some embodiments, the new potential template may be selected by analyzing the physiological signal. For example, the processing equipment may select a portion of the physiological signal between two peaks (e.g., two adjacent maxima), between two valleys (e.g., two adjacent minima), between two zero crossings, or other suitable portion of the physiological signal, or any combination thereof, to be a template. Identifying the new potential template may include locating a maximum or minimum signal value, a maximum or minimum value in a derivative of a signal, a zero crossing of a signal, a zero crossing in a derivative of a signal, any other suitable reference points, or any combination thereof. In some embodiments, the processing equipment may identify a new potential template based on the calculated rate of step 8210. For example, the processing equipment may determine a period P associated with the calculated rate of step 8210, and select a template having a length of P (or fraction or multiple thereof) from the physiological signal.

Step 8214 may include the processing equipment analyzing the new potential template of step 8212. In some embodiments, the analysis of step 8214 may include analyzing the shape of the template (e.g., a peak value, a peak to width ratio, a full width at half maximum value), the skewness of the template, the relative amplitude of the template, the correspondence of the template to one or more other templates, any other property of the template, or any combination thereof. In some embodiments, the analysis of step 8214 may include determining a noise metric and/or a confidence metric based on the physiological signal associated with the new potential template.

Step 8216 may include the processing equipment determining whether the new potential template of step 8212 is qualified based on the analysis of step 8214. In some embodiments, step 8216 may include comparing a metric determined at step 8214 with a threshold value to determine whether to qualify the new potential template. For example, a noise metric such as signal to noise ratio calculated at step 8214 may be compared to a noise threshold and if the noise metric is greater than the noise threshold, the template may be determined to be unqualified. Accordingly, under relatively low noise conditions, a new template may be qualified each time steps 8210-8216 are performed. As one or more noise metrics increase beyond some threshold value, the processing equipment may cease updating the template and continue to use the template qualified under the relatively low-noise conditions. In some embodiments, if the new potential template is disqualified at step 8216, the template may be discarded. For example, the new potential template may be erased from memory storage, or otherwise made unavailable for further consideration if disqualified at step 8216.

Step 8218 may include the processing equipment storing the qualified template of step 8216 in suitable memory. The qualified template may be stored, for example, in RAM 54 of system 10. In some embodiments, a qualified template may be stored in a database of templates. In some embodiments, the qualified template may be stored and indexed by the calculated rate value for subsequent use. Accordingly, a stored template may be recalled at step 8204 in circumstances where, for example, the index matches the initialization parameters and/or calculated rate of step 8202. In some embodiments, a stored template may have been derived from a subject's physiological signals. In some embodiments, a stored template may have been derived from a standard (e.g., typical) physiological signal shape, a mathematical function, or derived from any other suitable source, or any combination thereof.

In some embodiments, the processing equipment may combine metrics, qualifications/disqualifications, any other suitable information, or any combination thereof in a neural network to determine which Technique may be desired under some circumstances. In some embodiments, as system 300 processes data over time, the processing equipment may use a neural network, or any other suitable classifier, to adapt the Techniques and parameters thereof used by the processing equipment to determine physiological information of a subject. For example, as templates are qualified and/or disqualified at step 8216, the processing equipment may adjust or otherwise update thresholds, criterion, or analysis techniques to select initialization parameters or determine rates having higher probabilities of being qualified.

Figure 83:
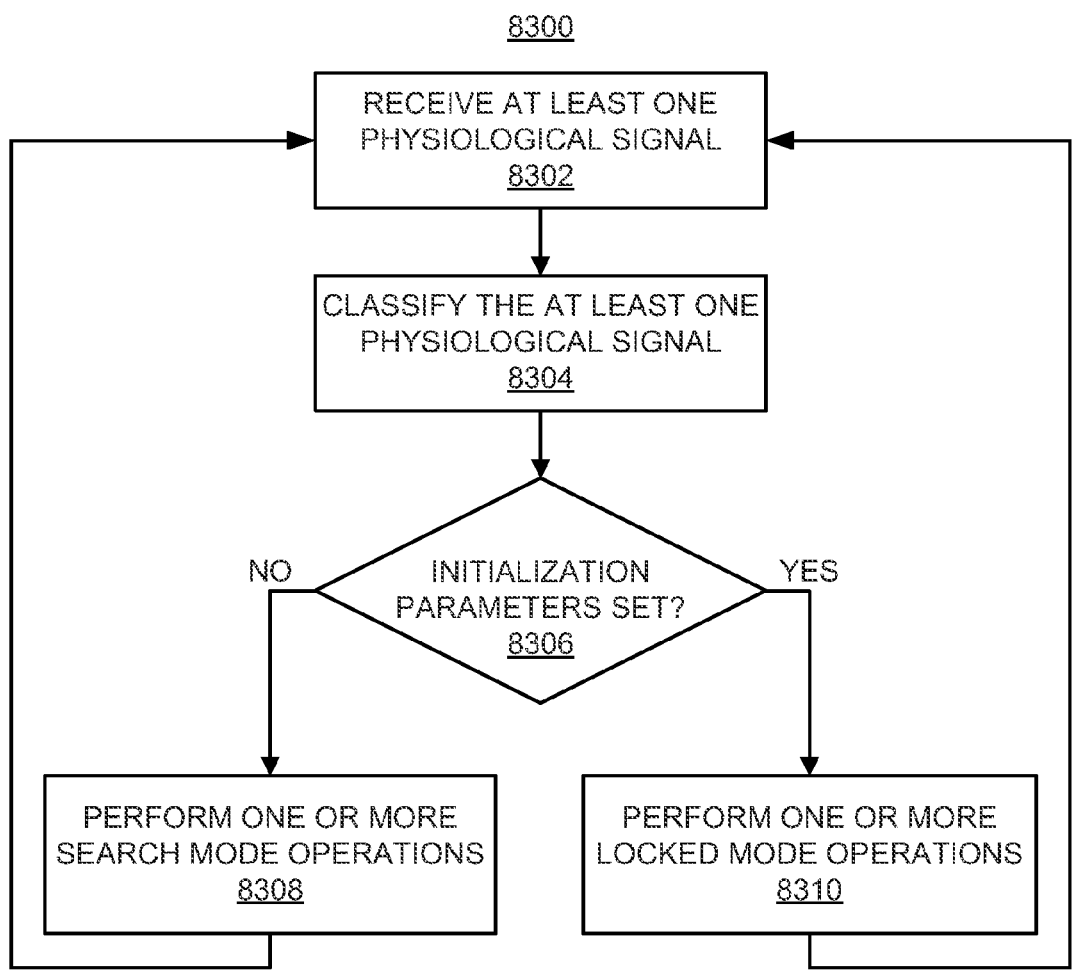
FIG. 83 is a flow diagram of illustrative steps for classifying a physiological signal to be used in Search Mode and/or Locked Mode, in accordance with some embodiments of the present disclosure.

FIG. 83 is a flow diagram 8300 of illustrative steps for classifying a physiological signal to be used in Search Mode and/or Locked Mode, in accordance with some embodiments of the present disclosure. Classification of a physiological signal may aid in determining initialization parameters and/or calculating a rate, by further directing the analysis of the physiological signal. For example, filter settings, expected pulse rate range, subject classification (e.g., neonate or adult), the presence of a dicrotic notch, pulse shape (e.g., skew), and/or any other suitable classification may be used to determine the type of analysis to perform on a physiological signal.

Step 8302 may include processing equipment receiving at least one physiological signal from a physiological sensor, memory, any other suitable source, or any combination thereof. For example, referring to system 300 of FIG. 3, the processing equipment may receive a physiological signal from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., memory of system 10 of FIGS. 1-2) after being pre-processed by pre-processor 320. In such cases, step 8302 may include recalling the signals from the memory for further processing.

The physiological signal of step 8302 may include a PPG signal, which may include a sequence of pulse waves and may exhibit motion artifacts, noise from ambient light, electronic noise, system noise, any other suitable signal component, or any combination thereof. Step 8302 may include receiving a particular time interval or corresponding number of samples of the physiological signal. In some embodiments, step 8302 may include receiving a digitized, sampled, and pre-processed physiological signal.

Step 8304 may include the processing equipment classifying the at least one received physiological signal of step 8302. The processing equipment may perform the classification using any suitable set of classes, which may be based on signal quality, signal properties, subject properties, any other suitable types of classes having any suitable number of classes, or combination thereof. Illustrative classifications may include, for example, subject age (e.g., neonate/child/adult), high/low motion artifact (e.g., motion of a subjects limbs), dicrotic notch/no dicrotic notch, high/low pulse skewness, likely pulse rate range, signal noisiness, any other suitable classification having any suitable number of classes, or any combination thereof. For example, the skewness S of n samples (e.g., corresponding to one or more pulse waves) may be determined using Eq. 31a:

$$S = \frac{\frac{1}{n}\left(\sum_{i=1}^{n}(x_i - \bar{\mu})^3\right)}{\left(\frac{1}{n}\left(\sum_{i=1}^{n}(x_i - \bar{\mu})^2\right)\right)^{3/2}} \quad (31a)$$

where $\bar{\mu}$ is the sample mean, and $x_i$ is sample i. In some embodiments, the processing equipment may use the classification to modify how Search and/or Locked Modes operate. For example, if a PPG signal is classified as a neonate PPG signal, the signal may be high passed or band-passed to reduce or eliminate frequencies less than about 85 BPM because neonates typically have rate higher than 100 BPM. In a further example, qualification tests to be performed may be changed, or the thresholds may be changed, based on the classification. For example, if a PPG signal is classified as having a dicrotic notch, additional or relatively more stringent tests may be applied to make sure the dicrotic notch is not causing the rate to be calculated as double the true rate. If double the true rate is detected, then the calculated rate may be halved and provided as an output. In some embodiments step 8304 may include receiving user input to user inputs 56 of system 10. For example, a user may indicate that the received physiological signal is from a neonate, has a dicrotic notch, and/or likely includes a pulse rate in a particular range. In some embodiments, in which the processing equipment is unable to classify a physiological signal and/or no user indication is received, the processing equipment need not classify the physiological signal and may proceed using any of the techniques disclosed herein.

Step 8306 may include the processing equipment determining whether initialization parameters have been set. In some embodiments, initialization parameters may include one or more algorithm settings such as, for example, indexes for inputting into a look-up table, filter settings, and/or templates. In some embodiments, initialization parameters may include one or more settings of a band pass filter such as, for example, a high and low frequency cutoff value (e.g., a frequency range), a representative frequency value, a set of one or more coefficients, any other suitable parameters, or any combination thereof. Physiological monitoring system 10 may use initialization parameters to improve data processing (e.g., reduce computational requirements, improve accuracy, reduce the effects of noise) to extract physiological information in the presence of noise. This may be accomplished by effectively limiting the bandwidth of data to be analyzed, performing a rough calculation to estimate a physiological pulse, or otherwise mathematically manipulating physiological data. In some embodiments, following a change in classification, the processing equipment may determine that initialization parameters are to be reset. In some embodiments, in which more than two classes exist, the processing equipment may determine whether initialization parameters are to be reset based on the relative change in classification. For example, a physiological signal may be classified by noise level, and the processing equipment may determine whether initialization parameters are set depending on the change in noise level. In some embodiments, step 8306 may be independent of the classification of step 8304.

Depending upon the determination of step 8306, the processing equipment may enter Search Mode at step 8308 or Locked Mode at step 8310. Step 8308 may include system 300 performing any suitable Search Mode operation such as, for example, performing signal conditioning, determining one or more initialization parameters, qualifying one or more initialization parameters, determining whether initialization parameters are qualified, any other suitable operations, or any combination thereof. Step 8310 may include system 300 performing any suitable Locked Mode operation such as, for example, performing signal conditioning, determining one or more initialization parameters, calculating a physiological rate, qualifying a calculated physiological rate, determining whether a physiological rate is qualified, filtering and/or outputting a calculated rate, any other suitable operations, or any combination thereof.

In an illustrative example, a physiological signal may be classified as having a dicrotic notch. The processing equipment may, accordingly, determine that a calculated value (e.g., a calculated rate and/or initialization parameters) corresponds to a harmonic of the physiological rate. In some such circumstances, the processing equipment may modify the calculated value to obtain the physiological rate when the classification of the physiological signal is a dicrotic notch classification. For example, if an intensity signal is classified as having a dicrotic notch, the processing equipment may determine that one half of the calculated value corresponds to the physiological rate.

Figure 84:
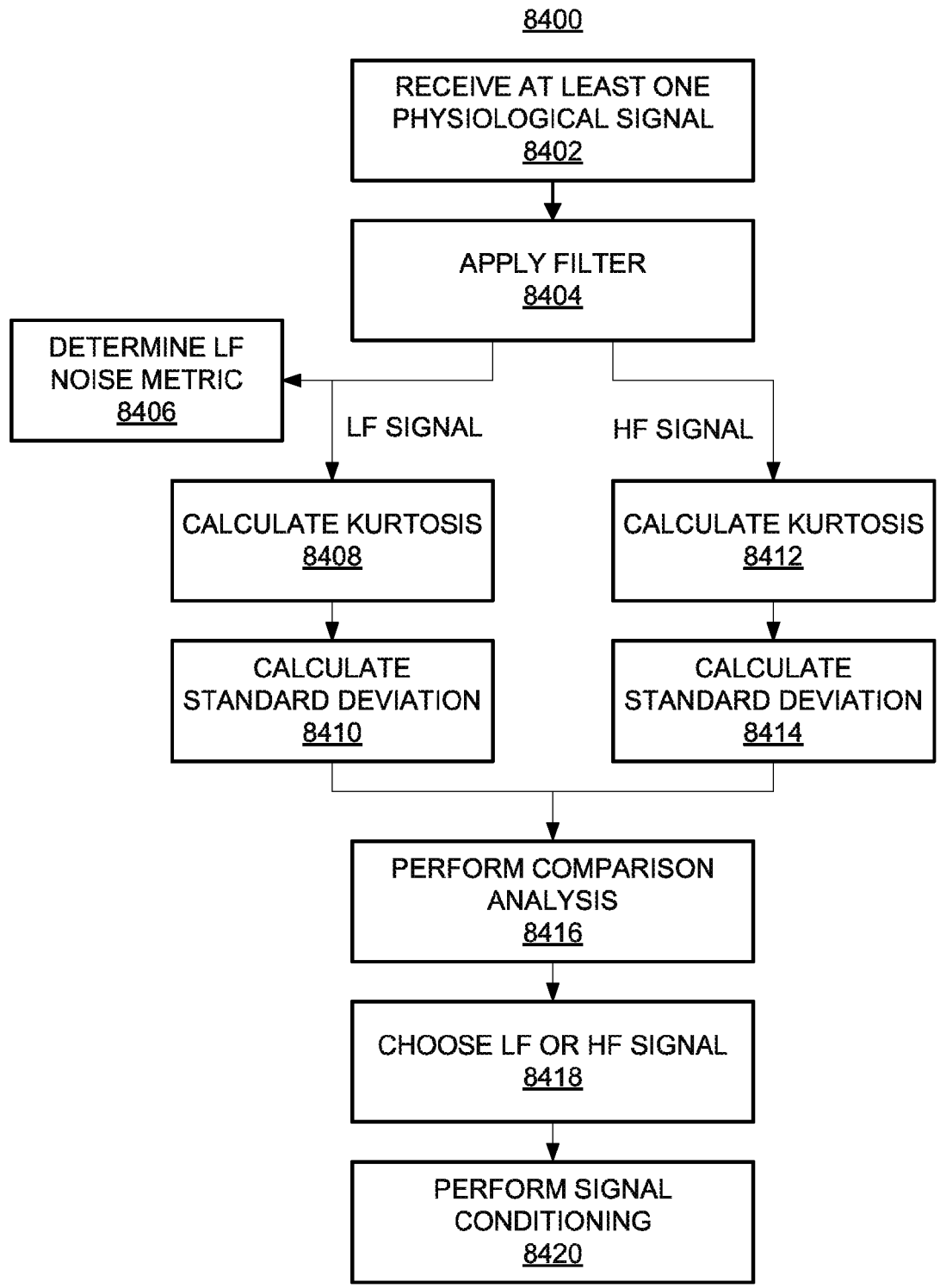
FIG. 84 is a flow diagram of illustrative steps for classifying a physiological signal, in accordance with some embodiments of the present disclosure.

FIG. 84 is a flow diagram 8400 of illustrative steps for classifying a physiological signal, in accordance with some embodiments of the present disclosure. The steps of illustrative flow diagram 8400 may provide an exemplary embodiment of step 8304 of flow diagram 8300.

Step 8402 may include processing equipment receiving at least one physiological signal from a physiological sensor, memory, any other suitable source, or any combination thereof. For example, referring to system 300 of FIG. 3, the processing equipment may receive a physiological signal from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2 or other suitable memory) after being pre-processed by pre-processor 320. In such cases, step 8402 may include recalling the signals from the memory for further processing.

Step 8404 may include the processing equipment applying a filter such as a low-pass filter (LPF) or high-pass filter (HPF) to the received physiological signal of step 8402. In some embodiments, applying the filter may include separating the physiological signal into a low frequency signal component and a high frequency signal component (i.e., relatively higher frequency activity), as shown in FIG. 84. The processing equipment may apply the filter having any suitable spectral character (e.g., the LPF may be a Bessel filter, Chebyshev filter, elliptic filter, Butterworth filter, or other suitable low-pass filter, having any suitable spectral cutoff). For example, the processing equipment may apply a LPF having a 75 BPM cut-off at step 8404 (e.g., which attenuates frequencies greater than approximately 75 BPM). In a further example, the processing equipment may apply a HPF having a 75 BPM cut-off at step 8404 (e.g., which attenuates frequencies less than approximately 75 BPM). The 75 BPM cut-off is exemplary and any other suitable BPM cutoff can be used to separate the intensity signal into high and low frequency components.

Step 8406 may include the processing equipment determining a noise metric based on the low frequency component outputted at step 8404. In some embodiments, the processing equipment may apply a LPF (separate from the filter of step 8404) to the LF signal, and then compare the input and output signals to the second LPF. For example, step 8404 may include applying a LPF with a cutoff of 75 BPM, and step 8406 may include the processing equipment applying a second LPF with a cutoff of 6 BPM. The processing equipment may determine the difference between the input and output signals of the 6 BPM LPF, and then determine a root mean square value of the difference as the noise metric.

Step 8408 may include the processing equipment calculating a kurtosis (e.g., the fourth standardized moment of a signal or corrected value thereof) of the LF signal output at step 8404. In some embodiments, for example, the processing equipment may calculate the kurtosis K for a signal of n samples using Eq. 31:

$$K = \frac{\frac{1}{n}\left(\sum_{i=1}^{n}(x_i - \bar{\mu})^4\right)}{\left(\frac{1}{n}\left(\sum_{i=1}^{n}(x_i - \bar{\mu})^2\right)\right)^2} - 3 \qquad (31b)$$

where $\bar{\mu}$ is the sample mean, and $x_i$ is sample i. The kurtosis of a signal may provide an indication of a relative measure of sharpness of a distribution (e.g., high kurtosis indicates a relatively sharp peak and relatively large tails).

Step 8410 may include the processing equipment calculating a standard deviation of the LF signal output at step 8404. In some embodiments, the processing equipment may calculate the standard deviation $\sigma$ for a signal of n samples using Eq. 32:

$$\sigma = \sqrt{\frac{1}{n}\left(\sum_{i=1}^{n}(x_i - \bar{\mu})^2\right)} \qquad (32)$$

where $\bar{\mu}$ is the sample mean, and $x_i$ is sample i. The standard deviation of a signal may provide an indication of sample variability about a mean value.

Step 8412 may include the processing equipment calculating a kurtosis of the HF output at step 8404. In some embodiments, the processing equipment may calculate the kurtosis K for a signal of n samples using Eq. 31, in which the samples and mean are based on the HF signal. Step 8414 may include the processing equipment calculating a standard deviation of the HF output at step 8404. In some embodiments, the processing equipment may calculate the standard deviation $\sigma$ for a signal of n samples using Eq. 32, in which the samples and mean are based on the HF signal.

It will be understood that steps 8406, 8408, 8410, 8412, and 8414 may be performed in any suitable order between steps 8404 and 8416.

Step 8416 may include the processing equipment performing comparison analysis between the LF signal and the HF signal output at step 8404. In some embodiments, step 8416 may include the processing equipment comparing one or more signal metrics from the LF signal and HF signal output at step 8404. In some embodiments, at step 8416, the processing equipment may compare the kurtosis (e.g., from steps 8408 and 8412), standard deviation (e.g., from steps 8410 and 8414), any other suitable signal metric, or any combination thereof. For example, the processing equipment may determine which of the LF signal and the HF signal has a larger kurtosis, standard deviation, and/or other signal metric. In some embodiments, step 8416 may include the processing equipment performing independent component analysis (ICA) using the LF signal, the HF signal, the at least one physiological signal of step 8402, or any combination thereof. For example, ICA analysis may be used to separate the component of a physiological signal associated with a physiological rate from a noise components or other undesired component of the signal.

Step 8418 may include the processing equipment selecting either the LF signal or the filter residual signal output at step 8404. In some embodiments, the processing equipment selecting between the LF and HF signals outputted at step 8404. In some embodiments, the processing equipment may select one signal component and disregard the other, non-selected signal component. For example, the processing equipment may determine at step 8416 that the LF signal has a higher kurtosis and/or standard deviation than the HF signal, and accordingly may select the LF signal for conditioning at step 8420.

Step 8420 may include the processing equipment performing signal conditioning on the selected signal component of step 8418. In some embodiments, step 8420 may include de-trending the selected signal component. For example, the processing equipment may subtract a quadratic fit (e.g., or any other suitable de-trending such as those discussed in flow diagrams 6100 or 6200) from the selected signal component of step 8418. In some embodiments, the processing equipment may proceed to enter Search Mode or Locked Mode, and perform further processing using the conditioned, selected signal of step 8418.

Figure 85:
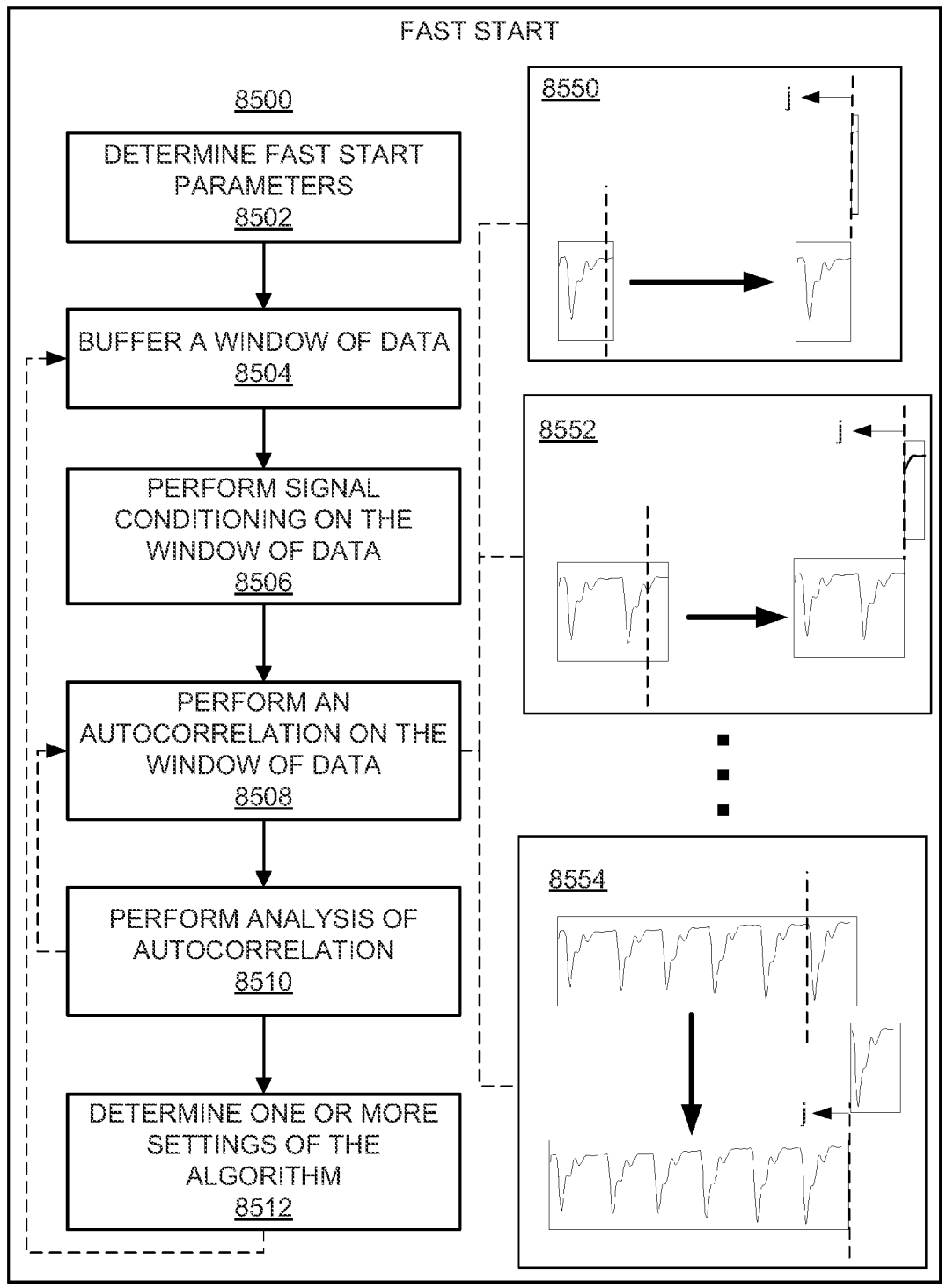
FIG. 85 is a flow diagram of illustrative steps for providing a Fast Start, in accordance with some embodiments of the present disclosure.

FIG. 85 is a flow diagram 8500 of illustrative steps for providing a Fast Start, in accordance with some embodiments of the present disclosure. Fast Start may be used in circumstances where a reduced-size window of data may be available and/or desired. In some embodiments, Fast Start allows system 300 or system 10 to start processing a physiological signal before an entire buffer (e.g., 6 or 7 seconds of data) is obtained. Fast Start may be especially useful during start-up, and/or start of data collection, of system 10 or system 300. An entire buffer of data (e.g., 6 seconds in this example, although an entire buffer may be any suitable length), for example, is typically only needed to accurately compute rates down to 20 BPM. Since most rates are 60 BPM or higher, system 300 or system 10 can begin processing sooner.

Step 8502 may include processing equipment determining Fast Start parameter(s). Fast Start parameters may include buffer sizes of a physiological signal, autocorrelation templates sizes, an increment of increase in buffer size and/or template size, a time and/or available buffer size to end Fast Start, autocorrelation analysis parameters, signal conditioning parameters, any other suitable parameters, or any combination thereof. For example, step 8502 may include determining a starting buffer and template size (e.g., a two second buffer and a half second template). In a further example, step 8502 may include determining how to increment the buffer and template size as more data is available and/or desired (e.g., increase the buffer size by one second for each calculation with the template being a fixed proportion of the buffer). In a further example, step 8502 may include determining that when a six second buffer of data is available, system 300 may transition out of Fast Start mode and begin normal operation. In a further example, step 8502 may include determining parameters used in the autocorrelation analysis of step 8510. In a further example, step 8502 may include determining signal conditioning parameters such as curve fit subtraction parameters. In some embodiments, step 8502 may include the processing equipment determining whether to operate in Fast Start mode.

Step 8504 may include the processing equipment buffering a window of data, derived from a physiological signal. In some embodiments, the window may include a particular time interval, as included in the Fast Start parameters of step 8502. Step 8504 may include pre-processing (e.g., using pre-processor 320) the output of a physiological sensor, and then storing a window of the processed data in any suitable memory or buffer (e.g., queue serial module 72 of FIG. 2), for further processing by the processing equipment. In some embodiments, the window of data may be recalled from data stored in memory (e.g., RAM 54 of FIG. 2 or other suitable memory) for subsequent processing. In some embodiments, the window size (e.g., the number of samples or time interval of data to be buffered) of data may be selected based on Fast Start parameters of step 8502. The window of data buffered during a Fast Start may be relatively smaller than the preferred buffer size during normal operation.

Step 8506 may include the processing equipment performing signal conditioning on the window of data of step 8504. Signal conditioning may include removing DC components, low frequency components, or both, from the window of data. In some embodiments, a varying baseline may be removed from the window of data (i.e., de-trending) to constrain the data average to zero. In some embodiments, the signal conditioning of step 8506 may be based on Fast Start parameters of step 8502.

Step 8508 may include the processing equipment performing an autocorrelation on the conditioned window of data of step 8506. In some embodiments, the autocorrelation of step 8508 may include correlating a first portion of the window of data (i.e., the template) with a second portion of the window of data. The first and second portions may be exclusive of one another, may share one or more samples, or may be selected by any other suitable partition of the window of data. In some embodiments, the processing equipment may pad the buffered window of data with zeros, or other suitable padding values such as white noise (e.g., to increase the buffer size in terms of time interval/sample number). For example, if the processing equipment is configured to perform an autocorrelation using six seconds of data (e.g., a window of data under non-Fast Start conditions), but only two seconds is available from the buffer during Fast Start, the processing equipment may pad the buffered data with four seconds of zeros to create the six second window. In a further example, if the processing equipment is configured to perform an autocorrelation using six seconds of data (e.g., a window of data under non-Fast Start conditions), but only two seconds is available from the buffer during Fast Start, the processing equipment may pad the buffered data with four seconds of suitably scaled random numbers to create the six second window. Padding may, in some circumstances, allow the processing equipment to perform an autocorrelation using fixed template sizes when data availability may be limited. In some embodiments, step 8508 may include the processing equipment performing a cross-correlation of the conditioned window of data and another waveform.

In an illustrative example, once the first second of data is obtained, the processing equipment may begin one or more operations of Search Mode or Locked Mode. For example, when one second of data may normally be used as the template for a six second buffer, Fast Start may select one sixth of the buffer size for the template. Accordingly, for the first second the template may be the most recent one sixth of a second of data, as shown by panel 8550. As the buffer increases in size, the template may also increase in size. As shown in panel 8552, when two seconds of data have been buffered, the processing equipment may again select the most recent one sixth of the buffer (i.e., one third of a second in this example) as a template and perform the autocorrelation. When sufficient data has been buffered such as, for example, six seconds of data as shown in panel 8554 (with a one second template), the processing equipment may leave Fast Start mode and begin normal operation. The duration for which system 300 is in Fast Start mode may depend on the true physiological rate, the buffer size, and/or the template size.

Step 8510 may include the processing equipment performing an analysis of the autocorrelation of step 8508. In some embodiments, step 8510 may include analyzing more than one autocorrelation, for example, corresponding to one or more buffer and/or template sizes used during Fast Start. Step 8510 may include the processing equipment determining a number of threshold crossings (e.g., as shown in flow diagram 500 of FIG. 5), identifying and analyzing a peak shape (e.g., as shown in flow diagram 900 of FIG. 9), performing a cross-correlation of the autocorrelation with a cross-correlation waveform (e.g., as shown in flow diagram 1800 of FIG. 18), any other suitable analysis of the autocorrelation of step 8508, or any combination thereof. In some embodiments, the output of step 8510 may be an estimate of a physiological rate, determined using any suitable technique. In some embodiments, the processing equipment may analyze the autocorrelation of step 8508 and determine that a different template should be used with the same buffered window of data. Accordingly, the processing equipment may perform step 8508 again using the different template, as shown by the dashed arrow.

Step 8512 of flow diagram 8500 may include the processing equipment determining one or more algorithm settings based on the analysis of step 8510. In some embodiments, the one or more algorithm settings may include one or more initialization parameters. For example, the processing equipment may determine a rate estimate, and thus suitable initialization parameters, based on a number of threshold crossings, a peak shape, a cross-correlation of the autocorrelation of step 8508 with a cross-correlation waveform, any other suitable analysis, or any combination thereof.

In some embodiments, one or more aspects of an algorithm may also be changed when system 300 or system 10 is in Fast Start mode, as compared to the algorithm used during normal operation. For example, if signal conditioning of step 8506 included a curve fit subtraction, Fast Start may include the processing equipment performing the subtraction over a smaller amount of signal. Accordingly, the curve fitting will likely remove relatively higher frequencies from the signal, which may be beneficial because typically only rates of around 120 BPM and higher are likely to be found when a one second buffer of data is used.

Figure 86:
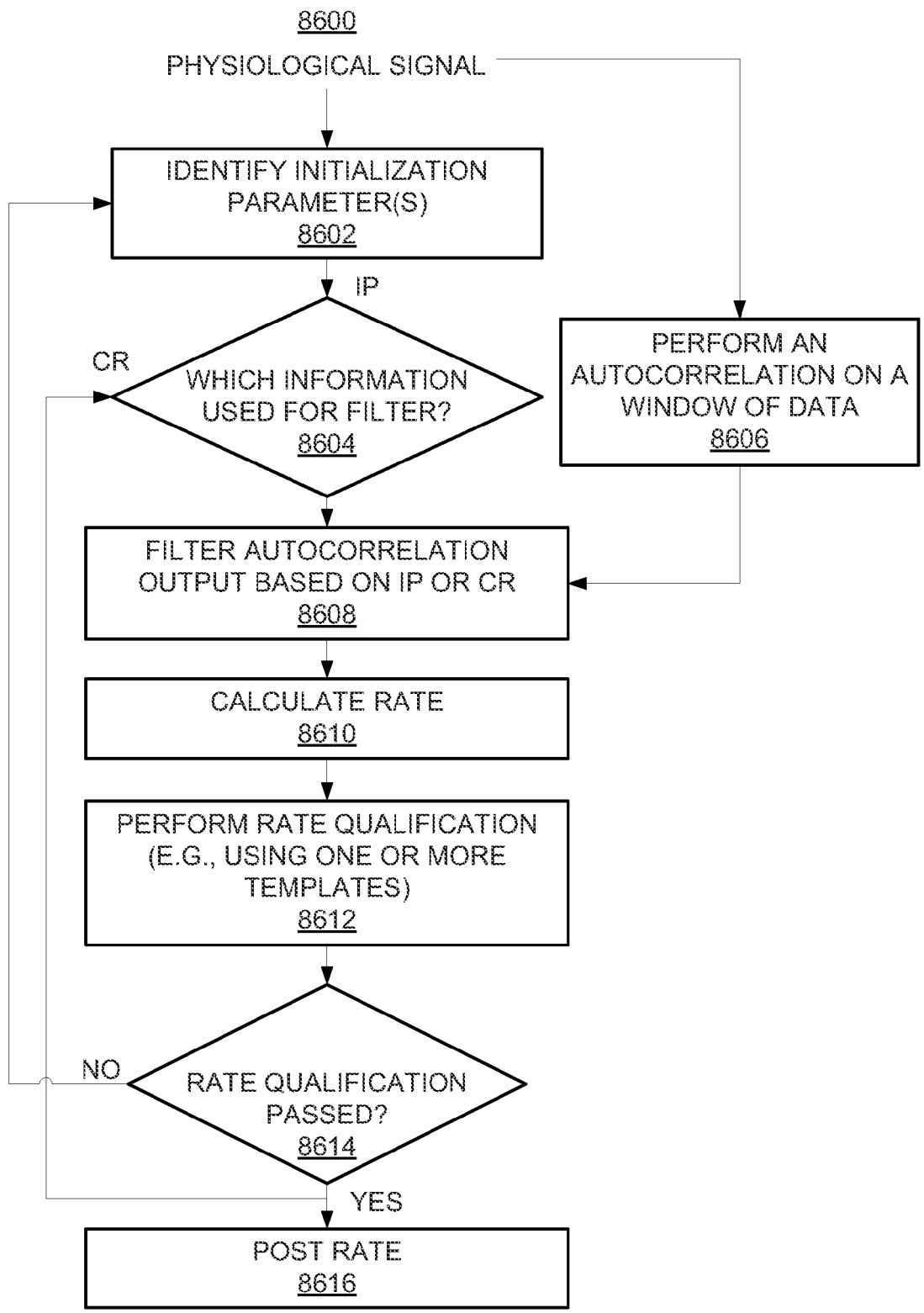
FIG. 86 is a flow diagram of illustrative steps for implementing Search Mode and Locked Mode, in accordance with some embodiments of the present disclosure.

FIG. 86 is a flow diagram 8600 of illustrative steps for implementing Search Mode and Locked Mode, in accordance with some embodiments of the present disclosure.

Step 8602 may include processing equipment identifying one or more initialization parameters for processing a received physiological signal. The processing equipment may use any suitable technique such as, for example, those described in the context of Search Mode, to identify one or more initialization parameters, in accordance with the present disclosure. In some embodiments, initialization parameters may include one or more settings of a band pass filter such as, for example, a high and low frequency cutoff value (e.g., a frequency range), a high or low cutoff for a respective low-pass filter or high-pass filter, a representative frequency value, a set of one or more coefficients, any other suitable parameters, or any combination thereof. In some embodiments, the initialization parameters may be determined based on the received physiological signal.

Step 8604 may include the processing equipment determining whether to use one or more initialization parameters (IP) identified at step 8602 or a previously calculated rate (CR) to filter an autocorrelation of a window of data buffered from the physiological signal. In some embodiments, the processing equipment may determine that a previously calculated rate, associated with a passed test at step 8614, may be used to provide filter information (e.g., a period P). In some embodiments, the processing equipment may determine that if the previously calculated rate is not associated with a passed test at step 8614, the one or more identified initialization parameters of step 8602 are to be used to provide filter information. In some embodiments, the processing equipment may determine that no previously calculated rate is available (e.g., during start-up, or instances of high-noise in the physiological signal), and may select the one or more identified initialization parameters of step 8602 to provide filter information. The determination of step 8604 may be based on the physiological signal or metric derived thereof (e.g., a noise metric or a confidence metric)

Step 8606 may include the processing equipment performing an autocorrelation on a window of data buffered from the physiological signal. In some embodiments, the autocorrelation of step 8606 may include correlating a first portion (e.g., a template) of the window of data with a second portion of the window of data. The first and second portions may be exclusive of one another, may share one or more samples, or may be selected by any other suitable partition of the window of data. In some embodiments, a stored template may be used to perform the autocorrelation (e.g., as discussed in the context of flow diagram 8200). The resulting autocorrelation output of step 8606 may exhibit one or more peaks. In some embodiments, step 8606 may include the processing equipment, pre-processor 320, or both, performing signal conditioning on the physiological signal and/or autocorrelation output. Signal conditioning may include filtering (e.g., low pass, high pass, band pass, notch, or any other suitable filter), amplifying, performing an operation on the received signal (e.g., taking a derivative, averaging), performing any other suitable signal conditioning, or any combination thereof. For example, in some embodiments, step 8606 may include removing a DC offset, low frequency components, or both, of the physiological signal. In a further example, step 8606 may include smoothing the received physiological signal (e.g., using a moving average or other smoothing technique). In some embodiments, step 8606 may include the processing equipment performing a cross-correlation of the window of data, or a portion thereof, and another waveform.

Step 8608 may include the processing equipment filtering the autocorrelation output of step 8606 based on either the IP or CR of step 8604. In some embodiments, the processing equipment may apply an adjustable band-pass filter to the autocorrelation output of step 8606. For example, the band-pass filter may be adjusted to center at a frequency selected at step 8604 (e.g., corresponding to either the previously calculated rate or the rate associated with the one or more initialization parameters). The processing equipment may apply any suitable type of filter at step 8608, having any suitable spectral characteristics (e.g., cut-off, roll-off shape and size, and/or bandwidth).

Step 8610 may include the processing equipment calculating a rate based on the filtered autocorrelation output of step 8608. The processing equipment may use any suitable technique such as, for example, those described in the context of Search Mode and/or Locked Mode, to calculate a rate based on an autocorrelation output, in accordance with the present disclosure. For example, step 8610 may include generating a threshold using a CFAR window and a binary signal to calculate the rate.

Step 8612 may include the processing equipment performing a Qualification for the calculated rate of step 8610. The processing equipment may implement any suitable qualification technique such as, for example, those techniques disclosed in the context of FIGS. 38-57. In some embodiments, for example, step 8612 may include the processing equipment performing a cross-correlation of the window of data buffered from the physiological signal and a cross-correlation template. The cross-correlation output may be analyzed using any suitable qualification test to qualify or disqualify a calculated rate.

Step 8614 may include the processing equipment determining whether to qualify or disqualify the calculated rate of step 8610. Step 8616 may include the processing equipment posting the rate calculated at step 8610 if it has been qualified at step 8614. Step 8616 may include displaying the posted rate (e.g., on display 20 of system 10), storing the rate in suitable memory, replacing a previously posted rate, performing any other suitable processing, or any combination thereof. If the calculated rate of step 8610 is disqualified at step 8614, the processing equipment may then repeat step 8602 and/or step 8604. In some embodiments, the calculated rate of step 8610 may be used in a further iteration at step 8604, if qualified at step 8614, after the rate has been posted at step 8616.

Figure 87:
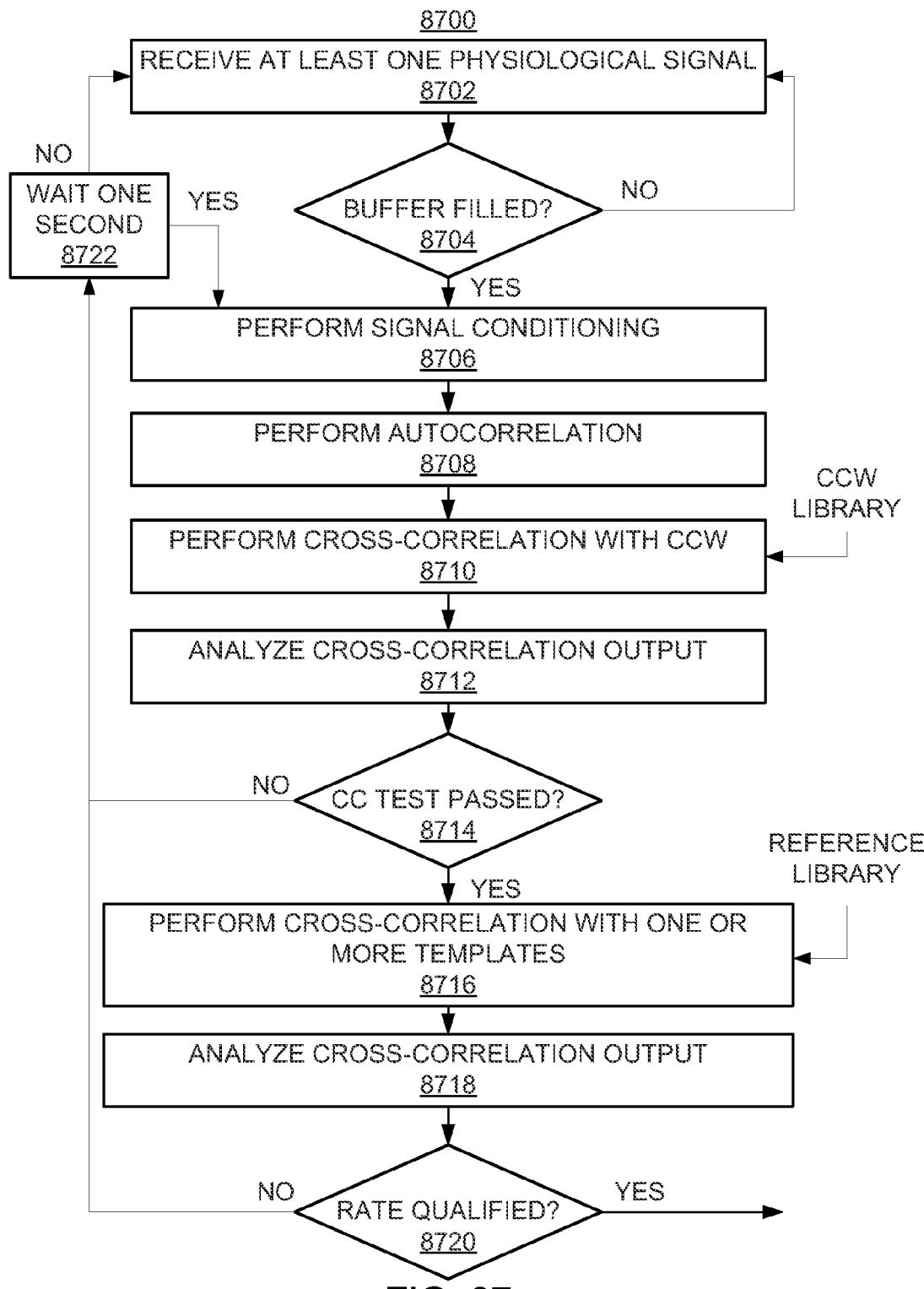
FIG. 87 is a flow diagram of illustrative steps for implementing Search Mode, in accordance with some embodiments of the present disclosure.

FIG. 87 is a flow diagram 8700 of illustrative steps for implementing Search Mode, in accordance with some embodiments of the present disclosure.

Step 8702 may include processing equipment receiving at least one physiological signal from a physiological sensor, memory, any other suitable source, or any combination thereof. For example, referring to system 300 of FIG. 3, the processing equipment may receive a physiological signal from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., any suitable memory of system 10 or system 300) after being pre-processed by pre-processor 320. In such cases, step 8702 may include recalling the signals from the memory for further processing. In some embodiments, step 8702 may include receiving a particular time interval or corresponding number of samples of the physiological signal. In some embodiments, step 8702 may include receiving a digitized, sampled, and pre-processed physiological signal. The physiological signal of step 8702 may include a PPG signal, which may include a sequence of pulse waves and may exhibit motion artifacts, noise from ambient light, electronic noise, system noise, any other suitable signal component, or any combination thereof.

Step 8704 may include the processing equipment determining whether a data storage buffer is filled. In some embodiments, the buffer may be determined to be filled when a full window of data of a desired length has been stored ("buffered"). For example, a six second window of data may be desired, and the processing equipment may wait as more data is buffered until the full six seconds is stored. In some embodiments, such as during Fast Start, the processing equipment may determine that the buffer is sufficiently filled to proceed to step 8706, although what would be considered a full window of data has not been buffered. In some embodiments, the buffer may continually store the data from the incoming physiological signal, and accordingly continually update the contents of at least a portion of the buffer.

Step 8706 may include the processing equipment performing signal conditioning on the buffered window of data of step 8704. Signal conditioning may include removing DC components, low frequency components, or both, from the window of data (e.g., by high-pass or band-pass filtering). In some embodiments, a varying baseline may be removed from the window of data (i.e., de-trending) to constrain the data average to zero. In some embodiments step 8706 may include calculating an ensemble average window of data of multiple windows of data. In some embodiments, step 8706 may include smoothing the physiological signal. For example, a moving average may be calculated and outputted as the conditioned signal. In some embodiments, step 8706 may include subtracting a quadratic fit and a cubic fit from the physiological signal to remove the DC and low frequency components.

Step 8708 may include the processing equipment performing an autocorrelation on a window of data buffered from the physiological signal. In some embodiments, the autocorrelation of step 8708 may include correlating a first portion (e.g., a template) of the window of data with a second portion of the window of data. The first and second portions may be exclusive of one another, may share one or more samples, or may be selected by any other suitable partition of the window of data. In some embodiments, a stored template may be used to perform the autocorrelation (e.g., as discussed in the context of flow diagram 8200). The resulting autocorrelation output of step 8708 may exhibit one or more peaks.

Step 8710 may include the processing equipment performing a cross-correlation of the autocorrelation of step 8708 with a cross-correlation waveform. In some embodiments, step 8710 may include the processing equipment performing a cross-correlation of the conditioned physiological signal of step 8706 with a cross-correlation waveform, and step 8708 need not be performed. The following discussion, and FIG. 87, will reference using the autocorrelation of step 8708 for illustration, although the same techniques will apply if step 8708 is omitted. The cross-correlation waveform may include a concatenation of segments, each including a waveform of a particular characteristic frequency. Further detail regarding generation of, use of, and properties of, the cross-correlation waveform is provided above in the discussion of FIGS. 18-20, for example. The output of step 8710 may be a cross-correlation output, exhibiting segments corresponding to the segments of the cross-correlation waveform.

Step 8712 may include the processing equipment analyzing the cross-correlation output of step 8710 to determine one or more algorithm settings. In some embodiments, step 8712 may include determining a maximum in the cross-correlation output, and identifying a segment of the cross-correlation waveform corresponding to the maximum. In some embodiments, step 8712 may include identifying a pattern in the cross-correlation. In some embodiments, characteristics of an upper envelope may be calculated, compared with threshold values, or otherwise analyzed to identify a physiological peak. In some embodiments, the processing equipment may use any of the cross-correlation analysis techniques disclosed in the context of the flow diagrams of FIGS. 18, 23, 25, 27, 29, and 33. For example, step 8712 may include the processing equipment identifying one or more peaks of the cross-correlation output. The analysis may provide one or more algorithm settings, such as a representative physiological rate, associated period, or likely ranges thereof.

Step 8714 may include the processing equipment determining whether one or more cross-correlation tests have been passed based on the analysis of step 8712. In some embodiments, the processing equipment may use any of the cross-correlation tests disclosed in the context of the flow diagrams of FIGS. 18, 23, 25, 27, 29, and 33. For example, step 8712 may include the processing equipment qualifying (i.e., passing the test) or disqualifying (i.e., not passing the test) one or more peaks of the cross-correlation output based on a threshold. For example, the peak height may be compared to a threshold equal to six times the standard deviation of the cross-correlation waveform. If the test is not passed at step 8714, the processing equipment may continue on to step 8722 and wait one second before performing one or more of steps 8706-8712 again. If the test is passed at step 8714, the processing equipment may continue on to step 8716.

Step 8716 may include the processing equipment performing a cross-correlation of the buffered window of data with one or more cross-correlation templates (e.g., stored in a reference library). The cross-correlation may be performed using any suitable algorithm. The output of step 8716 may be a cross-correlation output, which may include a series of cross-correlation values taken for a corresponding series of time lags (or sample number lags) between the predefined template and the physiological signal. In some embodiments, any of the disclosed techniques of flow diagram 3800 of FIG. 38 may be used by the processing equipment at step 8716, in accordance with the present disclosure.

Step 8718 may include the processing equipment analyzing the cross-correlation output(s) of step 8716 to qualify or disqualify the initialization parameters, a calculated rate, or both. A cross-correlation output of step 8716 may include one or more peaks, indicative of high correlation between the physiological signal and a predefined template. In some embodiments, step 8718 may include analyzing one or more peaks, segments, or portions thereof, of a cross-correlation waveform, determining one or more metric values, any other suitable analysis, or any combination thereof. In some embodiments, step 8718 may include using any of the techniques disclosed in FIGS. 43, 46, 48, and 53-57. For example, tests described above such as, for example, the Symmetry Test, Radius Test, Angle Test, Area Test, Area Similarity Test, Statistical Property Test, or any other suitable test, or combination thereof, may be performed at step 8718 to analyze the one or more cross-correlation output(s) of step 8716. The processing equipment may perform any suitable analysis at step 8718 to qualify or disqualify initialization parameters, a calculated rate, or both, associated with the one or more cross-correlation outputs.

Step 8720 may include the processing equipment qualifying or disqualifying initialization parameters, a calculated rate, or both, based on the analysis of step 8718. In some embodiments, qualification (or disqualification) may depend on a comparison between one or metrics computed at step 8718 and one or more threshold values. In some embodiments, a disqualification at step 8720 may trigger steps 8702-8718 to repeat after waiting one second at step 8722. In some embodiments, a disqualification at step 8720 may trigger an analysis different than that of flow diagram 8700 to be performed to either qualify or disqualify the initialization parameters, calculated rate, or both, associated with the cross-correlation output.

Step 8722 may include the processing equipment waiting one second, or any other suitable time period, before repeating any of the steps of flow diagram 8700 after a test fail at step 8714 and/or a rate disqualification at step 8720. In some embodiments, the wait time may allow data stored in the buffer to be updated (e.g., partially replaced with new data). For example, when the processing equipment determines that one second has passed since the test fail at step 8714 and/or the rate disqualification at step 8720, the processing equipment may then perform signal conditioning at step 8706 on the new window of data in the buffer. In a further example, when the processing equipment determines that one second has not yet passed since the test failed at step 8714 and/or the rate disqualification at step 8720, the processing equipment may proceed to step 8702 and allow further, more recent data to be stored in the buffer until filled (e.g., as determined at step 8704).

Figure 88:
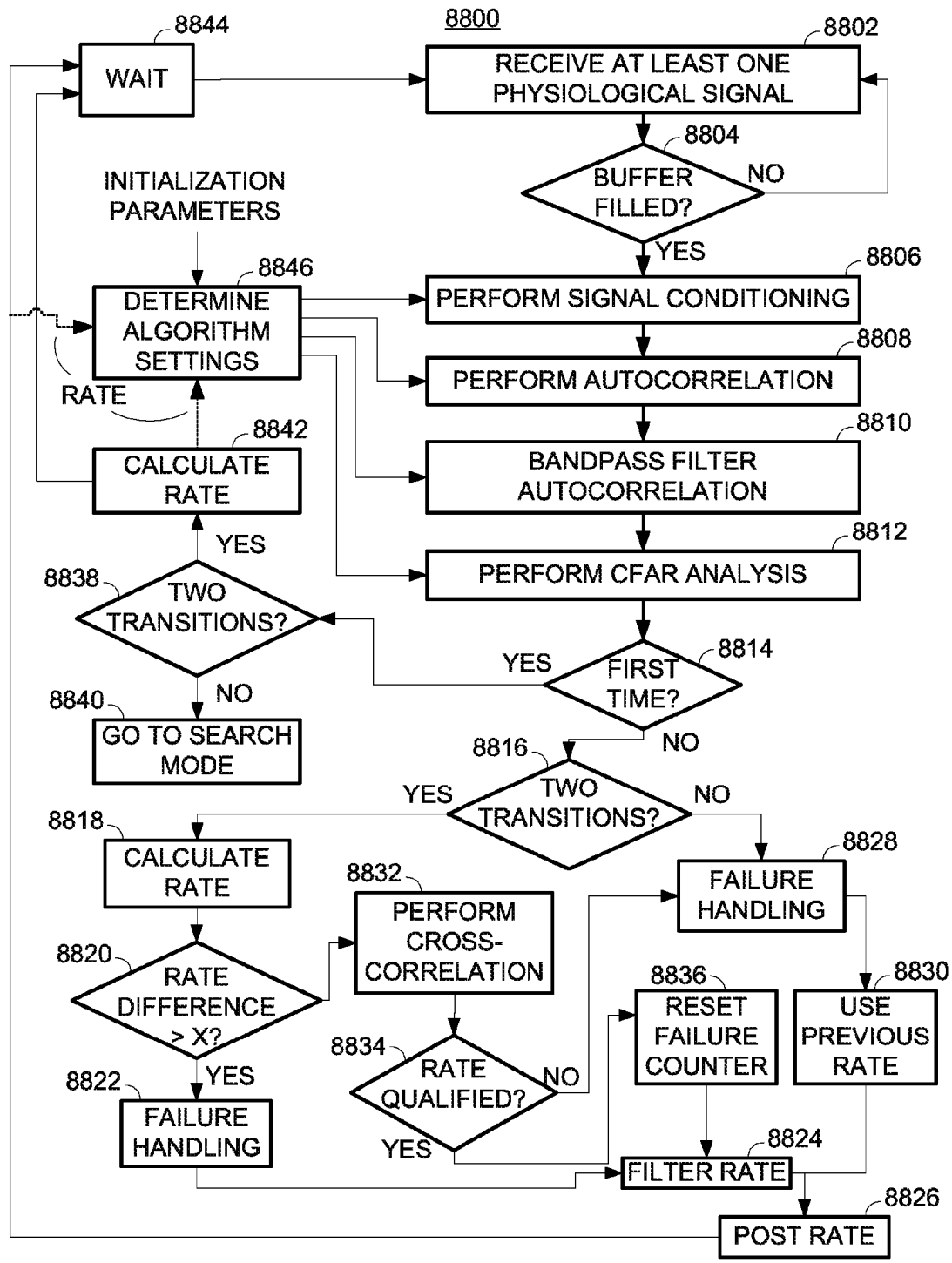
FIG. 88 is a flow diagram of illustrative steps for implementing Locked Mode, in accordance with some embodiments of the present disclosure.

FIG. 88 is a flow diagram 8800 of illustrative steps for implementing LOCKED MODE, in accordance with some embodiments of the present disclosure.

Step 8802 may include processing equipment receiving at least one physiological signal from a physiological sensor, memory, any other suitable source, or any combination thereof. For example, referring to system 300 of FIG. 3, processor 312 may receive a physiological signal from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., any suitable memory of system 10 or system 300) after being pre-processed by pre-processor 320. In such cases, step 8802 may include recalling the signals from the memory for further processing. In some embodiments, step 8802 may include receiving a particular time interval or corresponding number of samples of the physiological signal. In some embodiments, step 8802 may include receiving a digitized, sampled, and pre-processed physiological signal. The physiological signal of step 8802 may include a PPG signal, which may include a sequence of pulse waves and may exhibit motion artifacts, noise from ambient light, electronic noise, system noise, any other suitable signal component, or any combination thereof.

Step 8804 may include the processing equipment determining whether a data storage buffer is filled. In some embodiments, the buffer may be determined to be filled when a full window of data of a desired length has been buffered. For example, a six second window of data may be desired, and the processing equipment may wait as more data is buffered until the full six seconds is stored. In some embodiments, such as during Fast Start, the processing equipment may determine that the buffer is sufficiently filled to proceed to step 8806, although what would be considered a full window of data has not been buffered. In some embodiments, the buffer may continually store the data from the incoming physiological signal, and accordingly continually update the contents of at least a portion of the buffer.

Step 8806 may include the processing equipment performing signal conditioning on the buffered window of data of step 8804. Signal conditioning may include removing DC components, low frequency components, or both, from the window of data (e.g., by high-pass or band-pass filtering). In some embodiments, a varying baseline may be removed from the window of data (i.e., de-trending) to constrain the data average to zero. In some embodiments step 8806 may include calculating an ensemble average window of data of multiple windows of data. In some embodiments, step 8806 may include smoothing the physiological signal. For example, a moving average may be calculated and outputted as the conditioned signal. In some embodiments, 8806 may include subtracting a quadratic fit and a cubic fit from the physiological signal to remove the DC and low frequency components.

Step 8808 may include the processing equipment performing an autocorrelation on a window of data buffered from the physiological signal. In some embodiments, the autocorrelation of step 8808 may include correlating a first portion (e.g., a one second template) of the window of data with a second portion of the window of data. The first and second portions may be exclusive of one another, may share one or more samples, or may be selected by any other suitable partition of the window of data. In some embodiments, a stored template may be used to perform the autocorrelation (e.g., as discussed in the context of flow diagram 8200). The resulting autocorrelation output of step 8808 may exhibit one or more peaks. In some embodiments, step 8808 may include the processing equipment performing a cross-correlation of the window of data, or a portion thereof, and another waveform.

Step 8810 may include the processing equipment applying a band-pass filter to the autocorrelation output of step 8808. In some embodiments, coefficients of the band-pass filter may be fixed or adjustable. For example, the high and low cutoff frequencies of the band-pass filter may depend on one or more initialization parameters and/or calculated rates. In a further example, the band-pass filter may be adjusted to center at a frequency determined at step 8846 (e.g., corresponding to either the previously calculated rate or the rate associated with the one or more initialization parameters). The processing equipment may apply any suitable type of filter at step 8810, having any suitable spectral characteristics (e.g., cutoff, roll-off shape and size, and/or bandwidth).

Step 8812 may include the processing equipment performing CFAR analysis on the filtered autocorrelation output of step 8810. In some embodiments, the processing equipment may use any of the techniques disclosed in the context of FIG. 72 and FIG. 75. For example, step 8812 may include the processing equipment generating one or more thresholds using a CFAR window, and then optionally generating a binary signal based on crossings of the filtered autocorrelation of step 8810 and the threshold.

Step 8814 may include the processing equipment determining whether the current processing is the first instance. For example, the first time that step 8814 is performed, the processing equipment may determine "YES" at step 8814. In some embodiments, when it is the first time, a subsequently calculated rate need not be posted but rather used to determine one or more algorithm settings for the next iteration of flow diagram 8800 (e.g., see steps 8838-8846). In some embodiments, because the first rate is calculated based on initialization parameters, the first rate may not necessarily be as accurate as subsequently calculated rates that are based on previously calculated rates from Locked Mode. If the processing equipment determines that the current processing is not the first instance, then the processing equipment may proceed to step 8816.

Step 8816 may include the processing equipment determining whether there are two transitions in the binary signal generated at step 8812. For example, the presence of two or more transitions may indicate suitable crossings of the autocorrelation output and the threshold, and accordingly a rate may be calculated. If the processing equipment determines that the binary signal does not exhibit two transitions, then the processing equipment may proceed to perform failure handling at step 8828. Following failure handling step 8828, the processing equipment may continue to use and/or post the previously posted rate at step 8830. If the processing equipment determines that the binary signal does exhibit two or more transitions, then the processing equipment may proceed to calculate a rate at step 8818. Step 8818 may include the processing equipment performing any suitable rate calculation technique such as those disclosed in the context of FIG. 72. For example, the processing equipment may determine the period between successive peaks in the binary signal, and determine a rate corresponding to the period.

Step 8820 may include the processing equipment determining whether the difference between the rate calculated at step 8818 and the previously posted rate is greater than a difference threshold. In some embodiments, step 8820 may be used to prevent relatively large changes in the posted rate that are unlikely to correspond to an increase in the physiological rate. For example, a difference threshold of 24 BPM may be used at step 8820. In this illustrative example, a calculated rate of more than 24 BPM higher than the posted rate, or less than 24 BPM lower than the posted rate, may be limited to the previously posted rate plus or minus the 24 BPM, respectively. A calculated rate within a plus or minus 24 BPM range of the posted rate would be passed on to step 8832. If the rate difference is larger than the difference threshold, the processing equipment may perform failure handling at step 8822.

Step 8832 may include the processing equipment performing a cross-correlation of the buffered window of data with one or more cross-correlation templates (e.g., stored in a reference library). The cross-correlation may be performed using any suitable algorithm. The output of step 8832 may be a cross-correlation output, which may include a series of cross-correlation values taken for a corresponding series of time lags (or sample number lags) between the predefined template and the physiological signal. In some embodiments, any of the disclosed techniques of flow diagram 3800 of FIG. 38 may be used by the processing equipment at step 8832, in accordance with the present disclosure.

Step 8834 may include the processing equipment qualifying or disqualifying a calculated rate based on an analysis of the cross-correlation output of step 8832. A cross-correlation output of step 8832 may include one or more peaks, indicative of high correlation between the physiological signal and a predefined template. In some embodiments, step 8834 may include analyzing one or more peaks, segments, or portions thereof, of a cross-correlation waveform, determining one or more metric values, any other suitable analysis, or any combination thereof. In some embodiments, step 8834 may include using any of the techniques disclosed in FIGS. 43, 46, 48, and 54-57. For example, tests described above such as the Symmetry Test, Radius Test, Angle Test, Area Test, Area Similarity Test, Statistical Property Test, any other suitable test, or any combination thereof, may be performed at step 8834 to analyze the one or more cross-correlation output(s) of step 8832. The processing equipment may perform any suitable analysis at step 8834 to qualify or disqualify a calculated rate. In some embodiments, qualification (or disqualification) may depend on a comparison between one or more metrics and one or more threshold values. In some embodiments, a disqualification at step 8834 may trigger the processing equipment to perform failure handling at step 8828.

Following a qualification at step 8834, the processing equipment may reset a failure counter at step 8836. In some embodiments, the failure counter may store an index of the failure instances from step 8828 and/or step 8822. Step 8836 may include the processing equipment resetting the failure counter to zero.

Step 8824 may include the processing equipment filtering the calculated rate of step 8818. In some embodiments, the processing equipment may apply a filter to smooth, average, or otherwise limit the change of a rate to be posted at step 8826. For example, the processing equipment may apply an infinite impulse response filter (IIR) to the calculated rate. The filter may be a fixed or adjustable weight filter. For example, the filter weights may be adjusted based on signal confidence (e.g., based on an independent signal confidence metric, based on qualification metric values, based on CFAR analysis).

Step 8826 may include the processing equipment posting the filtered rate of step 8824 and/or the previous rate of step 8830. Step 8826 may include displaying the posted rate (e.g., on display 20 of system 10), storing the rate in suitable memory, replacing a previously posted rate, performing any other suitable processing, or any combination thereof.

Failure handling steps 8828 and 8822 may include incrementally increasing a counter to keep track of the number of failures. In some embodiments, failure handling step 8828 and/or failure handling step 8822 may include the processing equipment returning to Search Mode after a particular number of failures is reached.

If at step 8814 the processing equipment determines that the current processing is not the first instance, then the processing equipment may proceed to step 8838 and determine whether the binary signal of step 8812 exhibits two or more transitions. If at step 8838 the processing equipment determines that the binary signal of step 8812 does not exhibit two or more transitions, the processing equipment may proceed to operate in Search Mode at step 8840 to determine one or more new initialization parameters.

Step 8842 may include the processing equipment performing any suitable rate calculation technique such as those disclosed in the context of FIG. 72. For example, the processing equipment may determine the period between successive peaks in the binary signal, and determine a rate corresponding to the period.

Step 8844 may include the processing equipment waiting a suitable time period, before repeating any of the steps of flow diagram 8800 after calculating a rate at step 8842 and/or posting a rate at step 8826. In some embodiments, the wait time may allow data stored in the buffer to be updated (e.g., partially replaced with new data). For example, when the processing equipment determines that a wait time of one second has passed since the rate calculation of step 8842 and/or rate posting of step 8826, the processing equipment may then receive the most recent one second of data of the physiological signal at step 8802.

Step 8846 may include the processing equipment determining one or more algorithm settings based on a previously calculated rate, a posted rate, one or more initialization parameters, any other suitable information, or any combination thereof. Algorithm settings may include, for example, signal conditioning settings (e.g., de-trending parameters and curve fit type), autocorrelation settings (e.g., template size and or buffer size), filter settings (e.g., coefficients of a bandpass filter), CFAR settings (e.g., window size, guard size, and/or coefficients), any other suitable settings, or any combination thereof. The processing equipment may reset or adjust one or more algorithm settings based on a calculated rate.

It will be understood that flow diagrams 8700 and 8800 of FIGS. 87 and 88, respectively, are merely illustrative and various modifications can be made that are within the scope of the present disclosure. For example, the CFAR analysis at step 8812 need not generate a binary signal. Instead, the locations of the threshold crossings can be identified and used in the remaining steps of FIG. 88.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof which are within the spirit of the following claims.

What is claimed is:

1. A subject monitoring pulse oximetry system for determining physiological information of a subject, comprising:
   a pulse oximetry sensor configured to generate an intensity signal, wherein the pulse oximetry sensor detects light attenuated by the subject; and
   a pulse oximetry processor coupled to the pulse oximetry sensor, wherein the pulse oximetry processor is configured to:
      calculate a first autocorrelation sequence of an optical intensity signal derived from the intensity signal;
      calculate a second autocorrelation sequence of the optical intensity signal, wherein the second autocorrelation sequence uses a template of a different size than used in the calculation of the first autocorrelation sequence;
      combine the first autocorrelation sequence and the second autocorrelation sequence; and
      determine a value indicative of physiological information of the subject based on the combined autocorrelation sequence, wherein the physiological information comprises pulse rate; and
   a display configured to display the value indicative of the physiological information.

2. The system of claim 1, wherein the pulse oximetry processor is further configured to:
   calculate the first autocorrelation sequence using a first template of data; and
   calculate the second autocorrelation sequence using a second template of data, wherein the first template of data is based on a more recent portion of the optical intensity signal than the second template of data.

3. The system of claim 1, wherein the pulse oximetry processor is further configured to average the first autocorrelation sequence and the second autocorrelation sequence.

4. The system of claim 1, wherein the pulse oximetry processor is further configured to:
   bandpass filter the combined autocorrelation sequence; and
   determine the value indicative of the physiological information based on the bandpass filtered autocorrelation sequence.

5. The system of claim 1, wherein the pulse oximetry processor is further configured to:
   identify peaks in the combined autocorrelation sequence; and
   determine the value indicative of physiological information based on the identified peaks.

6. The system of claim 5, wherein the pulse oximetry processor is further configured to:
   determine a difference associated with at least two peaks; and
   determine the value indicative of physiological information based on the difference.

7. The system of claim 1, wherein the intensity signal is a photoplethysmograph signal.

8. A pulse oximeter module for determining physiological information of a subject, wherein the pulse oximeter module comprises a pulse oximetry processor configured to:
   receive an optical intensity signal derived from a detector output of a pulse oximetry sensor, wherein the pulse oximetry sensor detects light attenuated by the subject;
   calculate a first autocorrelation sequence of the optical intensity signal;
   calculate a second autocorrelation sequence of the optical intensity signal, wherein the second autocorrelation sequence uses a template of a different size than used in the calculation of the first autocorrelation sequence;
   combine the first autocorrelation sequence and the second autocorrelation sequence;
   determine a value indicative of physiological information of the subject based on the combined autocorrelation sequence, wherein the physiological information comprises pulse rate; and
   output the value indicative of the physiological information on a display.

9. The pulse oximeter module of claim 8, wherein the pulse oximetry processor is further configured to:
   calculate the first autocorrelation sequence using a first template of data; and
   calculate the second autocorrelation sequence using a second template of data, wherein the first template of data is based on a more recent portion of the optical intensity signal than the second template of data.

10. The pulse oximeter module of claim 8, wherein the pulse oximetry processor is further configured to average the first autocorrelation sequence and the second autocorrelation sequence.

11. The pulse oximeter module of claim 8, wherein the pulse oximetry processor is further configured to:
    bandpass filter the combined autocorrelation sequence; and
    determine the value indicative of the physiological information based on the bandpass filtered autocorrelation sequence.

12. The pulse oximeter module of claim 8, further wherein the pulse oximetry processor is configured to:
    identify peaks in the combined autocorrelation sequence; and
    determine the value indicative of physiological information based on the identified peaks.

13. The pulse oximeter module of claim 12, wherein the pulse oximetry processor is further configured to:
    determine a difference associated with at least two peaks; and determine the value indicative of physiological information based on the difference.

14. The processing module of claim 8, wherein the optical intensity signal is a photoplethysmograph signal.

15. A method for determining physiological information of a subject by a pulse oximeter, comprising:
    receiving, using a pulse oximetry processor, an optical intensity signal derived from a detector of a pulse oximetry sensor, wherein the pulse oximetry sensor detects light attenuated by the subject;
    calculating, using the pulse oximetry processor, a first autocorrelation sequence of the optical intensity signal;
    calculating, using the pulse oximetry processor, a second autocorrelation sequence of the optical intensity signal, wherein the second autocorrelation sequence uses a template of a different size than used in the calculation of the first autocorrelation sequence;

combining, using the pulse oximetry processor, the first autocorrelation sequence and the second autocorrelation sequence;

determining, using the pulse oximetry processor, a value indicative of physiological information of the subject based on the combined autocorrelation sequence, wherein the physiological information comprises pulse rate; and displaying, using a display, the value indicative of the physiological information.

16. The method of claim 15, wherein the calculation of the first autocorrelation sequence uses a first template of data, wherein the calculation of the second autocorrelation sequence uses a second template of data, and wherein the first template of data is based on a more recent portion of the optical intensity signal than the second template of data.

17. The method of claim 15, wherein combining the first autocorrelation sequence and the second autocorrelation sequence comprises averaging the first autocorrelation sequence and the second autocorrelation sequence.

18. The method of claim 15, further comprising bandpass filtering, using the pulse oximetry processor, the combined autocorrelation sequence, wherein determining the value indicative of the physiological information comprises determining the value indicative of the physiological information based on the bandpass filtered autocorrelation sequence.

19. The method of claim 15, further comprising identifying, using the pulse oximetry processor, peaks in the combined autocorrelation sequence, wherein the determining the value indicative of physiological information comprises determining the value indicative of physiological information based on the identified peaks.

20. The method of claim 19, further comprising determining, using the pulse oximetry processor, a difference associated with at least two peaks, wherein the determining the value indicative of physiological information comprises determining the value indicative of physiological information based on the difference.

21. The method of claim 15, wherein the optical intensity signal is a photoplethysmograph signal.

22. A non-transitory computer-readable medium for use in determining physiological information of a subject, the non-transitory computer-readable medium comprising:

computer program instructions recorded thereon for causing a pulse oximetry processor to:

receive an optical intensity signal derived from an output of a detector, wherein the detector detects light attenuated by the subject;

calculate a first autocorrelation sequence of the optical intensity signal;

calculate a second autocorrelation sequence of the optical intensity signal, wherein the second autocorrelation sequence uses a template of a different size than used in the calculation of the first autocorrelation sequence;

combine the first autocorrelation sequence and the second autocorrelation sequence;

determine a value indicative of physiological information of the subject based on the combined autocorrelation sequence, wherein the physiological information comprises pulse rate; and output the value indicative of the physiological information on a display.

23. The non-transitory computer-readable medium of claim 22, wherein the calculation of the first autocorrelation sequence uses a first template of data, wherein the calculation of the second autocorrelation sequence uses a second template of data, and wherein the first template of data is based on a more recent portion of the optical intensity signal than the second template of data.

24. The non-transitory computer-readable medium of claim 22, having further computer program instructions recorded thereon for causing the pulse oximetry processor to average the first autocorrelation sequence and the second autocorrelation sequence.

25. The non-transitory computer-readable medium of claim 22, having further computer program instructions recorded thereon for causing the pulse oximetry processor to:

bandpass filtering the combined autocorrelation sequence; and determining the value indicative of the physiological information based on the bandpass filtered autocorrelation sequence.

26. The non-transitory computer-readable medium of claim 22, having further computer program instructions recorded thereon for causing the pulse oximetry processor to:

identify peaks in the combined autocorrelation sequence; and determine the value indicative of physiological information based on the identified peaks.

27. The non-transitory computer-readable medium of claim 26, having further computer program instructions recorded thereon for causing the pulse oximetry processor to:

determine a difference associated with at least two peaks; and determine the value indicative of physiological information based on the difference.

28. The non-transitory computer-readable medium of claim 22, wherein the optical intensity signal is a photoplethysmograph signal.

* * * * *